United States Patent
Chen et al.

(10) Patent No.: US 11,168,334 B2
(45) Date of Patent: Nov. 9, 2021

(54) CONSTRUCTS AND METHODS TO IMPROVE ABIOTIC STRESS TOLERANCE IN PLANTS

(71) Applicants: PIONEER OVERSEAS CORPORATION, Johnston, IA (US); SINOBIOWAY BIO-AGRICULTURE GROUP CO., LTD., Beijing (CN)

(72) Inventors: Guangwu Chen, Beijing (CN); Chengfeng Du, Beijing (CN); Yang Gao, Beijing (CN); Zantang Li, Beijing (CN); Guihua Lu, Beijing (CN); Guanfan Mao, Beijing (CN); Changgui Wang, Beijing (CN); Guokui Wang, Beijing (CN)

(73) Assignees: SINOBIOWAY BIO-AGRICULTURE GROUP CO LTD; PIONEER OVERSEAS CORPORATION

( * ) Notice: Subject to any disclaimer, the term of this patent is extended or adjusted under 35 U.S.C. 154(b) by 0 days.

(21) Appl. No.: 16/342,794

(22) PCT Filed: Oct. 18, 2017

(86) PCT No.: PCT/CN2017/106665
§ 371 (c)(1),
(2) Date: Apr. 17, 2019

(87) PCT Pub. No.: WO2018/072706
PCT Pub. Date: Apr. 26, 2018

(65) Prior Publication Data
US 2019/0292557 A1   Sep. 26, 2019

(30) Foreign Application Priority Data
Oct. 19, 2016 (CN) .......................... 201610909055.3

(51) Int. Cl.
| | |
|---|---|
| *C12N 15/82* | (2006.01) |
| *C12N 9/22* | (2006.01) |
| *C12N 15/11* | (2006.01) |
| *C07K 14/415* | (2006.01) |
| *C12Q 1/68* | (2018.01) |
| *C12Q 1/6895* | (2018.01) |

(52) U.S. Cl.
CPC ........ *C12N 15/8273* (2013.01); *C07K 14/415* (2013.01); *C12N 9/22* (2013.01); *C12N 15/11* (2013.01); *C12N 15/8213* (2013.01); *C12N 15/8218* (2013.01); *C12N 15/8261* (2013.01); *C12N 15/8271* (2013.01); *C12Q 1/68* (2013.01); *C12Q 1/6895* (2013.01); *C12N 2310/20* (2017.05); *C12N 2800/80* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 2004/0123343 | A1* | 6/2004 | La Rosa | C07K 14/415 800/278 |
| 2006/0123505 | A1* | 6/2006 | Kikuchi | C07K 14/415 800/278 |
| 2007/0020621 | A1* | 1/2007 | Boukharov | C12N 15/8216 435/6.12 |

FOREIGN PATENT DOCUMENTS

| | | |
|---|---|---|
| CN | 102027111 A | 4/2011 |
| WO | 2016000644 A1 | 1/2016 |
| WO | 2016000645 A1 | 1/2016 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
McConnell et al. (Nature, 411:709-713, 2001).*
Hanzawa et al. (PNAS, 102:7748-7753, 2005).*
Wishart et al. (JBC, 270:26782-26785, 1995).*
Nishimura et al. (Plant Cell Physiol., 41 (5):583-590, 2000).*
Yang et al. (PNAS, 98:11438-11443, 2001).*
Ide et al. (J expt. Bot., 62:1483-1497, 2011).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Doerks et al., (TIG, 14:248-250, 1998).*
Smith et al. (Nature Biotechnology, 15:1222-1223, 1997).*
Bork et al. (TIG, 12:425-427, 1996).*
Tajada-Jim et al. (New Phytologist, 216:1223-1235; Published 2016).*
GenBank accession XP_015632211.1, Mar. 1, 2016.
GenBank accession XP_015789235.1, Mar. 1, 2016.
GenBank accession XP_015644811.1, Mar. 1, 2016.
GenBank accession XM_015769084.1, Mar. 1, 2016.

(Continued)

*Primary Examiner* — Vinod Kumar

(57) ABSTRACT

Isolated polynucleotides and polypeptides, and recombinant DNA constructs, suppression DNA constructs and CRISPR/Cas9 DNA constructs are provided. Compositions (such as plants or seeds) with modified expression or activity of the isolated polypeptides are obtained by transforming the regenerable plant cell with a suppression DNA construct or CRISPR/Cas construct. The plants with improving drought tolerance are obtained by decreasing the expression or activity of the isolated polynucleotide.

8 Claims, 21 Drawing Sheets

Specification includes a Sequence Listing.

(56) References Cited

OTHER PUBLICATIONS

GenBank accession XM_015624570.1, Mar. 1, 2016.
GenBank accession BAD53245.1, Dec. 16, 2008.
GenBank accession XM_015791956.1, Mar. 1, 2016.
GenBank accession XP_015647442.1, Mar. 1, 2016.
GenBank accession XM_015767245.1, Mar. 1, 2016.
GenBank accession XP_015622731.1, Mar. 1, 2016.
GenBank accession XP_015776725.1, Mar. 1, 2016.
International Search Report for PCT/CN2017/106665, dated Jan. 19, 2018.

* cited by examiner

|  | | SEQ ID NO: |
|---|---|---|
| Reference | GTCATCAATGTTGGGTAGCTCAATTGCTGCACGCTTGTTAGCCCGAAAGCTGAAGGTCGAAGGTTATATGCAGATCGTGTTTACAATATC | 94 |
| Mutation type 1 | GTCATCAATGTTGGGTAGCTCAATTGCTGCACGCTTGTTAGCCCGAAAGCATGAAGGTTATATGCAGATCGTGTTTACAATATC | 95 |
| Mutation type 2 | GTCATCAATGTTGGGTAGCTCAATTGCTGCACGCTTGTTAGCCCGAAAGCTTGAAGGTCGAAGGTTATATGCAGATCGTGTTTACAATATC | 96 |
| Mutation type 3 | GTCATCAATGTTGGGTAGCTCAATTGCTGCACGCTTGTTAGCCCGAAAGCCTGAAGGTCGAAGGTTATATGCAGATCGTGTTTACAATATC | 97 |
| Mutation type 4 | GTCATCAATGTTGGGTAGCTCAATTGCTGCACGCTTGTTAGCC----------GTCGAAGGTTATATGCAGATCGTGTTTACAATATC | 98 |
| Mutation type 5 | GTCATCAATGTTGGGTAGCTCAATTGCTGCACGCTTGTTAGC----------CTGAAGGTCGAAGGTTATATGCAGATCGTGTTTACAATATC | 99 |
| Mutation type 6 | GTCATCAATGTTGGGTAGCTCAATTGCTGCACGCTTGTTA----------GTCGAAGGTTATATGCAGATCGTGTTTACAATATC | 100 |
| Mutation type 7 | GTCATCAAT----------------------ATAAGGTCGAAGGTT ATATGCAGATCGTGTTTACAATATC | 101 |

FIG.19

| | | SEQ ID NO: |
|---|---|---|
| Reference | CACACGCACCGCACCCGAAATCCCAAGAAACGCGCGTATAAATCCCACCGGCTTGAGGAGTCGACTCGCCGATCCATCCACCCGCTT | 102 |
| Mutation type 1 | CACACGCACCGCACCCGAAATCCCAAGAAACGCGCGTATAAATCCCACCGGCTTGAGGAGTCGACTCGCCGATCCATCCACCCGCTT | 103 |
| Mutation type 2 | CACACGCACCGCACCCGAAATCCCAAGAAACGCGCGTATAAATCCCACCGGCCTTGAGGAGTCGACTCGCCGATCCATCCACCCGCTT | 104 |

FIG.20

SEQUENCE LISTING

```
<160> NUMBER OF SEQ ID NOS: 118

<210> SEQ ID NO 1
<211> LENGTH: 11934
<212> TYPE: DNA
<213> ORGANISM: Artificial Sequence
<220> FEATURE:
<223> OTHER INFORMATION: The nucleotide sequence of construct DP0158

<400> SEQUENCE: 1
gaattctcta gtcccgatct agtaacatag atgacaccgc gcgcgataat ttatcctagt      60
ttgcgcgcta tattttgttt tctatcgcgt attaaatgta taattgcggg actctaatca     120
taaaaaccca tctcataaat aacgtcatgc attacatgtt aattattaca tgcttaacgt     180
aattcaacag aaattatatg ataatcatcg caagaccggc aacaggattc aatcttaaga     240
aacgcggccg cttcagttgt ggcccagctt ggaggtcgac tcgcgaggat ctctgcagag     300
agatagattt gtagagagag actggtgatt tcagcgtgtc ctctccaaat gaaatgaact     360
tccttatata gaggaagggt cttgcgaagg atagtgggat tgtgcgtcat cccttacgtc     420
agtggagata tcacatcaat ccacttgctt tgaagacgtg gttggaacgt cttcttttc      480 cacgatgctc ctcgtgggtg ggggtccatc tttgggacca ctgtcggcag aggcatcttg     540
```

-continued

```
aacgatagcc tttcctttat cgcaatgatg gcatttgtag gtgccacctt ccttttctac    600
tgtccttttg atgaagtgac agatagctgg gcaatggaat ccgaggaggt ttcccgatat    660
tacccttttgt tgaaaagtct aatagccct ttggtcttct gagactgtat ctttgatatt    720
cttggagtag acgagagtgt cgtgctccac catgttcaca tcaatccact tgctttgaag    780
acgtggttgg aacgtcttct ttttccacga tgctcctcgt gggtggggt ccatctttgg    840
gaccactgtc ggcagaggca tcttgaacga tagccttcc tttatcgcaa tgatggcatt    900
tgtaggtgcc accttccttt tctactgtcc ttttgatgaa gtgacagata gctgggcaat    960
ggaatccgag gaggtttccc gatattaccc tttgttgaaa agtctcaata gcccttggt   1020
cttctgagac tgtatctttg atattcttgg agtagacgag agtgtcgtgc tccaccatgt   1080
tgccaagctg ctctaagctt tggcggccgc attcgcaaaa cacacctaga ctagatttgt   1140
tttgctaacc caattgatat taattatata tgattaatat ttatatgtat atggatttgg   1200
ttaatgaaat gcatctggtt catcaaagaa ttataaagac acgtgacatt catttaggat   1260
aagaaatatg gatgatctct ttctctttta ttcagataac tagtaattac acataacaca   1320
caactttgat gcccacatta tagtgattag catgtcacta tgtgtgcatc cttttatttc   1380
atacattaat taagttggcc aatccagaag atggacaagt ctaggttaac catgtggtac   1440
ctacgcgttc gaatatccat gggccgctac aggaacaggt ggtggcggcc ctcggtgcgc   1500
tcgtactgct ccacgatggt gtagtcctcg ttgtgggagg tgatgtccag cttggcgtcc   1560
acgtagtagt agccgggcag ctgcacgggc ttcttggcca tgtagatgga cttgaactcc   1620
accaggtagt ggccgccgtc cttcagcttc agggccttgt gggtctcgcc cttcagcacg   1680
ccgtcgcggg ggtacaggcg ctcggtggag gcctcccagc ccatggtctt cttctgcatc   1740
acggggccgt cggaggggaa gttcacgccg atgaacttca ccttgtagat gaagcagccg   1800
tcctgcaggg aggagtcctg ggtcacggtc gccacgccgc cgtcctcgaa gttcatcacg   1860
cgctcccact gaagccctc ggggaaggac agcttcttgt agtcgggat gtcggcgggg   1920
tgcttcacgt acaccttgga gccgtactgg aactgggggg acaggatgtc ccaggcgaag   1980
ggcagggggc cgcccttcgt caccttcagc ttcacggtgt tgtggccctc gtaggggcgg   2040
ccctcgccct cgccctcgat ctcgaactcg tggccgttca cggtgccctc catgcgcacc   2100
ttgaagcgca tgaactcggt gatgacgttc tcggaggagg ccatggtggc gaggatctac   2160
tcggctacac tcacacgctc gctctcgcag ttgcaggtgt aagtttctag ctagggcact   2220
cacggggtac gtatttgtag ccagccacgc acggtctgag ctcgccatgt gccgccatgc   2280
atgcgggggc acgtcgccag cgtacgcggc catcgtcgct gacgaaggta gcgcattcaa   2340
gtccggtcgg tagaggtcag ctgggtcgtt cgccgatggt agttgccgcc cggactcagt   2400
gggcggtagg cgaaggctag caagcagacg actccattca tgcgcatcat ccaaaggtga   2460
tgcaaagcct tccaaacgcg attgtctcat gatgtttccg tctcttgtta cgaggagtac   2520
aatttttttct tatacacgaa cgttacttta tgtcacattt ccatgccatg aacaccttgg   2580
cttcaaataa gtgagtgttt ttttttcacat tctgtggcat aaacagaatt tctagagtgg   2640
catttgtgat acattgtgaa agctaagagt ggtaaaagta aaataaaatt gttttgcttt   2700
tgccgcggaa tggaaattat ttgtcaaaac ctaagagtgg caaaactgaa atgtcaaaac   2760
ctagagtgac ataaacaaaa tttacccatc actaaatgag cacaaatat ttcaccacaa   2820
tggaggtatg tgaggtccga tgtactacta gagctcatcg gaaaagcatc ctcttgatga   2880
gtaaacctct tgaagtactg taccaccaca ttttatttat cctcatcggc ttattttag   2940
```

```
gccacggtta ttctcacgaa gagacggtta acccttctcg tagactacac atcgagatcc    3000
actagttcta gagcggccag cttcgaagct tggcactggc cgtcgtttta caacgtcgtg    3060
actgggaaaa ccctggcgtt acccaactta atcgccttgc agcacatccc cctttcgcca    3120
gctggcgtaa tagcgaagag gcccgcaccg atcgcccttc ccaacagttg cgcagcctga    3180
atggcgaatg ctagagcagc ttgagcttgg atcagattgt cgtttccgc cttcagttta     3240 aactatcagt gtttgacagg atatattggc gggtaaacct aagagaaaag agcgtttatt    3300
agaataatcg atatttaaa agggcgtgaa aaggtttatc cgttcgtcca tttgtatgtg     3360
catgccaacc acagggttcc cctcgggatc aaagtacttt gatccaaccc ctccgctgct    3420
atagtgcagt cggcttctga cgttcagtgc agccgtcttc tgaaaacgac atgtcgcaca    3480
agtcctaagt tacgcgacag gctgccgccc tgccctttc ctggcgtttt cttgtcgcgt     3540
gttttagtcg cataaagtag aatacttgcg actagaaccg gagacattac gccatgaaca    3600
agagcgccgc cgctggcctg ctgggctatg cccgcgtcag caccgacgac caggacttga    3660
ccaaccaacg ggccgaactg cacgcggccg gctgcaccaa gctgttttcc gagaagatca    3720
ccggcaccag gcgcgaccgc ccggagctgg ccaggatgct tgaccaccta cgccctggcg    3780
acgttgtgac agtgaccagg ctagaccgcc tggcccgcag cacccgcgac ctactggaca    3840
ttgccgagcg catccaggag gccggcgcgg gcctgcgtag cctggcagag ccgtgggccg    3900
acaccaccac gccggccggc cgcatggtgt tgaccgtgtt cgccggcatt gccgagttcg    3960
agcgttccct aatcatcgac cgcacccgga gcgggcgcga ggccgccaag gcccgaggcg    4020
tgaagtttgg ccccgccct accctcaccc cggcacagat cgcgcacgcc cgcgagctga    4080
tcgaccagga aggccgcacc gtgaaagagg cggctgcact gcttggcgtg catcgctcga    4140
ccctgtaccg cgcacttgag cgcagcgagg aagtgacgcc caccgaggcc aggcggcgcg    4200
gtgccttccg tgaggacgca ttgaccgagg ccgacgccct ggcggccgcc gagaatgaac    4260
gccaagagga caagcatga aaccgcacca ggacggccag gacgaaccgt ttttcattac    4320
cgaagagatc gaggcggaga tgatcgcggc cgggtacgtg ttcgagccgc ccgcgcacgt    4380
ctcaaccgtg cggctgcatg aaatcctggc cggtttgtct gatgccaagc tggcggcctg    4440
gccggccagc ttggccgctg aagaaaccga gcgccgccgt ctaaaaaggt gatgtgtatt    4500
tgagtaaaac agcttgcgtc atgcggtcgc tgcgtatatg atgcgatgag taaataaaca    4560
aatacgcaag gggaacgcat gaaggttatc gctgtactta accagaaagg cgggtcaggc    4620
aagacgacca tcgcaaccca tctagcccgc gccctgcaac tcgccggggc cgatgttctg    4680
ttagtcgatt ccgatcccca gggcagtgcc cgcgattggg cggccgtgcg gaagatcaa     4740 ccgctaaccg ttgtcggcat cgaccgcccg acgattgacc gcgacgtgaa ggccatcggc    4800
cggcgcgact tcgtagtgat cgacggagcg ccccaggcgg cggacttggc tgtgtccgcg    4860
atcaaggcag ccgacttcgt gctgattccg gtgcagccaa gcccttacga catatgggcc    4920
accgccgacc tggtggagct ggttaagcag cgcattgagg tcacggatgg aaggctacaa    4980
gcggcctttg tcgtgtcgcg ggcgatcaaa ggcacgcgca tcggcggtga ggttgccgag    5040
gcgctggccg gtacgagct gcccattctt gagtcccgta tcacgcagcg cgtgagctac      5100
ccaggcactg ccgccgccgg cacaaccgtt cttgaatcag aacccgaggg cgacgctgcc    5160
cgcgaggtcc aggcgctggc cgctgaaatt aaatcaaaac tcatttgagt taatgaggta    5220
aagagaaaat gagcaaaagc acaaacacgc taagtgccgg ccgtccgagc gcacgcagca    5280
```

```
gcaaggctgc aacgttggcc agcctggcag acacgccagc catgaagcgg gtcaactttc    5340
agttgccggc ggaggatcac accaagctga agatgtacgc ggtacgccaa ggcaagacca    5400
ttaccgagct gctatctgaa tacatcgcgc agctaccaga gtaaatgagc aaatgaataa    5460
atgagtagat gaattttagc ggctaaagga ggcggcatgg aaaatcaaga acaaccaggc    5520
accgacgccg tggaatgccc catgtgtgga ggaacgggcg gttggccagg cgtaagcggc    5580
tgggttgtct gccggccctg caatggcact ggaaccccca gcccgaggaa tcgcgtga     5640 cggtcgcaaa ccatccggcc cggtacaaat cggcgcggcg ctgggtgatg acctggtgga    5700
gaagttgaag gccgcgcagg ccgcccagcg gcaacgcatc gaggcagaag cacgccccgg    5760
tgaatcgtgg caagcggccg ctgatcgaat ccgcaaagaa tcccggcaac cgccggcagc    5820
cggtgcgccg tcgattagga agccgcccaa gggcgacgag caaccagatt ttttcgttcc    5880
gatgctctat gacgtgggca cccgcgatag tcgcagcatc atggacgtgg ccgttttccg    5940
tctgtcgaag cgtgaccgac gagctggcga ggtgatccgc tacgagcttc cagacgggca    6000
cgtagaggtt tccgcagggc cggccggcat ggccagtgtg tgggattacg acctggtact    6060
gatggcggtt tcccatctaa ccgaatccat gaaccgatac cgggaaggga agggagacaa    6120
gcccggccgc gtgttccgtc cacacgttgc ggacgtactc aagttctgcc ggcgagccga    6180
tggcggaaag cagaaagacg acctggtaga aacctgcatt cggttaaaca ccacgcacgt    6240
tgccatgcag cgtacgaaga aggccaagaa cggccgcctg gtgacggtat ccgagggtga    6300
agccttgatt agccgctaca agatcgtaaa gagcgaaacc gggcggccgg agtacatcga    6360
gatcgagcta gctgattgga tgtaccgcga gatcacagaa ggcaagaacc cggacgtgct    6420
gacggttcac cccgattact ttttgatcga tcccggcatc ggccgttttc tctaccgcct    6480
ggcacgccgc gccgcaggca aggcagaagc cagatggttg ttcaagacga tctacgaacg    6540
cagtggcagc gccggagagt tcaagaagtt ctgtttcacc gtgcgcaagc tgatcgggtc    6600
aaatgacctg ccggagtacg atttgaagga ggaggcgggg caggctggcc cgatcctagt    6660
catgcgctac cgcaacctga tcgagggcga agcatccgcc ggttcctaat gtacggagca    6720
gatgctaggg caaattgccc tagcagggga aaaaggtcga aaaggtctct ttcctgtgga    6780
tagcacgtac attgggaacc caaagccgta cattgggaac cggaacccgt acattgggaa    6840
cccaaagccg tacattggga accggtcaca catgtaagtg actgatataa aagagaaaaa    6900
aggcgatttt tccgcctaaa actctttaaa acttattaaa actcttaaaa cccgcctggc    6960
ctgtgcataa ctgtctggcc agcgcacagc cgaagagctg caaaaagcgc ctacccttcg    7020
gtcgctgcgc tccctacgcc ccgccgcttc gcgtcggcct atcgcggccg ctggccgctc    7080
aaaaatggct ggcctacggc caggcaatct accaggcgc ggacaagccg cgccgtcgcc    7140
actcgaccgc cggcgcccac atcaaggcac cctgcctcgc gcgtttcggt gatgacggtg    7200
aaaacctctg acacatgcag ctcccggaga cggtcacagc ttgtctgtaa gcggatgccg    7260
ggagcagaca gcccgtcag ggcgcgtcag cgggtgttgg cgggtgtcgg ggcgcagcca    7320
tgacccagtc acgtagcgat agcggagtgt atactggctt aactatgcgg catcagagca    7380
gattgtactg agagtgcacc atatgcggtg tgaaataccg cacagatgcg taaggagaaa    7440
ataccgcatc aggcgctctt ccgcttcctc gctcactgac tcgctgcgct cggtcgttcg    7500
gctgcggcga gcggtatcag ctcactcaaa ggcggtaata cggttatcca cagaatcagg    7560
ggataacgca ggaaagaaca tgtgagcaaa aggccagcaa aaggccagga accgtaaaaa    7620
ggccgcgttg ctggcgtttt tccataggct ccgcccccct gacgagcatc acaaaaatcg    7680
```

```
acgctcaagt cagaggtggc gaaacccgac aggactataa agataccagg cgtttccccc   7740
tggaagctcc ctcgtgcgct ctcctgttcc gaccctgccg cttaccggat acctgtccgc   7800
cttctctcct tcgggaagcg tggcgctttc tcatagctca cgctgtaggt atctcagttc   7860
ggtgtaggtc gttcgctcca agctgggctg tgtgcacgaa ccccccgttc agcccgaccg   7920
ctgcgcctta tccggtaact atcgtcttga gtccaacccg gtaagacacg acttatcgcc   7980
actggcagca gccactggta acaggattag cagagcgagg tatgtaggcg gtgctacaga   8040
gttcttgaag tggtggccta actacggcta cactagaagg acagtatttg gtatctgcgc   8100
tctgctgaag ccagttacct tcggaaaaag agttggtagc tcttgatccg gcaaacaaac   8160
caccgctggt agcggtggtt ttttcgtttg caagcagcag attacgcgca gaaaaaaagg   8220
atctcaagaa gatcctttga tcttttctac ggggtctgac gctcagtgga acgaaaactc   8280
acgttaaggg attttggtca tgcattctag gtactaaaac aattcatcca gtaaatata    8340
atattttatt ttctcccaat caggcttgat ccccagtaag tcaaaaaata gctcgacata   8400
ctgttcttcc ccgatatcct ccctgatcga ccggacgcag aaggcaatgt cataccactt   8460
gtccgccctg ccgcttctcc caagatcaat aaagccactt actttgccat ctttcacaaa   8520
gatgttgctg tctcccaggt cgccgtggga aaagacaagt tcctcttcgg cttttccgt    8580
cttttaaaaaa tcatacagct cgcgcggatc tttaaatgga gtgtcttctt cccagttttc   8640
gcaatccaca tcggccagat cgttattcag taagtaatcc aattcggcta agcggctgtc   8700
taagctattc gtatagggac aatccgatat gtcgatggag tgaaagagcc tgatgcactc   8760
cgcatacagc tcgataatct tttcagggct ttgttcatct tcatactctt ccgagcaaag   8820
gacgccatcg gcctcactca tgagcagatt gctccagcca tcatgccgtt caaagtgcag   8880
gaccttggga acaggcagct ttccttccag ccatagcatc atgtcctttt cccgttccac   8940
atcataggtg gtcccttat accggctgtc cgtcattttt aaatataggt ttcattttc    9000
tcccaccagc ttatatacct tagcaggaga cattccttcc gtatctttta cgcagcggta   9060
ttttcgatc agttttttca attccggtga tattctcatt ttagccattt attatttcct   9120
tcctcttttc tacagtattt aaagataccc caagaagcta attataacaa gacgaactcc   9180
aattcactgt tccttgcatt ctaaaacctt aaataccaga aaacagcttt ttcaaagttg   9240
ttttcaaagt tggcgtataa catagtatcg acggagccga ttttgaaacc gcggtgatca   9300
caggcagcaa cgctctgtca tcgttacaat caacatgcta ccctccgcga gatcatccgt   9360
gtttcaaacc cggcagctta gttgccgttc ttccgaatag catcggtaac atgagcaaag   9420
tctgccgcct tacaacggct ctcccgctga cgccgtcccg gactgatggg ctgcctgtat   9480
cgagtggtga ttttgtgccg agctgccggt cggggagctg ttggctggct ggtggcagga   9540
tatattgtgg tgtaaacaaa ttgacgctta gacaacttaa taacacattg cggacgtttt   9600
taatgtactg aattaacgcc gaattaattc ggggatctg gattttagta ctggattttg    9660
gttttaggaa ttagaaattt tattgataga agtattttac aaatacaaat acatactaag   9720
ggtttcttat atgctcaaca catgagcgaa accctatagg aaccctaatt cccttatctg   9780
ggaactactc acacattatt atggagaaac tcgagcttgt cgatcgacag atccggtcgg   9840
catctactct atttctttgc cctcggacga gtgctgggc gtcggtttcc actatcggcg   9900
agtacttcta cacagccatc ggtccagacg gccgcgcttc tgcgggcgat ttgtgtacgc   9960
ccgacagtcc cggctccgga tcggacgatt gcgtcgcatc gaccctgcgc ccaagctgca  10020
```

```
tcatcgaaat tgccgtcaac caagctctga tagagttggt caagaccaat gcggagcata    10080
tacgcccgga gtcgtggcga tcctgcaagc tccggatgcc tccgctcgaa gtagcgcgtc    10140
tgctgctcca tacaagccaa ccacggcctc cagaagaaga tgttggcgac ctcgtattgg    10200
gaatccccga acatcgcctc gctccagtca atgaccgctg ttatgcggcc attgtccgtc    10260
aggacattgt tggagccgaa atccgcgtgc acgaggtgcc ggacttcggg gcagtcctcg    10320
gcccaaagca tcagctcatc gagagcctgc gcgacgacg cactgacggt gtcgtccatc     10380
acagtttgcc agtgatacac atggggatca gcaatcgcgc atatgaaatc acgccatgta    10440
gtgtattgac cgattccttg cggtccgaat gggccgaacc cgctcgtctg gctaagatcg    10500
gccgcagcga tcgcatccat agcctccgcg accggttgta aacagcggg cagttcggtt      10560 tcaggcaggt cttgcaacgt gacaccctgt gcacggcggg agatgcaata ggtcaggctc    10620 tcgctaaaact ccccaatgtc aagcacttcc ggaatcggga gcgcggccga tgcaaagtgc   10680
cgataaacat aacgatcttt gtagaaacca tcggcgcagc tatttacccg caggacatat    10740
ccacgccctc ctacatcgaa gctgaaagca cgagattctt cgcctccga gagctgcatc      10800 aggtcggaga cgctgtcgaa cttttcgatc agaaacttct cgacagacgt cgcggtgagt    10860
tcaggctttt tcatatctca ttgccccccg ggatctgcga aagctcgaga gagatagatt    10920
tgtagagaga gactggtgat ttcagcgtgt cctctccaaa tgaaatgaac ttccttatat    10980
agaggaaggt cttgcgaagg atagtgggat tgtgcgtcat cccttacgtc agtggagata    11040
tcacatcaat ccacttgctt tgaagacgtg gttggaacgt cttcttttc cacgatgctc      11100 ctcgtgggtg ggggtccatc tttgggacca ctgtcggcag aggcatcttg aacgatagcc    11160
tttcctttat cgcaatgatg gcatttgtag gtgccacctt cctttctac tgtcctttg       11220 atgaagtgac agatagctgg gcaatggaat ccgaggaggt ttcccgatat tacccttttgt   11280 tgaaaagtct caatagccct ttggtcttct gagactgtat cttttgatatt cttggagtag    11340 acgagagtgt cgtgctccac catgttatca catcaatcca cttgctttga agacgtggtt    11400
ggaacgtctt ctttttccac gatgctcctc gtgggtgggg gtccatcttt gggaccactg    11460
tcggcagagg catcttgaac gatagccttt cctttatcgc aatgatggca tttgtaggtg    11520
ccaccttcct tttctactgt ccttttgatg aagtgacaga tagctgggca atggaatccg    11580
aggaggtttc ccgatattac ccttttgttga aaagtctcaa tagcccttttg gtcttctgag    11640 actgtatctt tgatattctt ggagtagacg agagtgtcgt gctccaccat gttggcaagc     11700
tgctctagcc aatacgcaaa ccgcctctcc ccgcgcgttg gccgattcat taatgcagct    11760
ggcacgacag gtttcccgac tggaaagcgg gcagtgagcg caacgcaatt aatgtgagtt    11820
agctcactca ttaggcaccc caggctttac actttatgct tccggctcgt atgttgtgtg    11880
gaattgtgag cggataacaa tttcacacag gaaacagcta tgaccatgat tacg           11934
```

<210> SEQ ID NO 2
<211> LENGTH: 567
<212> TYPE: DNA
<213> ORGANISM: Oryza sativa

<400> SEQUENCE: 2

```
actctcaccc agtatagttc tccattgagc aaactaccaa agggtactca tctgaaacag      60
aatccagtga tcgaccagca tggatgatcg taggtacggc tactcgtatc caccacccca    120
aggtaataag cattatgatc acttgcagag ttacattcat gatctatctc ctcgttgatt    180
ttacttgctt gattaatttg ggcttgcaat gcgtgcgtgc agggtactac aatgggccgc    240
```

| | |
|---|---|
| cggtgatggc gccgccgcag tacgcggctc cgccgccgag gcggccggag ccgagcttcc | 300 |
| tcgaaggatg gtaagaacga caaagccata tgcgagcata cgatcgtcag aatactgtct | 360 |
| ctgtcctttg cattctctct gctaatcatg gtgctaattt gtctgaataa tacagccttg | 420 |
| ctgctctctg ctgctgctgc ctcatcgacg agtgctgctg cgacccatcg gtcatatttg | 480 |
| tgacctaatt acggtcacag tggcgtctcg actggttgac gaggacgaac agtctgagtt | 540 |
| gagatataca ctgtacacgt gcttgcc | 567 |

<210> SEQ ID NO 3
<211> LENGTH: 204
<212> TYPE: DNA
<213> ORGANISM: Oryza sativa

<400> SEQUENCE: 3

| | |
|---|---|
| atggatgatc gtaggtacgg ctactcgtat ccaccacccc aagggtacta caatgggccg | 60 |
| ccggtgatgg cgccgccgca gtacgcggct ccgccgccga gcggccgga gccgagcttc | 120 |
| ctcgaaggat gccttgctgc tctctgctgc tgctgcctca tcgacgagtg ctgctgcgac | 180 |
| ccatcggtca tatttgtgac ctaa | 204 |

<210> SEQ ID NO 4
<211> LENGTH: 67
<212> TYPE: PRT
<213> ORGANISM: Oryza sativa

<400> SEQUENCE: 4

Met Asp Asp Arg Arg Tyr Gly Tyr Ser Tyr Pro Pro Pro Gln Gly Tyr
1               5                   10                  15

Tyr Asn Gly Pro Pro Val Met Ala Pro Pro Gln Tyr Ala Ala Pro Pro
            20                  25                  30

Pro Arg Arg Pro Glu Pro Ser Phe Leu Glu Gly Cys Leu Ala Ala Leu
        35                  40                  45

Cys Cys Cys Cys Leu Ile Asp Glu Cys Cys Cys Asp Pro Ser Val Ile
    50                  55                  60

Phe Val Thr
65

<210> SEQ ID NO 5
<211> LENGTH: 1351
<212> TYPE: DNA
<213> ORGANISM: Oryza sativa

<400> SEQUENCE: 5

| | |
|---|---|
| ctgatttggg cattggtgtt ggtggtggag gaggatgggg aactgcgtgg cgaggagcgg | 60 |
| gacggcggtg gatgcgggtg gtgatggagg ggaggatggg aagaggcgga ggaggaggtg | 120 |
| gaaggcgccg cgggaagatc agctcgggat ggtgcccggc cggatcttct ccaacgacgg | 180 |
| ccgcagccgg acgcgacggg tgtacacgca gcaaggcgc aagggatca accaggacgc | 240 |
| catgctcgtc tgggatgggt tcggcggcga ggacgacggc gtgctgtgcg gggtgttcga | 300 |
| cgggcacggg ccgcacgggc acgtggtggc gcggagggtc cgcgactcgc tgccgctgag | 360 |
| gctcatgtcc gcggcgcgcg acagcggggc ggacatgccg gccgccgcat ggaggaaggc | 420 |
| cttcgcgcgc gcctacaagg ccatggacaa ggacctccgg tcgcacccct ccctcgattg | 480 |
| cttctgcagc ggaagcactg ccgtcaccgt cctcaagctc ggctcggatc tctacatggc | 540 |
| caacattggg gactcgcgcg ccgtgctcgg ctccaggag gccaccggcg gcggcatggt | 600 |

-continued

| | |
|---|---|
| cgccgtgcag ctcaccgttg atctcaagcc ggatgtcccc agcgaagcgg agaggatcaa | 660 |
| gaagtgcagg ggcagggtgt tcgcgctgca ggacgagccg gaggtgccaa gggtctggct | 720 |
| gccgttcgac gacgcgccgg gcctcgcgat ggcgcgagcg ttcggggact tctgcctgaa | 780 |
| agattacggg gtcatctcgg tgccggaatt cttccactgg tctctcacag aaaaggacca | 840 |
| gttcgtcatt cttgcatcgg atggggtatg ggatgtcctc agcaatcaag aggctgttga | 900 |
| tatagtgtcc gcgtccccaa gcagatcaaa ggctgcaaaa tcccttgttg aggcagccac | 960 |
| tcgtgaatgg aaaaccaaat atccaacatc aaaatcgat gattgcgcgg ttgtttgctt | 1020 |
| atatttggat ggaaaaatgg accatgagcg tgactcaact gcctcattgg acaacatcag | 1080 |
| tattgaagag ggttcagttg cagatcctaa tgaacctcag gagcaggagc ccaccttaac | 1140 |
| tcggaatttc acagttagga cagttgcagg cagcacgcaa gagaagacct tagcaggggt | 1200 |
| ggatgcgagg attgctggtg tagcgaacga ccaaaattgg tcaggtctcg atggagtgac | 1260 |
| acgggtaaac tcacttgttc agcttcctag gttttctgaa gagagggcaa ttggctgagc | 1320 |
| tgcccatctt atatttaccc ccgttatttt c | 1351 |

<210> SEQ ID NO 6
<211> LENGTH: 1284
<212> TYPE: DNA
<213> ORGANISM: Oryza sativa

<400> SEQUENCE: 6

| | |
|---|---|
| atggggaact gcgtggcgag gagcgggacg gcggtggatg cgggtggtga tggaggggag | 60 |
| gatgggaaga ggcggaggag gaggtggaag gcgccgcggg aagatcagct cgggatggtg | 120 |
| cccggccgga tcttctccaa cgacggccgc agccggacgg cgacggtgta cacgcagcaa | 180 |
| gggcgcaagg ggatcaacca ggacgccatg ctcgtctggg atgggttcgg cggcgaggac | 240 |
| gacggcgtgc tgtgcggggt gttcgacggg cacgggccgc acgggcacgt ggtggcgcgg | 300 |
| agggtccgcg actcgctgcc gctgaggctc atgtccgcgg cgcgcgacag cggggcggac | 360 |
| atgccggccg ccgcatggag gaaggccttc gcgcgcgcct acaaggccat ggacaaggac | 420 |
| ctccggtcgc acccttccct cgattgcttc tgcagcggaa gcactgccgt caccgtcctc | 480 |
| aagctcggct cggatctcta catggccaac attggggact cgcgcgccgt gctcggctcc | 540 |
| agggaggcca ccgcggcgg catggtcgcc gtgcagctca ccgttgatct caagccggat | 600 |
| gtccccagcg aagcggagag gatcaagaag tgcaggggca gggtgttcgc gctgcaggac | 660 |
| gagccggagg tgccaagggt ctggctgccg ttcgacgacg cgccgggcct cgcgatggcg | 720 |
| cgagcgttcg ggacttctg cctgaaagat tacggggtca tctcggtgcc ggaattcttc | 780 |
| cactggtctc tcacagaaaa ggaccagttc gtcattcttg catcggatgg ggtatgggat | 840 |
| gtcctcagca atcaagaggc tgttgatata gtgtccgcgt ccccaagcag atcaaaggct | 900 |
| gcaaaatccc ttgttgaggc agccactcgt gaatggaaaa ccaaatatcc aacatccaaa | 960 |
| atcgatgatt gcgcggttgt tgcttatat ttggatggaa aaatggacca tgagcgtgac | 1020 |
| tcaactgcct cattggacaa catcagtatt gaagagggtt cagttgcaga tcctaatgaa | 1080 |
| cctcaggagc aggagcccac cttaactcgg aatttcacag ttaggacagt tgcaggcagc | 1140 |
| acgcaagaga gaccttagc aggggtggat gcgaggattg ctggtgtagc gaacgaccaa | 1200 |
| aattggtcag gtctcgatgg agtgacacgg gtaaactcac ttgttcagct tcctaggttt | 1260 |
| tctgaagaga gggcaattgg ctga | 1284 |

<210> SEQ ID NO 7
<211> LENGTH: 427
<212> TYPE: PRT
<213> ORGANISM: Oryza sativa

<400> SEQUENCE: 7

```
Met Gly Asn Cys Val Ala Arg Ser Gly Thr Ala Val Asp Ala Gly Gly
1               5                   10                  15

Asp Gly Gly Glu Asp Gly Lys Arg Arg Arg Arg Trp Lys Ala Pro
            20                  25                  30

Arg Glu Asp Gln Leu Gly Met Val Pro Gly Arg Ile Phe Ser Asn Asp
            35                  40                  45

Gly Arg Ser Arg Thr Ala Thr Val Tyr Thr Gln Gln Gly Arg Lys Gly
        50                  55                  60

Ile Asn Gln Asp Ala Met Leu Val Trp Asp Gly Phe Gly Gly Glu Asp
65                  70                  75                  80

Asp Gly Val Leu Cys Gly Val Phe Asp Gly His Gly Pro His Gly His
                    85                  90                  95

Val Val Ala Arg Arg Val Arg Asp Ser Leu Pro Leu Arg Leu Met Ser
                100                 105                 110

Ala Ala Arg Asp Ser Gly Ala Asp Met Pro Ala Ala Ala Trp Arg Lys
            115                 120                 125

Ala Phe Ala Arg Ala Tyr Lys Ala Met Asp Lys Asp Leu Arg Ser His
        130                 135                 140

Pro Ser Leu Asp Cys Phe Cys Ser Gly Ser Thr Ala Val Thr Val Leu
145                 150                 155                 160

Lys Leu Gly Ser Asp Leu Tyr Met Ala Asn Ile Gly Asp Ser Arg Ala
                    165                 170                 175

Val Leu Gly Ser Arg Glu Ala Thr Gly Gly Met Val Ala Val Gln
                180                 185                 190

Leu Thr Val Asp Leu Lys Pro Asp Val Pro Ser Glu Ala Glu Arg Ile
            195                 200                 205

Lys Lys Cys Arg Gly Arg Val Phe Ala Leu Gln Asp Glu Pro Glu Val
        210                 215                 220

Pro Arg Val Trp Leu Pro Phe Asp Asp Ala Pro Gly Leu Ala Met Ala
225                 230                 235                 240

Arg Ala Phe Gly Asp Phe Cys Leu Lys Asp Tyr Gly Val Ile Ser Val
                    245                 250                 255

Pro Glu Phe Phe His Trp Ser Leu Thr Glu Lys Asp Gln Phe Val Ile
                260                 265                 270

Leu Ala Ser Asp Gly Val Trp Asp Val Leu Ser Asn Gln Glu Ala Val
            275                 280                 285

Asp Ile Val Ser Ala Ser Pro Ser Arg Ser Lys Ala Lys Ser Leu
        290                 295                 300

Val Glu Ala Ala Thr Arg Glu Trp Lys Thr Lys Tyr Pro Thr Ser Lys
305                 310                 315                 320

Ile Asp Asp Cys Ala Val Val Cys Leu Tyr Leu Asp Gly Lys Met Asp
                    325                 330                 335

His Glu Arg Asp Ser Thr Ala Ser Leu Asp Asn Ile Ser Ile Glu Glu
                340                 345                 350

Gly Ser Val Ala Asp Pro Asn Glu Pro Gln Glu Gln Glu Pro Thr Leu
            355                 360                 365

Thr Arg Asn Phe Thr Val Arg Val Ala Gly Ser Thr Gln Glu Lys
        370                 375                 380
```

```
Thr Leu Ala Gly Val Asp Ala Arg Ile Ala Gly Val Ala Asn Asp Gln
385                 390                 395                 400

Asn Trp Ser Gly Leu Asp Gly Val Thr Arg Val Asn Ser Leu Val Gln
            405                 410                 415

Leu Pro Arg Phe Ser Glu Glu Arg Ala Ile Gly
            420                 425

<210> SEQ ID NO 8
<211> LENGTH: 2771
<212> TYPE: DNA
<213> ORGANISM: Oryza sativa

<400> SEQUENCE: 8
tgggtggcga ggaggatggg gtacctgccg tcgtcgctgg gcagcaaggc ggcgcacttc     60
gtgtccgacc tcaccaccgt catcctcaac ccaatctccg agcgcgagcc ttcctcccca    120
ctccccgtga gacccgagat ctctctctct ctctccatct ctcctctcta ccgttcctcg    180
tagtgcgggc agtttatatc tggttttgaa ttgtgatcgg tttgcggctc gcgtcctaga    240
tttgcgcgat cgggctgagt cggatgctgc cggtagagat atcagcgtgg tttggacttt    300
ttggagtgat ttcgccgcag ggatcatccc gttgctaggg ttttttgtgta ggttgctgaa    360 ttctctgcct gtctttgttt agttttctgt ggggtttgc cgcgatctgg atgagtggca     420
acggaattgg agaatgctga tagatagtgg acttcgtcgg gtggggatat ttgtgttctt    480
tttgacatga ttgaggactt gagaagttga ggtagctgca atagtaaagt tagctcacct    540
gtatgtttct acttgctacc tgaaagttgt tcttcgtatt gtcagcttct gctagtctcg    600 agagggaaa tagttctgtt ccatctcagt gcgcttttga aagcctaccc cagctgttta    660
tctgttgtct ttgttgatgt atccctttgc attctgttat agtttaaaga tggttttgcat    720 tgttgattgt ttgaaataaa ttgttactgc atgtgtttga tctttgatgc cagtttgtag    780
ctatgaattg ccgctaatca ctgacccgtg tttcactcac catcttgttt tccagtaagc    840
tcacatctca agttctttga tcgttgtagg aggtggacaa agacgaagaa aaatcagagg    900
atgacaaaga ttctgagcaa aattctgaca cccccgatgg ccctgacaca tcttccttta    960
gagcattctt gatctcattc ctgtcatcat ctggttctag taatggttcc atggagataa   1020
ttcctgatca gaatgggaa ttgggatacc caactttaac accaatgggg aagtcaaaaa    1080
agggaaagtc tgggctccta agtagaggaa acattccat ggaaaaatc attagcaaag      1140 cggctagaat tggtggtttc aaacaaaatg tggagcctaa gattgataga gaggtggtag    1200
atcatgttga atcagtttca cctgtattgg agcttgaaga atcaaaggaa gttgcttcct    1260
tcattaattt gccagctatg tcagaaccat ctgttctttt gtcagaagtg atgaggttca    1320 atattttatgc atctttcct gttcttgcca aaggaatgaa ctgggtcttg ctatacaggt     1380
ttaaaacatg tctgttattt aatatggtat gactatatgc attagctaaa gtctaatgtt    1440
tgcgttcaca attgtgcagc acatggaggc atggaatatc tttgtctact ctatacagaa    1500
ggagcatgct ttgccctggt tactctctct tggtattctt cttctgtagc ttgaagctgt    1560 ttgatttta tagtttaact ggtactccaa ggccagcagc cagtgtgcca atatacatat     1620
tgaagttcca atattcctta cgtgggtgat actgtgatag cactttattc caataaaatt    1680
ctatggttta aatatcggtc tccataattt tagctcatgt tagttcagtt tttacaaaac    1740 ttctttttt ttttgtttag taataataat aatattttcc ctaacaggta gttggggata     1800
aagaaggtgc agtttttggc ggtttagttg aggctccatt gcagccaacc agtgcaaaga   1860
```

```
aatatcaggt tccacctaca cattctgaat ttctgatacc cttttttct ggtttaatta    1920 ccttatgcag attatgatgg aatcttaata ttgcagggga gcaatagctg ctttgttttc    1980
actaatttac acagcaatcc tagtatatat cgaccgactg gtaatatttc acctcctgtt    2040
ttcatgttct ttgcataaga acatcaaaag ctgcgaaata ttttgttcc atttgaccct    2100 accttccaga ctactagatg tatttctctg tgtagcagtg acttatgatt gttttgtcc    2160 cctgattcct gttcaatata tataacacta gcatactcct acaaaaattc tgggggatca    2220
agttgctgaa tatattactg ttaacactag caaagactta actcaggaga gccctgagc    2280 attcatttct ggtattgcag gtgctaataa ctatttcaca gtgtgctcca ccgactattt    2340
ggcattagga ggtggaggtc atttcgcact ttatctagat gccgacctgt aatctcccac    2400
ctcttaagca tgtcttttcac gccgtcaaat ctgctggttt tattgccttt tgtcattgat    2460
agctctcatc ttttcttctg ggttacccct ttcaggttg agtggttcaa gttccaattc    2520
agagactttt aacaacatgt gtttatctca ttccccagac ttcgcggtaa agatgtcga    2580 ggtatctaat tgtgggcttc tggctgaatg ctatcatgtt catctgggat gcagatatgt    2640
aactgctgtt ttcttgcaa tgcagctgtg gggtttcgtc tatccttcca agtacgatga    2700
gacgctcgcc ctctgccgta ctgagaaacc aggaatttgc cggtggtgat ttggtggtcc    2760
ttgaaggctt g                                                          2771

<210> SEQ ID NO 9
<211> LENGTH: 1095
<212> TYPE: DNA
<213> ORGANISM: Oryza sativa

<400> SEQUENCE: 9
atggggtacc tgccgtcgtc gctgggcagc aaggcggcgc acttcgtgtc cgacctcacc      60
accgtcatcc tcaacccaat ctccgagcgc gagccttcct cccactccc cgaggtggac     120 aaagacgaag aaaaatcaga ggatgacaaa gattctgagc aaaattctga cacccccgat     180
ggccctgaca catcttcctt tagagcattc ttgatctcat tcctgtcatc atctggttct     240
agtaatggtt ccatggagat aattcctgat cagaatgggg aattgggata cccaacttta     300
acaccaatgg ggaagtcaaa aagggaaag tctgggctcc taagtagagg aaaacattcc     360
attggaaaaa tcattagcaa agcggctaga attggtggtt caaacaaaa tgtggagcct     420 aagattgata gagaggtggt agatcatgtt gaatcagttt cacctgtatt ggagcttgaa     480
gaatcaaagg aagttgcttc cttcattaat ttgccagcta tgtcagaacc atctgttctt     540
ttgtcagaag tgatgaggtt caatatttat gcatcttttc ctgttcttgc caaaggaatg     600
aactgggtct tgctatacag cacatggagg catggaatat ctttgtctac tctatacaga     660
aggagcatgc tttgccctgg ttactctctc ttggtagttg gggataaaga aggtgcagtt     720
tttggcggtt tagttgaggc tccattgcag ccaaccagtg caaagaaata tcaggggagc     780
aatagctgct ttgttttcac taatttacac agcaatccta gtatatatcg accgactggt     840
gctaataact atttcacagt gtgctccacc gactatttgg cattaggagg tggaggtcat     900
ttcgcacttt atctagatgc cgacctgttg agtggttcaa gttccaattc agagactttt     960
aacaacatgt gtttatctca ttccccagac ttcgcggtaa agatgtcga gctgtgggt     1020 ttcgtctatc cttccaagta cgatgagacg ctcgccctct gccgtactga gaaaccagga    1080
atttgccggt ggtga                                                      1095
```

<210> SEQ ID NO 10
<211> LENGTH: 364
<212> TYPE: PRT
<213> ORGANISM: Oryza sativa

<400> SEQUENCE: 10

```
Met Gly Tyr Leu Pro Ser Ser Leu Gly Ser Lys Ala Ala His Phe Val
1               5                   10                  15

Ser Asp Leu Thr Thr Val Ile Leu Asn Pro Ile Ser Glu Arg Glu Pro
            20                  25                  30

Ser Ser Pro Leu Pro Glu Val Asp Lys Asp Glu Glu Lys Ser Glu Asp
        35                  40                  45

Asp Lys Asp Ser Glu Gln Asn Ser Asp Thr Pro Asp Gly Pro Asp Thr
    50                  55                  60

Ser Ser Phe Arg Ala Phe Leu Ile Ser Phe Leu Ser Ser Gly Ser
65                  70                  75                  80

Ser Asn Gly Ser Met Glu Ile Ile Pro Asp Gln Asn Gly Glu Leu Gly
                85                  90                  95

Tyr Pro Thr Leu Thr Pro Met Gly Lys Ser Lys Gly Lys Ser Gly
            100                 105                 110

Leu Leu Ser Arg Gly Lys His Ser Ile Gly Lys Ile Ser Lys Ala
        115                 120                 125

Ala Arg Ile Gly Gly Phe Lys Gln Asn Val Glu Pro Lys Ile Asp Arg
    130                 135                 140

Glu Val Val Asp His Val Glu Ser Val Ser Pro Val Leu Glu Leu Glu
145                 150                 155                 160

Glu Ser Lys Glu Val Ala Ser Phe Ile Asn Leu Pro Ala Met Ser Glu
                165                 170                 175

Pro Ser Val Leu Leu Ser Glu Val Met Arg Phe Asn Ile Tyr Ala Ser
            180                 185                 190

Phe Pro Val Leu Ala Lys Gly Met Asn Trp Val Leu Leu Tyr Ser Thr
        195                 200                 205

Trp Arg His Gly Ile Ser Leu Ser Thr Leu Tyr Arg Arg Ser Met Leu
    210                 215                 220

Cys Pro Gly Tyr Ser Leu Leu Val Val Gly Asp Lys Glu Gly Ala Val
225                 230                 235                 240

Phe Gly Gly Leu Val Glu Ala Pro Leu Gln Pro Thr Ser Ala Lys Lys
                245                 250                 255

Tyr Gln Gly Ser Asn Ser Cys Phe Val Phe Thr Asn Leu His Ser Asn
            260                 265                 270

Pro Ser Ile Tyr Arg Pro Thr Gly Ala Asn Asn Tyr Phe Thr Val Cys
        275                 280                 285

Ser Thr Asp Tyr Leu Ala Leu Gly Gly Gly His Phe Ala Leu Tyr
    290                 295                 300

Leu Asp Ala Asp Leu Leu Ser Gly Ser Ser Asn Ser Glu Thr Phe
305                 310                 315                 320

Asn Asn Met Cys Leu Ser His Ser Pro Asp Phe Ala Val Lys Asp Val
                325                 330                 335

Glu Leu Trp Gly Phe Val Tyr Pro Ser Lys Tyr Asp Gly Thr Leu Ala
            340                 345                 350

Leu Cys Arg Thr Glu Lys Pro Gly Ile Cys Arg Trp
        355                 360
```

<210> SEQ ID NO 11

<211> LENGTH: 3370
<212> TYPE: DNA
<213> ORGANISM: Oryza sativa

<400> SEQUENCE: 11

```
ccattccatc tttctctctc tctcgcggag gtcggaggag ccatggaggt gttctactac      60
ctcgtgttcg ggggcctcgc cgccgtggtg gccgggctgg agctcggcaa gagcgccaag     120
gaccgggtca ccacctccca ggccttcaac tccttcaaga caactacgt cctcgtctac      180
tccctcatga tgtgtatgtc attcttcgat tcttggcgca ttttcgtcct cccggatctg     240
ggattcatgg ctttcatcaa tcttgtgcag ccggggactg gctgcaaggg ccgtacgtgt     300
actacctcta cagccagtac ggcttcgaca agggcgacat cggccgcctc ttcatcgccg     360
gcttcggatc ctccatgctc ttcggcacca tcgtcgatc actcgccgac aagcagtacg      420
tttcttcttc atcgatttcc tctccgattg tcacagattg tgccccgcgc tgagactgac     480
agaaaaatct gtgtgtttca ggggaggaa gagggcgtgc atcacctact gcatcagcta      540
catcctcagc tgcatcacca agcactcccc cgagtacaag atcctcatga tcggccgcgt     600
gctcggagga atcgccacct cgctactctt ctcggcgttc gagtcatggc tcgtcgcgga     660
gcacaacaag gtactggacg ctcacacatt tcaagattct accttcaaaa cattttgacg     720
gattttagt acaatatgaa ttaaattta cttgctaaaa gttatattat tggattgata       780
tttcaattta ctttcatagg gttataattt tattactata aaccttataa tatatgagaa     840
attataagat aaatattagt tttgacgatc gtgtcaagtt tgatcgtgtc ttatattatg     900
ggataaaggg agtaattagt attactgtaa ttatacgcag ggccagatct gcttgtcagt     960
gtccccctc acactgatgc tttgcagctg tgtctggtct gactttaact ttaatccaaa     1020
gtttcctctt ttttttagt tgtctatcta gaagggcatg ttctagtggt ataagaata      1080
catatttgga atgttttaac cttaagtaac taaaattatt cctatctttg ttgtgaataa    1140
actattagag cgtcatttgg attcattcac ataatcacat ccttgtcatc caagcgagct    1200
aggagcatag gagtactttt attttgggat gtttgactac ttactcaatt aggcacataa    1260
aaaaaggatt ttcagtttga gattaggact acacagtaaa aggtcatttt gtcaggatct    1320
gaaaagagaa gactgaaatc tagtactcct tccgtcccat tttgcaatta tcggtttcta    1380
tttcaatgtt tatctgtccg tcttatttaa aaatttatga aaaaaataaa aaataagtc     1440
acgcataaag tactacatat tttatcattc aataacaaca aaaaaaatat taatcataag    1500
aaaattttaa ataagacgaa tggtcaaacg ttggacacag aaatatataa ctgcacttag    1560
gatgggacgg aggcagtatg gagtatagct agtagttcta gtatagttgc aagctcatag    1620
ccaccatttt ttgtttttctt tctggtcatt gtgtcggtgg atcagaataa gatggttgca    1680
tcgtcacaag gataggcatt taacaagcat ggcccattta ataaagctgg agtatttagg    1740
atagcctcac actcactaca aattgtcctt ttattcggcc atgtgccgtc tcctatatgg    1800
atattaatct cggacatatt caataattca ttcaattatc aataagaatc caaggatcca    1860
ggtacagtat ctgttgcctg tgaggctgtg agtctgtgac acactactat gcagtgttct    1920
tcccgtgaca aaactgtcgt tttgattaac taactaataa atggtccttg tcgtttgcaa    1980
acttctccaa tgtattacag tcaatttctt atctgcgtta tcaattttc actgtaaagt     2040
ttaaccttgg catttccttt cacagagagg ttttgattca caatggctgt cgatcacatt    2100
ctccaaggct atatttcttg gcaatggcct ggtcgcaatt gtatccgggc tatttgcaaa    2160
cctgcttgcc gacaacttgg gctttggtcc cgtggcacca tttgatgctg ctgcatgctt    2220
```

```
cctggcaata ggcatggcta tcataatgtc ttcatggagt gaaaactatg gagacccatc    2280
tgaaagcaag gatttgatgt cccagttcaa ggttgcagcc aaagcaattg cttcaggtat    2340
gcttaactca tcttattgga ttgacagata aacagatatg tatcaaagtt gacaatcggc    2400
attctgacat catccttgaa atctttagat gaaaaaattg cattactggg agccatacag    2460
tcattgtttg agggctcaat gtatactttc gtcttcctct ggactccggc gttgagccca    2520
aatgaagaag atattcctca tggcttcata tttgccacat tcatgctgtc atcaatgttg    2580
ggtagctcaa ttgctgcacg cttgttagcc cgaaagctga aggtcgaagg ttatatgcag    2640
atcgtgttta caatatcagc cttcacccctt tccttcctg ttgtcaccaa cgtaagaaca    2700
ctgcttatac tgcctgtcaa ttttttctctt ataattcaga gcctaacatc cgtttgctaa    2760
atgttgaaca gattctagtg ccaacttctt cagtgaaagg aggtagcatc tcatttggag    2820
gcactctgca gctgcttggt ttctgtacct ttgaggcatg cgttggcata ttctggccat    2880
caatcatgaa gatgagatct caatatattc ctgaggaggc aagaagcaca atcatgaatt    2940
tcttccgcat accactgaac ttgtttgttt gtgtggtgct ttacaatgta agtgaaagtg    3000
ttcttactga atctcatgat tctaatctgt tgatttcctt caaaaataac atttttttct    3060
gtgaattttg caggtgaatg cattccctat cactgtcatg tttggcatgt gttctatctt    3120
cctcttcatg gcggcaatcc tgcagagacg gctaatggtt gtttctgacc tacacaaatc    3180
atcgacaagt atgcatcttt cttcattact ccacatataa aaactaaaat cgctttgcca    3240
atcaatttct ttgattccta actgttgggg ttaacatttt ctgcagaagc acaagagatg    3300
gttgatgaag atgagccact gaatccttaa ggattgatag gatcatacaa acagatcgaa    3360
tataagcatg                                                          3370
```

<210> SEQ ID NO 12
<211> LENGTH: 1374
<212> TYPE: DNA
<213> ORGANISM: Oryza sativa

<400> SEQUENCE: 12

```
atggaggtgt tctactacct cgtgttcggg ggcctcgccg ccgtggtggc cgggctggag      60
ctcggcaaga gcgccaagga ccgggtcacc acctcccagg ccttcaactc cttcaagaac     120
aactacgtcc tcgtctactc cctcatgatg tccggggact ggctgcaagg gccgtacgtg     180
tactacctct acagccagta cggcttcgac aagggcgaca tcggccgcct cttcatcgcc     240
ggcttcggat cctccatgct cttcggcacc atcgtcggat cactcgccga caagcagggg     300
aggaagaggg cgtgcatcac ctactgcatc agctacatcc tcagctgcat caccaagcac     360
tcccccgagt acaagatcct catgatcggc cgcgtgctcg gaggaatcgc cacctcgctg     420
ctcttctcgg cgttcgagtc atggctcgtc gcggagcaca acaagagagg ttttgattca     480
caatggctgt cgatcacatt ctccaaggct atatttcttg gcaatggcct ggtcgcaatt     540
gtatccgggc tatttgcaaa cctgcttgcc gacaacttgg gctttggtcc cgtggcacca     600
tttgatgctg ctgcatgctt cctggcaata ggcatggcta tcataatgtc ttcatggagt     660
gaaaactatg gagacccatc tgaaagcaag gatttgatgt cccagttcaa ggttgcagcc     720
aaagcaattg cttcagatga aaaaattgca ttactgggag ccatacagtc attgtttgag     780
ggctcaatgt atactttcgt cttcctctgg actccggcgt tgagcccaaa tgaagaagat     840
attcctcatg gcttcatatt tgccacattc atgctgtcat caatgttggg tagctcaatt     900
```

```
gctgcacgct tgttagcccg aaagctgaag gtcgaaggtt atatgcagat cgtgtttaca    960
atatcagcct tcacccttt ccttcctgtt gtcaccaaca ttctagtgcc aacttcttca    1020
gtgaaaggag gtagcatctc atttggaggc actctgcagc tgcttggttt ctgtacctt    1080 gaggcatgcg ttggcatatt ctggccatca atcatgaaga tgagatctca atatattcct    1140
gaggaggcaa gaagcacaat catgaatttc ttccgcatac cactgaactt gtttgtttgt    1200
gtggtgcttt acaatgtgaa tgcattccct atcactgtca tgtttggcat gtgttctatc    1260
ttcctcttca tggcggcaat cctgcagaga cggctaatgg ttgtttctga cctacacaaa    1320
tcatcgacaa aagcacaaga gatggttgat gaagatgagc cactgaatcc ttaa          1374
```

<210> SEQ ID NO 13
<211> LENGTH: 457
<212> TYPE: PRT
<213> ORGANISM: Oryza sativa

<400> SEQUENCE: 13

```
Met Glu Val Phe Tyr Tyr Leu Val Phe Gly Gly Leu Ala Ala Val Val
1               5                   10                  15

Ala Gly Leu Glu Leu Gly Lys Ser Ala Lys Asp Arg Val Thr Thr Ser
            20                  25                  30

Gln Ala Phe Asn Ser Phe Lys Asn Asn Tyr Val Leu Val Tyr Ser Leu
        35                  40                  45

Met Met Ser Gly Asp Trp Leu Gln Gly Pro Tyr Val Tyr Tyr Leu Tyr
    50                  55                  60

Ser Gln Tyr Gly Phe Asp Lys Gly Asp Ile Gly Arg Leu Phe Ile Ala
65                  70                  75                  80

Gly Phe Gly Ser Ser Met Leu Phe Gly Thr Ile Val Gly Ser Leu Ala
                85                  90                  95

Asp Lys Gln Gly Arg Lys Arg Ala Cys Ile Thr Tyr Cys Ile Ser Tyr
            100                 105                 110

Ile Leu Ser Cys Ile Thr Lys His Ser Pro Glu Tyr Lys Ile Leu Met
        115                 120                 125

Ile Gly Arg Val Leu Gly Gly Ile Ala Thr Ser Leu Leu Phe Ser Ala
    130                 135                 140

Phe Glu Ser Trp Leu Val Ala Glu His Asn Lys Arg Gly Phe Asp Ser
145                 150                 155                 160

Gln Trp Leu Ser Ile Thr Phe Ser Lys Ala Ile Phe Leu Gly Asn Gly
                165                 170                 175

Leu Val Ala Ile Val Ser Gly Leu Phe Ala Asn Leu Leu Ala Asp Asn
            180                 185                 190

Leu Gly Phe Gly Pro Val Ala Pro Phe Asp Ala Ala Cys Phe Leu
        195                 200                 205

Ala Ile Gly Met Ala Ile Ile Met Ser Ser Trp Ser Glu Asn Tyr Gly
    210                 215                 220

Asp Pro Ser Glu Ser Lys Asp Leu Met Ser Gln Phe Lys Val Ala Ala
225                 230                 235                 240

Lys Ala Ile Ala Ser Asp Glu Lys Ile Ala Leu Leu Gly Ala Ile Gln
                245                 250                 255

Ser Leu Phe Glu Gly Ser Met Tyr Thr Phe Val Phe Leu Trp Thr Pro
            260                 265                 270

Ala Leu Ser Pro Asn Glu Glu Asp Ile Pro His Gly Phe Ile Phe Ala
        275                 280                 285

Thr Phe Met Leu Ser Ser Met Leu Gly Ser Ser Ile Ala Ala Arg Leu
```

```
                290                 295                 300
Leu Ala Arg Lys Leu Lys Val Glu Gly Tyr Met Gln Ile Val Phe Thr
305                 310                 315                 320

Ile Ser Ala Phe Thr Leu Phe Leu Pro Val Val Thr Asn Ile Leu Val
                325                 330                 335

Pro Thr Ser Ser Val Lys Gly Gly Ser Ile Ser Phe Gly Gly Thr Leu
                340                 345                 350

Gln Leu Leu Gly Phe Cys Thr Phe Glu Ala Cys Val Gly Ile Phe Trp
            355                 360                 365

Pro Ser Ile Met Lys Met Arg Ser Gln Tyr Ile Pro Glu Glu Ala Arg
        370                 375                 380

Ser Thr Ile Met Asn Phe Phe Arg Ile Pro Leu Asn Leu Phe Val Cys
385                 390                 395                 400

Val Val Leu Tyr Asn Val Asn Ala Phe Pro Ile Thr Val Met Phe Gly
                405                 410                 415

Met Cys Ser Ile Phe Leu Phe Met Ala Ala Ile Leu Gln Arg Arg Leu
                420                 425                 430

Met Val Val Ser Asp Leu His Lys Ser Ser Thr Lys Ala Gln Glu Met
            435                 440                 445

Val Asp Glu Asp Glu Pro Leu Asn Pro
        450                 455

<210> SEQ ID NO 14
<211> LENGTH: 2421
<212> TYPE: DNA
<213> ORGANISM: Oryza sativa

<400> SEQUENCE: 14
cactctctca cacacacact ctctctctct gctagctcag ctctagatcc agcaatggcg    60
cctcctccgg ctgcagctgc ggcgttggcg gcgtgcattc tcgccgtcgc cgccaccctc   120
gccggcgccg acgacccta ccgcttcttc acctggaacg tcacctacgg cagcatcaac    180
cctctcggct ccaccccgca gcaggtgact gacaacgcca ctagatgttc ttcttcttct   240
tcttgcaaat gcagatgcag ttcttgaatt ctgtcattct ctctctctga taattgattt   300
ggttgcttgg ttgaatcgaa tcgaagggca tcttgatcaa tggccagttt cctgggccgc   360
gaatcgactg cgtgacgaac gacaacatca tcgtgaacgt gttcaacaac ctggacgagc   420
cgttcctcct gacatggaat ggcatcaagc agcgcaagaa ctcgtggcag acggcgtgc    480 tgggcaccaa ctgcccaatc cccctggcg ccaactacac ctacaagttc caggccaagg    540
accagatcgg caccttcgtc tacttcccct ccgtcgccat gcaccgcgcc gccggcggct   600
tcggcgcgct caacgtctac cagcgcccgg ccatccccgt cccgtacccg ccgcccgccg   660
gcgacttcac gctcctcgtc ggcgactggt acaaggccgg gcataagcag ctgaggcagg   720
cgctcgacgc cggcggcggt ggcgcgctcc cgccgcccga cgcgctgctc atcaatggca   780
tgccgtcggc ggcggcgttc gtcggcgacc aggggaggac gtacctgttc agggtgtcca   840
atgtcggggt gaagacgtcc gtcaatgtca ggatccaggg gcactcgctg aggttggtgg   900
aggtggaggg gacgcacccg gtgcagaacg tgtacgactc gctcgacgtc catgtcggcc   960
agtcggtggc gttcctcgtc acgctcgaca aggcggcgca ggactacgcc gtcgtggcgt  1020
ccgcgcggtt cagcccgggc gcgtcgccgc tgatggcgac ggggacgctg cactacagca  1080
gcgccgtgtc cagggcgccc ggcccgctcc cggcgccgcc gccggagcag gcggagtggt  1140
cgatgaacca ggcgaggtcg ttccggtgga acctgacggc gagcgcggcg aggcccaacc  1200
```

```
cgcagggtc gttccactac ggcaccatcg cgacgtcgag gacgctggtg ctcgccaact    1260
ccgcgccggt gctcgccggg cagcgccggt acgccgtcaa cggcgtgtcg ttcgtcgtcc    1320
ccgacacgcc gctcaagctc gtggacaact acaacatcgc caatgtcatc ggctgggaca    1380
gcgtcccggc gaggcccgac ggcgcggcgc cgcggtcggg gacgccggtg gtgaggctca    1440
acctgcacga gttcatcgag gtggtgttcc agaacacgga gaacgagctg cagtcttggc    1500
atctcgatgg atatgacttc tgggttgttg ggtaagctac attcccatca accactgaaa    1560
ctttcagatt ttcagttgca tcaattctca gatgaacatc aacatgagaa agatctgttc    1620
attcaccttt gatgatttct ttctctgata aatggattca ggtatggcaa tggtcagtgg    1680
actgagaatc agcggacaac ctacaacttg gttgatgcgc aagcgaggca tacagttcag    1740
gtatgtgttg acatactcgt aatgaatctg aacttctgaa gaacagttaa ttcagaaagc    1800
atgctttggc tttgttataa agctgggcc acatgggtgg tctgttatct aaaaaaaaag     1860
aaattctgaa atctgaaaat tcctaatgga tttgaataac aattaactct gaagtctgaa    1920
cattcctaat caatttgaag aacaattaat tctgaatctg aacattccta atcaatttga    1980
agaacactta gctctgaagt ctgaattctg aacattccta accaatttga agaacaatta    2040
actccttagt ctgaattctg aacattccta accaatttga agaagagtta attctgaagt    2100
ctgaacattc caatgcattt gaagaacagt taactctgaa gtctgaattc tgaacattga    2160
cgatgttcgt ttcatcaggt ttacccgaat ggatggtcgg caatcttggt gtcattggac    2220
aaccagggga tgtggaacct gaggtcgcg aactgggacc ggcaataacct cggccagcag    2280 ctgtacatga gagtgtggac gccgcagcag agcttctcca atgagtacag tatcccgacc    2340
aacgccatac tctgcggtag agctgccggc cttggacact gaggaagatg atgaagaaga    2400
aattcagagt tgcatagttc g                                             2421
```

<210> SEQ ID NO 15
<211> LENGTH: 1638
<212> TYPE: DNA
<213> ORGANISM: Oryza sativa

<400> SEQUENCE: 15

```
atggcgcctc ctccggctgc agctgcggcg ttggcggcgt gcattctcgc cgtcgccgcc      60
accctcgccg cgccgacga cccctaccgc ttcttcacct ggaacgtcac ctacggcagc     120
atcaaccctc tcggctccac cccgcagcag ggcatcttga tcaatggcca gtttcctggg    180
ccgcgaatcg actgcgtgac gaacgacaac atcatcgtga acgtgttcaa caacctggac    240
gagccgttcc tcctgacatg gaatggcatc aagcagcgca agaactcgtg gcaggacggc    300
gtgctgggca ccaactgccc aatccccct ggcgccaact acacctacaa gttccaggcc     360
aaggaccaga tcggcacctt cgtctacttc ccctccgtcg ccatgcaccg cgccgccggc    420
ggcttcggcg cgctcaacgt ctaccagcgc cggccatcc ccgtcccgta ccgccgcccc     480
gccggcgact tcacgctcct cgtcggcgac tggtacaagg ccgggcataa gcagctgagg    540
caggcgctcg acgccggcgg cggtggcgcg ctcccgccgc ccgacgcgct gctcatcaat    600
ggcatgccgt cggcggcggc gttcgtcggc gaccagggga ggacgtacct gttcagggtg    660
tccaatgtcg gggtgaagac gtccgtcaat gtcaggatcc aggggcactc gctgaggttg    720
gtggaggtgg aggggacgca cccggtgcag aacgtgtacg actcgctcga cgtccatgtc    780
ggccagtcgg tggcgttcct cgtcacgctc gacaaggcgg cgcaggacta cgccgtcgtg    840
```

-continued

```
gcgtccgcgc ggttcagccc gggcgcgtcg ccgctgatgg cgacgggggac gctgcactac    900
agcagcgccg tgtccagggc gcccggcccg ctcccggcgc cgccgccgga gcaggcggag    960
tggtcgatga accaggcgag gtcgttccgg tggaacctga cggcgagcgc ggcgaggccc   1020
aacccgcagg ggtcgttcca ctacggcacc atcgcgacgt cgaggacgct ggtgctcgcc   1080
aactccgcgc cggtgctcgc cgggcagcgc cggtacgccg tcaacggcgt gtcgttcgtc   1140
gtccccgaca cgccgctcaa gctcgtggac aactacaaca tcgccaatgt catcggctgg   1200
gacagcgtcc cggcgaggcc cgacggcgcg gcgccgcggt cggggacgcc ggtggtgagg   1260
ctcaacctgc acgagttcat cgaggtggtg ttccagaaca cggagaacga gctgcagtct   1320
tggcatctcg atggatatga cttctgggtt gttgggtatg caatggtca gtggactgag   1380
aatcagcgga caacctacaa cttggttgat cgcaagcga ggcatacagt tcaggtttac   1440
ccgaatggat ggtcggcaat cttggtgtca ttggacaacc aggggatgtg gaacctgagg   1500
tcggcgaact gggaccggca atacctcggc cagcagctgt acatgagagt gtggacgccg   1560
cagcagagct tctccaatga gtacagtatc ccgaccaacg ccatactctg cggtagagct   1620
gccggccttg gacactga                                                  1638
```

<210> SEQ ID NO 16
<211> LENGTH: 545
<212> TYPE: PRT
<213> ORGANISM: Oryza sativa

<400> SEQUENCE: 16

Met Ala Pro Pro Ala Ala Ala Ala Leu Ala Ala Cys Ile Leu
1               5                   10                  15

Ala Val Ala Ala Thr Leu Ala Gly Ala Asp Asp Pro Tyr Arg Phe Phe
                20                  25                  30

Thr Trp Asn Val Thr Tyr Gly Ser Ile Asn Pro Leu Gly Ser Thr Pro
            35                  40                  45

Gln Gln Gly Ile Leu Ile Asn Gly Gln Phe Pro Gly Pro Arg Ile Asp
        50                  55                  60

Cys Val Thr Asn Asp Asn Ile Ile Val Asn Val Phe Asn Asn Leu Asp
65                  70                  75                  80

Glu Pro Phe Leu Leu Thr Trp Asn Gly Ile Lys Gln Arg Lys Asn Ser
                85                  90                  95

Trp Gln Asp Gly Val Leu Gly Thr Asn Cys Pro Ile Pro Pro Gly Ala
            100                 105                 110

Asn Tyr Thr Tyr Lys Phe Gln Ala Lys Asp Gln Ile Gly Thr Phe Val
        115                 120                 125

Tyr Phe Pro Ser Val Ala Met His Arg Ala Ala Gly Gly Phe Gly Ala
    130                 135                 140

Leu Asn Val Tyr Gln Arg Pro Ala Ile Pro Val Pro Tyr Pro Pro Pro
145                 150                 155                 160

Ala Gly Asp Phe Thr Leu Leu Val Gly Asp Trp Tyr Lys Ala Gly His
                165                 170                 175

Lys Gln Leu Arg Gln Ala Leu Asp Ala Gly Gly Gly Ala Leu Pro
            180                 185                 190

Pro Pro Asp Ala Leu Leu Ile Asn Gly Met Pro Ser Ala Ala Ala Phe
        195                 200                 205

Val Gly Asp Gln Gly Arg Thr Tyr Leu Phe Arg Val Ser Asn Val Gly
    210                 215                 220

Val Lys Thr Ser Val Asn Val Arg Ile Gln Gly His Ser Leu Arg Leu

```
                225                 230                 235                 240
        Val Glu Val Glu Gly Thr His Pro Val Gln Asn Val Tyr Asp Ser Leu
                            245                 250                 255

Asp Val His Val Gly Gln Ser Val Ala Phe Leu Val Thr Leu Asp Lys
                            260                 265                 270

Ala Ala Gln Asp Tyr Ala Val Ala Ser Ala Arg Phe Ser Pro Gly
                            275                 280                 285

Ala Ser Pro Leu Met Ala Thr Gly Thr Leu His Tyr Ser Ser Ala Val
                290                 295                 300

Ser Arg Ala Pro Gly Pro Leu Pro Ala Pro Pro Glu Gln Ala Glu
        305                 310                 315                 320

Trp Ser Met Asn Gln Ala Arg Ser Phe Arg Trp Asn Leu Thr Ala Ser
                            325                 330                 335

Ala Ala Arg Pro Asn Pro Gln Gly Ser Phe His Tyr Gly Thr Ile Ala
                            340                 345                 350

Thr Ser Arg Thr Leu Val Leu Ala Asn Ser Ala Pro Val Leu Ala Gly
                            355                 360                 365

Gln Arg Arg Tyr Ala Val Asn Gly Val Ser Phe Val Val Pro Asp Thr
                370                 375                 380

Pro Leu Lys Leu Val Asp Asn Tyr Asn Ile Ala Asn Val Ile Gly Trp
        385                 390                 395                 400

Asp Ser Val Pro Ala Arg Pro Asp Gly Ala Ala Pro Arg Ser Gly Thr
                            405                 410                 415

Pro Val Val Arg Leu Asn Leu His Glu Phe Ile Glu Val Val Phe Gln
                            420                 425                 430

Asn Thr Glu Asn Glu Leu Gln Ser Trp His Leu Asp Gly Tyr Asp Phe
                            435                 440                 445

Trp Val Val Gly Tyr Gly Asn Gly Gln Trp Thr Glu Asn Gln Arg Thr
                            450                 455                 460

Thr Tyr Asn Leu Val Asp Ala Gln Ala Arg His Thr Val Gln Val Tyr
        465                 470                 475                 480

Pro Asn Gly Trp Ser Ala Ile Leu Val Ser Leu Asp Asn Gln Gly Met
                            485                 490                 495

Trp Asn Leu Arg Ser Ala Asn Trp Asp Arg Gln Tyr Leu Gly Gln Gln
                            500                 505                 510

Leu Tyr Met Arg Val Trp Thr Pro Gln Gln Ser Phe Ser Asn Glu Tyr
                            515                 520                 525

Ser Ile Pro Thr Asn Ala Ile Leu Cys Gly Arg Ala Ala Gly Leu Gly
                530                 535                 540

His
        545

<210> SEQ ID NO 17
<211> LENGTH: 1583
<212> TYPE: DNA
<213> ORGANISM: Oryza sativa

<400> SEQUENCE: 17
ctaccaagct ctctcttcct ctgatcaact ccactataat tagctatagc ttagctagct      60
gagtgatcag tgagcaggtc gatagcttaa ttagcttcca attaatttga ttaagagctt     120
aagatggtag gcaagccaca tcaccatggc tcctcctcgc ttgtggcgga ggagctcaac     180
ctcttgcacg gcggcggcga tggcggccgc ggcggcggcg ggctggggca gtggaagtgc     240
cggctgctgg gctcgctggc cggcctcggc cggccgcggc gggcgcggtg cgtcgtgtgc     300
```

```
ctccaggtgc agcacgtcac cggcctcccc ccggcggcgg aagggcgcgg cgtggtggtg    360
gggtggcgca gcaggggcgg cgaggggag cacacgtcgc cggtgcgcgc gtcgcgcggc     420
gccgccgcgt tcgacgaggt gttcctcaac tatttcgtcg ccggcggcgc cacgctgcgg    480
agcttcgccg tgtgggcggc gctcgtggac gacctggcgt cgacggcgag gggcggcggc    540
gacctcggct ccttccccgt cgacctcacc gagatcgcca ccgcggagag ctccaacccg    600
cggttcggcg gcaaggccct cagcttcccg ctcggcggcg cggccgccgg cgccgtgctc    660
accgtcagcg tctactgcag agtgatggag cgtgaggaaa accatggcgg cgccaatggt    720
aataaggaag aaacgaaacc ctagctagcc tagttaatca cttaattatg gcgctaaata    780
acagtgtagt ggttaattaa ttgcgaatta agaagtaaat actaattaat tactacgtgt    840
atcgatcacg aacaggccat gcaagagcgg agaggaagaa caaggggaag ggatcctacg    900
cgtcgtgcct gccggatctg agctgcctcc ggaaccggcc gtctccggcg gcggcggcgg    960
cgtcggggtc ggctcggcgg gcggcgtcgc tccgatccga tcgaggcggg ttcatcacga    1020
tcgagaactc ggtggcggag atggagggcg gcggcgcgtt cgggcgcgtg gaggacgtgg    1080
acgaggaggg cgcggggttc atcacgatgg agaagggcac catctcgtct tcgcggtcgc    1140
ggtctcgccg gccggcgggc gaggacgacg aggccggcga catggaggac gagaagccgt    1200
gcctgctgat ggagctggcg ccggaggagg cggcggcggc gttcgaggtg gagaaggtgg    1260
aggaggagtt cctggcgatg ctggaggaca agtactgggc gaggagcaag gagatcgaga    1320
aggggttggg cgtgagcctg gacatggggc tcgatctggg gctggacctc gactcgctca    1380
tcaaggacgc ggagatggag ctcgccaagg cggagcaggc gtggcggagc aaggtcggcg    1440
ccgccatcgt cgaggaggag gagtacatgg acctcgtccg ccgctggagc gcccgcgacg    1500
ccgccgccgc gtgctggccg gccgccgcct tcgccttcgg gagccccatc taggctatct    1560
taatttgttc tgctcgatcg atc                                           1583

<210> SEQ ID NO 18
<211> LENGTH: 1293
<212> TYPE: DNA
<213> ORGANISM: Oryza sativa

<400> SEQUENCE: 18
atggtaggca agccacatca ccatggctcc tcctcgcttg tggcggagga gctcaacctc     60
ttgcacggcg gcggcgatgg cggccgcggc ggcggcgggc tggggcagtg gaagtgccgg    120
ctgctgggct cgctggccgg cctcggccgg ccgcggcggg cgcggtgcgt cgtgtgcctc    180
caggtgcagc acgtcaccgg cctcccccg gcggcggaag ggcgcggcgt ggtggtgggg    240
tggcgcagca gggcggcga ggggagcac acgtcgccgg tgcgcgtc gcgcggcgcc       300 gccgcgttcg acgaggtgtt cctcaactat ttcgtcgccg gcggcgccac gctgcggagc    360
ttcgccgtgt gggcggcgct cgtggacgac ctggcgtcga cggcgagggg cggcggcgac    420
ctcggctcct tccccgtcga cctcaccgag atcgccaccg cggagagctc caacccgcgg    480
ttcggcggca aggccctcag cttcccgctc ggcggcgcgg ccgccggcgc cgtgctcacc    540
gtcagcgtct actgcagagt gatggagcgt gaggaaaacc atggcggcgc caatggccat    600
gcaagagcgg agaggaagaa caaggggaag ggatcctacg cgtcgtgcct gccggatctg    660
agctgcctcc ggaaccggcc gtctccggcg gcggcgcg cgtcggggtc ggctcggcgg      720
gcggcgtcgc tccgatccga tcgaggcggg ttcatcacga tcgagaactc ggtggcggag    780
```

-continued

```
atggagggcg gcggcgcgtt cgggcgcgtg gaggacgtgg acgaggaggg cgcggggttc    840
atcacgatgg agaagggcac catctcgtct tcgcggtcgc ggtctcgccg gccggcgggc    900
gaggacgacg aggccggcga catggaggac gagaagccgt gcctgctgat ggagctggcg    960
ccggaggagg cggcggcggc gttcgaggtg gagaaggtgg aggaggagtt cctggcgatg   1020
ctggaggaca gtactgggc gaggagcaag gagatcgaga aggggttggg cgtgagcctg   1080
gacatggggc tcgatctggg gctggacctc gactcgctca tcaaggacgc ggagatggag   1140
ctcgccaagg cggagcaggc gtggcggagc aaggtcggcg ccgccatcgt cgaggaggag   1200
gagtacatgg acctcgtccg ccgctggagc gcccgcgacg ccgccgccgc gtgctggccg   1260
gccgccgcct tcgccttcgg gagccccatc tag                                1293
```

<210> SEQ ID NO 19
<211> LENGTH: 430
<212> TYPE: PRT
<213> ORGANISM: Oryza sativa

<400> SEQUENCE: 19

```
Met Val Gly Lys Pro His His Gly Ser Ser Leu Val Ala Glu
1               5                   10                  15

Glu Leu Asn Leu His Gly Gly Gly Asp Gly Gly Arg Gly Gly
                20                  25                  30

Gly Leu Gly Gln Trp Lys Cys Arg Leu Leu Gly Ser Leu Ala Gly Leu
            35                  40                  45

Gly Arg Pro Arg Arg Ala Arg Cys Val Val Cys Leu Gln Val Gln His
        50                  55                  60

Val Thr Gly Leu Pro Pro Ala Ala Glu Gly Arg Gly Val Val Val Gly
65                  70                  75                  80

Trp Arg Ser Arg Gly Gly Glu Gly Glu His Thr Ser Pro Val Arg Ala
                85                  90                  95

Ser Arg Gly Ala Ala Ala Phe Asp Glu Val Phe Leu Asn Tyr Phe Val
            100                 105                 110

Ala Gly Gly Ala Thr Leu Arg Ser Phe Ala Val Trp Ala Ala Leu Val
        115                 120                 125

Asp Asp Leu Ala Ser Thr Ala Arg Gly Gly Gly Asp Leu Gly Ser Phe
130                 135                 140

Pro Val Asp Leu Thr Glu Ile Ala Thr Ala Glu Ser Ser Asn Pro Arg
145                 150                 155                 160

Phe Gly Gly Lys Ala Leu Ser Phe Pro Leu Gly Gly Ala Ala Ala Gly
                165                 170                 175

Ala Val Leu Thr Val Ser Val Tyr Cys Arg Val Met Glu Arg Glu Glu
            180                 185                 190

Asn His Gly Gly Ala Asn Gly His Ala Arg Ala Glu Arg Lys Asn Lys
        195                 200                 205

Gly Lys Gly Ser Tyr Ala Ser Cys Leu Pro Asp Leu Ser Cys Leu Arg
    210                 215                 220

Asn Arg Pro Ser Pro Ala Ala Ala Ala Ser Gly Ser Ala Arg Arg
225                 230                 235                 240

Ala Ala Ser Leu Arg Ser Asp Arg Gly Gly Phe Ile Thr Ile Glu Asn
                245                 250                 255

Ser Val Ala Glu Met Glu Gly Gly Ala Phe Gly Arg Val Glu Asp
            260                 265                 270

Val Asp Glu Glu Gly Ala Gly Phe Ile Thr Met Glu Lys Gly Thr Ile
        275                 280                 285
```

```
Ser Ser Ser Arg Ser Arg Ser Arg Arg Pro Ala Gly Glu Asp Asp Glu
    290                 295                 300

Ala Gly Asp Met Glu Asp Glu Lys Pro Cys Leu Leu Met Glu Leu Ala
305                 310                 315                 320

Pro Glu Glu Ala Ala Ala Phe Glu Val Glu Lys Val Glu Glu Glu
                325                 330                 335

Phe Leu Ala Met Leu Glu Asp Lys Tyr Trp Ala Arg Ser Lys Glu Ile
                340                 345                 350

Glu Lys Gly Leu Gly Val Ser Leu Asp Met Gly Leu Asp Leu Gly Leu
            355                 360                 365

Asp Leu Asp Ser Leu Ile Lys Asp Ala Glu Met Glu Leu Ala Lys Ala
                370                 375                 380

Glu Gln Ala Trp Arg Ser Lys Val Gly Ala Ala Ile Val Glu Glu Glu
385                 390                 395                 400

Glu Tyr Met Asp Leu Val Arg Arg Trp Ser Ala Arg Asp Ala Ala Ala
                405                 410                 415

Ala Cys Trp Pro Ala Ala Ala Phe Ala Phe Gly Ser Pro Ile
                420                 425                 430
```

```
<210> SEQ ID NO 20
<211> LENGTH: 27
<212> TYPE: DNA
<213> ORGANISM: Artificial Sequence
<220> FEATURE:
<223> OTHER INFORMATION: Forward primer for cloning gDNA of OsPRP1 gene

<400> SEQUENCE: 20
actctcaccc agtatagttc tccattg                                      27

<210> SEQ ID NO 21
<211> LENGTH: 27
<212> TYPE: DNA
<213> ORGANISM: Artificial Sequence
<220> FEATURE:
<223> OTHER INFORMATION: Reverse primer for cloning gDNA of OsPRP1 gene

<400> SEQUENCE: 21
ggcaagcacg tgtacagtgt atatctc                                      27

<210> SEQ ID NO 22
<211> LENGTH: 27
<212> TYPE: DNA
<213> ORGANISM: Artificial Sequence
<220> FEATURE:
<223> OTHER INFORMATION: Forward primer for cloning cDNA of OsPP2C64
      gene

<400> SEQUENCE: 22
ctgatttggg cattggtgtt ggtggtg                                      27

<210> SEQ ID NO 23
<211> LENGTH: 29
<212> TYPE: DNA
<213> ORGANISM: Artificial Sequence
<220> FEATURE:
<223> OTHER INFORMATION: Reverse primer for cloning cDNA of OsPP2C64
      gene

<400> SEQUENCE: 23
gaaaataacg ggggtaaata taagatggg                                    29
```

<210> SEQ ID NO 24
<211> LENGTH: 24
<212> TYPE: DNA
<213> ORGANISM: Artificial Sequence
<220> FEATURE:
<223> OTHER INFORMATION: Forward primer for cloning gDNA of OsOPPL1 gene

<400> SEQUENCE: 24
tgggtggcga ggaggatggg gtac                                           24

<210> SEQ ID NO 25
<211> LENGTH: 29
<212> TYPE: DNA
<213> ORGANISM: Artificial Sequence
<220> FEATURE:
<223> OTHER INFORMATION: Reverse primer for cloning gDNA of OsOPPL1 gene

<400> SEQUENCE: 25
caagccttca aggaccacca aatcaccac                                      29

<210> SEQ ID NO 26
<211> LENGTH: 27
<212> TYPE: DNA
<213> ORGANISM: Artificial Sequence
<220> FEATURE:
<223> OTHER INFORMATION: Forward primer for cloning gDNA of OsMFS9 gene

<400> SEQUENCE: 26
ccattccatc tttctctctc tctcgcg                                        27

<210> SEQ ID NO 27
<211> LENGTH: 27
<212> TYPE: DNA
<213> ORGANISM: Artificial Sequence
<220> FEATURE:
<223> OTHER INFORMATION: Reverse primer for cloning gDNA of OsMFS9 gene

<400> SEQUENCE: 27
catgcttata ttcgatctgt ttgtatg                                        27

<210> SEQ ID NO 28
<211> LENGTH: 29
<212> TYPE: DNA
<213> ORGANISM: Artificial Sequence
<220> FEATURE:
<223> OTHER INFORMATION: Forward primer for cloning gDNA of OsLAO1 gene

<400> SEQUENCE: 28
cactctctca cacacacact ctctctctc                                      29

<210> SEQ ID NO 29
<211> LENGTH: 26
<212> TYPE: DNA
<213> ORGANISM: Artificial Sequence
<220> FEATURE:
<223> OTHER INFORMATION: Reverse primer for cloning gDNA of OsLAO1 gene

<400> SEQUENCE: 29
cgaactatgc aactctgaat ttcttc                                         26

<210> SEQ ID NO 30
<211> LENGTH: 29
<212> TYPE: DNA
<213> ORGANISM: Artificial Sequence
<220> FEATURE:
<223> OTHER INFORMATION: Forward primer for cloning gDNA of OsDN-DSP1
      gene

<400> SEQUENCE: 30
ctaccaagct ctctcttcct ctgatcaac                                              29

<210> SEQ ID NO 31
<211> LENGTH: 34
<212> TYPE: DNA
<213> ORGANISM: Artificial Sequence
<220> FEATURE:
<223> OTHER INFORMATION: Reverse primer for cloning gDNA of OsDN-DSP1
      gene

<400> SEQUENCE: 31
gatcgatcga gcagaacaaa ttaagatagc ctag                                        34

<210> SEQ ID NO 32
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsPRP1 gene

<400> SEQUENCE: 32
tgatcgtagg tacggctact c                                                      21

<210> SEQ ID NO 33
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsPRP1 gene

<400> SEQUENCE: 33
agcaaggcat ccttcgag                                                          18

<210> SEQ ID NO 34
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsPP2C64 gene

<400> SEQUENCE: 34
tcacagttag gacagttgca g                                                      21

<210> SEQ ID NO 35
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      OsPP2C64 gene

<400> SEQUENCE: 35
cctaggaagc tgaacaagtg ag                                                     22

<210> SEQ ID NO 36
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsOPPL1 gene

<400> SEQUENCE: 36
ctagatgccg acctgttgag                                                      20

<210> SEQ ID NO 37
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      OsOPPL1 gene

<400> SEQUENCE: 37
cttggaagga tagacgaaac cc                                                   22

<210> SEQ ID NO 38
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsMFS9 gene

<400> SEQUENCE: 38
ggaggtagca tctcatttgg ag                                                   22

<210> SEQ ID NO 39
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsMFS9 gene

<400> SEQUENCE: 39
gccagaatat gccaacgc                                                        18

<210> SEQ ID NO 40
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsLAO1 gene

<400> SEQUENCE: 40
ggcaatcttg gtgtcattgg                                                      20

<210> SEQ ID NO 41
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      OsLAO1 gene

<400> SEQUENCE: 41
gtcgggatac tgtactcatt gg                                                   22

<210> SEQ ID NO 42
<211> LENGTH: 18
<212> TYPE: DNA
<213> ORGANISM: Artificial Sequence
<220> FEATURE:
<223> OTHER INFORMATION: Forward primer for real-time RT-PCR analysis of
      OsDN-DSP1 gene

<400> SEQUENCE: 42

```
ggcaccatct cgtcttcg                                                   18

<210> SEQ ID NO 43
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsDN-DSP1 gene

<400> SEQUENCE: 43
cctccacctt ctccacctc                                                  19

<210> SEQ ID NO 44
<211> LENGTH: 199
<212> TYPE: DNA
<213> ORGANISM: Artificial Sequence
<220> FEATURE:
<223> OTHER INFORMATION: The nucleotide sequence of intron used for
      constructing RNAi construct

<400> SEQUENCE: 44
gtacggaccg tactactcta ttcgtttcaa tatatttatt tgtttcagct gactgcaaga     60
ttcaaaaatt tctttattat tttaaatttt gtgtcactca aaaccagata aacaatttga    120
tatagaggca ctatatatat acatattctc gattatatat gtaaatgagt taacctttt     180 ttccacttaa attatatag                                                 199

<210> SEQ ID NO 45
<211> LENGTH: 161
<212> TYPE: DNA
<213> ORGANISM: Oryza sativa

<400> SEQUENCE: 45
gctactcgta tccaccaccc caagggtact acaatgggcc gccggtgatg gcgccgccgc     60
agtacgcggc tccgccgccg aggcggccgg agccgagctt cctcgaagga tgccttgctg    120
ctctctgctg ctgctgcctc atcgacgagt gctgctgcga c                        161

<210> SEQ ID NO 46
<211> LENGTH: 105
<212> TYPE: DNA
<213> ORGANISM: Oryza sativa

<400> SEQUENCE: 46
gaagatcagc tcgggatggt gcccggccgg atcttctcca cgacggccg cagccggacg      60 gcgacggtgt acacgcagca agggcgcaag gggatcaacc aggac                    105

<210> SEQ ID NO 47
<211> LENGTH: 173
<212> TYPE: DNA
<213> ORGANISM: Oryza sativa

<400> SEQUENCE: 47
agaggatgac aaagattctg agcaaaattc tgacaccccc gatggccctg acacatcttc     60
ctttagagca ttcttgatct cattcctgtc atcatctggt tctagtaatg gttccatgga    120
gataattcct gatcagaatg gggaattggg atacccaact ttaacaccaa tgg           173

<210> SEQ ID NO 48
<211> LENGTH: 195
<212> TYPE: DNA
```

<213> ORGANISM: Oryza sativa

<400> SEQUENCE: 48

```
atcacattct ccaaggctat atttcttggc aatggcctgg tcgcaattgt atccgggcta    60
tttgcaaacc tgcttgccga caacttgggc tttggtcccg tggcaccatt tgatgctgct   120
gcatgcttcc tggcaatagg catggctatc ataatgtctt catggagtga aaactatgga   180
gacccatctg aaagc                                                    195
```

<210> SEQ ID NO 49
<211> LENGTH: 173
<212> TYPE: DNA
<213> ORGANISM: Oryza sativa

<400> SEQUENCE: 49

```
ctcatcaatg gcatgccgtc ggcggcggcg ttcgtcggcg accaggggag gacgtacctg    60
ttcagggtgt ccaatgtcgg ggtgaagacg tccgtcaatg tcaggatcca ggggcactcg   120
ctgaggttgg tggaggtgga ggggacgcac ccggtgcaga acgtgtacga ctc          173
```

<210> SEQ ID NO 50
<211> LENGTH: 264
<212> TYPE: DNA
<213> ORGANISM: Oryza sativa

<400> SEQUENCE: 50

```
gtgttcctca actatttcgt cgccggcggc gccacgctgc ggagcttcgc cgtgtgggcg    60
gcgctcgtgg acgacctggc gtcgacggcg aggggcggcg cgacctcgg ctccttcccc    120
gtcgacctca ccgagatcgc caccgcggag agctccaacc cgcggttcgg cggcaaggcc   180
ctcagcttcc cgctcggcgg cgcggccgcc ggcgccgtgc tcaccgtcag cgtctactgc   240
agagtgatgg agcgtgagga aaac                                          264
```

<210> SEQ ID NO 51
<211> LENGTH: 33
<212> TYPE: DNA
<213> ORGANISM: Artificial Sequence
<220> FEATURE:
<223> OTHER INFORMATION: Forward primer for cloning sense strand cDNA of
      OsPRP1 gene for constructing RNAi construct

<400> SEQUENCE: 51

```
ctgctgaggg ctactcgtat ccaccacccc aag                                 33
```

<210> SEQ ID NO 52
<211> LENGTH: 32
<212> TYPE: DNA
<213> ORGANISM: Artificial Sequence
<220> FEATURE:
<223> OTHER INFORMATION: Reverse primer for cloning sense strand cDNA of
      OsPRP1 gene for constructing RNAi construct

<400> SEQUENCE: 52

```
gcttgctgag ggtcgcagca gcactcgtcg at                                  32
```

<210> SEQ ID NO 53
<211> LENGTH: 33
<212> TYPE: DNA
<213> ORGANISM: Artificial Sequence
<220> FEATURE:
<223> OTHER INFORMATION: Forward primer for cloning antisense strand
      cDNA of OsPRP1 gene for constructing RNAi construct

```
<400> SEQUENCE: 53
ccgctgaggg ctactcgtat ccaccacccc aag                           33

<210> SEQ ID NO 54
<211> LENGTH: 32
<212> TYPE: DNA
<213> ORGANISM: Artificial Sequence
<220> FEATURE:
<223> OTHER INFORMATION: Reverse primer for cloning antisense strand
      cDNA of OsPRP1 gene for constructing RNAi construct

<400> SEQUENCE: 54
gcctgctgag ggtcgcagca gcactcgtcg at                            32

<210> SEQ ID NO 55
<211> LENGTH: 28
<212> TYPE: DNA
<213> ORGANISM: Artificial Sequence
<220> FEATURE:
<223> OTHER INFORMATION: Forward primer for cloning sense strand cDNA of
      OsPP2C64 gene for constructing RNAi construct

<400> SEQUENCE: 55
ctgctgaggg aagatcagct cgggatgg                                 28

<210> SEQ ID NO 56
<211> LENGTH: 30
<212> TYPE: DNA
<213> ORGANISM: Artificial Sequence
<220> FEATURE:
<223> OTHER INFORMATION: Reverse primer for cloning sense strand cDNA of
      OsPP2C64 gene for constructing RNAi construct

<400> SEQUENCE: 56
gcttgctgag ggtcctggtt gatccccttg                               30

<210> SEQ ID NO 57
<211> LENGTH: 28
<212> TYPE: DNA
<213> ORGANISM: Artificial Sequence
<220> FEATURE:
<223> OTHER INFORMATION: Forward primer for cloning antisense strand
      cDNA of OsPP2C64 gene for constructing RNAi construct

<400> SEQUENCE: 57
ccgctgaggg aagatcagct cgggatgg                                 28

<210> SEQ ID NO 58
<211> LENGTH: 30
<212> TYPE: DNA
<213> ORGANISM: Artificial Sequence
<220> FEATURE:
<223> OTHER INFORMATION: Reverse primer for cloning antisense strand
      cDNA of OsPP2C64 gene for constructing RNAi construct

<400> SEQUENCE: 58
gcctgctgag ggtcctggtt gatccccttg                               30

<210> SEQ ID NO 59
<211> LENGTH: 33
<212> TYPE: DNA
<213> ORGANISM: Artificial Sequence
<220> FEATURE:
<223> OTHER INFORMATION: Forward primer for cloning sense strand cDNA of
      OsOPPL1 gene for constructing RNAi construct

<400> SEQUENCE: 59
```

```
ctgctgagga gaggatgaca aagattctga gca                                 33
```

<210> SEQ ID NO 60
<211> LENGTH: 36
<212> TYPE: DNA
<213> ORGANISM: Artificial Sequence
<220> FEATURE:
<223> OTHER INFORMATION: Reverse primer for cloning sense strand cDNA of
      OsOPPL1 gene for constructing RNAi construct

<400> SEQUENCE: 60

```
gcttgctgag gccattggtg ttaaagttgg gtatcc                              36
```

<210> SEQ ID NO 61
<211> LENGTH: 33
<212> TYPE: DNA
<213> ORGANISM: Artificial Sequence
<220> FEATURE:
<223> OTHER INFORMATION: Forward primer for cloning antisense strand
      cDNA of OsOPPL1 gene for constructing RNAi construct

<400> SEQUENCE: 61

```
ccgctgagga gaggatgaca aagattctga gca                                 33
```

<210> SEQ ID NO 62
<211> LENGTH: 36
<212> TYPE: DNA
<213> ORGANISM: Artificial Sequence
<220> FEATURE:
<223> OTHER INFORMATION: Reverse primer for cloning antisense strand
      cDNA of OsOPPL1 gene for constructing RNAi construct

<400> SEQUENCE: 62

```
gcctgctgag gccattggtg ttaaagttgg gtatcc                              36
```

<210> SEQ ID NO 63
<211> LENGTH: 29
<212> TYPE: DNA
<213> ORGANISM: Artificial Sequence
<220> FEATURE:
<223> OTHER INFORMATION: Forward primer for cloning sense strand cDNA of
      OsMFS9 gene for constructing RNAi construct

<400> SEQUENCE: 63

```
ctgctgagga tcacattctc caaggctat                                      29
```

<210> SEQ ID NO 64
<211> LENGTH: 29
<212> TYPE: DNA
<213> ORGANISM: Artificial Sequence
<220> FEATURE:
<223> OTHER INFORMATION: Reverse primer for cloning sense strand cDNA of
      OsMFS9 gene for constructing RNAi construct

<400> SEQUENCE: 64

```
gcttgctgag ggctttcaga tgggtctcc                                      29
```

<210> SEQ ID NO 65
<211> LENGTH: 29
<212> TYPE: DNA
<213> ORGANISM: Artificial Sequence
<220> FEATURE:
<223> OTHER INFORMATION: Forward primer for cloning antisense strand
      cDNA of OsMFS9 gene for constructing RNAi construct

<400> SEQUENCE: 65
ccgctgagga tcacattctc caaggctat                                    29

<210> SEQ ID NO 66
<211> LENGTH: 29
<212> TYPE: DNA
<213> ORGANISM: Artificial Sequence
<220> FEATURE:
<223> OTHER INFORMATION: Reverse primer for cloning antisense strand
      cDNA of OsMFS9 gene for constructing RNAi construct

<400> SEQUENCE: 66
gcctgctgag ggctttcaga tgggtctcc                                    29

<210> SEQ ID NO 67
<211> LENGTH: 30
<212> TYPE: DNA
<213> ORGANISM: Artificial Sequence
<220> FEATURE:
<223> OTHER INFORMATION: Forward primer for cloning sense strand cDNA of
      OsLAO1 gene for constructing RNAi construct

<400> SEQUENCE: 67
ctgctgaggc tcatcaatgg catgccgtcg                                   30

<210> SEQ ID NO 68
<211> LENGTH: 34
<212> TYPE: DNA
<213> ORGANISM: Artificial Sequence
<220> FEATURE:
<223> OTHER INFORMATION: Reverse primer for cloning sense strand cDNA of
      OsLAO1 gene for constructing RNAi construct

<400> SEQUENCE: 68
gcttgctgag ggagtcgtac acgttctgca ccgg                              34

<210> SEQ ID NO 69
<211> LENGTH: 30
<212> TYPE: DNA
<213> ORGANISM: Artificial Sequence
<220> FEATURE:
<223> OTHER INFORMATION: Forward primer for cloning antisense strand
      cDNA of OsLAO1 gene for constructing RNAi construct

<400> SEQUENCE: 69
ccgctgaggc tcatcaatgg catgccgtcg                                   30

<210> SEQ ID NO 70
<211> LENGTH: 34
<212> TYPE: DNA
<213> ORGANISM: Artificial Sequence
<220> FEATURE:
<223> OTHER INFORMATION: Reverse primer for cloning antisense strand
      cDNA of OsLAO1 gene for constructing RNAi construct

<400> SEQUENCE: 70
gcctgctgag ggagtcgtac acgttctgca ccgg                              34

<210> SEQ ID NO 71
<211> LENGTH: 33
<212> TYPE: DNA
<213> ORGANISM: Artificial Sequence
<220> FEATURE:
<223> OTHER INFORMATION: Forward primer for cloning sense strand cDNA of
      OsDN-DSP1 gene for constructing RNAi construct

<400> SEQUENCE: 71
ctgctgaggg tgttcctcaa ctatttcgtc gcc                               33

```
<210> SEQ ID NO 72
<211> LENGTH: 36
<212> TYPE: DNA
<213> ORGANISM: Artificial Sequence
<220> FEATURE:
<223> OTHER INFORMATION: Reverse primer for cloning sense strand cDNA of
      OsDN-DSP1 gene for constructing RNAi construct

<400> SEQUENCE: 72
gcttgctgag ggttttcctc acgctccatc actctg                                 36

<210> SEQ ID NO 73
<211> LENGTH: 33
<212> TYPE: DNA
<213> ORGANISM: Artificial Sequence
<220> FEATURE:
<223> OTHER INFORMATION: Forward primer for cloning antisense strand
      cDNA of OsDN-DSP1 gene for constructing RNAi construct

<400> SEQUENCE: 73
ccgctgaggg tgttcctcaa ctatttcgtc gcc                                    33

<210> SEQ ID NO 74
<211> LENGTH: 36
<212> TYPE: DNA
<213> ORGANISM: Artificial Sequence
<220> FEATURE:
<223> OTHER INFORMATION: Reverse primer for cloning antisense strand
      cDNA of OsDN-DSP1 gene for constructing RNAi construct

<400> SEQUENCE: 74
gcctgctgag ggttttcctc acgctccatc actctg                                 36

<210> SEQ ID NO 75
<211> LENGTH: 20
<212> TYPE: DNA
<213> ORGANISM: Artificial Sequence
<220> FEATURE:
<223> OTHER INFORMATION: Nucleotide sequence of gRNA2 for target site
      sequence for OsMFS9 promoter

<400> SEQUENCE: 75
gcccggatac aattgcgacc                                                   20

<210> SEQ ID NO 76
<211> LENGTH: 20
<212> TYPE: DNA
<213> ORGANISM: Artificial Sequence
<220> FEATURE:
<223> OTHER INFORMATION: Nucleotide sequence of gRNA3 for target site
      sequence for OsMFS9 promoter

<400> SEQUENCE: 76
gagccgagtc gcacacggtt                                                   20

<210> SEQ ID NO 77
<211> LENGTH: 20
<212> TYPE: DNA
<213> ORGANISM: Artificial Sequence
<220> FEATURE:
<223> OTHER INFORMATION: Nucleotide sequence of gRNA3 for target site
      sequence for OsMFS9 promoter

<400> SEQUENCE: 77
gttggttagt tatttcaggg                                                   20
```

```
<210> SEQ ID NO 78
<211> LENGTH: 20
<212> TYPE: DNA
<213> ORGANISM: Artificial Sequence
<220> FEATURE:
<223> OTHER INFORMATION: Nucleotide sequence of gRNA4 for target site
      sequence for OsMFS9 promoter

<400> SEQUENCE: 78
gctggcttag gtagtttaag                                                    20

<210> SEQ ID NO 79
<211> LENGTH: 20
<212> TYPE: DNA
<213> ORGANISM: Artificial Sequence
<220> FEATURE:
<223> OTHER INFORMATION: Nucleotide sequence of gRNA5 for target site
      sequence for OsMFS9 promoter

<400> SEQUENCE: 79
gtataaatcc caccggcttg                                                    20

<210> SEQ ID NO 80
<211> LENGTH: 20
<212> TYPE: DNA
<213> ORGANISM: Artificial Sequence
<220> FEATURE:
<223> OTHER INFORMATION: Nucleotide sequence of gRNA6 for target site
      sequence for OsMFS9 promoter

<400> SEQUENCE: 80
gcgcgctgtg aaacaagtgt                                                    20

<210> SEQ ID NO 81
<211> LENGTH: 20
<212> TYPE: DNA
<213> ORGANISM: Artificial Sequence
<220> FEATURE:
<223> OTHER INFORMATION: Nucleotide sequence of gRNA7 for target site
      sequence for OsMFS9 promoter

<400> SEQUENCE: 81
tatgtgtgtt cagtttacgg                                                    20

<210> SEQ ID NO 82
<211> LENGTH: 20
<212> TYPE: DNA
<213> ORGANISM: Artificial Sequence
<220> FEATURE:
<223> OTHER INFORMATION: Nucleotide sequence of gRNA8 for target site
      sequence for OsMFS9 promoter

<400> SEQUENCE: 82
gatttatacg cgcgtttctt                                                    20

<210> SEQ ID NO 83
<211> LENGTH: 20
<212> TYPE: DNA
<213> ORGANISM: Artificial Sequence
<220> FEATURE:
<223> OTHER INFORMATION: Nucleotide sequence of gRNA9 for target site
      sequence for OsMFS9 promoter

<400> SEQUENCE: 83
gtgcgtgccg gccgaagatt                                                    20
```

<210> SEQ ID NO 84
<211> LENGTH: 20
<212> TYPE: DNA
<213> ORGANISM: Artificial Sequence
<220> FEATURE:
<223> OTHER INFORMATION: Nucleotide sequence of gRNA10 for target site
      sequence for OsMFS9 promoter

<400> SEQUENCE: 84
gaagtttcgg aaccttaccg                                              20

<210> SEQ ID NO 85
<211> LENGTH: 20
<212> TYPE: DNA
<213> ORGANISM: Artificial Sequence
<220> FEATURE:
<223> OTHER INFORMATION: Nucleotide sequence of gRNA11 for target site
      sequence for OsMFS9 promoter

<400> SEQUENCE: 85
ttatccaatg ggattacccg                                              20

<210> SEQ ID NO 86
<211> LENGTH: 20
<212> TYPE: DNA
<213> ORGANISM: Artificial Sequence
<220> FEATURE:
<223> OTHER INFORMATION: Nucleotide sequence of gRNA12 for target site
      sequence for OsMFS9 gene

<400> SEQUENCE: 86
gctcttgccg agctccagcc                                              20

<210> SEQ ID NO 87
<211> LENGTH: 20
<212> TYPE: DNA
<213> ORGANISM: Artificial Sequence
<220> FEATURE:
<223> OTHER INFORMATION: Nucleotide sequence of gRNA13 for target site
      sequence for OsMFS9 gene

<400> SEQUENCE: 87
ccatgaatcc cagatccggg                                              20

<210> SEQ ID NO 88
<211> LENGTH: 20
<212> TYPE: DNA
<213> ORGANISM: Artificial Sequence
<220> FEATURE:
<223> OTHER INFORMATION: Nucleotide sequence of gRNA14 for target site
      sequence for OsMFS9 gene

<400> SEQUENCE: 88
gatggtgccg aagagcatgg                                              20

<210> SEQ ID NO 89
<211> LENGTH: 20
<212> TYPE: DNA
<213> ORGANISM: Artificial Sequence
<220> FEATURE:
<223> OTHER INFORMATION: Nucleotide sequence of gRNA15 for target site
      sequence for OsMFS9 gene

<400> SEQUENCE: 89
ctaccttcaa aacattttga                                              20

<210> SEQ ID NO 90

```
<211> LENGTH: 20
<212> TYPE: DNA
<213> ORGANISM: Artificial Sequence
<220> FEATURE:
<223> OTHER INFORMATION: Nucleotide sequence of gRNA16 for target site
      sequence for OsMFS9 gene

<400> SEQUENCE: 90
cttgttagcc cgaaagctga                                               20

<210> SEQ ID NO 91
<211> LENGTH: 20
<212> TYPE: DNA
<213> ORGANISM: Artificial Sequence
<220> FEATURE:
<223> OTHER INFORMATION: Nucleotide sequence of gRNA17 for target site
      sequence for OsMFS9 gene

<400> SEQUENCE: 91
atagacaact aaaaaaaaag                                               20

<210> SEQ ID NO 92
<211> LENGTH: 20
<212> TYPE: DNA
<213> ORGANISM: Artificial Sequence
<220> FEATURE:
<223> OTHER INFORMATION: Nucleotide sequence of gRNA18 for target site
      sequence for OsMFS9 gene

<400> SEQUENCE: 92
gtcggtggat cagaataaga                                               20

<210> SEQ ID NO 93
<211> LENGTH: 20
<212> TYPE: DNA
<213> ORGANISM: Artificial Sequence
<220> FEATURE:
<223> OTHER INFORMATION: Nucleotide sequence of gRNA19 for target site
      sequence for OsMFS9 gene

<400> SEQUENCE: 93
ccaacttctt cagtgaaagg                                               20

<210> SEQ ID NO 94
<211> LENGTH: 20
<212> TYPE: DNA
<213> ORGANISM: Artificial Sequence
<220> FEATURE:
<223> OTHER INFORMATION: Nucleotide sequence of gRNA20 for target site
      sequence for OsMFS9 gene

<400> SEQUENCE: 94
acacaaacaa acaagttcag                                               20

<210> SEQ ID NO 95
<211> LENGTH: 20
<212> TYPE: DNA
<213> ORGANISM: Artificial Sequence
<220> FEATURE:
<223> OTHER INFORMATION: Nucleotide sequence of gRNA21 for target site
      sequence for OsMFS9 gene

<400> SEQUENCE: 95
gcaggattgc cgccatgaag                                               20

<210> SEQ ID NO 96
<211> LENGTH: 20
```

```
<212> TYPE: DNA
<213> ORGANISM: Artificial Sequence
<220> FEATURE:
<223> OTHER INFORMATION: Nucleotide sequence of gRNA22 for target site
      sequence for OsMFS9 gene

<400> SEQUENCE: 96
gcaaatgtag taggcacgag                                                    20

<210> SEQ ID NO 97
<211> LENGTH: 1934
<212> TYPE: DNA
<213> ORGANISM: Zea may

<400> SEQUENCE: 97
cagtgcagcg tgacccggtc gtgcccctct ctagagataa tgagcattgc atgtctaagt        60
tataaaaaat taccacatat ttttttttgtc acacttgttt gaagtgcagt ttatctatct       120
ttatacatat atttaaactt tactctacga ataatataat ctatagtact acaataatat       180
cagtgtttta gagaatcata taaatgaaca gttagacatg gtctaaagga caattgagta       240
ttttgacaac aggactctac agttttatct ttttagtgtg catgtgttct cctttttttt       300
tgcaaatagc ttcacctata taatacttca tccattttat tagtacatcc atttaggggtt      360 tagggttaat ggttttttata gactaatttt tttagtacat ctattttatt ctattttagc      420
ctctaaatta agaaaactaa aactctattt tagttttttt atttaataat ttagatataa       480
aatagaataa aataaagtga ctaaaaatta aacaaatacc ctttaagaaa ttaaaaaaac       540
taaggaaaca tttttcttgt ttcgagtaga taatgccagc ctgttaaacg ccgtcgacga       600
gtctaacgga caccaaccag cgaaccagca gcgtcgcgtc gggccaagcg aagcagacgg       660
cacggcatct ctgtcgctgc ctctggaccc ctctcgagag ttccgctcca ccgttggact       720
tgctccgctg tcggcatcca gaaattgcgt ggcggagcgg cagacgtgag ccggcacggc       780
aggcggcctc ctcctcctct cacggcaccg gcagctacgg gggattcctt tcccaccgct       840
ccttcgcttt cccttcctcg cccgccgtaa taaatagaca ccccctccac accctctttc       900
cccaacctcg tgttgttcgg agcgcacaca cacacaacca gatctccccc aaatccaccc       960
gtcggcacct ccgcttcaag gtacgccgct cgtcctcccc cccccccctc tctaccttct      1020
ctagatcggc gttccggtcc atggttaggg cccggtagtt ctacttctgt tcatgttttgt     1080 gttagatccg tgtttgtgtt agatccgtgc tgctagcgtt cgtacacgga tgcgacctgt     1140
acgtcagaca cgttctgatt gctaacttgc cagtgtttct cttggggaat cctgggatgg     1200
ctctagccgt tccgcagacg ggatcgattt catgattttt tttgtttcgt tgcatagggt     1260
ttggtttgcc cttttccttt atttcaatat atgccgtgca cttgtttgtc gggtcatctt     1320
ttcatgcttt tttttgtctt ggttgtgatg atgtggtctg gttgggcggt cgttctagat     1380
cggagtagaa ttctgtttca aactacctgg tggatttatt aatttttggat ctgtatgtgt     1440 gtgccataca tattcatagt tacgaattga agatgatgga tggaaatatc gatctaggat     1500
aggtatacat gttgatgcgg gttttactga tgcatataca gagatgcttt ttgttcgctt     1560
ggttgtgatg atgtggtgtg gttgggcggt cgttcattcg ttctagatcg gagtagaata     1620
ctgtttcaaa ctacctggtg tatttattaa ttttggaact gtatgtgtgt gtcatacatc     1680
ttcatagtta cgagtttaag atggatggaa atatcgatct aggataggta tacatgttga     1740
tgtgggtttt actgatgcat atacatgatg gcatatgcag catctattca tatgctctaa     1800
ccttgagtac ctatctatta taataaacaa gtatgtttta taattatttt gatcttgata     1860
```

| | |
|---|---|
| tacttggatg atggcatatg cagcagctat atgtggattt ttttagccct gccttcatac | 1920 |
| gctatttatt tgct | 1934 |

<210> SEQ ID NO 98
<211> LENGTH: 4206
<212> TYPE: DNA
<213> ORGANISM: Artificial Sequence
<220> FEATURE:
<223> OTHER INFORMATION: The nucleotide sequence of nuclear localization sequence

<400> SEQUENCE: 98

| | |
|---|---|
| atggcccta agaagaagag aaaggtcggt attcacggcg ttcctgcggc gatggacaag | 60 |
| aagtatagta ttggtctgga cattgggacg aattccgttg ctgggccgt gatcaccgat | 120 |
| gagtacaagg tcccttccaa gaagtttaag gttctgggga caccgatcg gcacagcatc | 180 |
| aagaagaatc tcattggagc cctcctgttc gactcaggcg agaccgccga agcaacaagg | 240 |
| ctcaagagaa ccgcaaggag acggtataca agaaggaaga ataggatctg ctacctgcag | 300 |
| gagattttca gcaacgaaat ggcgaaggtg gacgattcgt tctttcatag attggaggag | 360 |
| agtttcctcg tcgaggaaga taagaagcac gagaggcatc ctatctttgg caacattgtc | 420 |
| gacgaggttg cctatcacga aaagtacccc acaatctatc atctgcggaa gaagcttgtg | 480 |
| gactcgactg ataaggcgga ccttagattg atctacctcg ctctggcaca catgattaag | 540 |
| ttcaggggcc attttctgat cgaggggat cttaacccgg acaatagcga tgtggacaag | 600 |
| ttgttcatcc agctcgtcca aacctacaat cagctctttg aggaaaaccc aattaatgct | 660 |
| tcaggcgtcg acgccaaggc gatcctgtct gcacgccttt caaagtctcg ccggcttgag | 720 |
| aacttgatcg ctcaactccc gggcgaaaag aagaacggct gttcgggaa tctcattgca | 780 |
| ctttcgttgg ggctcacacc aaacttcaag agtaattttg atctcgctga ggacgcaaag | 840 |
| ctgcagctt ccaaggacac ttatgacgat gacctggata accttttggc ccaaatcggc | 900 |
| gatcagtacg cggacttgtt cctcgccgcg aagaatttgt cggacgcgat cctcctgagt | 960 |
| gatattctcc gcgtgaacac cgagattaca aaggcccgc tctcggcgag tatgatcaag | 1020 |
| cgctatgacg agcaccatca ggatctgacc cttttgaagg ctttggtccg gcagcaactc | 1080 |
| ccagagaagt acaaggaaat cttctttgat caatccaaga acggctacgc tggttatatt | 1140 |
| gacggcgggg catcgcagga ggaattctac aagtttatca agccaattct ggagaagatg | 1200 |
| gatggcacag aggaactcct ggtgaagctc aataggagg accttttgcg gaagcaaaga | 1260 |
| actttcgata acggcagcat ccctcaccag attcatctcg gggagctgca cgccatcctg | 1320 |
| agaaggcagg aagacttcta cccctttctt aaggataacc gggagaagat cgaaaagatt | 1380 |
| ctgacgttca gaattccgta ctatgtcgga ccactcgccc ggggtaattc cagatttgcg | 1440 |
| tggatgacca gaaagagcga ggaaaccatc acaccttgga acttcgagga agtggtcgat | 1500 |
| aagggcgctt ccgcacagag cttcattgag cgcatgacaa attttgacaa gaacctgcct | 1560 |
| aatgagaagg tccttcccaa gcattccctc ctgtacgagt atttcactgt ttataacgaa | 1620 |
| ctcacgaagg tgaagtatgt gaccgaggga atgcgcaagc ccgccttcct gagcggcgag | 1680 |
| caaaagaagg cgatcgtgga ccttttgttt aagaccaatc ggaaggtcac agttaagcag | 1740 |
| ctcaaggagg actacttcaa gaagattgaa tgcttcgatt ccgttgagat cagcggcgtg | 1800 |
| gaagacaggt ttaacgcgtc actggggact taccacgatc tcctgaagat cattaaggat | 1860 |
| aaggacttct tggacaacga ggaaaatgag gatatcctcg aagacattgt cctgactctt | 1920 |

```
acgttgtttg aggataggga aatgatcgag gaacgcttga agacgtatgc ccatctcttc   1980
gatgacaagg ttatgaagca gctcaagaga agaagataca ccggatgggg aaggctgtcc   2040
cgcaagctta tcaatggcat tagagacaag caatcaggga agacaatcct tgactttttg   2100
aagtctgatg gcttcgcgaa caggaatttt atgcagctga ttcacgatga ctcacttact   2160
ttcaaggagg atatccagaa ggctcaagtg tcgggacaag gtgacagtct gcacgagcat   2220
atcgccaacc ttgcgggatc tcctgcaatc aagaagggta ttctgcagac agtcaaggtt   2280
gtggatgagc ttgtgaaggt catgggacgg cataagcccg agaacatcgt tattgagatg   2340
gccagagaaa atcagaccac acaaaagggt cagaagaact cgagggagcg catgaagcgc   2400
atcgaggaag gcattaagga gctggggagt cagatcctta aggagcaccc ggtggaaaac   2460
acgcagttgc aaaatgagaa gctctatctg tactatctgc aaaatggcag ggatatgtat   2520
gtggaccagg agttggatat taaccgcctc tcggattacg acgtcgatca tatcgttcct   2580
cagtccttcc ttaaggatga cagcattgac aataaggttc tcaccaggtc cgacaagaac   2640
cgcgggaagt ccgataatgt gcccagcgag gaagtcgtta agaagatgaa gaactactgg   2700
aggcaacttt tgaatgccaa gttgatcaca cagaggaagt tgataaccct cactaaggcc   2760
gagcgcggag gtctcagcga actggacaag gcgggcttca ttaagcggca actggttgag   2820
actagacaga tcacgaagca cgtggcgcag attctcgatt cacgcatgaa cacgaagtac   2880
gatgagaatg acaagctgat ccgggaagtg aaggtcatca ccttgaagtc aaagctcgtt   2940
tctgacttca ggaaggattt ccaatttat aaggtgcgcg agatcaacaa ttatcaccat   3000
gctcatgacg catacctcaa cgctgtggtc ggaacagcat tgattaagaa gtacccgaag   3060
ctcgagtccg aattcgtgta cggtgactat aaggtttacg atgtgcgcaa gatgatcgcc   3120
aagtcagagc aggaaattgg caaggccact gcgaagtatt tcttttactc taacattatg   3180
aatttcttta agactgagat cacgctggct aatggcgaaa tccggaagag accacttatt   3240
gagaccaacg gcgagacagg ggaaatcgtg tgggacaagg ggagggattt cgccacagtc   3300
cgcaaggttc tctctatgcc tcaagtgaat attgtcaaga agactgaagt ccagacgggc   3360
gggttctcaa aggaatctat tctgcccaag cggaactcgg ataagcttat cgccagaaag   3420
aaggactggg acccgaagaa gtatggaggt ttcgactcac caacggtggc ttactctgtc   3480
ctggttgtgg caaaggtgga gaaggaaaag tcaagaagc tcaagtctgt caaggagctc   3540
ctgggtatca ccattatgga gaggtccagc ttcgaaaaga tccgatcga ttttctcgag   3600 gcgaagggat ataaggaagt gaagaaggac ctgatcatta agcttccaaa gtacagtctt   3660
ttcgagttgg aaaacggcag gaagcgcatg ttggcttccg caggagagct ccagaagggt   3720
aacgagcttg ctttgccgtc caagtatgtg aacttcctct atctggcatc ccactacgag   3780
aagctcaagg gcagcccaga ggataacgaa cagaagcaac tgtttgtgga gcaacacaag   3840
cattatcttg acgagatcat tgaacagatt tcggagttca gtaagcgcgt catcctcgcc   3900
gacgcgaatt tggataaggt tctctcagcc tacaacaagc accgggacaa gcctatcaga   3960
gagcaggcgg aaaatatcat tcatctcttc accctgacaa accttggggc tcccgctgca   4020
ttcaagtatt ttgacactac gattgatcgg aagagataca cttctacgaa ggaggtgctg   4080
gatgcaaccc ttatccacca atcgattact ggcctctacg agacgcggat cgacttgagt   4140
cagctcgggg gggataagag accagcggca accaagaagg caggacaagc gaagaagaag   4200
aagtag                                                              4206
```

<210> SEQ ID NO 99
<211> LENGTH: 367
<212> TYPE: DNA
<213> ORGANISM: Cauliflower mosaic virus

<400> SEQUENCE: 99

| | |
|---|---|
| cggtacgctg aaatcaccag tctctctcta caaatctatc tctctctatt ttctccataa | 60 |
| ataatgtgtg agtagtttcc cgataaggga aattagggtt cttataggtt ttcgctcatg | 120 |
| tgttgagcat ataagaaacc cttagtatgt atttgtattt gtaaatact tctatcaata | 180 |
| aaatttctaa ttcctaaaac caaaatccag tactaaaatc cagatctcct aaagtcccta | 240 |
| tagatctttg tcgtgaatat aaaccagaca cgagacgact aaacctggag cccagacgcc | 300 |
| gttcgaagct agaagtaccg cttaggcagg aggccgttag ggaaaagatg ctaaggcagg | 360 |
| gttggtt | 367 |

<210> SEQ ID NO 100
<211> LENGTH: 742
<212> TYPE: DNA
<213> ORGANISM: Oryza sativa

<400> SEQUENCE: 100

| | |
|---|---|
| ctcattagcg gtatgcatgt tggtagaagt cggagatgta ataatttttc attatataaa | 60 |
| aaaggtactt cgagaaaaat aaatgcatac gaattaattc ttttatgtt ttttaaacca | 120 |
| agtatataga atttattgat ggttaaaatt tcaaaaatat gacgagagaa aggttaaacg | 180 |
| tacggcatat acttctgaac agagagggaa tatggggttt ttgttgctcc caacaattct | 240 |
| taagcacgta aaggaaaaaa gcacattatc cacattgtac ttccagagat atgtacagca | 300 |
| ttacgtaggt acgttttctt tttcttcccg gagagatgat acaataatca tgtaaaccca | 360 |
| gaatttaaaa aatattcttt actataaaaa ttttaattag ggaacgtatt attttttaca | 420 |
| tgacacccttt tgagaaagag ggacttgtaa tatgggacaa atgaacaatt tctaagaaat | 480 |
| gggcatatga ctctcagtac aatggaccaa attccctcca gtcggcccag caatacaaag | 540 |
| ggaaagaaat gaggggggccc acaggccacg gcccactttt ctccgtggtg gggagatcca | 600 |
| gctagaggtc cggcccacaa gtggcccttg ccccgtggga cggtgggatt gcagagcgcg | 660 |
| tgggcggaaa caacagttta gtaccacctc gctcacgcaa cgacgcgacc acttgcttat | 720 |
| aagctgctgc gctgaggctc ag | 742 |

<210> SEQ ID NO 101
<211> LENGTH: 83
<212> TYPE: DNA
<213> ORGANISM: Artificial Sequence
<220> FEATURE:
<223> OTHER INFORMATION: The nucleotide sequence of gRNA scaffold

<400> SEQUENCE: 101

| | |
|---|---|
| gttttagagc tagaaatagc aagttaaaat aaggctagtc cgttatcaac ttgaaaaagt | 60 |
| ggcaccgagt cggtgctttt ttt | 83 |

<210> SEQ ID NO 102
<211> LENGTH: 1182
<212> TYPE: DNA
<213> ORGANISM: Oryza sativa

<400> SEQUENCE: 102

| | |
|---|---|
| cctcctctct ccctctctcc gcgattcgat ctcaccggcg ccgtagcgcg cggggcggtg | 60 |

```
gagagcgtgg gatttctccg cgggtaatcc cattggataa acatggcgcg tttgggtggt      120
tcggtcgccg caccacgcaa cgcgacgcag tgcgcgtgag cgtgcctaac cgtgtgcgac      180
tcggctcgac aaaaaaccaa accaaaccga tcagatcgca ttagaaaatc tctccaccgc      240
ttgcaattgc aagctagctg cagtggttta gggccaaaca tgctgcaagt gtgagtcgtt      300
gaccaaagag gacatcacat tcggagtcag agatgggaga ccgccagtgc aatgctagtc      360
ataaccacga tatcaaatgc caaggagtta agaaatgat  agtttgtgaa cttgtgagtt      420
gtgatggacc gggacgatga gcatgggtga gctaggcatt gtctctgcgc aagcactggt      480
gtactgccgc tgccagggta gatccaccgt ccattgcagt ggtccattgc ctcaccctca      540
cgccgacact tgtttcacag cgcgcaagta attaacttga tccattcgag agagatgagg      600
agagaaaacg aacaaggttt ggttgatctg cactgggcc accgccaatc cgatgttcgt      660
tccaccgact gtactacagt actagtatcc ggcagtctgg ctacgcggta tactactata      720
cgtgtcattg tctactcaac caagaaaaat tcgctgacga tcgagaattg tgtcagtaac      780
gccgccaagc agaagaacac ccaaaatcca tctatccacc accactggga ctggattcat      840
catcatcaat tggaagaaat ctcaaccacc gttgggcccc agacgcacag acacacacaa      900
acacatccga tcccgcggcg gcagcagcaa gcgcaattcc catcaaccgc aagtgcgtgc      960
cggccgaaga tttggcgcac gcacactcaa acccccact  ccactgcccc caaacccaa     1020 cccccaacca gccagaatta ccacacacac gcaccgcacc cgaaatccca agaaacgcgc     1080
gtataaatcc caccggcttg aggagtcgac tcgccgatcc atccaccgc  gcttcgtcca     1140 ttccatcttt ctctctctct cgcggaggtc ggaggagcca tg                        1182
```

<210> SEQ ID NO 103
<211> LENGTH: 2500
<212> TYPE: DNA
<213> ORGANISM: Oryza sativa

<400> SEQUENCE: 103

```
ccatcacctg aaatgttgag tagctgttca aagaactgat gcatattgct cacgtgaagg       60
catctgatgc agagactaaa ttcttgagga ctgacggaaa tgggacaagg ttgccaatt      120 agggcacata caaatttct  gcgtgccatt gcactaatat aggcacaaaa agattcagat      180
ttacaagccc atctcaaaac acccaagagg aagaaggcaa aaatgctta  ggttgccaat      240 gagagaattt tcttcctggt aaatgatcaa gcttcagcga gcaatatatc ttgataatgg      300
aacaagaatg ctttgaaaaa atggccaagg atagaacaaa tctgtgaaac atatccaatc      360
actaattact ggaaagcgga atttgaactg aaaggaaaa  cactcagccc cttgttagaa      420
tacaagtata caacagagag atgtctctcc acttaatggc actaagttca aatattcaga      480
acaaaggaac tagcgaaaac cgaaaagttt taaatttgtg aaatagaaaa ctgttctgat      540
taatcatcaa gccaacacac gcaacacttc agtggtgttt ggatgaagt  gattattcta      600 gacactagaa ctggtgcaaa ctgaagtctc tgaacatctg ttgctatggt gagcaaaact      660
acatcgccgt gcacaaatcc attgtcaatc taggtatcta actgagttca agttccggca      720
aatgcgagaa ccaatcatta ctacaacgat cgtttactag aaaaaaaaat gtggcggctt      780
tgaacgggac cggggcttac ttgtgagggc gatagcgtgg gcgccaccgc cggcgacgaa      840
ggaaaccaga ccgcggcagc gaggtggcag gaggagcggc tgcgggagat ggtggtcctg      900
gaagccgccg ttcccgagct gcccgtccgt tcccgcgccc caactccacg cccacaccgc      960
```

| | |
|---|---|
| ctcctcctcc tcctcctccg ccgccgccgc cgcctccatg cccccgaacc ggtgcgaaga | 1020 |
| aagttccacg ggactccggt ccttcggtta tccgaaggac ttcacttccc tgcgtgacac | 1080 |
| gtgtcccggc acgaatctca gagcactatt cctctctttc tccgaccagg atggcctttg | 1140 |
| cccacaagac cgtatttgga atttttcttg caggggaatc cgttcaactt atgtgtgcaa | 1200 |
| tactgtgact tttcctcaag acaagaatcc ttctggattt tgcaacaagt gagacagcgt | 1260 |
| gtggtcttct agttctagca agtagtactg attctcgaat ttgattccct tttaaaacgt | 1320 |
| gtttgatctt cgttctctct ctcaaaaatt ctgctaatta accgggttag tagacggaaa | 1380 |
| gtcagacgct tgagctcgag cgagttcttt acgttctctc cttaaccgga tcgccaaatt | 1440 |
| aaagcagcac atcgccttct gcaatctgca cctccggatc atttccattt gcccaaaagg | 1500 |
| agggcaaatt ggcctagcta gcaaggccac cgaaagctca cgacaatggc ggtcgatcaa | 1560 |
| tctggtctgt acttttttcg acggtgtgaa agaaacaaga cccgaccag catctgctga | 1620 |
| tctccgatcg atgcttagtg tccgcgagaa ccagcgagct accttggttt gtagtgcttc | 1680 |
| gattcgagat cttggaacga gctcgcaatc agcttcctc gccggcctgc cggacgattc | 1740 |
| tcggcgtcac gtcgcggtcg aatctctcat cgcctcatct ttgatgaaga attcaagata | 1800 |
| aaagtgctta actaggatcg ccgttcacat tgcatttaga ggtgggaaaa tatttaactc | 1860 |
| gagaggacat cctttccttt tatacatatt atttaaatgg ttattttttt acaagatata | 1920 |
| ttaatatgtg ataagtcact ctacaaacat gtaagatgaa tatacgtaag tcatactccc | 1980 |
| aatgaatgac atgcaaacaa cgaggggtga tccctcgaga atttagaatc cactccctac | 2040 |
| gaccatcggt ttctgacttt caccagcttc aacgttggca tcaacattgt tctctctttt | 2100 |
| acggcctttt ttttttctga attctgaaca cttctactat tgaacttttg ttacggttgt | 2160 |
| attaggcatt gcgtgccttg aagttaaggg caggaacaat ccgaaaaggt aaaaaggtga | 2220 |
| cgaatatata tcgagcttta ttcgtttccc tccgatccat cacacgcact cgccgatgga | 2280 |
| tcagctgctg acagcggcgc acgcaggatg gtggccgggt tggaacttgg aagctccaaa | 2340 |
| caccgcgaga agcatcatca ctcagctgca acctgaagca ccgtggtcta taaatatagc | 2400 |
| tccaggacag gctctcttct tactctcacc cagtatagtt ctccattgag caaactacca | 2460 |
| aagggtactc atctgaaaca gaatccagtg atcgaccagc | 2500 |

<210> SEQ ID NO 104
<211> LENGTH: 2500
<212> TYPE: DNA
<213> ORGANISM: Oryza sativa

<400> SEQUENCE: 104

| | |
|---|---|
| gtttggtttg caatcctacc aaaattttga taggacaaat tttggtaggg tagcaattta | 60 |
| aattggccct aactctcggc gacagctaca aagaggccat atacaaattt tcgagatacg | 120 |
| caatacggcg atttccatt gcaaggggc gcaactctag cataatccgg acgaacactt | 180 |
| gcctccacac agagcgaacc aaatgcacgg gttaagtagt accagtacga cgtgtccatc | 240 |
| ccgttcaaca cttgccccc gctctgaccg ccgctgccgc caaggcgacc cggtcggcgg | 300 |
| tctcccctgc tcgccgcttg tttattcctc gcagtccgcg ctccctcctc ccggtaaaca | 360 |
| aacgactcct gcagcctgca ggctactcct accgctacat caaccgagga aaaacgtctg | 420 |
| tcgcatgtgg tgtgtgtgca ttaataaaaa aaaatactat ttataatatt cgtaagtaaa | 480 |
| ttgtactccc tccgtctcaa aataagtaca gttttacact attcatgttc aacgtttgac | 540 |
| cgtccatctt attgaaaat ttttatgat tagtattttt attgctatta gataataaaa | 600 |

```
catgaatagt actttatgtg tgactaaatg ttttaattt tttcacaaat ttttaaata      660 agacggacgg tcaaacgttg aacgtgaata gtgcaaaact gcacttatta taggacggag    720
gtagtaacat aaatttatta aacctaatta atttttatt agcacatgtt tactatagca     780
tcatattgtc aaatcatgga gcaattatga ttaaaatatt tctcgtaaat tagtcgcaat    840
ctatgtaatt ggagtagtta cttccttcat cccacaatac ttgtctttct agcattcaaa   900
agttgtccca aaatattatc acttgaaagt agtacttgcc acattaacca cttctaattc    960
aaatttcttc tcattatact cccaaccacc atcttacatc caactatact ccctccgtct   1020
tttaaaaaaa agtaaactct ggctatgctt tttttacgg agggagcaca ttagttacta    1080
aaggatatta tagtcttttt ctcttaatct tagtatatgc taaacaaacct agaattatat   1140 gtattttgct acggaggggg tatatttttt aacttatggg tgtatttagt tcacgccaaa   1200
attgtaagtt tgattgaaat ttgaacgatg tgacgggaaa gttggaaggt gtgtgtagga   1260 aagtttgat gtgatggaaa agttggaagt ttaaaaaaaa agtttggaac taaactcagc    1320
ctatatttaa tactccctct gtcccataat ataagggact ttgagttttt tttcattgtt   1380
tgaccactcg tcttattcaa aaatttgtgc aaatataaaa aacgaaaagt tgtgcttaag   1440
tgctttggat aataaagtaa gtcaaaaaaa ataattctaa atttttttga ataagacgag   1500
tggtcaaaca gcaccagcaa aaacttaaaa tcccttgtat tatgaaacgg agggagtact   1560
ttggtatatg tgttcagacg ttcgatgtga cgggatgtaa aattttaacg tggatctaaa   1620
cagacgatca acaacatcg acgaggagta aggccctgtt tagatgggac taaaactttt     1680
aagtccctat cacatcggat gtttgaaaat taattataaa tattaaacgt agactattaa   1740
taaaacccat ccataatctt ggactaattt gcgagacgaa tctaatgagc ctaattaatc   1800
catgattagc ctatgtgatg ctacagtaaa cattctctaa ttatagatta attaggctta   1860
aaaaatttgt ctcgtgattt agcttttatt tatgtaatta gttttgtaag tagtctatat   1920
ttaatactct aaattagtgt ttaaagacag ggagacaggg actagtccct gatgtaaaca   1980
ccacctgaaa caacgaccgc tacgctaggt ccatggtcgt ggcaacggca gcgcgtcggg   2040
agacgagctg agcaagcgag acacgagacc atcggcggcc acgctcttac acgccatcaa   2100
ccgcgagaca cgactcacac gagactcccc acccatcctc ctccgtgcgc gctggaggag   2160
gtggaggtgg aggtggtggt gtccgctgcc ccccgcaata aataagccta cctccatgtt   2220
cccacccccc tctctctctc ttctccgtct cgcctcgtca cctcacctcg gcatcaccca   2280
ggtgggaggg ggtccgcctt gacttttcgt gttcgggttt gggtttgagt gccgcatctg   2340
caagcttgtg cgaggggga atctctcttc cttgctgtgg tggcggcggg cggagggcg    2400 gcgttgattt cgttggggtt tgcgttgcgt gcggaggacg gggttgtgtt tgtgtgtgtg   2460
tttgtgctga tttgggcatt ggtgttggtg gtggaggagg                         2500
```

<210> SEQ ID NO 105
<211> LENGTH: 2500
<212> TYPE: DNA
<213> ORGANISM: Oryza sativa

<400> SEQUENCE: 105

```
aagtttcgag tccacgtttg agataggaag taatcacttt gaagatccac tgtggtcttc    60
agtttgctta ccagatgccc agctagtacc aagcagctgt ctcttggaca ataccaattt   120
gtcaactgtt tcgaatgaga gcacaacaaa gtctatatta tcatcagttt cagtttccga   180
```

```
tactactagt gctgaaccat tgttccttga tcaggtactt ccaaactttt gatctttcta      240
attgatttcc ccctaatttt ataggttaga tgatgccgag ggtttcttcc ccagggtagc      300
ttctcttgtc attccgagag tcaagatctc tggcctcttc aatatgcaac aaatctccag      360
atcatatgtt tcctcaaaat aatcttggtt ccatatagga acattttaac atttctcttc      420
aatttatctc tgcagaataa tatggcaaat cctatcaaca tacaacaacc acccagcaaa      480
ggaagaagtt cggcaacttt gaatcatgaa gcacttgcct gttcttccgg ggaaatcgag      540
cgattttcac aacattcaga tgttgatgtt ttctacccat ttgacaatgt aacaagctcg      600
gaacgcataa gtggctgtga gggactagag gctatctttt gcacaaatca ggaaatgcta      660
gccccaacaa catcaagcat catgtgtgat gatgaaattg tatcttcatc gactttctca      720
gcaccggatc tcgttgcaac ctacgttccg cgttcgatga agagatctca tgatccactg      780
aatggaactc cagacatgat cctcgacgaa atggctggaa atccactaga gatgtatttc      840
cctccatcat tgactgcata tgaacaccca gaacatctga ataacgttac tttgacacaa      900
acacaccagt ttcctgaagg atttgcaggt gacgatgttc tgaaaagtgc agacttacag      960
ttcctctcga agggaaagac ttcagcagac ttatgtgtga accttgctc accactgatt     1020 ctagaagctg tgccagttaa ggatcttggc ttccataagc ttcaggaagg catgaatcag     1080
gtatactaat agtatcagta acttagaaca ccctcttgca cccttctag ctatgttgca     1140 ttcttcagga atttgtgaat gcaattagct attattcagg ttgataatat ttcagattgt     1200
ccatgataag tattcagctc ttgtatcctt ccaatgtact ttgcagttgg acgtggcatc     1260
caaagctcgc ataagagatg ccttgtatcg attggccaat tgtgttgagc ataggcatcg     1320
cattgctagt acaacagaga ccgttaacca acttggagtt atggaatcat cagcttcaaa     1380
gaggtacaac ggtttaatgt gatcttcaat tatgtttagg acacttgaag tgatcgacag     1440
ctgagttttt gtgaagtgta attttctgac atgttcaaat caaacaggtg gagagaaatt     1500
cagatgatga accctatgga tcgctcagtg gcacagctgc ttctccagaa accgctccac     1560
cataaatctc cacctgattc ggcgctcggc attggtccct gaattgtact gcaccgtgaa     1620
aaacacgtag gagtggctgc tgatgcgatg tggtttttt tactgcacat gtctgatcga     1680
ttgagcattc taggtccggc aatttttttt ccctctcggt tccggtacgc atgtatatac     1740
agtaatcact aaagagtaca gacttactag atgaaatgta atgtgatagc aacgctttgc     1800
tgttcagaga tgtgattcta aatagaaact acagtgtttt tttttttgttg tcttcagcat     1860 ttacctgtga cttgtcagat gccccattgt accgtccaaa aatttcctct attgacggtt     1920
accccttggt cgcagattta cacggtttct cttattgacg gttaccatgg taattaggct     1980
tatcacgtgt gcggaaacga taagtgccgg ataattctac caagttcaaa gaaacttaaa     2040
tgtaaactct ctccagtttt ttcacggttc atcacgataa ccgcaatggt taccgcggtc     2100
gttggagata aaccctgtcg ccgaaccgag gccgcctgtg cactaaccgc caattagagg     2160
aaaggaaaca aatcttgcaa gtgtgcaagt gaccgggcta gataatccaa tcttgacttg     2220
gcagttgtgt tcgccaccga acggcaggag aagcgaagcg tggggaggaa aaggcccaaa     2280
tcctcgcctc ctcctgcctg caaccaccgc ctccgtcgtc tcgtctcccc cggcagagga     2340
atccccaacc cggaagcttt cgggagtcgg acagctcgc cttgactcgc gtcccctcc     2400 ctcgcgcgcg cgcgcgctcg tcgcctccta aacttagcgg ccgcgcggga cgcggagggg     2460
cgctcccctc cagaaatagg cggggtgggt ggcgaggagg                          2500
```

<210> SEQ ID NO 106
<211> LENGTH: 2500
<212> TYPE: DNA
<213> ORGANISM: Oryza sativa

<400> SEQUENCE: 106

| | | | | | |
|---|---|---|---|---|---|
| gggtatgtct | ttgtggataa | ctaattgggc | aattagttca | tatctgtaaa | gtgtaaaata | 60 |
| tactatcatt | atataagaga | cacacattcc | ttttagaaaa | gaaaaaaaag | catgtgtatc | 120 |
| aggggctggt | tgttggatga | ccaaagttca | gatctttaaa | accagaatat | tcttgtcatt | 180 |
| tttcttttaa | acaagtgggt | tttcacggcc | gtctatacct | ccgtgaggga | gggaccacac | 240 |
| actcctttgt | aaagccacga | attctacatt | agcttacatt | gaatttcaca | taaattaaaa | 300 |
| tgatttattt | tgtgtacaaa | aaagaagaaa | gattcatgtg | ttttaagcga | gccaaatgca | 360 |
| aaactagtgc | caacaccaat | gagaaacttc | gatgcaaatg | cagttagcgt | gacacaccat | 420 |
| tttctattag | aacctgtttg | agatagctaa | aatttatgca | caatctaatt | cttttatagt | 480 |
| tattggaggg | tacaaacaaa | tcaattaatt | attagaaaaa | ttaaaatgtt | gctttagaaa | 540 |
| agtgtttcaa | ggaaatttta | tatacttttaa | attttacga | aacacaccgt | gtagtaagtt | 600 |
| aagaattgtt | ttaaaatacc | agaattaaaa | aaaaagaaca | gggcctcaag | gcaaggtagt | 660 |
| ggtggatcat | tatacatgtg | cccatcaaaa | gagttacaca | tatgcatgtt | aacttgttcc | 720 |
| cttcttttct | ttatcttctt | gcctttaaat | tttccctctt | ttgactgttg | tgcatacttg | 780 |
| taagcacctt | ttcattttgg | ttgtcttcca | agctaagggt | cctgtgaaag | aatttaatta | 840 |
| ttgtagagta | cacaagagcc | actcctacat | aggatcatct | agaactatcg | cccactcgta | 900 |
| gaagcaaaag | ccgaacaaaa | tgaaagaaa | agaagaaga | agaaataaag | aaataaacaa | 960 |
| aagaaataaa | gaaagaaaga | gggtcgatga | aattgcaggc | agttaattac | actaggtctc | 1020 |
| gtgttcgaac | atggttgaaa | acttctcctc | ccgcacacgt | aaaatgaagt | gattcattag | 1080 |
| tatatgatta | attaagtatt | agctagtttt | tttaaaaaag | attaatataa | ttttaaaaa | 1140 |
| caacctctta | tattttttat | aaaaaaatac | attgtttagc | gggttcagaa | aatgtatgtg | 1200 |
| tgaaaaatga | ggaggtagaa | attgaaaatt | tgcgctgccg | aatgcacctt | tctttactcc | 1260 |
| aagttaaaac | gttttgaaa | aacctgctct | atcaatatat | atgaggcaaa | acttttgccc | 1320 |
| tccctttttt | ttaaaaaaaa | cttttttccaa | accgtaccat | tcatccatgc | attgttcatg | 1380 |
| ccatttgctt | aggccttgtt | tagtttcaaa | cttttttcttc | aaactttcaa | ttttttcatc | 1440 |
| acatcaaaac | tttcctacat | atgtaaactt | tcaacttttt | cattacatta | ttctaatttc | 1500 |
| aatcaaattt | tcaattttag | catgaactaa | acacacccctt | agttaagatt | acttggtaca | 1560 |
| attactacgg | aatacggatg | gaggagttga | ttgatacgag | gccaagaatg | gaggttcttt | 1620 |
| tggacaaaaa | aattcagctc | tgtactgcga | cgtacacacg | tggcaagtgc | atttcctccc | 1680 |
| gattcaccctt | cagatttgt | tctcgtcgat | taatttccct | ggtaaatacg | aaatgttcat | 1740 |
| ggtccgtgat | gaaatgatga | tacggtcgag | cacataatgc | gccctgaaac | tgtaattgca | 1800 |
| gtacagaaaa | tgggtaacat | attcttgaat | aattttggca | caaccaaaaa | aaaaagccgt | 1860 |
| cttttgttca | ttcttgaacc | gtaggaattg | ttacaatttt | catgttcatg | aactttttt | 1920 |
| gcagaaacaa | agaaacccc | ttttgttaa | ttcctcaacc | gtaggaattg | ttgttaccat | 1980 |
| gttcatgaaa | attcttggca | gaaaacaaat | cctcctcctt | taaattcttc | aatagctgta | 2040 |
| cagtatctag | cacattgaga | tgtacgacag | cgtaatgccg | gattcaacaa | gcaagtcagc | 2100 |
| agcagcatca | ctgcgtcact | gatcactgta | ctggagagag | agatggccag | agagaaagat | 2160 |

| | | | | |
|---|---|---|---|---|
| ggtagccatg | gaggagagga | ggagacaggc | tgggccgcca | tgttcctcgc gaccttaatt | 2220 |
| tactcctcca | atggccgccg | ctgctgcgaa | acgcggagaa | ttctcttcca atttaaagcg | 2280 |
| ccccatctgt | ccatcttctc | caccaccact | agcattcttc | ttctccatcc atccatccat | 2340 |
| ccatctacgc | gtagattttg | cttttctttg | ctttgctttc | cagttgtaat tttgtgtacg | 2400 |
| agtacagcac | aagctcagct | cagctgcttc | agctataaaa | gcttctcact ctctcacaca | 2460 |
| cacactctct | ctctctgcta | gctcagctct | agatccagca | | 2500 |

<210> SEQ ID NO 107
<211> LENGTH: 2500
<212> TYPE: DNA
<213> ORGANISM: Oryza sativa

<400> SEQUENCE: 107

| | | | | |
|---|---|---|---|---|
| ggtctggctg | agtgaagttg | tgtagctatt | acttttttct | tctaatatat tgacgtgtaa | 60 |
| tcgttttaca | cgttcgagaa | aaaaaaacta | gaaagctgct | tctcggaatc tcgagcttct | 120 |
| caaacaaagt | cattgcctac | aaacacaaac | aagctaagtt | gtggcatcaa atttgatggc | 180 |
| cacaacttta | caattgggca | cacaaatgtt | tagatgttct | tggtctatca aacaaataac | 240 |
| ctctggtaat | aattcgcagc | cacatacata | ctggcaatca | cgcttaattt ggggtagaaa | 300 |
| cagaactagc | tagttagaga | tatactatcc | attctggagg | ggaacaaagt acatgtgcca | 360 |
| tgcagaaagt | gagggagctt | agcacaagaa | ctatgcagaa | ttaatccaaa ataatagtac | 420 |
| caatatcctt | ttgtggtcct | gctaacccat | ggtgatggt | gactaattaa gtaccaatta | 480 |
| agtagagtct | aggtgtcaat | taagtaaagc | agccaagtta | catgacaact gacaattgtc | 540 |
| acaagggcca | aggccatccc | caaattcttt | ttgccatgga | caccagcaaa ggacgtagta | 600 |
| ctagcttgaa | gggtcatcaa | gttcatcctt | ggacttagcc | aattctttcc tcttctcatg | 660 |
| cacctgcgcg | ccgtttcatc | ttttccttgt | ttgattagac | gttttcaaaa ggattaatag | 720 |
| gggtccagtt | ctagggagga | gattatatta | cttgttgatt | tgatataacc cctatttgca | 780 |
| tgcacacacc | acctgtactg | tacacgtctt | gaggttgggg | ttgagagctt aggtacactc | 840 |
| atatcaatgt | tttgacttga | tgtgagtgtc | gaattatata | attactccag taagcaaaat | 900 |
| tgtagtactc | catatatatc | ttagtaccTT | cggtaggatt | tctgatttct accaccacat | 960 |
| ttaattagtt | tcactgaaag | tacattgctt | tcctactagt | taatccggaa attaattttg | 1020 |
| ttgtttttat | taattagtgt | gaatcatgac | tcgatgtgat | cgtaacatac atgtggtgag | 1080 |
| tctcaaattt | tctgaagacg | ggataaaatg | cgcaaagatg | agtattatca gggtgtgttt | 1140 |
| agttcacgtt | aaaattggaa | gtttgattgg | aattgaaacg | atgtgacgga aaaattagaa | 1200 |
| gtttgtatgt | gtgtaggaaa | attttgatgt | gatggaaaag | ttggaggttt gaagaaaaag | 1260 |
| ttggaaacta | aaccaggcct | cagatgccaa | tttctaagcg | ggaatgctag ggggcagttg | 1320 |
| cctgatcgcc | tacttccaca | ccatcctgcc | ttctgactgc | atccccgtcc atccatctat | 1380 |
| ccattgtgca | agatcaaatc | tggcgagatg | gtcagtggtg | gtgtggatga agcgtatgtg | 1440 |
| acgaggatag | agccaccaag | gagcagctca | tcaccccctt | ggtctttcac attgttgggt | 1500 |
| gagcactcac | ttcgatctcc | cttttcatct | ctatcgtctt | cttcgatggg gaaagaagga | 1560 |
| ggaagtgacg | aatggggaag | tagggagat | gagatggtgg | cattggcgag cgtgatggaa | 1620 |
| ggaagtctta | tgctactcct | ctttgatgtg | agctcgtcac | taccacggtt atcctctcat | 1680 |
| gaaatcgaat | aatcatactc | aaccaaatgc | atcaacattg | gtgaactgat tggtagttat | 1740 |
| aggtattagg | cacgtaccac | tagtatcagg | cctgatacac | cacaagtatc tagtatcagg | 1800 |

```
ccatgataca ccacaaatat ctagtatcat gcctgataca caagtatgaa ggacgtctta    1860
tactgacggg tatcaattga tacctatggg tatcggtctg gtaccgatgg ggtaccagat    1920
cgacagatct gatatctaca tagtattatc atatttgaac gggatcgcgt atattatcat    1980
ggttaattga gcaatccaga tcccaacttg ctagtagata atgagaacag atctagaagc    2040
ataggccatc catctttttc cttacaagtt agctagctag ctagcaatcc ttcattctaa    2100
agttttgccc tccacagtca gccctcttgt tcaagtaaca catgagagct aaacaatggt    2160
gcaaaaccct aacactggtc ctccctttcc acattagggc tccccatata tcctgcctcc    2220
acaattccca tcagatcaaa gctactagct aatagccact gcacatgcca tgctacccaa    2280
atcatcacct cccttgtacc tttattatat tattcctagc taatctccac ttaattacag    2340
tagtgttcaa tctcatataa gcatatgcat ctcctagcta ccaagctctc tcttcctctg    2400
atcaactcca ctataattag ctatagctta gctagctgag tgatcagtga gcaggtcgat    2460
agcttaatta gcttccaatt aatttgatta agagcttaag                         2500
```

<210> SEQ ID NO 108
<211> LENGTH: 90
<212> TYPE: DNA
<213> ORGANISM: Oryza sativa

<400> SEQUENCE: 108

```
gtcatcaatg ttgggtagct caattgctgc acgcttgtta gcccgaaagc tgaaggtcga    60
aggttatatg cagatcgtgt ttacaatatc                                    90
```

<210> SEQ ID NO 109
<211> LENGTH: 91
<212> TYPE: DNA
<213> ORGANISM: Oryza sativa

<400> SEQUENCE: 109

```
gtcatcaatg ttgggtagct caattgctgc acgcttgtta gcccgaaagc atgaaggtcg    60
aaggttatat gcagatcgtg tttacaatat c                                  91
```

<210> SEQ ID NO 110
<211> LENGTH: 91
<212> TYPE: DNA
<213> ORGANISM: Oryza sativa

<400> SEQUENCE: 110

```
gtcatcaatg ttgggtagct caattgctgc acgcttgtta gcccgaaagc ttgaaggtcg    60
aaggttatat gcagatcgtg tttacaatat c                                  91
```

<210> SEQ ID NO 111
<211> LENGTH: 91
<212> TYPE: DNA
<213> ORGANISM: Oryza sativa

<400> SEQUENCE: 111

```
gtcatcaatg ttgggtagct caattgctgc acgcttgtta gcccgaaagc ctgaaggtcg    60
aaggttatat gcagatcgtg tttacaatat c                                  91
```

<210> SEQ ID NO 112
<211> LENGTH: 78
<212> TYPE: DNA
<213> ORGANISM: Oryza sativa

<400> SEQUENCE: 112
gtcatcaatg ttgggtagct caattgctgc acgcttgtta gccgtcgaag gttatatgca        60
gatcgtgttt acaatatc        78

<210> SEQ ID NO 113
<211> LENGTH: 83
<212> TYPE: DNA
<213> ORGANISM: Oryza sativa

<400> SEQUENCE: 113
gtcatcaatg ttgggtagct caattgctgc acgcttgtta gcctgaaggt cgaaggttat        60
atgcagatcg tgtttacaat atc        83

<210> SEQ ID NO 114
<211> LENGTH: 75
<212> TYPE: DNA
<213> ORGANISM: Oryza sativa

<400> SEQUENCE: 114
gtcatcaatg ttgggtagct caattgctgc acgcttgtta gtcgaaggtt atatgcagat        60
cgtgtttaca atatc        75

<210> SEQ ID NO 115
<211> LENGTH: 49
<212> TYPE: DNA
<213> ORGANISM: Oryza sativa

<400> SEQUENCE: 115
gtcatcaata taaggtcgaa ggttatatgc agatcgtgtt tacaatatc        49

<210> SEQ ID NO 116
<211> LENGTH: 89
<212> TYPE: DNA
<213> ORGANISM: Oryza sativa

<400> SEQUENCE: 116
cacacgcacc gcacccgaaa tcccaagaaa cgcgcgtata atcccaccg gcttgaggag        60 tcgactcgcc gatccatcca cccgcgctt        89

<210> SEQ ID NO 117
<211> LENGTH: 90
<212> TYPE: DNA
<213> ORGANISM: Oryza sativa

<400> SEQUENCE: 117
cacacgcacc gcacccgaaa tcccaagaaa cgcgcgtata atcccaccg gctttgagga        60 gtcgactcgc cgatccatcc acccgcgctt        90

<210> SEQ ID NO 118
<211> LENGTH: 90
<212> TYPE: DNA
<213> ORGANISM: Oryza sativa

<400> SEQUENCE: 118
cacacgcacc gcacccgaaa tcccaagaaa cgcgcgtata atcccaccg gccttgagga        60 gtcgactcgc cgatccatcc acccgcgctt        90

CONSTRUCTS AND METHODS TO IMPROVE ABIOTIC STRESS TOLERANCE IN PLANTS

FIELD

The field of the disclosure relates to plant breeding and genetics and, in particular, relates to constructs and methods useful in plants for improving abiotic stress tolerance, such as drought stress.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) *Science* 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and have to adjust to the prevailing environmental conditions of their surroundings. This has led to their development of a great plasticity in gene regulation, morphogenesis, and metabolism. Adaption and defense strategies involve the activation of genes encoding proteins important in the acclimation or defense towards the different stresses.

Drought (insufficient available water) is one of the major abiotic stresses that limit crop productivity worldwide, and exposure of plants to a water-limiting environment during various developmental stages appears to activate various physiological and developmental changes. Although many reviews on molecular mechanisms of abiotic stress responses and genetic regulatory networks of drought stress tolerance have been published (Valliyodan, B., and Nguyen, H. T. (2006) *Curr. Opin. Plant Biol.* 9:189-195; Wang, W., et al. (2003) *Planta* 218:1-14; Vinocur, B., and Altman, A. (2005) *Curr. Opin. Biotechnol.* 16:123-132; Chaves, M. M., and Oliveira, M. M. (2004) *J. Exp. Bot.* 55:2365-2384; Shinozaki, K., et al. (2003) *Curr. Opin. Plant Biol.* 6:410-417; Yamaguchi-Shinozaki, K. and Shinozaki, K. (2005) *Trends Plant Sci.* 10:88-94; Farooq, M. et al. (2009) *Agron. Sustain. Dev.* 29: 185-212; and Drought Stress Tolerance in Plants—Vol 1 edited by Hossain, M. A., Wani, S. H., Bhattacharjee, S., Burritt, D. J., Tran, L.-S. P. (2016)), it remains a major challenge in biology to understand the basic biochemical and molecular mechanisms for drought stress perception, signal transduction and tolerance. Molecular marker-assisted breeding has led to improved drought tolerance in crops. Transgenic approaches to engineering drought tolerance in crops have made progress (Vinocur B. and Altman A. (2005) *Curr. Opin. Biotechnol.* 16:123-132; Lawlor D W. (2013) *J. Exp. Bot.* 64:83-108).

Activation tagging can be utilized to identify genes with the ability to affect a trait, and this approach has been used in *Arabidopsis thaliana* (the model plant species) (Weigel, D., et al. (2000) *Plant Physiol.* 122:1003-1013) and rice (Lu et al. (2014) *Plant Cell Rep.* 33:617-631). Insertions of transcriptional enhancer elements can dominantly activate and/or elevate the expression of nearby endogenous genes, so this method can be used to select genes involved in agronomically important phenotypes, including abiotic stress tolerance such as improved drought tolerance and cold tolerance.

SUMMARY

The following embodiments are among those encompassed by the disclosure:

In one embodiment, the present disclosure includes an isolated polynucleotide, comprising: (a) a polynucleotide with nucleotide sequence of at least 85% sequence identity to SEQ ID NO: 2, 5, 8, 11, 14 or 17; (b) a polynucleotide with nucleotide sequence of at least 85% sequence identity to SEQ ID NO: 3, 6, 9, 12, 15 or 18; (c) a polynucleotide encoding a polypeptide with an amino acid sequence of at least 90% sequence identity to SEQ ID NO: 4, 7, 10, 13, 16 or 19; or (d) the full complement of the nucleotide sequence of (a), (b) or (c), wherein decreasing the expression of the polynucleotide enhances drought tolerance in a plant. The isolated polynucleotide comprises the nucleotide sequence of SEQ ID NO: 2, 3, 5, 6, 8, 9, 11, 12, 14, 15, 17 or 18; and the said isolated polynucleotide encodes a polypeptide comprising the amino acid sequence of SEQ ID NO: 4, 7, 10, 13, 16 or 19.

In another embodiment, the present disclosure includes a recombinant DNA construct comprising the isolated polynucleotide operably linked to at least one heterologous regulatory element, wherein the polynucleotide comprises (a) a polynucleotide with nucleotide sequence of at least 85% sequence identity to SEQ ID NO: 2, 3, 5, 6, 8, 9, 11, 12, 14, 15, 17 or 18; (b) a polynucleotide encoding a polypeptide with an amino acid sequence of at least 90% sequence identity to SEQ ID NO: 4, 7, 10, 13, 16 or 19; or (c) the full complement of the nucleotide sequence of (a) or (b).

In another embodiment, the present disclosure includes a suppression DNA construct comprising at least one heterologous regulatory element operably linked to suppression elements, wherein the suppression elements comprise (a) a polynucleotide with nucleotide sequence of at least 85% sequence identity to SEQ ID NO: 3, 6, 9, 12, 15 or 18; (b) a polynucleotide encoding a polypeptide with an amino acid sequence of at least 90% sequence identity to SEQ ID NO: 4, 7, 10, 13, 16 or 19; or (c) the full complement of the nucleotide sequence of (a) or (b); the suppression elements suppress the expression of an endogenous target comprising a polynucleotide region represented by SEQ ID NO: 3 (PRP1), SEQ ID NO: 6 (PP2C64), SEQ ID NO: 9 (OPPL1), SEQ ID NO: 12 (MFS9), SEQ ID NO: 15 (LAO1) or SEQ ID NO: 18 (DN-DSP1). The suppression elements comprise (a) a polynucleotide with nucleotide sequence of SEQ ID NO: 3, 6, 9, 12, 15 or 18; (b) a polynucleotide encoding a polypeptide with an amino acid sequence of SEQ ID NO: 4, 7, 10, 13, 16 or 19; or (c) the full complement of the nucleotide sequence of (a) or (b). Further, the suppression elements comprise the polynucleotide of SEQ ID NO: 45, 46, 47, 48, 49, or 50.

In another embodiment, the present disclosure includes a CRISPR/Cas construct comprising: a polynucleotide encoding a Cas9 enzyme, a polynucleotide encoding nuclear localization signal and at least one heterologous regulatory element operably linked to gRNA, wherein the gRNA is targeted to the genomic region of a target comprising endogenous PRP1, PP2C64, OPPL1, MFS9, LAO1 or DN-DSP1 gene and its regulatory elements to reduce the expression or the activity of endogenous PRP1, PP2C64, OPPL1, MFS9, LAO1 or DN-DSP1 polypeptide. Further the gRNA is targeted to the genomic region containing the polynucleotide with nucleotide sequence of SEQ ID NO: 3, 6, 9, 12, 15, 18, 102, 103, 104, 105, 106 or 107.

In another embodiment, the present disclosure includes a plant in which the expression or the activity of an endogenous PRP1, PP2C64, OPPL1, MFS9, LAO1 or DN-DSP1 polypeptide is decreased, when compared to the expression or the activity of wild-type PRP1, PP2C64, OPPL1, MFS9, LAO1 or DN-DSP1 polypeptide in a control plant, wherein the plant exhibits at least one phenotype selected from the group consisting of: increased drought tolerance, increased grain yield, increased abiotic stress tolerance and increased biomass, compared to the control plant, wherein the plant is obtained by steps of (a) introducing a suppression DNA construct comprising at least one heterologous regulatory element operably linked to suppression elements that reduces the expression of an endogenous PRP1, PP2C64, OPPL1, MFS9, LAO1 or DN-DSP1 polypeptide selected from the group consisting of SEQ ID NO: 4, 7, 10, 13, 16 or 19, or a sequence that is 95% identical to SEQ ID NO: 4, 7, 10, 13, 16 or 19; or (b)(i) introducing a DNA fragment, deleting a DNA fragment or replacing a DNA fragment, or (ii) introducing one or more nucleotide changes in the genomic region comprising the endogenous PRP1, PP2C64, OPPL1, MFS9, LAO1 or DN-DSP1 gene and its regulatory elements to reduce the expression or the activity of the endogenous PRP1, PP2C64, OPPL1, MFS9, LAO1 or DN-DSP1 polypeptide. Further, the plant comprising a suppression DNA construct, wherein the suppression DNA construct comprises at least one regulatory element operably linked to the suppression elements, wherein the suppression elements comprise at least 100 contiguous base pairs of (a) a polynucleotide with nucleotide sequence of at least 85% sequence identity to SEQ ID NO: 3, 6, 9, 12, 15 or 18; (b) a polynucleotide encoding a polypeptide with amino acid sequence of at least 90% sequence identity to SEQ ID NO: 4, 7, 10, 13, 16 or 19; or (c) the full complement of the nucleotide sequence of (a) or (b). Further, the suppression elements comprise (a) a polynucleotide with nucleotide sequence of SEQ ID NO: 3, 6, 9, 12, 15 or 18; (b) a polynucleotide encoding a polypeptide with amino acid sequence of SEQ ID NO: 4, 7, 10, 13, 16 or 19; or (c) the full complement of the nucleotide sequence of (a) or (b). The suppression elements comprise the nucleotide sequence of SEQ ID NO: 45, 46, 47, 48, 49, or 50.

The plant comprising a mutated PRP1, PP2C64, OPPL1, MFS9, LAO1 or DN-DSP1 gene, wherein the expression of the PRP1, PP2C64, OPPL1, MFS9, LAO1 or DN-DSP1 gene is decreased in the plant, or the activity of the PRP1, PP2C64, OPPL1, MFS9, LAO1 or DN-DSP1 polypeptide is decreased or eliminated in the plant when compared to a control plant, and wherein the plant is obtained by (i) introducing a DNA fragment, deleting a DNA fragment or replacing a DNA fragment, or (ii) introducing one or more nucleotide changes in the genomic region comprising the a sequence of SEQ ID NO: 3, 6, 9, 12, 15 or 18 or a sequence with identity of at least 90% to SEQ ID NO: 3, 6, 9, 12, 15 or 18 to reduce the expression or the activity of the endogenous OsPRP1, OsPP2C64, OsOPPL1, OsMFS9, OsLAO1 or OsDN-DSP1 polypeptide. The nucleotide sequence of mutant PRP1, PP2C64, OPPL1, MFS9, LAO1 or DN-DSP1 gene is at least 95% sequence identity to SEQ ID NO: 3, 6, 9, 12, 15 or 18. The plant is obtained by introducing nucleotide changes in the genomic region containing a sequence of SEQ ID NO: 12 by gRNA with sequence of SEQ ID NO:90 to reduce the activity of the endogenous OsMFS9 polypeptide.

The plant comprising a mutated PRP1, PP2C64, OPPL1, MFS9, LAO1 or DN-DSP1 regulatory elements, wherein the expression of the PRP1, PP2C64, OPPL1, MFS9, LAO1 or DN-DSP1 gene is decreased in the plant, when compared to a control plant, and wherein the plant is obtained by (i) introducing a DNA fragment, deleting a DNA fragment or replacing a DNA fragment, or (ii) introducing one or more nucleotide changes in the genomic region at the upstream of the endogenous PRP1, PP2C64, OPPL1, MFS9, LAO1 or DN-DSP1 gene to reduce the expression of the endogenous PRP1, PP2C64, OPPL1, MFS9, LAO1 or DN-DSP1 polypeptide. Further, the plant is obtained by (i) introducing a DNA fragment, deleting a DNA fragment or replacing a DNA fragment, or (ii) introducing one or more nucleotide changes in the genomic region comprising a sequence of SEQ ID NO: 102, 103, 104, 105, 106, 107 to reduce the expression of the endogenous OsPRP1, OsPP2C64, OsOPPL1, OsMFS9, OsLAO1 or OsDN-DSP1 polypeptide. The plant is obtained by introducing one nucleotide in the genomic region containing a sequence of SEQ ID NO: 102 by gRNA with sequence of SEQ ID NO: 79 to reduce the expression of the endogenous OsMFS9 polypeptide. The plant is obtained by deleting a DNA fragment in the genomic region containing a sequence of SEQ ID NO: 102 by gRNA with sequence of SEQ ID NO: 80 and 83, or by gRNA with sequence of SEQ ID NO: 76 and 83, or by gRNA with sequence of SEQ ID NO: 79 and 83 to reduce the expression of the endogenous OsMFS9 polypeptide.

The plant exhibits an increase in abiotic stress tolerance, and the abiotic stress is drought stress. In another embodiment, the present disclosure includes any of the plants of the disclosure, wherein the plant is selected from the group consisting of rice, maize, soybean, sunflower, sorghum, canola, wheat, alfalfa, cotton, barley, millet, sugar cane and switchgrass.

In another embodiment, methods of making a plant in which the expression or the activity of an endogenous PRP1, PP2C64, OPPL1, MFS9, LAO1 or DN-DSP1 polypeptide is decreased, when compared to the expression or the activity of wild-type PRP1, PP2C64, OPPL1, MFS9, LAO1 or DN-DSP1 polypeptide in a control plant are provided, and wherein the plant exhibits at least one phenotype selected from the group consisting of: increased drought tolerance, increased grain yield, increased abiotic stress tolerance, increased biomass and a combination of thereof compared to the control plant, wherein the method comprises a genetic modification performed by the steps of (a) introducing a suppression DNA construct comprising at least one heterologous regulatory sequence operably linked to suppression elements that reduces the expression of PRP1, PP2C64, OPPL1, MFS9, LAO1 or DN-DSP1 polypeptide; (b)(i) introducing a DNA fragment, deleting a DNA fragment or replacing a DNA fragment, or (ii) introducing one or more nucleotide changes in the genomic region comprising the endogenous PRP1, PP2C64, OPPL1, MFS9, LAO1 or DN-DSP1 gene and its regulatory elements, wherein these alterations are effective for decreasing the expression or the activity of the endogenous PRP1, PP2C64, OPPL1, MFS9, LAO1 or DN-DSP1 polypeptide.

Further, the method comprises introducing a suppression DNA construct comprising at least one heterologous regulatory element operably linked to suppression elements that reduces the expression of an endogenous PRP1, PP2C64, OPPL1, MFS9, LAO1 or DN-DSP1 polynucleotide, wherein the suppression elements comprise at least 100 contiguous base pairs of (a) a polynucleotide with nucleotide sequence of at least 85% sequence identity to SEQ ID NO: 3, 6, 9, 12, 15 or 18; (b) a polynucleotide encoding a polypeptide with an amino acid sequence of at least 90% sequence identity to SEQ ID NO: 4, 7, 10, 13, 16 or 19; or (c) the full complement of the nucleotide sequence of (a) or (b). The suppression elements comprise at least 100 contiguous base pairs of (a) a polynucleotide with nucleotide sequence of SEQ ID NO: 3, 6, 9, 12, 15 or 18; (b) a polynucleotide encoding a polypeptide with amino acid sequence of SEQ ID NO: 4, 7, 10, 13, 16 or 19; or (c) the full complement of the nucleotide sequence of (a) or (b). The suppression elements comprise sequence of SEQ ID NO: 45, SEQ ID NO: 46, SEQ ID NO: 47, SEQ ID NO: 48, SEQ ID NO: 49 or SEQ ID NO: 50.

The method comprises (i) introducing a DNA fragment, deleting a DNA fragment or replacing a DNA fragment, or (ii) introducing one or more nucleotide changes in the genomic region comprising the endogenous PRP1, PP2C64, OPPL1, MFS9, LAO1 or DN-DSP1 gene or its regulatory elements, wherein these alterations are effective for decreasing the expression or the activity of the endogenous PRP1, PP2C64, OPPL1, MFS9, LAO1 or DN-DSP1 polypeptide.

These alterations are introduced using zinc finger nuclease, Transcription Activator-Like Effector Nuclease (TALEN), CRISPR/Cas/Cpf1, guided Cas endonuclease, meganuclease, or CRISPR-Cas ribonucleoprotein complexes. Further, these alterations are introduced using CRISPR/Cas system.

In another embodiment, methods are provided for increasing drought tolerance in a plant, comprising: (a) introducing into a regenerable plant cell a construct to reduce the expression or the activity of endogenous PRP1, PP2C64, OPPL1, MFS9, LAO1 or DN-DSP1 polypeptide; (b) regenerating a modified plant from the regenerable plant cell after step (a); and (c) obtaining a progeny plant derived from the modified plant of step (b), wherein said progeny plant exhibits increased drought tolerance when compared to a control plant.

The said construct comprising at least one regulatory element operably linked to suppression elements, wherein the suppression elements comprise at least 100 contiguous base pairs of (a) a polynucleotide with nucleotide sequence of at least 85% sequence identity to SEQ ID NO: 3, 6, 9, 12, 15 or 18; (b) a polynucleotide encoding a polypeptide with amino acid sequence of at least 90% sequence identity to SEQ ID NO: 4, 7, 10, 13, 16 or 19; or (c) the full complement of the nucleotide sequence of (a) or (b). The suppression elements further comprise at least 100 contiguous base pairs of (a) a polynucleotide with nucleotide sequence of SEQ ID NO: 3, 6, 9, 12, 15 or 18; (b) a polynucleotide encoding a polypeptide with amino acid sequence of SEQ ID NO: 4, 7, 10, 13, 16 or 19; or (c) the full complement of the nucleotide sequence of (a) or (b). The said suppression elements further comprise the polynucleotide with nucleotide sequence of SEQ ID NO: 45, 46, 47, 48, 49, or 50.

The said construct comprising a polynucleotide encoding a Cas9 enzyme, a polynucleotide encoding nuclear localization signal and at least one heterologous regulatory sequence operably linked to gRNA, wherein the gRNA is targeted to a genomic region of a target comprising endogenous PRP1, PP2C64, OPPL1, MFS9, LAO1 or DN-DSP1 gene or its regulatory elements to reduce the expression or the activity of endogenous PRP1, PP2C64, OPPL1, MFS9, LAO1 or DN-DSP1 polypeptide. The gRNA is targeted to SEQ ID NO: 3, 6, 9, 12, 15, 18, 102, 103, 104, 105, 106 or 107 to reduce the expression or the activity of endogenous PRP1, PP2C64, OPPL1, MFS9, LAO1 or DN-DSP1polypeptide. Further, the gRNA comprises the nucleotide sequence of SEQ ID NO: 79 and 82, the targeted site is between Chr3:842668-842698 in rice genome, wherein the edit results in one nucleotide insertion in Chr3:842668-842698 in rice genome and resulted in reducing the expression of OsMFS9 gene.

In another embodiment, methods are provided for enhancing grain yield in a rice plant, when compared to a control plant, wherein the plant exhibits enhanced grain yield under stress conditions, the method comprising the step of decreasing the expression of the endogenous PRP1, PP2C64, OPPL1, MFS9, LAO1 or DN-DSP1 gene or a heterologous PRP1, PP2C64, OPPL1, MFS9, LAO1 or DN-DSP1 gene in the rice plant.

In another embodiment, method are provided for identifying one or more alleles associated with increased grain yield in a population of rice plants, the method comprising the steps of: (a) detecting in a population of rice plants one or more polymorphisms in (i) a genomic region encoding a polypeptide or (ii) a regulatory region controlling expression of the polypeptide, wherein the polypeptide comprises the amino acid sequence selected from the group consisting of SEQ ID NO: 4, 7, 10, 13, 16 or 19, or a sequence that is 90% identical to SEQ ID NO: 4, 7, 10, 13, 16 or 19, wherein the one or more polymorphisms in the genomic region encoding the polypeptide or in the regulatory region controlling expression of the polypeptide is associated with grain yield; and (b) identifying one or more alleles at the one or more polymorphisms that are associated with increased grain yield. Wherein the one or more alleles associated with increased grain yield is used for marker assisted selection of a rice plant with increased grain yield, the regulatory region is a promoter.

BRIEF DESCRIPTION OF THE DRAWINGS AND SEQUENCE LISTING

The disclosure can be more fully understood from the following detailed description and the accompanying drawings and Sequence Listing which form a part of this application.

Figure 6:
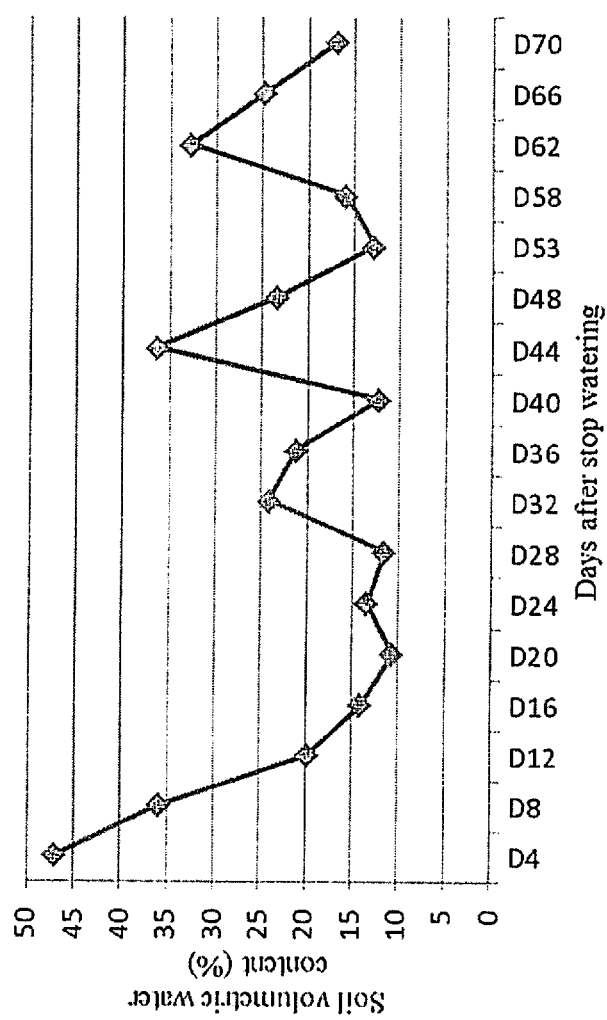

FIG. 6 shows changes of soil volumetric water content in Ningxia field for drought testing OsOPPL1 over-expressed transgenic rice. The OsOPPL1 over-expressed transgenic rice started heading 57 days after stopping watering and matured 88 days after stopping watering.

Figure 7:
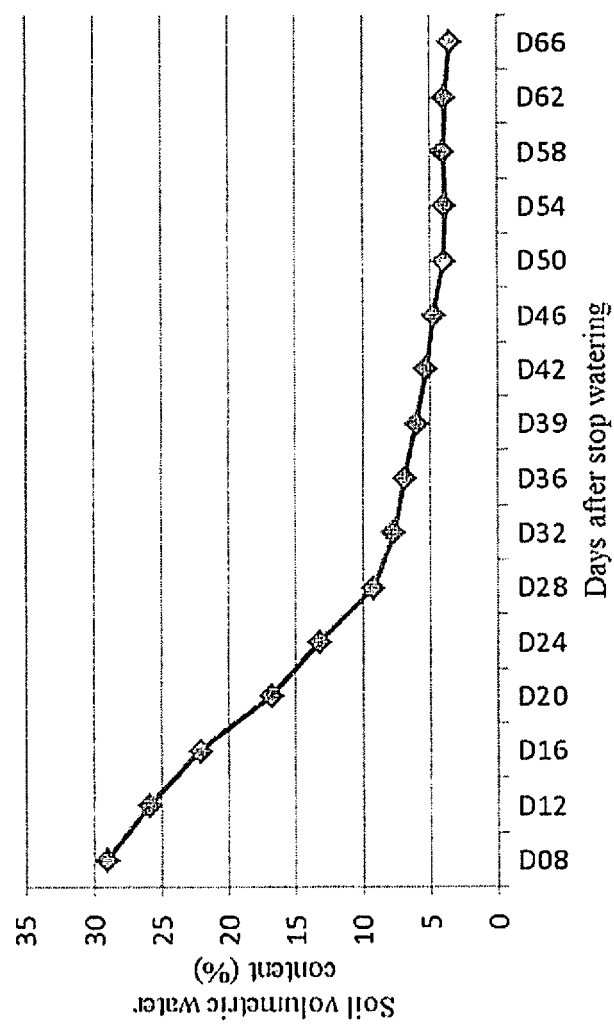

FIG. 7 shows changes of soil volumetric water content in Hainan field for drought testing OsMFS9 over-expressed transgenic rice. The OsMFS9 over-expressed transgenic rice started heading 40 days after stopping watering and matured 73 days after stopping watering.

Figure 8:
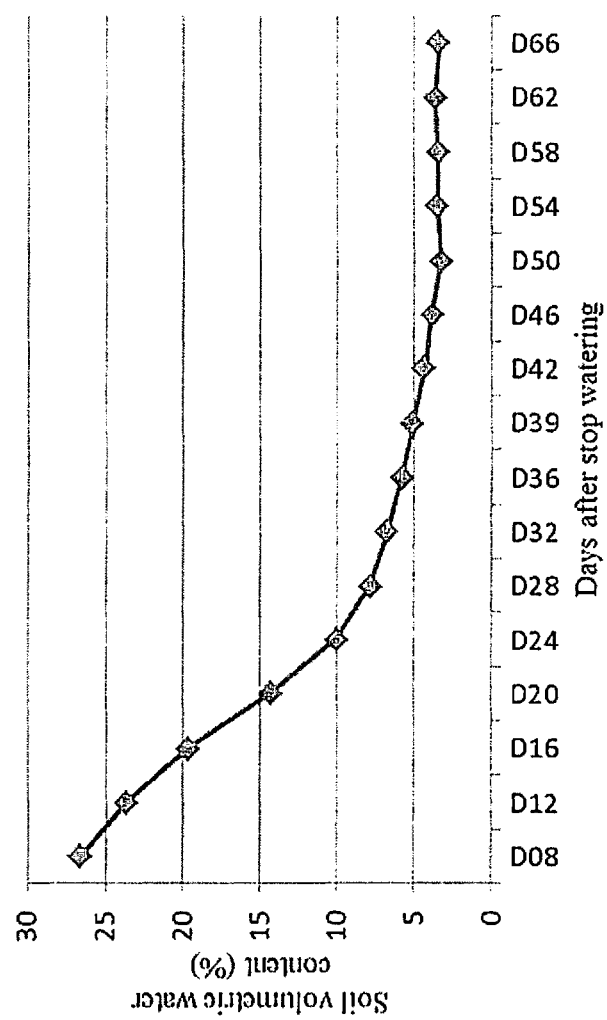

FIG. 8 shows changes of soil volumetric water content in Hainan field for drought testing OsLAO1 over-expressed transgenic rice in the second experiment. The OsLAO1 over-expressed transgenic rice started heading 40 days after stopping watering and matured 73 days after stopping watering.

Figure 9:
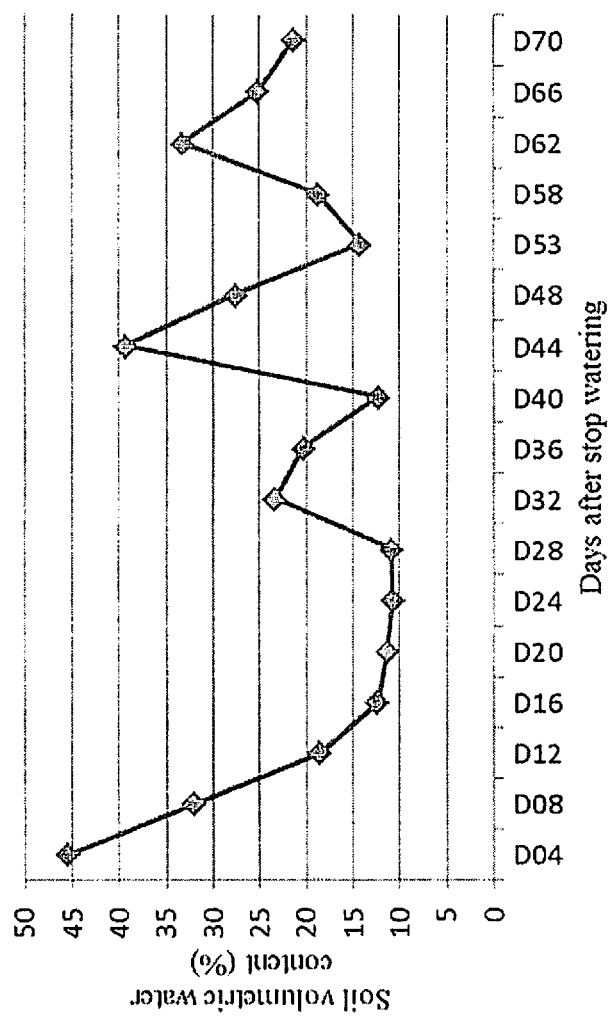

FIG. 9 shows changes of soil volumetric water content in Ningxia field for drought testing OsOPPL1 and OsDN-DSP1 over-expressed transgenic rice. The OsOPPL1 and OsDN-DSP1 transgenic rice started heading 46 days after stopping watering and matured 86 days after stopping watering.

Figure 10:
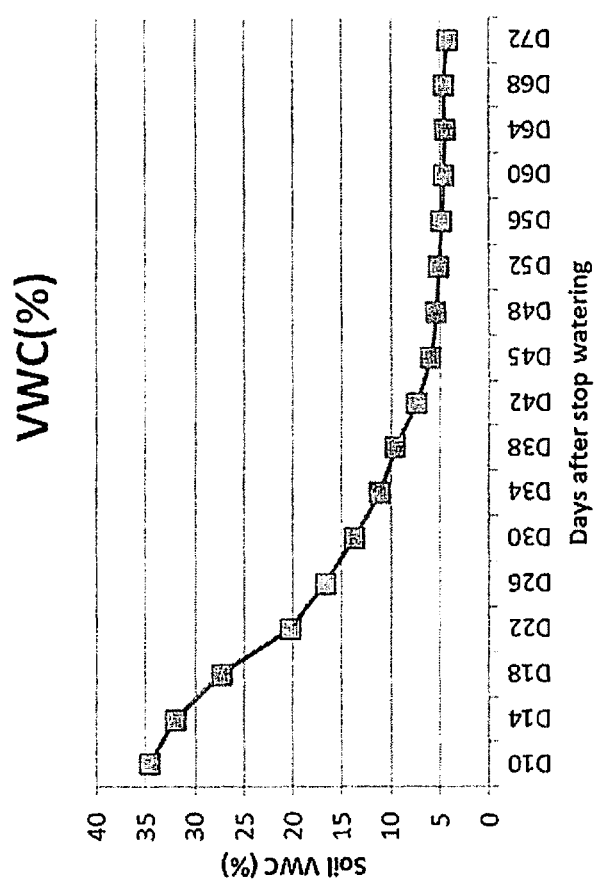

FIG. 10 shows changes of soil volumetric water content in Hainan field for drought testing OsDN-DSP1 over-expressed transgenic rice. The OsDN-DSP1 over-expressed transgenic rice started heading 36 days after stopping watering and matured 86 days after stopping watering.

Figure 11:
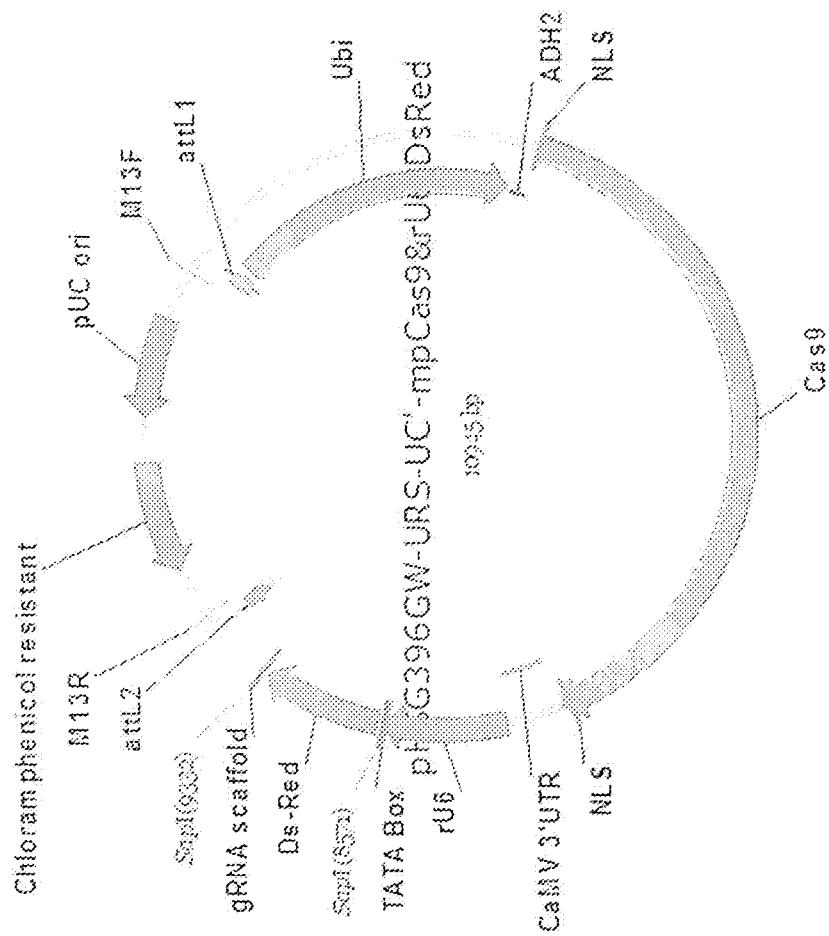

FIG. 11 shows the structure of construct for CRISPR/Cas system.

Figure 12:
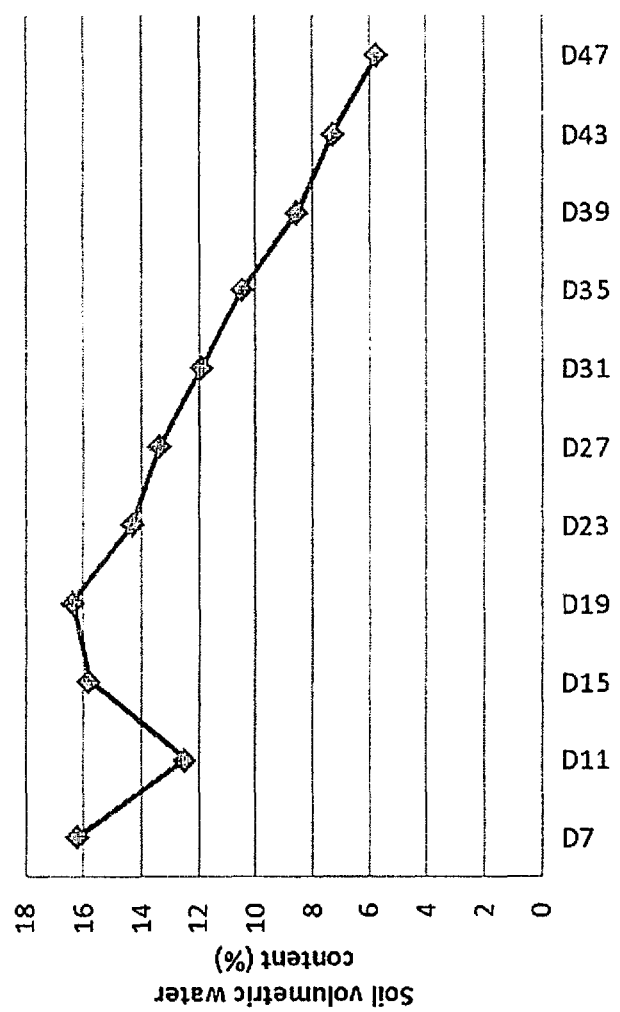

FIG. 12 shows changes of soil volumetric water content in Hainan field for drought testing RNAi construct transgenic rice. The suppressed transgenic rice started heading 29 days after stopping watering and matured 80 days after stopping watering.

Figure 13:
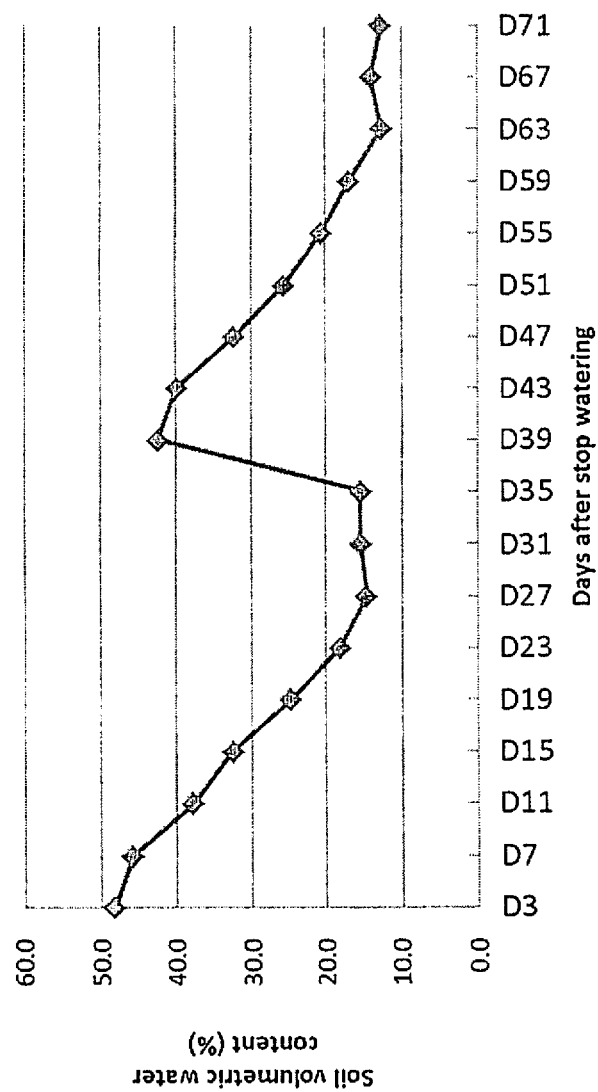

FIG. 13 shows changes of soil volumetric water content for drought testing OsMFS9 suppressed transgenic rice in the first experiment. The OsMFS9 suppressed transgenic rice started heading 31 days after stopping watering and matured 64 days after stopping watering. The field is re-watered at Day 27 to avoid total loss of seed.

Figure 14:
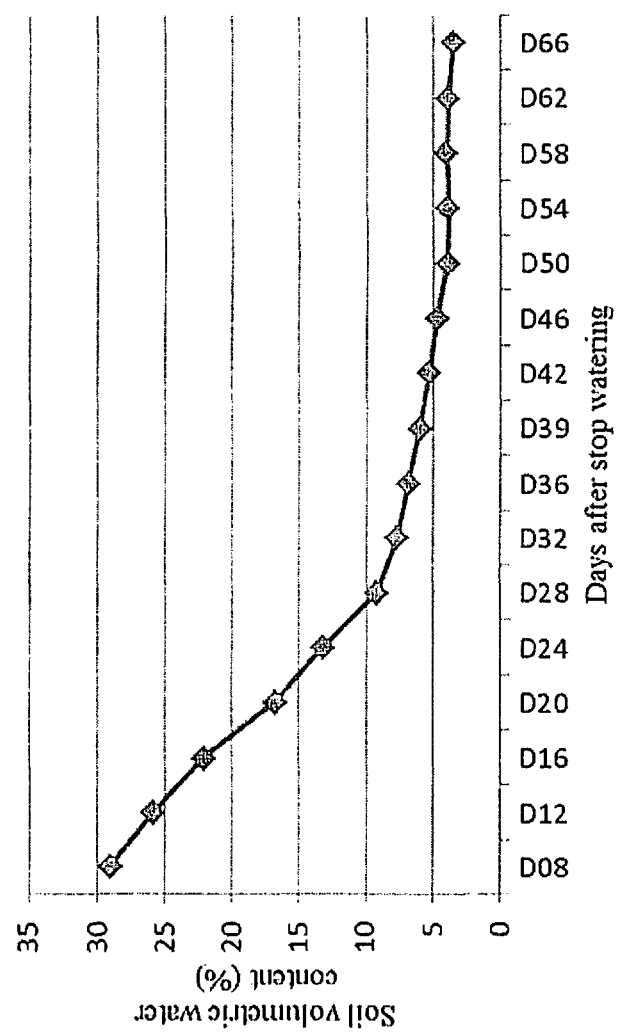

FIG. 14 shows changes of soil volumetric water content for drought testing OsMFS9 suppressed transgenic rice in the second experiment. The OsMFS9 suppressed transgenic rice started heading 25 days after stopping watering and matured 83 days after stopping watering.

Figure 15:
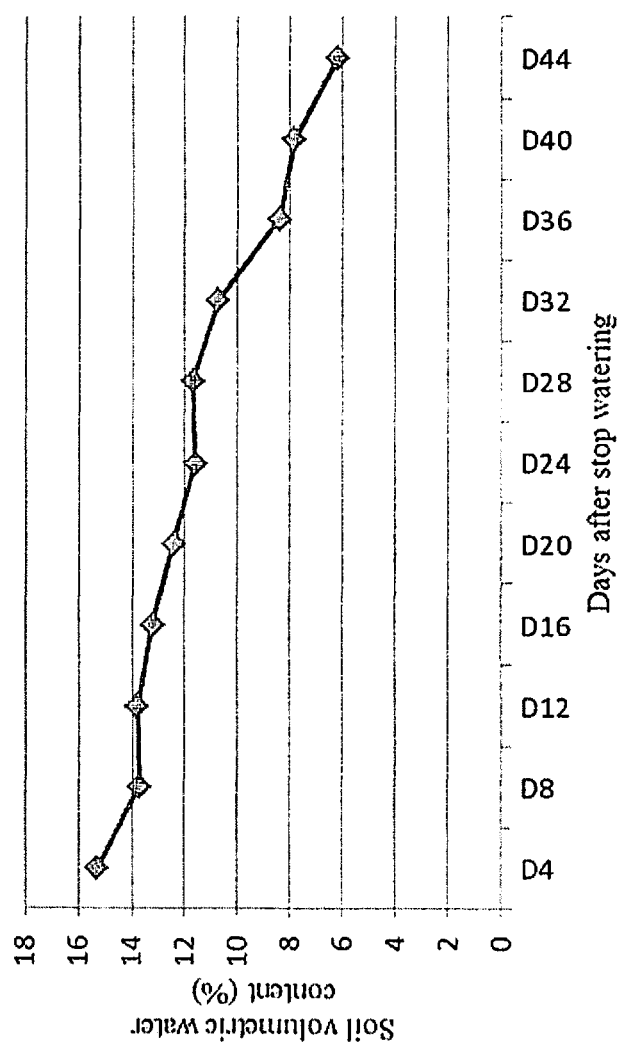

FIG. 15 shows changes of soil volumetric water content in Hainan field for drought testing DP2421 rice. The DP2421 rice started heading 22 days after stopping watering and matured 76 days after stopping watering.

Figure 16:
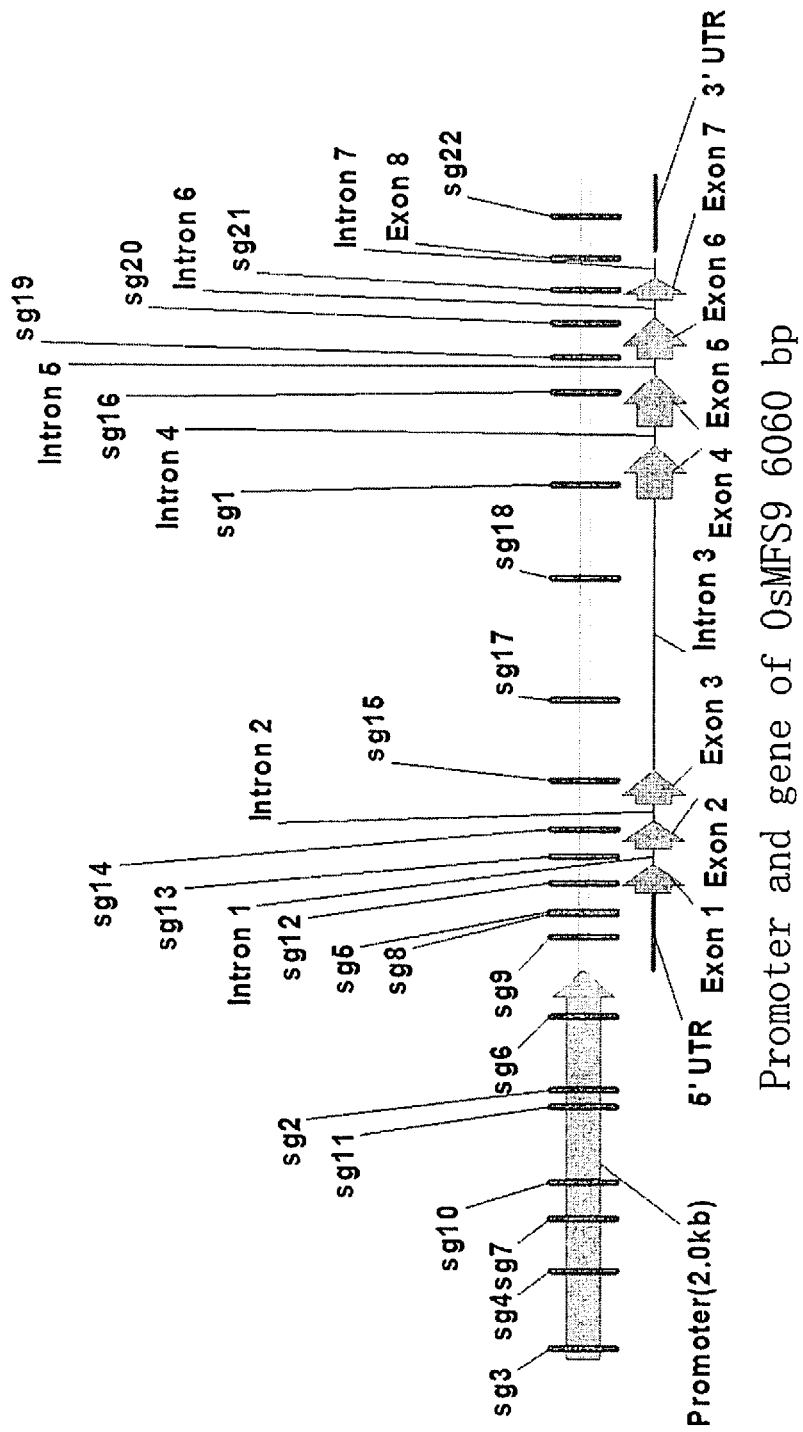

FIG. 16 shows the schematic of sgRNA distribution in the genome of rice OsMFS9 gene.

Figure 17:
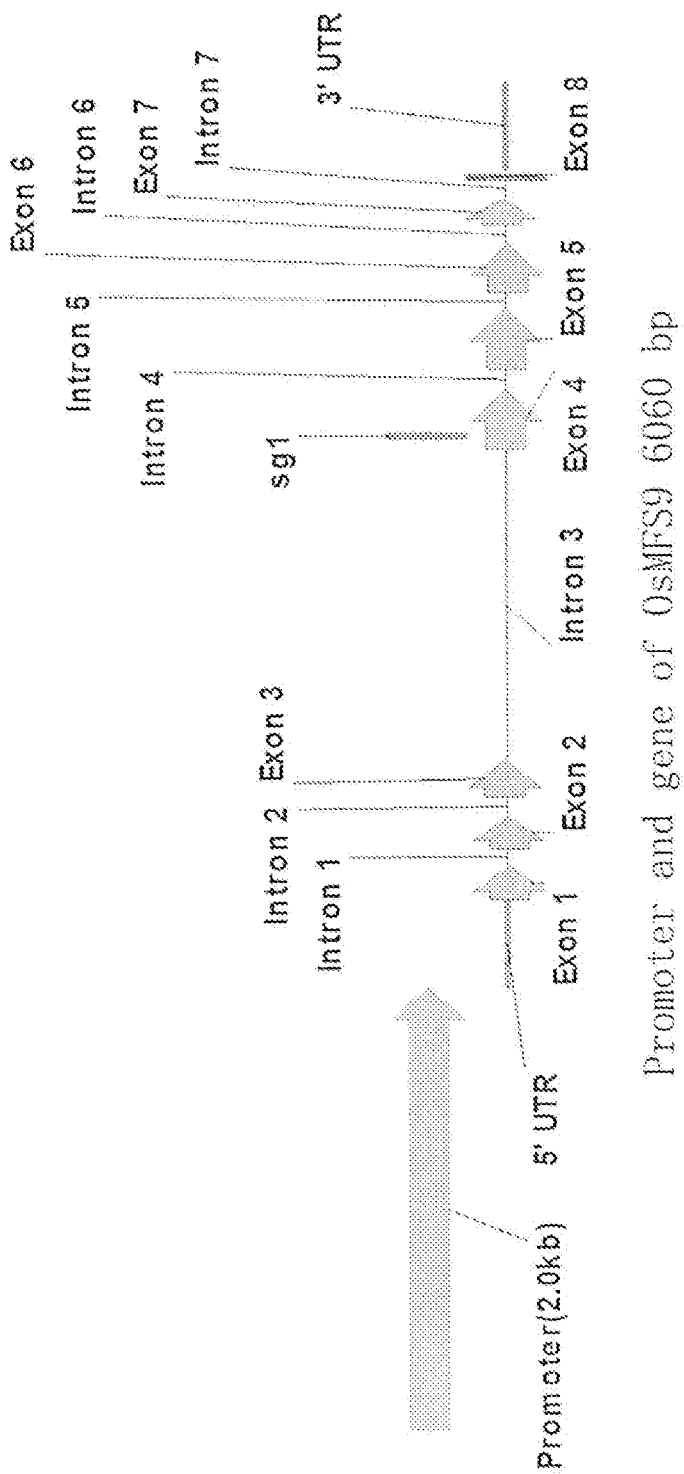

FIG. 17 shows an example of single sgRNA distribution in the genome of rice OsMFS9 gene.

Figure 18:
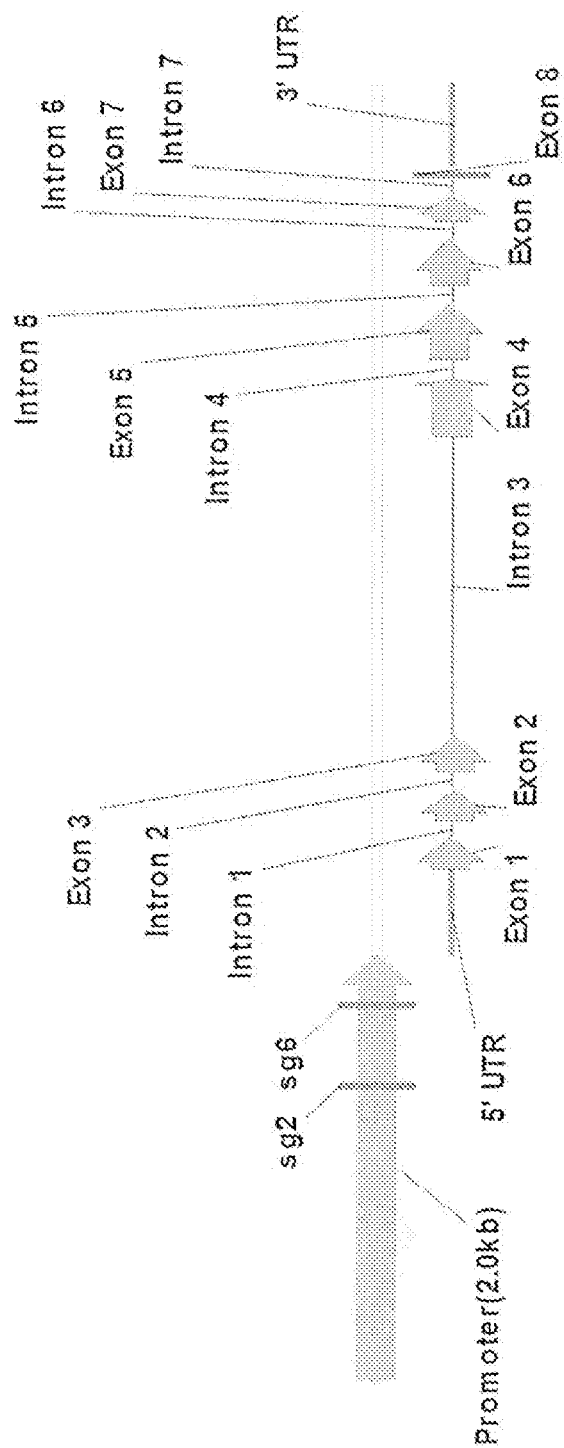

FIG. 18 shows an example of two sgRNAs distribution in the genome of rice OsMFS9 gene.

FIG. 19 shows an alignment of mutation induced by CRISPR-Cas construct DP2389 in rice plant. The mutations were identified by PCR and sequencing. The reference sequence represents the unmodified locus with each target site underlined. The PAM sequence and expected site of cleavage are also indicated. Deletion, insertion or replacement is shown by a "-", an italicized underlined nucleotide or bolded italicized nucleotide, respectively. The reference and mutations 1-7 of target site correspond to SEQ ID NO: 108-115, respectively.

FIG. 20 shows an alignment of mutation induced by CRISPR-Cas construct DP2421. The mutations were identified by PCR and sequencing. The reference sequence represents the unmodified locus with each target site underlined. The PAM sequence and expected site of cleavage are also indicated. Deletion, insertion or replacement is shown by a "-", an italicized underlined nucleotide or bolded italicized nucleotide, respectively. The reference and mutations 1-15 of target site correspond to SEQ ID NO: 117-118, respectively.

Figure 21:
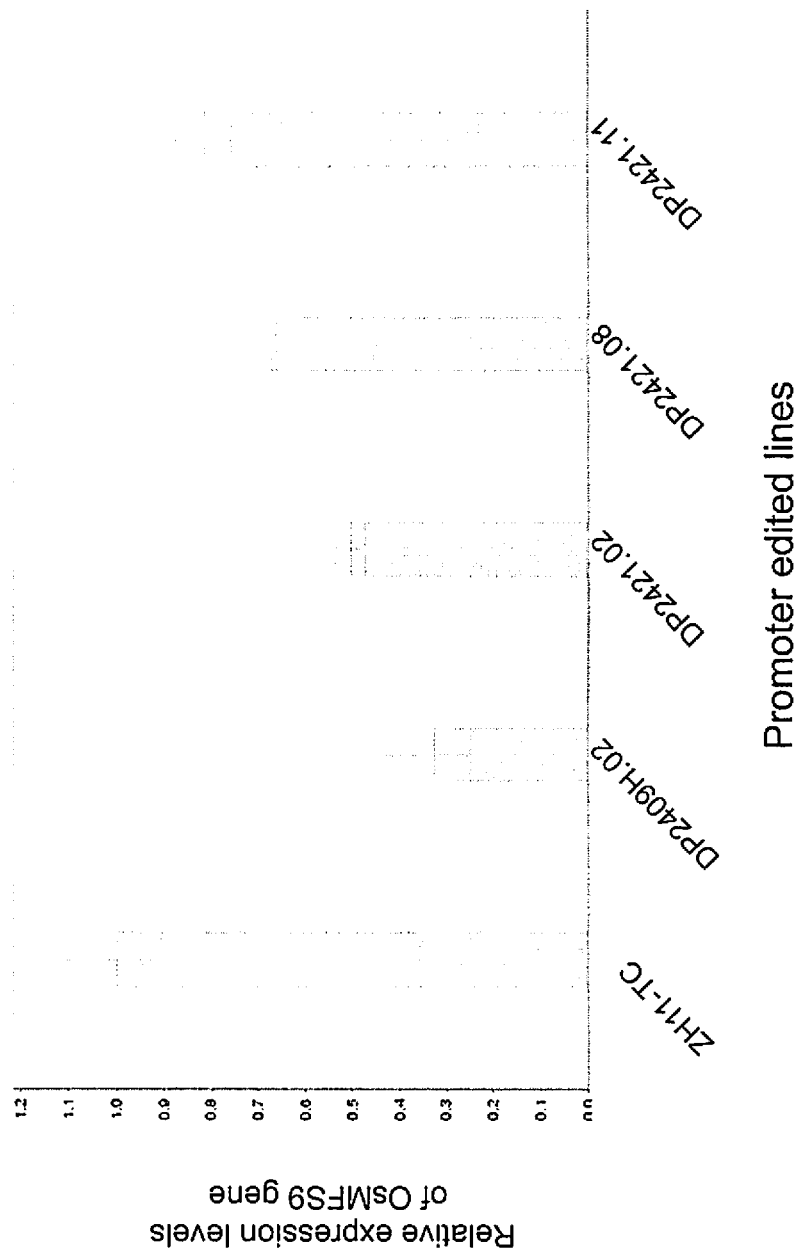

FIG. 21 shows the relative expression levels of OsMFS9 gene in leaves of different genome edited rice lines by real-time PCR analyses. The base expression level in ZH11-TC is set at 1.00, the numbers on the top of the columns are fold-changes compared to ZH11-TC rice. ZH11-TC is tissue cultured Zhonghua 11.

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Artificial | DP0158 construct | 1 | n/a |
| Oryza sativa | OsPRP1 | 2, 3 | 4 |
| Oryza sativa | OsPP2C64 | 5, 6 | 7 |
| Oryza sativa | OsOPPL1 | 8, 9 | 10 |
| Oryza sativa | OsMFS9 | 11, 12 | 13 |
| Oryza sativa | OsLAO1 | 14, 15 | 16 |
| Oryza sativa | OsDN-DSP1 | 17, 18 | 19 |
| Lycopersicon esculintum | intron | 44 | n/a |
| Oryza sativa | Sense strand OsPRP1 fragment for constructing RNAi vector | 45 | n/a |
| Oryza sativa | Sense strand OsPP2C64 fragment for constructing RNAi vector | 46 | n/a |
| Oryza sativa | Sense strand OsOPPL1 fragment for constructing RNAi vector | 47 | n/a |
| Oryza sativa | Sense strand OsMFS9 fragment for constructing RNAi vector | 48 | n/a |
| Oryza sativa | Sense strand OsLAO1 fragment for constructing RNAi vector | 49 | n/a |
| Oryza sativa | Sense strand OsDN-DSP1 fragment for constructing RNAi vector | 50 | n/a |
| Artificial | Primers | 20-31, 51-74 | n/a |
| Artificial | gRNA | 75-96 | n/a |
| Zea May | Ubiqutin Promoter | 97 | n/a |
| Artificial | Nucleus localization sequence | 98 | n/a |
| Cauliflower mosaic virus | CaMV 3'UTR | 99 | n/a |
| Oryza sativa | rU6-Promoter | 100 | n/a |
| Artificial | gRNA scaffold | 101 | n/a |
| Oryza sativa | OsMFS9 promoter | 102-107 | n/a |
| Oryza sativa | Mutation sequence | 108-118 | n/a |

The Sequence Listing contains the one-letter code for nucleotide sequences and the three-letter code for amino acid sequences as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsPRP1 (proline-rich protein 1)" refers to a rice polypeptide that confers drought sensitive phenotype when over-expressing it and is encoded by the rice gene locus LOC_Os01g57004.1. "PRP1 polypeptide" refers herein to the OsPRP1 polypeptide and its homologs from other organisms.

The OsPRP1 polypeptide (SEQ ID NO: 4) is encoded by the coding sequence (CDS) (SEQ ID NO: 3) or nucleotide sequence (SEQ ID NO: 2) at rice gene locus LOC_Os01g57004.1. This polypeptide is annotated as "adhesive/proline-rich protein, putative, expressed" in TIGR (the internet at plant biology msu.edu/index.shtml), however does not have any prior assigned function.

The term "OsPP2C64 (protein phosphatase 2C 64)" refers to a rice polypeptide that confers drought sensitive phenotype when over-expressing it and is encoded by the rice gene locus LOC_Os07g37890.1. "PP2C64 polypeptide" refers herein to the OsPP2C64 polypeptide and its homologs from other organisms.

The OsPP2C64 polypeptide (SEQ ID NO: 7) is encoded by the coding sequence (CDS) (SEQ ID NO: 6) or nucleotide sequence (SEQ ID NO: 5) at rice gene locus LOC_Os07g37890.1. This polypeptide is annotated as "protein phosphatase 2C, putative, expressed" in TIGR and "probable protein phosphatase 2C 64" in NCBI, however does not have any prior assigned function.

The term "OsOPPL1 (oxidation protection protein-like 1)" is a rice polypeptide and refers to a rice polypeptide that confers drought sensitive phenotype when over-expressing it and is encoded by the rice gene locus LOC_Os02g51770.1. "OPPL1 polypeptide" refers herein to the OsOPPL1 polypeptide and its homologs from other organisms.

The OsOPPL1 polypeptide (SEQ ID NO: 10) is encoded by the coding sequence (CDS) (SEQ ID NO: 9) or nucleotide sequence (SEQ ID NO: 8) at rice gene locus LOC_Os02g51770.1. This polypeptide is annotated as "TLD family protein, putative, expressed" in TIGR and annotated as "oxidation protection protein-like" in NCBI.

The term "OsMFS9 (major facilitator superfamily 9)" refers to a rice polypeptide that confers drought sensitive phenotype when over-expressing it and is encoded by the rice gene locus LOC_Os03g02380.1. "MFS9 polypeptide" refers herein to the OsMFS9 polypeptide and its homologs from other organisms.

The OsMFS9 polypeptide (SEQ ID NO: 13) is encoded by the coding sequence (CDS) (SEQ ID NO: 12) or nucleotide sequence (SEQ ID NO: 11) at rice gene locus LOC_Os03g02380.1. This polypeptide is annotated as "Major facilitator superfamily domain-containing protein 5, putative, expressed" in TIGR and "Molybdate-anion transporter" in NCBI, however does not have any prior assigned function.

The term "OsLAO1 (L-ascorbate oxidase 1)" refers to a rice polypeptide that confers drought sensitive phenotype when over-expressing it and is encoded by the rice gene locus LOC_Os07g02810.1. "LAO1 polypeptide" refers herein to the OsLAO1 polypeptide and its homologs from other organisms.

The OsLAO1 polypeptide (SEQ ID NO: 16) is encoded by the coding sequence (CDS) (SEQ ID NO: 15) or nucleotide sequence (SEQ ID NO: 14) at rice gene locus LOC_Os07g02810.1. This polypeptide is annotated as "ascorbate oxidase homolog precursor, putative, expressed" in TIGR and is annotated as "L-ascorbate oxidase homolog" in NCBI.

The term "OsDN-DSP1 (drought sensitive protein 1)" refers to a rice polypeptide that confers drought sensitive phenotype when over-expressing it and is encoded by the rice gene locus LOC_Os02g57210.1. "DN-DSP1 polypeptide" refers herein to the OsDN-DSP1 polypeptide and its homologs from other organisms.

The OsDN-DSP1 polypeptide (SEQ ID NO: 19) is encoded by the coding sequence (CDS) (SEQ ID NO: 18) or nucleotide sequence (SEQ ID NO: 17) at rice gene locus LOC_Os02g57210.1. This polypeptide is annotated as "expressed protein" in TIGR and is annotated as "uncharacterized protein" in NCBI.

The terms "monocot" and "monocotyledonous plant" are used interchangeably herein. A monocot of the current disclosure includes plants of the Gramineae family.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

The term "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

Increased biomass can be measured, for example, as an increase in plant height, plant total leaf area, plant fresh weight, plant dry weight or plant seed yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products. Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits, such as in the forms of greater yield or improved screening.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell in which genetic alteration, such as transformation, has been affected as to a gene of interest. A subject plant or plant cell may be descended from a plant or cell so altered and will comprise the alteration.

"Genome" as it applies to plant cells encompasses not only chromosomal DNA found within the nucleus, but also organelle DNA found within subcellular components (e.g., mitochondria, plastid) of the cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct. A T0 plant is directly recovered from the transformation and regeneration process. Progeny of T0 plants are referred to as T1 (first progeny generation), T2 (second progeny generation), etc. The modified gene or promoter may be insertion or deletion of a single or several or a fragment of deoxy nucleotide in the plant genome.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Messenger RNA (mRNA)" refers to the RNA which has no intron and can be translated into protein by the cell.

"cDNA" refers to a DNA that is complementary to and synthesized from an mRNA template using reverse transcriptase. The cDNA can be single-stranded or converted into the double-stranded form using the Klenow fragment of DNA polymerase I.

"Mature" protein refers to a post-translationally processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogenous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and influencing the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Suppression element" and "repression element" are used interchangeably herein, and refer a fragment of about 21 bp to about 1500 bp or more that selectively binds the mRNA sequence expressed from the endogenous locus and thereby down regulates the expression.

"gRNA" is guide RNA, refers a RNA fragment about 20 bp which is complementary with mRNA and guide the insertion or deletion of nucleotide.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel. (1992) *Plant Phys.* 100:1627-1632). A "mitochondrial signal peptide" is an amino acid sequence which directs a precursor protein into the mitochondria (Zhang and Glaser. (2002) *Trends Plant Sci* 7:14-21).

Methods to determine the relationship of various polynucleotide and polypeptide sequences are known. As used herein, "reference sequence" is a defined sequence used as a basis for sequence comparison. A reference sequence may be a subset or the entirety of a specified sequence, such as a segment of a full-length cDNA or gene sequence, or may be the complete cDNA or gene sequence. As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100 or longer. Those of skill in the art understand that to avoid a high similarity to a reference sequence due to inclusion of gaps in the sequence, a gap penalty is typically introduced and is subtracted from the number of matches.

Alignments using the programs can be performed using the default parameters. The CLUSTAL program is well described by Higgins, et al. (1988) *Gene* 73:237-244; Higgins, et al. (1989) *CABIOS* 5:151-153; Corpet, et al. (1988) *Nucleic Acids Res.* 16:10881-10890; Huang, et al. (1992) *CABIOS* 8:155-165 and Pearson, et al. (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al. (1990) *J. Mol. Biol.* 215:403 are based on the algorithm of Karlin and Altschul. (1990) supra. BLAST nucleotide searches can be performed with the BLASTN program, score=100, wordlength=12, to obtain nucleotide sequences homologous to a nucleotide sequence encoding a protein of the disclosures. BLAST protein searches can be performed with the BLASTX program, score=50, wordlength=3, to obtain amino acid sequences homologous to a protein or polypeptide of the disclosures. To obtain gapped alignments for comparison purposes, Gapped BLAST (in BLAST 2.0) can be utilized as described in Altschul, et al. (1997) *Nucleic Acids Res.* 25:3389. Alternatively, PSI-BLAST (in BLAST 2.0) can be used to perform an iterated search that detects distant relationships between molecules (Altschul, et al. (1997) supra). When utilizing BLAST, Gapped BLAST, PSI-BLAST and the default parameters of the respective programs (e.g., BLASTN for nucleotide sequences, BLASTX for proteins) can be used (the National Center for Biotechnology Information of the National Library of Medicine of the National Institutes of Health of the U.S. government). Alignment may also be performed by manual inspection.

Paired sequence identity/similarity values can be obtained using GAP Version 10 with the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch. (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

Unless stated otherwise, multiple alignments of the sequences provided herein are performed using the Clustal V method of alignment (Higgins and Sharp. (1989) *CABIOS.* 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Embodiments include isolated polynucleotides and polypeptides, and suppression DNA constructs and CRISPR/Cas9 constructs useful for conferring drought tolerance; compositions (such as plants or seeds) comprising these suppression DNA constructs and CRISPR/Cas9 constructs; and methods utilizing these constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. Over-expression of the encoded polypeptide decreases plant drought tolerance, and suppression of the encoded polypeptide enhances the drought tolerance activity.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15 or 18; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 2, 5, 8, 11, 14 or 17; or (iii) a full complement of the nucleic acid sequence of (i) or (ii). Any of the foregoing isolated polynucleotides may be utilized in any recombinant DNA constructs of the present disclosure. The isolated polynucleotide preferably encodes a PRP1, PP2C64, OPPL1, MFS9, LAO1 or DN-DSP1 polypeptide. Over-expression of the polypeptide decreases plant drought tolerance, and suppression of the polypeptide improves drought tolerance activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19. The polypeptide is preferably a PRP1, PP2C64, OPPL1, MFS9, LAO1 or DN-DSP1 polypeptide. Over-expression of the polypeptide decreases plant drought tolerance, and suppressed expression of the polypeptide increases plant drought tolerance activity.

Recombinant DNA Constructs, Suppression DNA Constructs and CRISPR/Cas Constructs:

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15 or 18; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 2, 5, 8, 11, 14 or 17; or (iii) a full complement of the nucleic acid sequence of (i) or (ii).

In another embodiment, a recombinant DNA construct comprises a polynucleotide operably linked to at least one regulatory sequence (e.g., a promoter functional in a plant), wherein said polynucleotide encodes a PRP1, PP2C64, OPPL1, MFS9, LAO1 or DN-DSP1 polypeptide. The polypeptide preferably has drought sensitive activity. The polypeptide may be from, for example, *Oryza sativa, Arabidopsis thaliana, Zea mays, Glycine max, Glycine tabacina, Glycine soja* or *Glycine tomentella*.

In another aspect, the present disclosure includes suppression DNA constructs.

A suppression DNA construct may comprise at least one regulatory sequence (e.g., a promoter functional in a plant) operably linked suppression element, wherein the suppression elements comprise at least 100 contiguous base pairs of to (a) all or part of: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19; or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to said all or part of a sense strand or antisense strand from which said region is derived, and wherein said target gene of interest encodes a drought sensitive polypeptide; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15 or 18; or (ii) a full complement of the nucleic acid sequence of (c)(i). The suppression DNA construct may comprise an antisense construct, viral-suppression construct, hairpin suppression construct, stem-loop suppression construct, double-stranded RNA-producing construct, RNAi construct, or small RNA construct (e.g., a siRNA construct or a miRNA construct).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive of, and not limited to, anti-sense, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 81%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (for example, U.S. Pat. No. 5,107,065). The complementarity of an antisense RNA may be with respect to any part of the specific gene transcript, i.e., at the 5' non-coding sequence, 3' non-coding sequence, introns, or the coding sequence.

RNA interference (RNAi) refers to the process of sequence-specific post-transcriptional gene silencing (PTGS) in animals mediated by short interfering RNAs (siRNAs) (Fire et al. (1998) Nature 391:806). The corresponding process in plants is commonly referred to as PTGS or RNA silencing and is also referred to as quelling in fungi. The process of PTGS is thought to be an evolutionarily-conserved cellular defense mechanism used to prevent the expression of foreign genes and is commonly shared by diverse flora and phyla (Fire et al. (1999) Trends Genet. 15:358).

Small RNAs play an important role in controlling gene expression, for example, small RNAs regulate many developmental processes which include flowering. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to 24 nucleotides (nt) in length that have been identified in both animals and plants (Lagos-Quintana et al. (2001) Science 294:853-858, Lagos-Quintana et al. (2002) Curr. Biol. 12:735-739; Lau et al. (2001) Science 294:858-862; Lee and Ambros. (2001) Science 294:862-864; Llave et al. (2002) Plant Cell 14:1605-1619; Mourelatos et al. (2002) Genes Dev. 16:720-728; Park et al. (2002) Curr. Biol. 12:1484-1495; Reinhart et al. (2002) Genes Dev. 16: 1616-1626). They are processed from longer precursor transcripts that range in size from approximately 70 to 200 nt, and these precursor transcripts have the ability to form stable hairpin structures.

miRNAs appear to regulate target genes by binding to complementary sequences located in the transcripts produced by these genes. It seems likely that miRNAs can enter at least two pathways of target gene regulation: (1) translational inhibition; and (2) RNA cleavage. miRNAs entering the RNA cleavage pathway are analogous to the 21-25 nt siRNAs generated during RNAi in animals and PTGS in plants, and likely are incorporated into an RNA-induced silencing complex (RISC) that is similar or identical to that seen for RNAi.

In another aspect, the present disclosure includes genome editing construct which including a CRISPR/Cas construct A CRISPR/Cas construct comprises a polynucleotide encoding a Cas enzyme, a polynucleotide encoding nuclear localization signal and at least one heterologous regulatory sequence operably linked to gRNA, wherein the gRNA is targeted to the genomic region containing endogenous PRP1, PP2C64, OPPL1, MFS9, LAO1 or DN-DSP1 gene and its regulatory elements to reduce the expression or activity of endogenous PRP1, PP2C64, OPPL1, MFS9, LAO1 or DN-DSP1 polypeptide. The gRNA is targeted to the genomic region containing the polynucleotide with nucleotide sequence of SEQ ID NO: 3, 6, 9, 12, 15, 18, 102, 103, 104, 105, 106 or 107.

A regulatory element driving the endogenous gene expression or the coding sequence itself, for example, may be edited or inserted into a plant by genome editing using a CRISPR/Cas9 system.

Genome-editing techniques such as designer zinc fingers, transcription activator-like effectors (TALEs), or homing meganucleases are available for producing targeted genome perturbations.

In general, "CRISPR system" refers collectively to transcripts and other elements involved in the expression of or directing the activity of CRISPR-associated ("Cas") genes, including sequences encoding a Cas gene, a tracr (tracr-activating CRISPR) sequence, a tracr-mate sequence, a guide sequence or other sequence and transcripts from a CRISPR locus.

CRISPR loci (Clustered Regularly Interspaced Short Palindromic Repeats) (also known as SPIDRs-SPacer Interspersed Direct Repeats, SRSR-Short Regularly Spaced Repeats, or LCTR-Large Cluster of 20-nt Tandem Repeat sequences) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas gene relates to a gene that is generally coupled, associated or close to or in the vicinity of flanking CRISPR loci. The terms "Cas gene" and "CRISPR-associated (Cas) gene" are used interchangeably herein (Haft et al. (2005), PLoS Comput Biol 474-483). As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. 2015/0082478). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence. The Cas endonuclease can be introduced directly into a cell by any method known in the art, for example, but not limited to transient introduction methods, transfection and/or topical application.

As used herein, the term "guide RNA" (gRNA) relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. 2015/0082478). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

DNA nucleases and other mutation enzyme domains may be fused with DNA binding domains to produce the double strand break (DSBs) in the target DNA. DNA binding domains include, for example, an array specific DNA binding domain or a site-specific DNA binding domain. Site specific DNA binding domains include but are not limited to a TAL (Transcription Activator-Like Effector) or a zinc finger binding domain.

Examples of DNA-binding domains fused to DNA nucleases include but are not limited to TALEN and multiple TALENs. Transcription Activator-Like Effector Nucleases (TALENs) are artificial restriction enzymes generated by fusing the TAL effector DNA binding domain to a DNA enzyme domain. TAL proteins are produced by bacteria and include a highly conserved 33-34 amino acid DNA binding domain sequence (PCT publication No. WO2014127287; US Patent Publication No. US20140087426).

The original TALEN chimera were prepared using the wild-type Fok1 endonuclease domain. However, TALEN may also include chimera made from Fok1 endonuclease domain variants with mutations designed to improve cleavage specificity and cleavage activity. In some instances multiple TALENs can be expressed to target multiple genomic regions.

A zinc finger is another type of DNA binding domain that can be used for introducing mutations into the target DNA.

Zinc finger nucleases and transcription activator-like effector nucleases are artificial fusion proteins comprising an engineered DNA-binding domain fused to the nonspecific nuclease domain of the rescription enzyme Fok1 (Radek Jankele and Petr Svoboda, (2014) *Brief Funct Genomics* 13:409-419; N J Palpant and D Dudzinski, (2013) *Gene Therapy* 20:121-127). Various protein engineering techniques can be used to alter the DNA-binding specificity of zinc fingers and tandem repeats of such engineered zinc fingers can be used to target desired genomic DNA sequences. Fusing a second protein domain such as a transcriptional repressor to a zinc finger that can bind near the promoter of the YEP gene can change the expression levels of PRP1, PP2C64, OPPL1, MFS9, LAO1 or DN-DSP1 gene.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Regulatory Elements:

A recombinant DNA construct (including a suppression DNA construct) of the present disclosure may comprise at least one regulatory element.

A regulatory element may be a promoter.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) *Plant J.* 12(2):255-265; Kwon et al. (1994) *Plant Physiol.* 105:357-367; Yamamoto et al. (1994) *Plant Cell Physiol.* 35(5):773-778; Gotor et al. (1993) *Plant J.* 3:509-518; Orozco et al. (1993) *Plant Mol. Biol.* 23(6): 1129-1138; and Matsuoka et al. (1993) *Proc. Natl. Acad. Sci. USA* 90(20):9586-9590).

Promoters which are seed or embryo-specific and may be useful in the disclosure include soybean Kunitz trypsin inhibitor (Kti3, Jofuku and Goldberg. (1989) *Plant Cell* 1:1079-1093), convicilin, vicilin, and legumin (pea cotyledons) (Rerie, W. G., et al. (1991) *Mol. Gen. Genet.* 259: 149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7:L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in certain embodiments include the following: 1) the stress-inducible promoter RD29A (Kasuga et al. (1999) *Nature Biotechnol.* 17:287-291); 2) the stress-inducible promoter Rab17 (Vilardell et al. (1991) *Plant Mol. Bio.* 17:985-993; Kamp Busk et al. (1997) *Plant J* 11(6): 1285-1295); 3) the barley promoter B22E whose expression is specific to the pedicel in developing maize kernels ("Primary Structure of a Novel Barley Gene Differentially Expressed in Immature Aleurone Layers". Klemsdal, S. S. et al. (1991) *Mol. Gen. Genet.* 228(½):9-16); and 4) maize promoter Zag2 ("Identification and molecular characterization of ZAG1, the maize homolog of the *Arabidopsis* floral homeotic gene AGAMOUS", Schmidt, R. J. et al. (1993) *Plant Cell* 5(7):729-737; "Structural characterization, chromosomal localization and phylogenetic evaluation of two pairs of AGAMOUS-like MADS-box genes from maize", Theissen et al. (1995) *Gene* 156(2):155-166; NCBI GenBank Accession No. X80206)). Zag2 transcripts can be detected 5 days prior to pollination to 7 to 8 days after pollination ("DAP"), and directs expression in the carpel of developing female inflorescences and CimI which is specific to the nucleus of developing maize kernels. CimI transcript is detected 4 to 5 days before pollination to 6 to 8 DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, CimI that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664).

Recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message RNA that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

Any plant can be selected for the identification of regulatory sequences and polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, vine, watermelon, wheat, yams, and zucchini.

Compositions:

A composition of the present disclosure is a plant comprising in its genome any of the recombinant DNA constructs (including any of the suppression DNA constructs) of the present disclosure (such as any of the constructs discussed above), or a plant comprising a modified PRP1, PP2C64, OPPL1, MFS9, LAO1 or DN-DSP1 gene, or a plant in which PRP1, PP2C64, OPPL1, MFS9, LAO1 or DN-DSP1 gene's regulatory element is modified. Compositions also include any progeny of the plant, and any seed obtained from the plant or its progeny, wherein the progeny or seed comprises within its genome the recombinant DNA construct (or suppression DNA construct), or modified PRP1, PP2C64, OPPL1, MFS9, LAO1 or DN-DSP1 gene or its regulatory element. Progeny includes subsequent generations obtained by self-pollination or out-crossing of a plant. Progeny also includes hybrids and inbreds.

In hybrid seed propagated crops, mature modified plants can be self-pollinated to produce a homozygous inbred plant. The inbred plant produces seed containing the newly introduced recombinant DNA construct (or suppression DNA construct), or modified PRP1, PP2C64, OPPL1, MFS9, LAO1 or DN-DSP1 gene or its regulatory promoter. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant, and the modification in the gene or promoter may be stably inherited in the plant.

Particular embodiments include but are not limited to the following:

1. A plant (for example, a rice or maize or soybean plant) comprising in its genome a suppression DNA construct comprising at least one regulatory element operably linked to a suppression element, wherein the suppression element derived from all or part of a sense strand or antisense strand of a target gene of interest, said suppression element having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to said all or part of a sense strand or antisense strand from which said suppression element is derived, and wherein said target gene of interest encodes a drought sensitive polypeptide, and wherein said plant exhibits enhanced drought tolerance compared to a control plant and further the said plant exhibits an alteration of at least one agronomic characteristic when compared to a control plant.

2. A plant (for example, a rice or maize or soybean plant) comprising in its genome a suppression DNA construct comprising at least one regulatory element operably linked to at least 100 contiguous base pairs of (a) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16 or 19; or (b) a full complement of the nucleic acid sequence of (a), and wherein said plant exhibits enhanced drought tolerance compared to a control plant. The plant may further exhibit an alteration of at least one agronomic characteristic when compared to a control plant.

3. A plant (for example, a rice or maize or soybean plant) comprising in its genome a suppression DNA construct comprising at least one regulatory element operably linked to at least 100 contiguous base pairs of (a) a polynucleotide with nucleotide sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15 or 18; or (b) a full complement of the nucleic acid sequence of (a), and wherein said plant exhibits enhanced drought tolerance compared to a control plant. The plant may further exhibit an alteration of at least one agronomic characteristic when compared to a control plant.

4. A plant (for example, a rice or maize or soybean plant) comprising in its genome a suppression DNA construct comprising at least one regulatory element operably linked to (a) the polynucleotide of SEQ ID NO: 45, 46, 47, 48, 49 or 50, or (b) a full complement of the nucleic acid sequence of (a), and wherein said plant exhibits enhanced drought tolerance compared to a control plant. The plant may further exhibit an alteration of at least one agronomic characteristic when compared to a control plant.

5. A modified plant (for example, a rice or maize or soybean plant) comprising (a) a modified polynucleotide with nucleotide sequence of at least 85% sequence identity to SEQ ID NO: 2, 5, 8, 11, 14 or 17; (b) a modified polynucleotide with nucleotide sequence of at least 85% sequence identity to SEQ ID NO: 3, 6, 9, 12, 15 or 18; or (c) the full complement of the nucleotide sequence of (a) or (b), wherein the plant exhibits enhanced drought tolerance.

6. A modified plant (for example, a rice or maize or soybean plant) comprising (a) a modified polynucleotide with nucleotide sequence of at least 95% sequence identity to SEQ ID NO: 2, 5, 8, 11, 14 or 17; (b) a modified polynucleotide with nucleotide sequence of at least 95% sequence identity to SEQ ID NO: 3, 6, 9, 12, 15 or 18; or (c) the full complement of the nucleotide sequence of (a) or (b), wherein the plant exhibits enhanced drought tolerance.

7. A modified plant, wherein expression of the PRP1, PP2C64, OPPL1, MFS9, LAO1 or DN-DSP1 gene is decreased in the plant, when compared to a control plant, and wherein the plant exhibits at least one phenotype selected from the group consisting of: increased grain yield, increased abiotic stress tolerance, increased biomass and a combination of thereof compared to the control plant, the plant exhibits an increase in abiotic stress tolerance, and the abiotic stress is drought stress.

8. A plant with modified PRP1, PP2C64, OPPL1, MFS9, LAO1 or DN-DSP1 gene's regulatory element, wherein the expression of the PRP1, PP2C64, OPPL1, MFS9, LAO1 or DN-DSP1 gene is decreased in the plant, when compared to a control plant, and wherein the plant exhibits at least one phenotype selected from the group consisting of: increased grain yield, increased abiotic stress tolerance, increased biomass and a combination of thereof compared to the control plant, the plant exhibits an increase in abiotic stress tolerance, and the abiotic stress is drought stress.

9. Any progeny of the above plants in embodiment 1-8, any seeds of the above plants in embodiment 1-8, any seeds of progeny of the above plants in embodiment 1-8, and cells from any of the above plants in embodiment 1-8 and progeny thereof.

In any of the foregoing embodiment 1-9 or other embodiments, the drought sensitive polypeptide may be from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Zea mays, Glycine max, Glycine tabacina, Glycine soja* or *Glycine tomentella*.

In any of the foregoing embodiment 1-9 or other embodiments, the recombinant DNA construct, suppression DNA construct or CRISPR/Cas9 construct may comprise at least a promoter functional in a plant as a regulatory element.

In any of the foregoing embodiment 1-9 or other embodiments, the alteration of at least one agronomic characteristic is either an increase or decrease.

In any of the foregoing embodiment 1-9 or other embodiments, the plant may exhibit the alteration of at least one agronomic characteristic when compared, under water limiting conditions, to a control plant.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Environmental conditions" refer to conditions under which the plant is grown, such as the availability of water, availability of nutrients, or the presence of insects or disease.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

The Examples below describe some representative protocols and techniques for simulating drought conditions and/or evaluating drought tolerance; and simulating oxidative conditions.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been affected as to a gene of interest. A subject plant or plant cell may be descended from a plant or cell so altered and will comprise the alteration. One of ordinary skill in the art would readily recognize a suitable control or reference plant to be utilized when assessing or measuring an agronomic characteristic or phenotype of a transgenic plant using compositions or methods as described herein. For example, by way of non-limiting illustrations:

1. Progeny of a modified plant which is hemizygous with respect to a recombinant DNA construct (or suppression DNA construct) or modified polynucleotide, such that the progeny are segregating into plants either comprising or not comprising the recombinant DNA construct (or suppression DNA construct) or modified polynucleotide: the progeny comprising the recombinant DNA construct (or suppression DNA construct) or modified polynucleotide would be typically measured relative to the progeny not comprising the recombinant DNA construct (or suppression DNA construct) or modified polynucleotide. The progeny not comprising the recombinant DNA construct (or the suppression DNA construct) or modified polynucleotide is the control or reference plant.

2. Introgression of a recombinant DNA construct (or suppression DNA construct) or modified polynucleotide into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct (or suppression DNA construct) or modified polynucleotide: the second hybrid line would typically be measured relative to the first hybrid line (i.e., the first hybrid line is the control or reference plant).

4. A plant comprising a recombinant DNA construct (or suppression DNA construct) or modified polynucleotide: the plant may be assessed or measured relative to a control plant not comprising the recombinant DNA construct (or suppression DNA construct) or modified polynucleotide but otherwise having a comparable genetic background to the plant (e.g., sharing at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity of nuclear genetic material compared to the plant comprising the recombinant DNA construct (or suppression DNA construct)) or modified polynucleotide. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

A control plant or plant cell may comprise, for example: (a) a wild-type (WT) plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimulus that would induce expression of the gene of interest or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

In this disclosure, ZH11-TC, DP0158 and Negative indicate control plants, ZH11-TC represents rice plants generated from tissue cultured Zhonghua 11, DP0158 represents plants transformed with empty vector of DP0158, and Negative represents genome edited negative rice plants which went through the transformation process and have the wild-type.

Methods:

Methods include but are not limited to methods for modifying or altering the host endogenous genomic gene or promoter, methods for altering the expression and activity of endogenous polypeptide, methods for increasing drought tolerance in a plant, methods for evaluating drought tolerance in a plant, methods for increasing paraquat tolerance, methods for altering an agronomic characteristic in a plant, methods for determining an alteration of an agronomic characteristic in a plant, and methods for producing seed. The plant may be a monocotyledonous or dicotyledonous plant, for example, rice, maize or soybean plant. The plant may also be sunflower, canola, wheat, alfalfa, cotton, barley, millet, sugar cane or sorghum. The seed may be a maize or soybean seed, for example, a maize hybrid seed or maize inbred seed.

Methods for modifying or altering the host endogenous genomic DNA includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9:39; The CRISPR/Cas system allows targeted cleavage of genomic DNA guided by a customizable small noncoding RNA.

Methods include but are not limited to the following:

A method for transforming a cell comprising transforming a cell with any one or more of the isolated polynucleotides, or the RNAi vector, or the CRISPR/Cas vector of the present disclosure, wherein, in particular embodiments, the cell is eukaryotic cell, e.g., a yeast, insect or plant cell; or prokaryotic cell, e.g., a bacterial cell.

A method for producing a modified plant comprising transforming a plant cell with any of the isolated polynucleotides or recombinant DNA constructs (including suppression DNA constructs) or CRISPR/Cas construct of the present disclosure and regenerating a modified plant from the transformed plant cell, wherein, the modified plant and the modified seed obtained by this method may be used in other methods of the present disclosure.

A method for altering the expression level of a polypeptide of the disclosure in a plant comprising: (a) transforming a regenerable plant cell with a recombinant DNA construct of the present disclosure; and (b) regenerating a transgenic plant from the regenerable plant cell after step (a); and (c) growing the transformed plant under conditions that are suitable for the expression of the recombinant DNA construct, wherein the expression of the recombinant DNA construct results in production of altered levels of the polypeptide of the disclosure in the transformed plant.

A method for altering the expression level of a polypeptide of the disclosure in a plant comprising: (a) transforming a regenerable plant cell with a suppression DNA construct of the present disclosure; and (b) regenerating a transgenic plant from the regenerable plant cell after step (a); and (c) growing the transformed plant, wherein the expression of the suppression DNA construct results in production of altered levels of the polypeptide of the disclosure in the transformed plant.

A method for altering the expression level of a polypeptide of the disclosure in a plant comprising: (a) transforming a regenerable plant cell with a CRISPR/Cas construct of the present disclosure; and (b) regenerating a transgenic plant from the regenerable plant cell after step (a), wherein the plant gene were edited; and (c) growing the transformed plant, wherein the transformation of the CRISPR/Cas construct results in production of altered levels of the polypeptide of the disclosure in the transformed plant.

A method of making a plant in which the expression or the activity of an endogenous PRP1, PP2C64, OPPL1, MFS9, LAO1 or DN-DSP1 polypeptide is decreased, when compared to the activity of wild-type PRP1, PP2C64, OPPL1, MFS9, LAO1 or DN-DSP1 polypeptide in a control plant, and wherein the plant exhibits at least one phenotype selected from the group consisting of: increased drought tolerance, increased grain yield, increased abiotic stress tolerance and increased biomass, compared to the control plant, wherein the method comprises the steps of (i) introducing a DNA fragment, deleting a DNA fragment or replacing a DNA fragment, or (ii) introducing one or more nucleotide changes in the genomic region comprising the endogenous PRP1, PP2C64, OPPL1, MFS9, LAO1 or DN-DSP1 gene, wherein these alterations are effective for decreasing the expression or the activity of the endogenous PRP1, PP2C64, OPPL1, MFS9, LAO1 or DN-DSP1 polypeptide.

A method of making a plant in which the expression or the activity of an endogenous MFS9 polypeptide is decreased, when compared to the expression or the activity of wild-type MFS9 polypeptide in a control plant, and wherein the plant exhibits at least one phenotype selected from the group consisting of: increased drought tolerance, increased grain yield, increased abiotic stress tolerance and increased biomass, compared to the control plant, wherein the method comprises the steps of (i) introducing a DNA fragment, deleting a DNA fragment or replacing a DNA fragment, or (ii) introducing one or more nucleotide changes in the genomic region comprising the endogenous MFS9 gene and its regulatory element, wherein these alterations are effective for decreasing the expression or the activity of the endogenous MFS9 polypeptide.

A method of increasing drought tolerance and/or paraquat tolerance in a plant, comprising: (a) introducing into a regenerable plant cell a suppression DNA construct comprising at least one regulatory element (for example, a promoter functional in a plant) operably linked to at least 100 contiguous base pairs of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 4, 7, 10, 13, 16 or 19, or (ii) a full complement of the nucleic acid sequence of (a)(i); (b) obtaining a progeny plant derived from said transgenic plant, wherein the progeny plant comprises in its genome the suppression DNA construct and exhibits increased drought tolerance and/or paraquat tolerance when compared to a control plant.

A method of increasing drought tolerance and/or paraquat tolerance in a plant, comprising: (a) introducing into a regenerable plant cell a suppression DNA construct comprising at least one regulatory element (for example, a promoter functional in a plant) operably linked to at least 100 contiguous base pairs of (i) a polynucleotide with nucleotide sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 3, 6, 9, 12, 15 or 18, or (ii) a full complement of the nucleic acid sequence of (a)(i); (b) obtaining a progeny plant derived from said transgenic plant, wherein the progeny plant comprises in its genome the suppression DNA construct and exhibits increased drought tolerance when compared to a control plant.

A method of increasing drought tolerance and/or paraquat tolerance in a plant, comprising: (a) introducing into a regenerable plant cell a suppression DNA construct comprising at least one regulatory element (for example, a promoter functional in a plant) operably linked to (i) a polynucleotide with nucleotide sequence of SEQ ID NO: 45, 46, 47, 48, 49 or 50, or (ii) a full complement of the nucleic acid sequence of (a)(i); (b) obtaining a progeny plant derived from said transgenic plant, wherein the progeny plant comprises in its genome the suppression DNA construct and exhibits increased drought tolerance when compared to a control plant.

A method of increasing drought tolerance and/or paraquat tolerance in a plant, comprising: (a) introducing into a regenerable plant cell a CRISPR/Cas construct comprising a polynucleotide encoding a Cas9 enzyme, a polynucleotide encoding nuclear localization signal and at least one heterologous regulatory element operably linked to gRNA, wherein the gRNA is targeted to the genomic region comprising PRP1, PP2C64, OPPL1, MFS9, LAO1 or DN-DSP1 gene and its regulatory element; (b) obtaining a progeny plant derived from said modified plant, wherein the progeny plant comprises in its genome the modified PRP1, PP2C64, OPPL1, MFS9, LAO1 or DN-DSP1 gene or its regulatory element and exhibits increased drought tolerance when compared to a control plant.

A method of increasing drought tolerance and/or paraquat tolerance in a plant, comprising: (a) introducing into a regenerable plant cell a CRISPR/Cas construct comprising a polynucleotide encoding a Cas9 enzyme, a polynucleotide encoding nuclear localization signal and at least one heterologous regulatory sequence operably linked to gRNA, wherein the gRNA is targeted to SEQ ID NO: 3, 6, 9, 12, 15, 18, 102, 103, 104, 105, 106 or 107; (b) obtaining a progeny plant derived from said modified plant, wherein the progeny plant comprises in its genome the modified OsPRP1, OsPP2C64, OsOPPL1, OsMFS9, OsLAO1 or OsDN-DSP1 gene or regulatory element and exhibits increased drought tolerance when compared to a control plant.

A method of evaluating drought tolerance in a plant comprising (a) obtaining a transgenic plant, wherein the transgenic plant comprises in its genome a suppression DNA construct comprising at least one regulatory element (for example, a promoter functional in a plant) operably linked to at least 100 contiguous base pairs of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 4, 7, 10, 13, 16 or 19, or (ii) a full complement of the nucleic acid sequence of (a)(i); (b) obtaining a progeny plant derived from said transgenic plant, wherein the progeny plant comprises in its genome the suppression DNA construct; and (c) evaluating the progeny plant for drought tolerance compared to a control plant.

A method of evaluating drought tolerance in a plant comprising (a) obtaining a transgenic plant, wherein the transgenic plant comprises in its genome a suppression DNA construct comprising at least one regulatory element (for example, a promoter functional in a plant) operably linked to the polynucleotide of SEQ ID NO: 45, 46, 47, 48, 49 or 50, or (ii) a full complement of the nucleic acid sequence of (a)(i); (b) obtaining a progeny plant derived from said transgenic plant, wherein the progeny plant comprises in its genome the suppression DNA construct; and (c) evaluating the progeny plant for drought tolerance compared to a control plant.

A method of determining an alteration of an agronomic characteristic in a plant comprising (a) obtaining a transgenic plant which comprises in its genome a suppression DNA construct comprising a polynucleotide operably linked to at least one regulatory element (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 4, 7, 10, 13, 16 or 19; (b) obtaining a progeny plant derived from said transgenic plant, wherein the progeny plant comprises in its genome the suppression DNA construct; and (c) determining whether the progeny plant exhibits an alteration in at least one agronomic characteristic when compared, optionally under water limiting conditions, to a control plant.

A method of producing seed comprising any of the preceding methods, and further comprising obtaining seeds from said progeny plant, wherein said seeds comprise in their genome said suppression DNA construct, or modified PRP1, PP2C64, OPPL1, MFS9, LAO1 or DN-DSP1 gene or its regulatory element.

In any of the preceding methods or any other embodiments of methods of the present disclosure, in said introducing step, the said regenerable plant cell may comprise a callus cell, an embryogenic callus cell, a gametic cell, a meristematic cell, or a cell of an immature embryo. The regenerable plant cells may derive from an inbred maize plant or rice.

In any of the preceding methods or any other embodiments of methods of the present disclosure, said regenerating step may comprise the following: (i) culturing said transformed plant cells in a medium comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the step of determining an alteration of an agronomic characteristic in a modified plant, if applicable, may comprise determining whether the modified plant exhibits an alteration of at least one agronomic characteristic when compared, under varying environmental conditions, to a control plant not comprising the suppression DNA construct or the wild-type plant.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the suppression DNA construct or the wild-type plant.

In any of the preceding methods or any other embodiments of methods of the present disclosure, the plant may exhibit the alteration of at least one agronomic characteristic when compared under water limiting conditions to a control plant.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant or suppression DNA constructs or CRSIPR-Cas construct of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Cloning and Vector Construction of Drought Sensitive Genes

Based on our preliminary screening of rice activation tagging population and the sequence information of gene IDs shown in Table 2, primers were designed for cloning rice drought sensitive genes OsPRP1, OsPP2C64, OsOPPL1, OsMFS9, OsLAO1 and OsDN-DSP1. The primers and the expected-lengths of the amplified genes are shown in Table 3.

For OsPP2C64, its cDNA was cloned using pooled cDNA from leaf, stem and root tissues of Zhonghua 11 plant as the template. For OsPRP1, OsOPPL1, OsMFS9, OsLAO1 and OsDN-DSP1, their gDNAs were cloned, and amplified using genomic DNA of Zhonghua 11 as the template. The PCR reaction mixtures and PCR procedures are shown in Table 4 and Table 5.

TABLE 2

Rice gene names, Gene IDs (from TIGR) and Construct IDs

| Gene name | LOC ID | Construct ID |
|---|---|---|
| OsPRP1 | LOC_Os01g57004.1 | DP0086 |
| OsPP2C64 | LOC_Os07g37890.1 | DP0297 |
| OsOPPL1 | LOC_Os02g51770 | DP0328 |
| OsMFS9 | LOC_Os03g02380 | DP0343 |
| OsLAO1 | LOC_Os07g02810.1 | DP0451 |
| OsDN-DSP1 | LOC_Os02g57210.1 | DP0505 |

TABLE 3

Primers for cloning rice drought sensitive genes

| Primer | Sequence | SEQ ID NO: | Gene name | Length of amplified fragment (bp) |
|---|---|---|---|---|
| gc-706 | 5'-ACTCTCACCCAGTATAG TTCTCCATTG-3' | 20 | OsPRP1 | 567 |
| gc-707 | 5'-GGCAAGCACGTGTACAG TGTATATCTC-3' | 21 | | |
| gc-2288 | 5'-CTGATTTGGGCATTGGT GTTGGTGGTG-3' | 22 | OsPP2C64 | 1351 |
| gc-2289 | 5'-GAAAATAACGGGGGTAA ATATAAGATGGG-3' | 23 | | |
| gc-3203 | 5'-TGGGTGGCGAGGAGGAT GGGGTAC-3' | 24 | OsOPPL1 | 2771 |
| gc-3204 | 5'-CAAGCCTTCAAGGACCA CCAAATCACCAC-3' | 25 | | |
| gc-3233 | 5'-CCATTCCATCTTTCTCT CTCTCTCGCG-3' | 26 | OsMFS9 | 3370 |
| gc-3234 | 5'-CATGCTTATATTCGATC TGTTTGTATG-3' | 27 | | |
| gc-4573 | 5'-CACTCTCTCACACACAC ACTCTCTCTCTC-3' | 28 | OsLAO1 | 2421 |
| gc-4574 | 5'-CGAACTATGCAACTCTG AATTTCTTC-3' | 29 | | |
| gc-3328 | 5'-CTACCAAGCTCTCTCTT CCTCTGATCAAC-3' | 30 | OsDN-DSP1 | 1583 |
| gc-6509 | 5'-GATCGATCGAGCAGAAC AAATTAAGATAGCCTAG-3' | 31 | | |

TABLE 4

PCR reaction mixture for cloning drought sensitive genes

| Reaction mix | 50 µL |
|---|---|
| Template | 1 µL |
| TOYOBO KOD-FX (1.0 U/µL) | 1 µL |
| 2 × PCR buffer for KOD-FX | 25 µL |
| 2 mM dNTPs (0.4 mM each) | 10 µL |
| Primer-F/R (10 µM) | 2 µL each |
| ddH$_2$O | 9 µL |

TABLE 5

PCR cycle conditions

| | | |
|---|---|---|
| 94° C. | 3 min | |
| 98° C. | 10 s | |
| 58° C. | 30 s | ×30 |
| 68° C. | (1 Kb/min) 1 min | |
| 68° C. | 5 min | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0158 (pCAMBIA1300-DsRed) (SEQ ID NO: 1).

The cloned nucleotide sequence in construct of DP0086 and coding sequence of OsPRP1 are provided as SEQ ID NO: 2 and 3, the encoded amino acid sequence of OsPRP1 is SEQ ID NO: 4; the cloned nucleotide sequence in construct of DP0297 and coding sequence of OsPP2C64 are provided as SEQ ID NO: 5 and 6, the encoded amino acid sequence of OsPP2C64 is SEQ ID NO: 7; the cloned nucleotide sequence in construct of DP0328 and coding sequence of OsOPPL1 are provided as SEQ ID NO: 8 and 9, the encoded amino acid sequence of OsOPPL1 is SEQ ID NO: 10; the cloned nucleotide sequence in construct of DP0343 and coding sequence of OsMFS9 are provided as SEQ ID NO: 11 and 12, the encoded amino acid sequence of OsMFS9 is SEQ ID NO: 13; the cloned nucleotide sequence in construct of DP0451 and coding sequence of OsLAO1 are provided as SEQ ID NO: 14 and 15, the encoded amino acid sequence of OsLAO1 is SEQ ID NO: 16; and the cloned nucleotide sequence in construct of DP0505 and coding sequence of OsDN-DSP1 are provided as SEQ ID NO: 17 and 18, the encoded amino acid sequence of OsDN-DSP1 is SEQ ID NO: 19.

Example 2

Transformation to Get Transgenic Rice Lines

In this research, all of the over-expression vectors and empty vector (DP0158) were transformed into the Zhonghua 11 (*Oryza sativa* L.) by Agrobacteria-mediated method as described by Lin and Zhang ((2005) *Plant Cell Rep.* 23:540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with Agrobacteria with the vector. The transgenic seedlings (T0) generated in transformation laboratory are transplanted in the field to get T1 seeds. The T1 and T2 seeds are stored at cold room (4° C.). The over-expression vectors contain DsRED and HYG genes. T1 and T2 seeds which showed red color under green fluorescent light were transgenic seeds and were used in the following trait screening.

Example 3

Gene Expression Analysis

The gene expression levels in the transgenic rice plants were analyzed. A standard RT-PCR or a real-time RT-PCR procedure, such as the QuantiTect® Reverse Transcription Kit from Qiagen® and Real Time-PCR (SYBR$^R$Premix Ex Taq™, TaKaRa), was used. EF-1α gene was used as an internal control to show that the amplification and loading of samples from the transgenic rice and wild-type were similar. Gene expression was normalized based on the EF-1α mRNA levels.

The relative expression levels of OsPRP1 gene in leaves of different transgenic rice lines were determined by real-time PCR analyses. The base level of expression in ZH11-TC was set at 1.00, and the expression levels in other OsPRP1 lines ranged from about 8-2954-fold-increases compared to ZH11-TC. ZH11-TC is tissue cultured ZH11 rice and DP0158 is empty vector transformed ZH11 rice plants. The primers for real-time RT-PCR for the OsPRP1 gene in the over-expression transgenic rice are listed as SEQ ID NO: 32 and 33.

```
DP0086-F1:
                                    (SEQ ID NO: 32)
5'-TGATCGTAGGTACGGCTACTC-3'

DP0086-R1:
                                    (SEQ ID NO: 33)
5'-AGCAAGGCATCCTTCGAG-3'
```

The relative expression levels of OsPP2C64 gene in leaves of different transgenic rice lines were determined by real-time PCR analyses and ranged from about 2 to 113 as compared to the base expression level in ZH11-TC (control, set at 1.00). OsPP2C64 over-expressed in most the tested transgenic rice lines. The primers used for the real-time PCR are as below:

```
DP0297-F1:
                                    (SEQ ID NO: 34)
5'-TCACAGTTAGGACAGTTGCAG-3'

DP0297-R1:
                                    (SEQ ID NO: 35)
5'-CCTAGGAAGCTGAACAAGTGAG-3'
```

The relative expression levels of OsOPPL1 gene in leaves of different transgenic rice lines were determined by real-time PCR analyses and ranged from about 3 to 78 as compared to the base expression level in ZH11-TC (control, set at 1.00). OsOPPL1 over-expressed in most the transgenic lines. The primers used for the real-time PCR are as below:

```
DP0328-F1:
                                    (SEQ ID NO: 36)
5'-CTAGATGCCGACCTGTTGAG-3'

DP0328-R1:
                                    (SEQ ID NO: 37)
5'-CTTGGAAGGATAGACGAAACCC-3'
```

The relative expression levels of OsMFS9 gene in leaves of different transgenic rice lines were determined by real-time PCR analyses and ranged from 16 to 618 as compared to the base expression level in ZH11-TC (control, set at 1.00). OsMFS9 over-expressed in all the transgenic lines.

```
DP0343-F1:
                                    (SEQ ID NO: 38)
5'-GGAGGTAGCATCTCATTTGGAG-3'

DP0343-R1:
                                    (SEQ ID NO: 39)
5'-GCCAGAATATGCCAACGC-3'
```

The relative expression levels of OsLAO1 gene in leaves of different transgenic rice lines were determined by real-time PCR analyses. The base expression level in ZH11-TC is set at 1.00, and the expression levels in other OsLAO1 lines ranged from about 3246-12946-fold-increases compared to ZH11-TC. The primers used for the real-time PCR are as below:

```
DP0451-F1:
                                    (SEQ ID NO: 40)
5'-GGCAATCTTGGTGTCATTGG-3'

DP0451-R1:
                                    (SEQ ID NO: 41)
5'-GTCGGGATACTGTACTCATTGG-3'
```

The relative expression levels of OsDN-DSP1 gene in leaves of different transgenic rice lines were determined by real-time PCR analyses. The base expression level in ZH11-TC is set at 1.00, and the expression levels in other OsDN-DSP1 lines ranged from about 225-474-fold-increases compared to ZH11-TC. The primers used for the real-time PCR are as below:

```
DP0505-F1:
                                    (SEQ ID NO: 42)
5'-GGCACCATCTCGTCTTCG-3'

DP0505-R1:
                                    (SEQ ID NO: 43)
5'-CCTCCACCTTCTCCACCTC-3'
```

Example 4

Field Drought Assays of Transgenic Rice Plants

Flowering stage drought stress is an important problem in agriculture practice. The transgenic rice plants were tested under field drought conditions.

Method:

For the Field drought assays of mature rice plants, 9-12 transgenic lines from each gene construct were tested. T2 Transgenic seeds were sterilized by 800 ppm carbendazol for 8 h at 32° C. and washed 3-5 times with distilled water, then soaked in water for 16 h at 32° C., germinated for 18 h at 35-37° C. in an incubator. The germinated seeds were planted in a seedbed field. At 3-leaf stage, the seedlings were transplanted into the testing field, with 4 replicates and 10 plants per replicate for each transgenic line, and the 4 replicates were planted in the same block. ZH11-TC and DP0158 were nearby the transgenic lines in the same block, and were used as controls in the statistical analysis.

The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain weight per plant was measured. The grain weight data were statistically analyzed using mixed linear model. Positive transgenic lines were selected based on the analysis (P<0.1).

Figure 1:
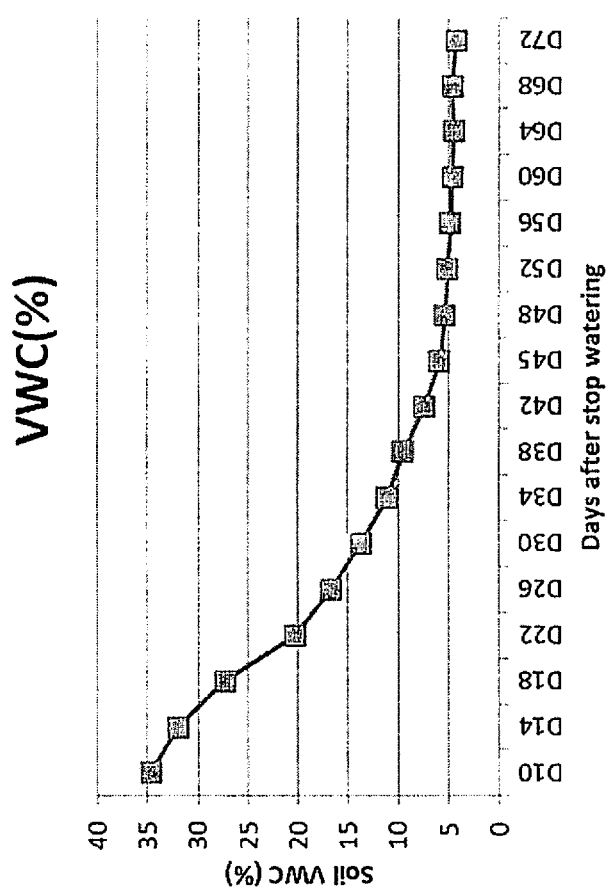
FIG. 1 shows changes of soil volumetric water content in Hainan field in the first field experiment for drought testing OsPRP1 over-expressed transgenic rice. The OsPRP1 over-expressed transgenic rice started heading 36 days after stopping watering and matured 79 days after stopping watering.
Figure 2:
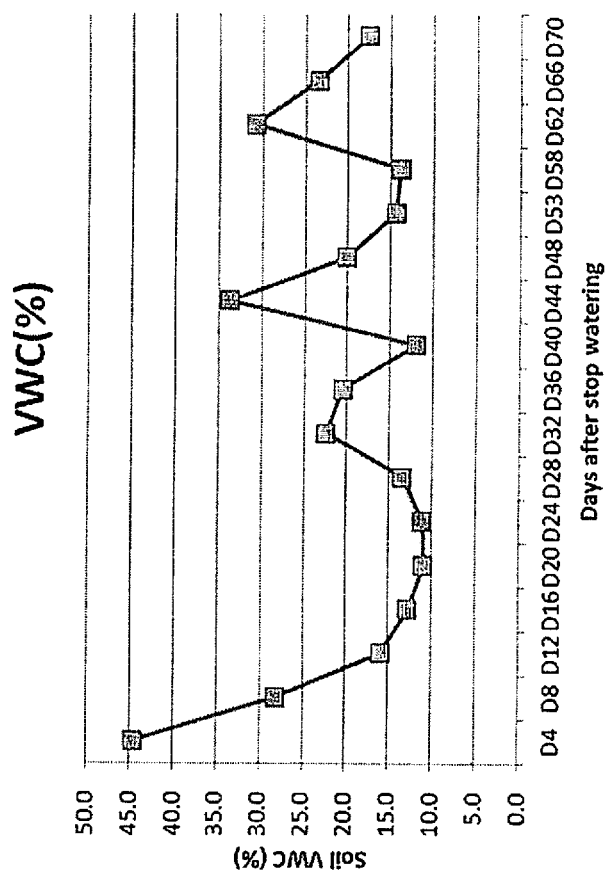
FIG. 2 shows changes of soil volumetric water content in Ningxia field in the second field experiment for drought testing OsPRP1 over-expressed transgenic rice. The OsPRP1 over-expressed transgenic rice started heading 57 days after stopping watering and matured 88 days after stopping watering.

Field Drought Assay Results:

1) Field DRT (Drought Tolerance) Validation Results of OsPRP1 Over-Expressed (DP0086) Transgenic Rice Twelve OsPRP1 transgenic lines were tested in Hainan Province in the first experiment, ZH11-TC and DP0158 rice plants (empty vector control) planted nearby were used as controls. Watering was stopped when the panicles of main stems reached panicle initiation stage IV and the tiller panicles reached the panicle initiation stage I. 19 days after stopping watering, the main stem panicles were at panicle initiation stage IX, the tiller panicles were at panicle initiation stage VII, and the rice plants started to show leaf rolling phenotype. During this process, the soil volumetric water content decreased from 35% to 20% (FIG. 1). 35 days after stopping watering, the rice plants headed, and the soil water content decreased to 10%. The transgenic rice lines showed drought sensitive phenotypes such as leaf rolling and less greenness except transgenic lines DP0086.07, DP0086.27 and DP0086.36. The grain weights per plant were measured and were shown in Table 6. The OsPRP1 transgenic rice plants showed less grain yield per plant than ZH11-TC and DP0158 control plants at the construct level. Nine lines obtained less grain yields per plant than ZH11-TC and DP0158 controls, three transgenic lines showed significantly less grain yield per plants than ZH11-TC rice plants at the line level. These results demonstrate that OsPRP1 transgenic rice plant showed drought sensitive phenotype at the vegetative stage and obtained less grain yield per plant than control after drought stress.

to show leaf rolling phenotype. The soil volumetric water content decreased from 40% to 12% during this process (FIG. 2). The rice plants reached heading stage 46 days after stopping watering. Nine transgenic lines at the vegetative stage showed drought sensitive phenotypes such as leaf rolling and dry leaf; and the transgenic lines DP0086.07 and DP0086.27 grow normally compared the ZH11-TC and DP0158 rice plants, during the drought stress. The transgenic line DP0086.36 showed better seed setting rates at maturation stage. OsPRP1 transgenic rice exhibited less grain yield per plant than ZH11-TC and DP0158 control plants at the construct level. As shown in Table 7, ten

TABLE 6

Grain yield analysis of OsPRP1 transgenic rice plants under field drought conditions
($1^{st}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0086 (Construct) | | | 5.75 | −0.86 | 0.366 | | −2.46 | 0.009 | Y |
| ZH11-TC | 40 | 24 | 6.61 | | | | | | |
| DP0158 | 37 | 24 | 8.21 | | | | | | |
| DP0086.01 | 40 | 25 | 3.62 | −2.99 | 0.005 | Y | −4.59 | 0.000 | Y |
| DP0086.02 | 40 | 24 | 5.86 | −0.75 | 0.477 | | −2.35 | 0.026 | Y |
| DP0086.03 | 39 | 25 | 5.28 | −1.33 | 0.207 | | −2.93 | 0.005 | Y |
| DP0086.05 | 38 | 23 | 4.39 | −2.21 | 0.036 | Y | −3.82 | 0.000 | Y |
| DP0086.06 | 40 | 24 | 5.97 | −0.63 | 0.573 | | −2.23 | 0.046 | Y |
| DP0086.07 | 40 | 24 | 8.62 | 2.01 | 0.057 | | 0.41 | 0.698 | |
| DP0086.24 | 40 | 24 | 5.07 | −1.54 | 0.145 | | −3.14 | 0.003 | Y |
| DP0086.27 | 40 | 24 | 8.24 | 1.64 | 0.120 | | 0.03 | 0.975 | |
| DP0086.28 | 39 | 24 | 5.20 | −1.40 | 0.183 | | −3.01 | 0.004 | Y |
| DP0086.33 | 39 | 24 | 4.32 | −2.28 | 0.030 | Y | −3.89 | 0.000 | Y |
| DP0086.35 | 37 | 24 | 5.51 | −1.09 | 0.300 | | −2.69 | 0.011 | Y |
| DP0086.36 | 40 | 24 | 6.91 | 0.30 | 0.775 | | −1.30 | 0.217 | |

The second experiment was performed in Ningxia province; twelve OsPRP1 transgenic lines were tested. Watering was stopped when 20% of the main stem panicles reached panicle initiation stage II. 18 days later, the main stem panicles reached panicle initiation stage V, the tiller panicles reached panicle initiation stage IV, and the rice plants begun OsPRP1 transgenic lines had less grain yields per plant than ZH11-TC control, and eleven lines had less grain yields per plant than DP0158 control. These results further demonstrate that OsPRP1 rice plant is sensitive to drought, and over-expression of OsPRP1 decreases the grain yield per plant after drought stress at flowering and heading stage.

TABLE 7

Grain yield analysis of OsPRP1 transgenic rice plants under field drought conditions
($2^{nd}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0086 (Construct) | | | 1.62 | −0.40 | 0.415 | | −1.19 | 0.017 | Y |
| ZH11-TC | 40 | 24 | 2.03 | | | | | | |
| DP0158 | 40 | 23 | 2.81 | | | | | | |
| DP0086.01 | 40 | 20 | 0.90 | −1.13 | 0.043 | Y | −1.91 | 0.001 | Y |
| DP0086.02 | 39 | 16 | 1.77 | −0.26 | 0.645 | | −1.04 | 0.062 | Y |
| DP0086.03 | 40 | 12 | 1.10 | −0.93 | 0.148 | | −1.71 | 0.008 | Y |
| DP0086.05 | 40 | 13 | 1.72 | −0.31 | 0.601 | | −1.09 | 0.065 | Y |
| DP0086.06 | 40 | 12 | 1.49 | −0.54 | 0.401 | | −1.32 | 0.039 | Y |
| DP0086.07 | 40 | 24 | 2.35 | 0.33 | 0.557 | | −0.46 | 0.408 | |
| DP0086.24 | 40 | 17 | 1.40 | −0.63 | 0.289 | | −1.41 | 0.017 | Y |
| DP0086.25 | 40 | 12 | 0.77 | −1.25 | 0.051 | Y | −2.04 | 0.002 | Y |
| DP0086.27 | 39 | 12 | 1.32 | −0.71 | 0.272 | | −1.49 | 0.020 | Y |
| DP0086.28 | 40 | 12 | 1.68 | −0.34 | 0.595 | | −1.13 | 0.080 | Y |

TABLE 7-continued

Grain yield analysis of OsPRP1 transgenic rice plants under field drought conditions
($2^{nd}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0086.33 | 40 | 17 | 1.90 | −0.13 | 0.821 | | −0.91 | 0.102 | |
| DP0086.36 | 40 | 24 | 3.05 | 1.03 | 0.063 | | 0.24 | 0.662 | |

Figure 3:
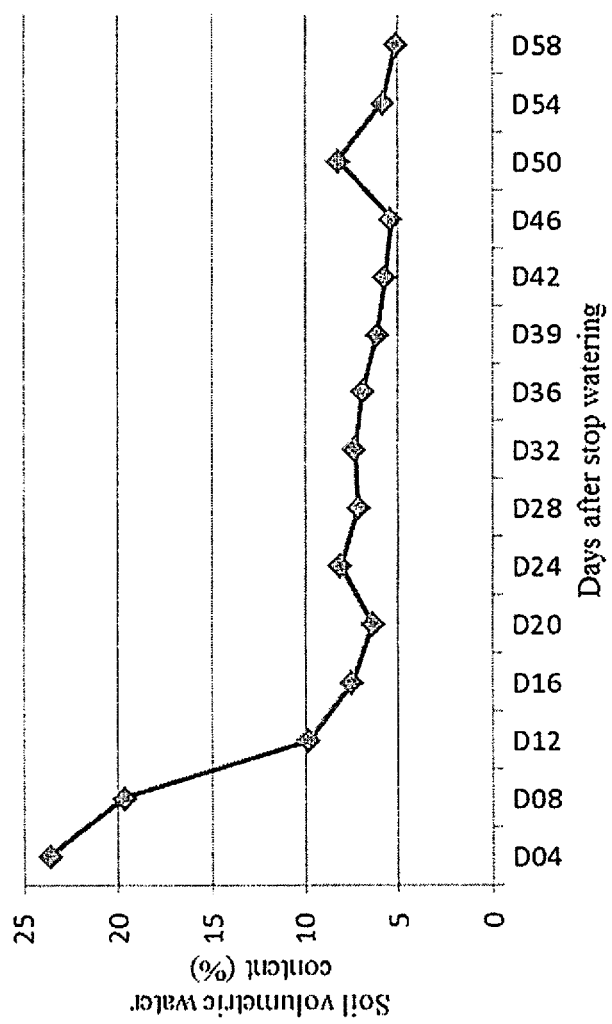
FIG. 3 shows changes of soil volumetric water content in Hainan field for drought testing OsPP2C64 over-expressed transgenic rice. The over-expressed transgenic rice started heading 39 days after stopping watering and matured 88 days after stopping watering.

2) Field DRT Validation Results of OsPP2C64 Over-Expressed (DP0297) Transgenic Rice Twelve OsPP2C64 transgenic rice plants were tested in Hainan field. ZH11-TC and DP0158 rice plants planted were used as control. Watering was stopped from panicle initiation stage I of the main stem panicle. The rice plants began to show leaf rolling phenotype 17 days after stopping watering, and the main stem panicles reached panicle initiation stage VI. The rice plants started heading after stopping watering for 29 days. The soil volumetric water content decreased from 25% to 7% during the main stem panicle heading stage (FIG. 3).

The grain yield per plant was measured. As shown in Table 8, the grain yield per plant of OsPP2C64 transgenic rice was less than ZH11-TC and DP0158 control at the construct level. Nine lines exhibited less grain yield per plant than ZH11-TC and DP0158 controls. These results indicate that OsPP2C64 transgenic rice plant is sensitive to drought condition and over-expression of OsPP2C64 decreased the grain yield per plant after drought stress at flowering stage.

Figure 4:
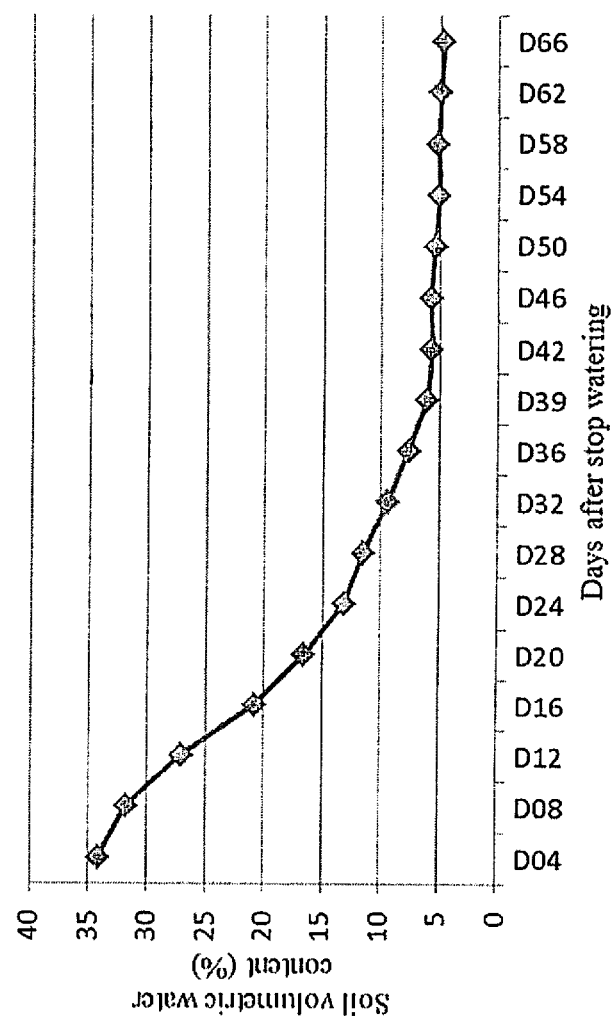
FIG. 4 shows changes of soil volumetric water content in Hainan field for drought testing OsPP2C64 over-expressed transgenic rice in the second experiment. The OsPP2C64 over-expressed transgenic rice started heading 57 days after stopping watering and matured 88 days after stopping watering.

Ten OsPP2C64 transgenic rice plants were tested in Hainan field again. Watering was stopped when the main stem panicles were at panicle initiation stage III and the tiller panicles were at panicle initiation stage I. After stopping watering for 19 days, the main stem panicles were at panicle initiation stage VIII, the tiller panicles were at initiation stage VI, and the rice plants began to show leaf rolling phenotype. The rice plants started heading after stopping watering for 35 days. The soil volumetric water content decreased from 35% to 7% during the main stem panicle heading stage (FIG. 4). Five OsPP2C64 transgenic lines (DP0297.04, DP0297.05, DP0297.10, DP0297.14 and DP0297.21) showed heavier leaf rolling degree than controls during drought stress.

As shown in Table 9, the grain yield per plant of OsPP2C64 transgenic rice was significantly less than ZH11-TC control and less than DP0158 control at the construct level. All the ten transgenic lines showed less grain yield per plant than ZH11-TC rice plants and eight lines exhibited less grain yield per plant than DP0158 control. These results further demonstrate that OsPP2C64 transgenic rice plant is

TABLE 8

Grain yield analysis of OsPP2C64 transgenic rice plants under field drought conditions
($1^{st}$ experiment)

Figure 5:
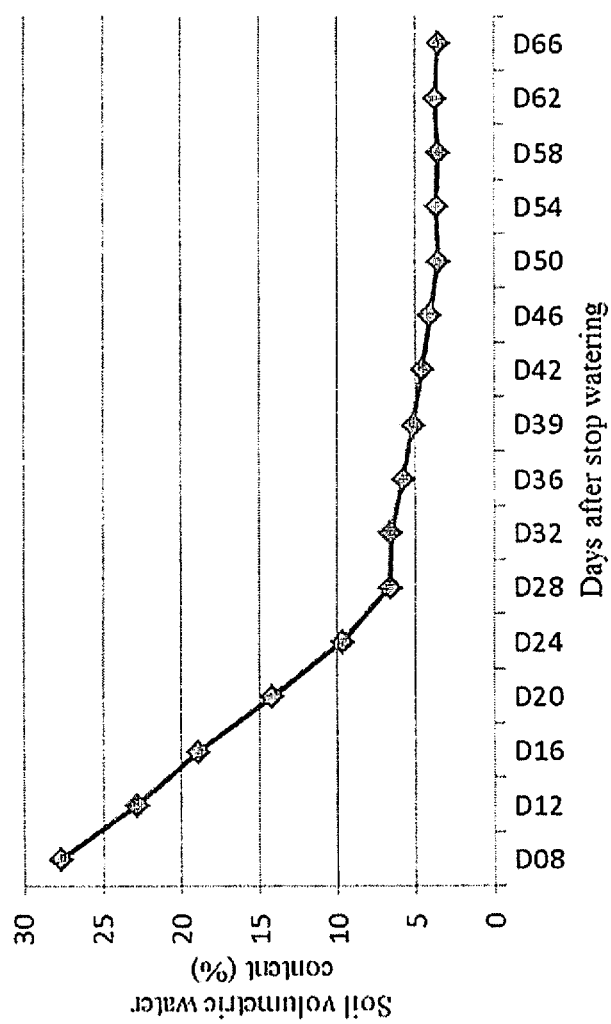
FIG. 5 shows changes of soil volumetric water content in Hainan field in the first field experiment for drought testing OsOPPL1 over-expressed transgenic rice. The OsOPPL1 over-expressed transgenic rice started heading 40 days after stopping watering and matured 83 days after stopping watering.

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0297 (Construct) | | | 6.70 | −0.97 | 0.282 | | −1.20 | 0.183 | |
| ZH11-TC | 24 | 18 | 7.67 | | | | | | |
| DP0158 | 24 | 18 | 7.90 | | | | | | |
| DP0297.01 | 24 | 18 | 8.24 | 0.57 | 0.604 | | 0.34 | 0.761 | |
| DP0297.04 | 24 | 18 | 5.80 | −1.87 | 0.090 | Y | −2.10 | 0.056 | Y |
| DP0297.05 | 24 | 18 | 5.48 | −2.19 | 0.049 | Y | −2.43 | 0.030 | Y |
| DP0297.06 | 24 | 18 | 6.14 | −1.53 | 0.169 | | −1.77 | 0.114 | |
| DP0297.07 | 24 | 18 | 6.94 | −0.73 | 0.510 | | −0.96 | 0.383 | |
| DP0297.09 | 24 | 16 | 6.47 | −1.20 | 0.278 | | −1.43 | 0.198 | |
| DP0297.10 | 24 | 17 | 6.86 | −0.81 | 0.466 | | −1.05 | 0.350 | |
| DP0297.11 | 24 | 17 | 7.82 | 0.15 | 0.892 | | −0.08 | 0.940 | |
| DP0297.14 | 24 | 12 | 6.83 | −0.84 | 0.441 | | −1.07 | 0.326 | |
| DP0297.15 | 24 | 18 | 8.06 | 0.39 | 0.727 | | 0.15 | 0.890 | |
| DP0297.16 | 24 | 18 | 5.44 | −2.23 | 0.041 | Y | −2.47 | 0.025 | Y |
| DP0297.21 | 24 | 18 | 6.34 | −1.33 | 0.229 | | −1.56 | 0.158 | | sensitive to drought condition at vegetative stage and over-expression of OsPP2C64 resulted in decreased grain yield per plant after drought stress at flowering stage.

days later, the main stem panicles headed out, and the tiller panicles reached panicles initiation stage VI. The soil volumetric water content decreased to 30% from 10% (FIG. 5),

TABLE 9

Grain yield analysis of OsPP2C64 transgenic rice plants under field drought conditions ($2^{nd}$ experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0297 (construct) | | | 4.38 | −2.91 | 0.000 | Y | −0.97 | 0.238 | |
| ZH11-TC | 40 | 24 | 7.29 | | | | | | |
| DP0158 | 40 | 24 | 5.35 | | | | | | |
| DP0297.01 | 40 | 24 | 5.38 | −1.65 | 0.055 | Y | 0.29 | 0.774 | |
| DP0297.04 | 40 | 24 | 2.55 | −3.75 | 0.000 | Y | −1.81 | 0.071 | Y |
| DP0297.05 | 37 | 23 | 1.67 | −3.96 | 0.000 | Y | −2.02 | 0.057 | Y |
| DP0297.06 | 40 | 24 | 3.44 | −3.24 | 0.000 | Y | −1.30 | 0.197 | |
| DP0297.07 | 40 | 24 | 4.10 | −2.72 | 0.002 | Y | −0.78 | 0.440 | |
| DP0297.09 | 40 | 24 | 4.45 | −2.34 | 0.006 | Y | −0.40 | 0.687 | |
| DP0297.10 | 40 | 18 | 1.57 | −4.56 | 0.000 | Y | −2.62 | 0.009 | Y |
| DP0297.11 | 40 | 24 | 6.74 | −0.44 | 0.606 | | 1.51 | 0.132 | |
| DP0297.14 | 40 | 22 | 3.04 | −3.61 | 0.000 | Y | −1.67 | 0.098 | Y |
| DP0297.21 | 39 | 23 | 3.22 | −3.46 | 0.000 | Y | −1.52 | 0.129 | |

The third experiment showed the same trend. The OsPP2C64 transgenic rice plants exhibited lower grain yield per plant than ZH11-TC control and significantly lower grain yield per plant than DP0158 control at the construct level, and the five transgenic lines showed lower grain yield per plant than both ZH11-TC and DP0158 control rice plants (Table 10). All these results showed that over-expression OsPP2C64 in rice resulted in drought sensitivity and reduced the grain yield after drought stress.

and the transgenic rice plants started to show drought sensitive phenotypes such as leaf rolling. During the earlier stage of the drought stress, two OsOPPL1 transgenic lines DP0328.15 and DP0328.48 showed increased leaf rolling degrees compared to ZH11-TC and DP0158 plants.

The grain yield results showed that the OsOPPL1 transgenic rice plants obtained more grain yield per plant than both ZH11-TC and DP0158 plants at the construct level after

TABLE 10

Grain yield analysis of OsPP2C64 transgenic rice plants under field drought conditions ($3^{rd}$ experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0297 (Construct) | | | 1.59 | −0.56 | 0.315 | | −1.53 | 0.006 | Y |
| ZH11-TC | 40 | 24 | 2.15 | | | | | | |
| DP0158 | 39 | 23 | 3.12 | | | | | | |
| DP0297.01 | 40 | 20 | 1.34 | −0.81 | 0.146 | | −1.78 | 0.002 | Y |
| DP0297.06 | 40 | 12 | 1.06 | −1.09 | 0.066 | Y | −2.06 | 0.001 | Y |
| DP0297.07 | 40 | 23 | 1.92 | −0.23 | 0.684 | | −1.19 | 0.034 | Y |
| DP0297.10 | 40 | 7 | 1.76 | −0.39 | 0.544 | | −1.36 | 0.036 | Y |
| DP0297.11 | 40 | 21 | 1.85 | −0.30 | 0.591 | | −1.27 | 0.024 | Y |
| DP0297.14 | 30 | 11 | 1.60 | −0.55 | 0.395 | | −1.52 | 0.020 | Y |

3) Field DRT Validation Results of OsOPPL1 Over-Expressed (DP0328) Transgenic Rice Twelve OsOPPL1 transgenic rice plants were tested in Hainan field in the first experiment. Watering was stopped from panicle initiation stage II of the main stem panicles. 23 drought stress. Further analysis in the line level showed that nine lines exhibited greater grain yields per plant than both ZH11-TC and DP0158 controls (Table 11). These results indicate that OsOPPL1 transgenic rice were drought sensitive at the vegetative stage.

TABLE 11

Grain yield analysis of OsOPPL1 transgenic rice plants under field drought conditions (1st experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0328 (Construct) | | | 2.80 | 0.38 | 0.494 | | 0.38 | 0.496 | |
| ZH11-TC | 35 | 19 | 2.42 | | | | | | |
| DP0158 | 36 | 17 | 2.42 | | | | | | |
| DP0328.13 | 36 | 18 | 3.23 | 0.81 | 0.201 | | 0.81 | 0.200 | |
| DP0328.15 | 36 | 20 | 1.84 | −0.58 | 0.337 | | −0.58 | 0.352 | |
| DP0328.16 | 35 | 20 | 3.26 | 0.84 | 0.167 | | 0.84 | 0.178 | |
| DP0328.17 | 36 | 19 | 2.99 | 0.57 | 0.362 | | 0.57 | 0.366 | |
| DP0328.21 | 36 | 20 | 3.38 | 0.96 | 0.120 | | 0.96 | 0.132 | |
| DP0328.25 | 36 | 18 | 3.02 | 0.59 | 0.329 | | 0.59 | 0.345 | |
| DP0328.30 | 36 | 20 | 2.34 | −0.08 | 0.893 | | −0.08 | 0.895 | |
| DP0328.32 | 36 | 20 | 2.56 | 0.13 | 0.834 | | 0.13 | 0.833 | |
| DP0328.40 | 35 | 20 | 2.43 | 0.01 | 0.987 | | 0.01 | 0.987 | |
| DP0328.44 | 36 | 20 | 3.73 | 1.30 | 0.038 | | 1.30 | 0.032 | |
| DP0328.48 | 36 | 18 | 2.17 | −0.25 | 0.686 | | −0.25 | 0.678 | |
| DP0328.49 | 36 | 19 | 2.67 | 0.25 | 0.692 | | 0.25 | 0.687 | |

The second experiment was performed in Ningxia province, and the same 12 OsOPPL1 transgenic lines were tested. Watering was stopped when 20% of the main stem panicles reached panicle initiation stage II. 18 days later, the main stem panicles reached panicle initiation stage V, the tiller panicles reached panicle initiation stage IV. The soil volumetric water content decreased from 47% to 10% (FIG. 6) during heading stage. The rice plants showed stressed phenotype. Eight OsOPPL1 transgenic rice line DP0328.13, DP0328.15, DP0328.16, DP0328.30, DP0328.32, DP0328.40, DP0328.48 and DP0328.49 showed greater leaf rolling degree and less greenness. The OsOPPL1 transgenic rice exhibited less grain yield per plant than ZH11-TC and greater grain yield per plant than DP0158 control at the construct level. At the transgenic line level, ten OsOPPL1 transgenic lines exhibited less grain yields per plant than ZH11-TC control (Table 12). These results further indicate that OsOPPL1 transgenic rice plant were drought sensitive during the vegetative stage.

4) Field DRT Validation Results of OsMFS9 Over-Expressed (DP0343) Transgenic Rice Twelve OsMFS9 transgenic lines were tested in Hainan Province in the first experiment, ZH11-TC and DP0158 rice plants planted nearby were used as controls. Watering was stopped when the main stem panicles reached panicle initiation stage III. 23 days after stopping watering, the main stem panicles headed out, the tiller panicles were at panicle initiation stage VII, and the rice plants started to show leaf rolling phenotype. During this process, the soil volumetric water content decreased from 30% to 13% (FIG. 7). 38 days after stopping watering, the rice plants were at heading stage, and the soil water content decreased to 6%.

The grain weights per plant were measured and were shown in Table 13. The OsMFS9 transgenic rice plants showed less grain yield per plant than ZH11-TC rice plants and greater grain yield per plant than DP0158 rice plants at the construct level. Nine lines obtained less grain yields per plant than ZH11-TC control, and five transgenic lines

TABLE 12

Grain yield analysis of OsOPPL1 transgenic rice plants under field drought conditions (2nd experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0328 (Construct) | | | 1.97 | −0.63 | 0.283 | | 0.54 | 0.330 | |
| ZH11-TC | 40 | 21 | 2.59 | | | | | | |
| DP0158 | 40 | 21 | 1.42 | | | | | | |
| DP0328.13 | 36 | 15 | 1.61 | −0.99 | 0.157 | | 0.18 | 0.791 | |
| DP0328.15 | 30 | 6 | 1.25 | −1.34 | 0.109 | | −0.17 | 0.835 | |
| DP0328.16 | 40 | 17 | 1.64 | −0.96 | 0.165 | | 0.21 | 0.754 | |
| DP0328.17 | 35 | 18 | 3.21 | 0.62 | 0.348 | | 1.79 | 0.006 | |
| DP0328.21 | 30 | 16 | 3.27 | 0.67 | 0.302 | | 1.84 | 0.005 | |
| DP0328.25 | 39 | 20 | 2.28 | −0.32 | 0.628 | | 0.85 | 0.186 | |
| DP0328.30 | 34 | 15 | 1.74 | −0.85 | 0.188 | | 0.32 | 0.621 | |
| DP0328.32 | 37 | 11 | 1.60 | −0.99 | 0.153 | | 0.18 | 0.795 | |
| DP0328.40 | 40 | 12 | 2.11 | −0.48 | 0.513 | | 0.69 | 0.313 | |
| DP0328.44 | 40 | 18 | 2.18 | −0.41 | 0.526 | | 0.76 | 0.219 | |
| DP0328.48 | 31 | 8 | 1.33 | −1.27 | 0.090 | Y | −0.10 | 0.892 | |
| DP0328.49 | 40 | 23 | 1.40 | −1.19 | 0.070 | Y | −0.02 | 0.971 | | showed significantly less grain yield per plants than ZH11-TC rice plants at the line level. These results demonstrate that OsMFS9 transgenic rice plant showed drought sensitive and obtained less grain yield per plant than control after drought stress.

TABLE 13

Grain yield analysis of OsMFS9 transgenic rice plants under field drought conditions ($1^{st}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0343 (Construct) | | | 4.59 | −1.29 | 0.086 | Y | 0.91 | 0.226 | |
| ZH11-TC | 36 | 20 | 5.88 | | | | | | |
| DP0158 | 36 | 20 | 3.68 | | | | | | |
| DP0343.01 | 36 | 20 | 5.14 | −0.74 | 0.396 | | 1.46 | 0.093 | |
| DP0343.02 | 36 | 20 | 6.31 | 0.43 | 0.623 | | 2.63 | 0.003 | |
| DP0343.03 | 33 | 19 | 6.66 | 0.78 | 0.359 | | 2.98 | 0.001 | |
| DP0343.06 | 36 | 19 | 3.70 | −2.18 | 0.012 | Y | 0.02 | 0.980 | |
| DP0343.07 | 36 | 20 | 3.09 | −2.79 | 0.001 | Y | −0.59 | 0.497 | |
| DP0343.08 | 36 | 20 | 2.33 | −3.56 | 0.000 | Y | −1.36 | 0.119 | |
| DP0343.10 | 36 | 16 | 4.46 | −1.42 | 0.101 | | 0.78 | 0.372 | |
| DP0343.12 | 36 | 19 | 4.95 | −0.93 | 0.285 | | 1.27 | 0.142 | |
| DP0343.16 | 36 | 20 | 4.51 | −1.37 | 0.111 | | 0.82 | 0.330 | |
| DP0343.17 | 36 | 19 | 5.89 | 0.01 | 0.992 | | 2.21 | 0.009 | |
| DP0343.18 | 36 | 20 | 4.34 | −1.54 | 0.073 | Y | 0.66 | 0.445 | |
| DP0343.20 | 35 | 19 | 3.71 | −2.17 | 0.010 | Y | 0.03 | 0.969 | |

The second experiment was performed in Ningxia province; the same twelve OsMFS9 transgenic lines were tested. Watering was stopped when 20% of the main stem panicles reached panicle initiation stage II. 18 days later, the main stem panicles reached panicle initiation stage V, the tiller panicles reached panicle initiation stage IV, and the rice plants begun to show leaf rolling phenotype. The soil volumetric water content decreased from 47% to 12% during this process (FIG. 6). The rice plants reached heading stage 46 days after stopping watering. Two transgenic lines DP0343.01 and DP0343.16 showed drought sensitive phenotypes such as leaf rolling and dry leaf compared the ZH11-TC and DP0158 rice plants, during the drought stress. OsMFS9 transgenic rice exhibited greater grain yield per plant than ZH11-TC and DP0158 control plants at the construct level. As shown in Table 14, eight OsMFS9 transgenic lines had less grain yields per plant than ZH11-TC control. These results indicate that OsMFS9 rice plant is sensitive to drought at vegetable stage.

TABLE 14

Grain yield analysis of OsMFS9 transgenic rice plants under field drought conditions ($2^{nd}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0343 (Construct) | | | 2.86 | 0.14 | 0.828 | | 1.70 | 0.024 | |
| ZH11-TC | 40 | 18 | 2.72 | | | | | | |
| DP0158 | 40 | 12 | 1.15 | | | | | | |
| DP0343.01 | 40 | 12 | 2.09 | −0.63 | 0.374 | | 0.94 | 0.256 | |
| DP0343.02 | 37 | 12 | 3.21 | 0.49 | 0.490 | | 2.06 | 0.014 | |
| DP0343.03 | 40 | 14 | 4.67 | 1.95 | 0.008 | | 3.52 | 0.000 | |
| DP0343.06 | 34 | 12 | 5.39 | 2.67 | 0.001 | | 4.24 | 0.000 | |
| DP0343.07 | 40 | 14 | 1.53 | −1.19 | 0.089 | Y | 0.38 | 0.655 | |
| DP0343.08 | 34 | 14 | 1.82 | −0.90 | 0.224 | | 0.67 | 0.431 | |
| DP0343.10 | 38 | 17 | 3.85 | 1.13 | 0.113 | | 2.70 | 0.001 | |
| DP0343.12 | 37 | 14 | 2.22 | −0.50 | 0.503 | | 1.07 | 0.214 | |
| DP0343.16 | 38 | 18 | 2.21 | −0.51 | 0.465 | | 1.05 | 0.200 | |
| DP0343.17 | 39 | 18 | 2.63 | −0.09 | 0.895 | | 1.47 | 0.082 | |
| DP0343.18 | 40 | 16 | 2.03 | −0.69 | 0.283 | | 0.88 | 0.287 | |
| DP0343.20 | 40 | 12 | 2.61 | −0.11 | 0.885 | | 1.45 | 0.075 | |

5) Field DRT Validation Results of OsLAO1 Over-Expressed (DP0451) Transgenic Rice Twelve OsLAO1 transgenic lines were tested in Hainan Province in the first experiment. Watering was stopped when the main stem panicles reached panicle initiation stage III. 23 days after stopping watering, the main stem panicles headed out, the tiller panicles were at panicle initiation stage VII, and the rice plants started to show leaf rolling phenotype. During this process, the soil volumetric water content decreased from 26% to 10% (FIG. 8). 40 days after stopping watering, the rice plants were at heading stage, and the soil water content decreased to 5%. Three transgenic rice lines DP0451.07, DP0451.08 and DP0451.12 showed drought sensitive phenotypes such as leaf rolling and less greenness. The grain yields per plant were measured and were shown in Table 15. The OsLAO1 transgenic rice plants showed greater grain yield per plant than ZH11-TC and DP0158 control plants at the construct level. These results demonstrate that OsLAO1 transgenic rice plant showed drought sensitive phenotype at the vegetative stage after drought stress.

TABLE 15

Grain yield analysis of OsLAO1 transgenic rice plants under field drought conditions (1st experiment)

| Line ID | Number of survived plants | Number of harvested plants | Yield per plant (g) | CK = ZH11-TC | | | CK = DP0158 | | |
| --- | --- | --- | --- | --- | --- | --- | --- | --- | --- |
| | | | | Diff | P value | P ≤ 0.1 | Diff | P value | P ≤ 0.1 |
| DP0451 (Construct) | | | 2.78 | 0.19 | 0.769 | | 1.06 | 0.097 | |
| ZH11-TC | 36 | 20 | 2.59 | | | | | | |
| DP0158 | 36 | 20 | 1.71 | | | | | | |
| DP0451.01 | 36 | 20 | 2.94 | 0.35 | 0.644 | | 1.22 | 0.103 | |
| DP0451.02 | 36 | 20 | 2.14 | −0.45 | 0.552 | | 0.43 | 0.558 | |
| DP0451.03 | 36 | 20 | 4.44 | 1.86 | 0.014 | | 2.73 | 0.000 | |
| DP0451.04 | 36 | 20 | 2.38 | −0.21 | 0.779 | | 0.67 | 0.374 | |
| DP0451.05 | 36 | 20 | 3.18 | 0.60 | 0.416 | | 1.47 | 0.049 | |
| DP0451.07 | 36 | 19 | 2.36 | −0.23 | 0.754 | | 0.65 | 0.385 | |
| DP0451.08 | 36 | 19 | 2.60 | 0.02 | 0.983 | | 0.89 | 0.219 | |
| DP0451.09 | 36 | 19 | 3.09 | 0.50 | 0.489 | | 1.38 | 0.062 | |
| DP0451.12 | 36 | 20 | 1.77 | −0.81 | 0.278 | | 0.06 | 0.933 | |
| DP0451.13 | 36 | 20 | 2.71 | 0.12 | 0.871 | | 1.00 | 0.184 | |
| DP0451.14 | 36 | 20 | 3.13 | 0.54 | 0.474 | | 1.41 | 0.056 | |
| DP0451.15 | 36 | 19 | 2.57 | −0.02 | 0.977 | | 0.86 | 0.252 | |

The second experiment was performed in Ningxia province; the same twelve OsLAO1 transgenic lines were tested. Watering was stopped when 20% of the main stem panicles reached panicle initiation stage II. 18 days later, the main stem panicles reached panicle initiation stage VI, the tiller panicles reached panicle initiation stage V, and the rice plants begun to show leaf rolling phenotype. The soil volumetric water content decreased from 45% to 12% during this process (FIG. 9). The rice plants reached heading stage 46 days after stopping watering. OsLAO1 transgenic rice exhibited greater grain yield per plant than ZH11-TC and DP0158 control plants at the construct level. As shown in Table 16, three OsLAO1 transgenic lines had less grain yields per plant than ZH11-TC control, and nine lines had less grain yields per plant than DP0158 control. These results indicate that OsLAO1 rice plant may be sensitive to drought.

TABLE 16

Grain yield analysis of OsLAO1 transgenic rice plants under field drought conditions (2nd experiment)

| Line ID | Number of survived plants | Number of harvested plants | Yield per plant (g) | CK = ZH11-TC | | | CK = DP0158 | | |
| --- | --- | --- | --- | --- | --- | --- | --- | --- | --- |
| | | | | Diff | P value | P ≤ 0.1 | Diff | P value | P ≤ 0.1 |
| DP0451 (Construct) | | | 2.38 | 0.45 | 0.536 | | 0.03 | 0.968 | |
| ZH11-TC | 40 | 22 | 1.93 | | | | | | |
| DP0158 | 39 | 18 | 2.35 | | | | | | |
| DP0451.01 | 39 | 24 | 3.56 | 1.62 | 0.053 | | 1.21 | 0.192 | |
| DP0451.02 | 40 | 24 | 2.14 | 0.21 | 0.804 | | −0.21 | 0.822 | |
| DP0451.03 | 39 | 24 | 2.09 | 0.16 | 0.854 | | −0.26 | 0.776 | |

TABLE 16-continued

Grain yield analysis of OsLAO1 transgenic rice plants under field drought conditions
(2$^{nd}$ experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0451.04 | 39 | 16 | 1.82 | −0.11 | 0.903 | | −0.52 | 0.584 | |
| DP0451.05 | 39 | 23 | 3.57 | 1.63 | 0.049 | | 1.22 | 0.182 | |
| DP0451.07 | 40 | 15 | 2.04 | 0.11 | 0.895 | | −0.31 | 0.748 | |
| DP0451.08 | 40 | 24 | 1.92 | −0.01 | 0.988 | | −0.43 | 0.642 | |
| DP0451.09 | 40 | 24 | 2.31 | 0.38 | 0.654 | | −0.04 | 0.966 | |
| DP0451.12 | 40 | 12 | 2.09 | 0.16 | 0.863 | | −0.25 | 0.802 | |
| DP0451.13 | 39 | 24 | 1.72 | −0.21 | 0.805 | | −0.63 | 0.499 | |
| DP0451.14 | 40 | 24 | 2.99 | 1.06 | 0.207 | | 0.64 | 0.473 | |
| DP0451.15 | 40 | 21 | 2.33 | 0.40 | 0.636 | | −0.02 | 0.983 | |

6) Field DRT Validation Results of OsDN-DSP1 Over-Expressed (DP0505) Transgenic Rice Twelve OsDN-DSP1 transgenic rice plants were tested in Hainan field. ZH11-TC and DP0158 rice plants planted were used as control. Watering was stopped when the main stem panicles were at panicle initiation stage IV and the tiller panicles were at panicle initiation stage I. The rice plants began to show leaf rolling phenotype 19 days after stopping watering, and the main stem panicles reached panicle initiation stage VIII. The rice plants started heading after stopping watering for 37 days. The soil volumetric water content decreased from 35% to 10% during the main stem panicle heading stage (FIG. 3). The OsDN-DSP1 transgenic lines showed increased leaf rolling degrees and less green leaf than ZH11-TC and DP0158 controls except DP0505.05, DP0505.08 and DP0505.09.

The grain yield per plant was measured. As shown in Table 17, the grain yield per plant of OsDN-DSP1 transgenic rice was significantly less than ZH11-TC and less than DP0158 control at the construct level. All the OsDN-DSP1 transgenic lines exhibited less grain yield per plant than ZH11-TC and eight lines less than DP0158 controls. These results indicate that OsDN-DSP1 transgenic rice plant is sensitive to drought condition and over-expression of OsDN-DSP1 increased drought sensitive at vegetative stage and resulted in decreased grain yield per plant after drought stress at flowering stage.

TABLE 17

Grain yield analysis of OsDN-DSP1 transgenic rice plants under field drought conditions
(1$^{st}$ experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0505 (Construct) | | | 3.12 | −4.09 | 0.000 | Y | −0.09 | 0.876 | |
| ZH11-TC | 38 | 24 | 7.20 | | | | | | |
| DP0158 | 40 | 24 | 3.21 | | | | | | |
| DP0505.01 | 39 | 24 | 3.11 | −4.09 | 0.000 | Y | −0.10 | 0.879 | |
| DP0505.02 | 39 | 24 | 1.39 | −5.82 | 0.000 | Y | −1.82 | 0.006 | Y |
| DP0505.03 | 40 | 22 | 2.98 | −4.23 | 0.000 | Y | −0.23 | 0.726 | |
| DP0505.04 | 40 | 25 | 2.37 | −4.84 | 0.000 | Y | −0.84 | 0.198 | |
| DP0505.05 | 40 | 24 | 5.17 | −2.03 | 0.001 | | 1.96 | 0.003 | |
| DP0505.07 | 40 | 24 | 2.70 | −4.50 | 0.000 | Y | −0.51 | 0.413 | Y |
| DP0505.08 | 40 | 25 | 3.81 | −3.40 | 0.000 | Y | 0.60 | 0.363 | |
| DP0505.09 | 40 | 24 | 4.70 | −2.50 | 0.000 | Y | 1.49 | 0.019 | |
| DP0505.11 | 40 | 24 | 3.48 | −3.72 | 0.000 | Y | 0.27 | 0.666 | |
| DP0505.12 | 40 | 23 | 3.15 | −4.05 | 0.000 | Y | −0.06 | 0.930 | |
| DP0505.13 | 39 | 24 | 2.49 | −4.71 | 0.000 | Y | −0.72 | 0.257 | |
| DP0505.15 | 40 | 24 | 2.06 | −5.15 | 0.000 | Y | −1.15 | 0.071 | Y |

The second experiment was performed in Ningxia province, and the same 12 OsOPPL1 transgenic lines were tested. Watering was stopped when 20% of the main stem panicles reached panicle initiation stage II. 18 days later, the main stem panicles reached panicle initiation stage V, the tiller panicles reached panicle initiation stage IV. The soil volumetric water content decreased from 45% to 10% during heading stage (FIG. 9). The rice plants showed stressed phenotype. The same nine OsDN-DSP1 transgenic rice lines showed greater leaf rolling degree and less greenness during drought stress. The grain yield analysis showed that the OsDN-DSP1 transgenic rice exhibited significantly less grain yield per plant than ZH11-TC and little greater grain yield per plant than DP0158 control at the construct level. At the transgenic line level, all the twelve transgenic lines exhibited significantly less grain yields per plant than ZH11-TC control and six lines showed less grain yield per plant than DP0158 rice plants (Table 18). These results further indicate that OsDN-DSP1 transgenic rice plant were drought sensitive during the vegetative stage; over-expression of OsDN-DSP1 resulted in lower grain yield per plant after drought stress.

TABLE 18

Grain yield analysis of OsDN-DSP1 transgenic rice plants under field drought conditions ($2^{nd}$ experiment)

| Line ID | Number of survived plants | Number of harvested plants | Yield per plant (g) | CKZH11-TC Diff | P value | P ≤ 0.1 | CK = DP0158 Diff | P value | P ≤ 0.1 |
|---|---|---|---|---|---|---|---|---|---|
| DP0505 (Construct) | | | 2.19 | −3.33 | 0.000 | Y | 0.15 | 0.843 | |
| ZH11-TC | 40 | 24 | 5.51 | | | | | | |
| DP0158 | 36 | 24 | 2.04 | | | | | | |
| DP0505.01 | 40 | 12 | 2.28 | −3.24 | 0.001 | Y | 0.24 | 0.804 | |
| DP0505.02 | 40 | 12 | 1.64 | −3.87 | 0.000 | Y | −0.40 | 0.679 | |
| DP0505.03 | 40 | 12 | 2.06 | −3.46 | 0.000 | Y | 0.02 | 0.983 | |
| DP0505.04 | 31 | 12 | 2.01 | −3.50 | 0.000 | Y | −0.02 | 0.982 | |
| DP0505.05 | 40 | 24 | 3.61 | −1.90 | 0.024 | Y | 1.58 | 0.061 | |
| DP0505.07 | 40 | 12 | 1.79 | −3.73 | 0.000 | Y | −0.25 | 0.794 | |
| DP0505.08 | 39 | 18 | 2.87 | −2.65 | 0.003 | Y | 0.83 | 0.337 | |
| DP0505.09 | 39 | 18 | 2.98 | −2.53 | 0.004 | Y | 0.94 | 0.281 | |
| DP0505.11 | 40 | 12 | 2.52 | −3.00 | 0.002 | Y | 0.48 | 0.618 | |
| DP0505.12 | 39 | 12 | 1.61 | −3.90 | 0.000 | Y | −0.43 | 0.656 | |
| DP0505.13 | 37 | 12 | 1.46 | −4.05 | 0.000 | Y | −0.58 | 0.546 | |
| DP0505.15 | 38 | 12 | 1.42 | −4.09 | 0.000 | Y | −0.61 | 0.522 | |

Example 5

Drought Screening of Transgenic Rice Plants in Greenhouse

The transgenic rice plants were screened in greenhouse drought assays. Two types of lamps were provided as light source, i.e. sodium lamp and metal halide lamp with the ratio of 1:1. Lamps provided the 16 h/8 h period of day/night, and were placed approximately 1.5 m above the seedbed. The light intensity 30 cm above the seedbed was measured as 10,000-20,000 lx in sunny day, while 6,000-10,000 lx in cloudy day, the relative humidity ranged from 30% to 90%, and the temperature ranged from 20 to 35° C.

Drought Screening Method:

T2 Transgenic seeds were sterilized by 800 ppm carbendazol for 8 h at 32° C. and washed 3-5 times with distilled water, then soaked in water for 16 h at 32° C., germinated for 18 h at 35-37° C. in an incubator. The germinated seeds were sowed in one tray filled with mixture of organic soil, vermiculite and sand (V:V:V=3:3:2). The seedlings were grown under normal greenhouse condition and watered by modified IRRI solution. After all the seedlings grew to 3-leaf stage, watering was stopped and the trays were kept in a dry place until the leaves became dry and curved (approximately 9-15 days depending on the seasons). The trays were transferred into water pool to recover the seedlings for 5-7 days, and then plants were scored for the degree of recovery. The following scoring system was used: more than half green stem=1, more than two third green leaf=1, less than two third but more than one third green leaf=0.5, less than one third green leaf=0.2, no green leaf or less than half green stem=0. The recovery degree was the sum of the score of the green tissues, and the data were statistically analyzed using Mixed Model. The lines which showed significant better than controls (P<0.05) were considered as positive ones. Survival rate (percentage of survived plants over the total plant number) was also used as a parameter for drought screening.

Randomized block design was used for validating the drought tolerance or sensitivity of the transformed rice from construct level. The wild-type control (Zhonghua 11) from tissue culture procedure (ZH11-TC) and/or empty vector (DP0158) transgenic control in the same were used as controls. 9-12 transgenic lines from the same construct were planted in one experimental unit to evaluate the transgene at construct level by Mixed Model considering construct, line and environment effects. If the survival rates or recovery degrees of the transgenic rice plants were significantly greater or lower than control (P<0.05), the gene was considered having drought tolerant function or was considered to resulted in drought sensitive.

GH Drought Assay Results:

1) GH DRT Validation Results of OsPRP1 Over-Expressed (DP0086) Transgenic Rice

Nine OsPRP1 transgenic lines were tested in the first experiment and repeated for twice. When the plants grew to 3-leaf stage, the plants were removed to a dry place. 17 days later, the leaf of the plants curved and was dry, these plants were transferred into water and recovered for 5 days, and then the recovery degrees were counted. Table 19 shows that OsPRP1 transgenic rice had lower survival rates and significantly lower recovery degrees than ZH11-TC and DP0158 control plants at the construct level. Seven OsPRP1 transgenic lines showed lower survival rates and six transgenic lines showed significantly lower recovery degrees than both ZH11-TC and DP0158 control plants at the line level. These results indicate that OsPRP1 transgenic rice were drought sensitive.

TABLE 19

Drought tolerance assay of OsPRP1 transgenic rice plants under greenhouse conditions (1st experiment)

| Line ID | Number of survived plants | Number of total plants | Survival rate (%) | Average recovery degree | CK = ZH11-TC P value | CK = ZH11-TC P ≤ 0.05 | CK = DP0158 P value | CK = DP0158 P ≤ 0.05 |
|---|---|---|---|---|---|---|---|---|
| DP0086 (Construct) | 92 | 216 | 42.6 | 0.48 | 0.0013 | Y | 0.0203 | Y |
| ZH11-TC | 29 | 48 | 60.4 | 0.84 | | | | |
| DP0158 | 14 | 24 | 58.3 | 0.81 | | | | |
| DP0086.01 | 7 | 24 | 29.2 | 0.37 | 0.0006 | Y | 0.0069 | Y |
| DP0086.02 | 8 | 24 | 33.3 | 0.40 | 0.0011 | Y | 0.0108 | Y |
| DP0086.05 | 6 | 24 | 25.0 | 0.34 | 0.0003 | Y | 0.0039 | Y |
| DP0086.06 | 9 | 24 | 37.5 | 0.42 | 0.0019 | Y | 0.0152 | Y |
| DP0086.07 | 12 | 24 | 50.0 | 0.50 | 0.0129 | Y | 0.0565 | |
| DP0086.25 | 10 | 24 | 41.7 | 0.48 | 0.0080 | Y | 0.0409 | Y |
| DP0086.27 | 14 | 24 | 58.3 | 0.67 | 0.2223 | | 0.3943 | |
| DP0086.33 | 10 | 24 | 41.7 | 0.46 | 0.0052 | Y | 0.0302 | Y |
| DP0086.36 | 16 | 24 | 66.7 | 0.67 | 0.2088 | | 0.3775 | |

In the second experiment, and the same nine lines were tested. When grown to 3-leaf stage, the plants were first drought stressed for 20 days and recovered in water for five days, and then were drought stressed for another 17 days. After recovered in water for 5 days, the recovery degrees were scored. As shown in Table 20, 52 of the 108 OsPRP1 transgenic seedlings survived, and the survival rate and recovery degree of OsPRP1 transgenic rice was lower than ZH11-TC control and DP0158 control at construct level. Analysis at transgenic line level showed that eight lines exhibited lower survival rates than both ZH11-TC and DP0158 controls, and seven lines exhibited lower recovery degrees than both ZH11-TC and DP0158 controls (Table 20). These results further demonstrate that OsPRP1 transgenic plants are drought sensitive, and over-expression of OsPRP1 gene resulted drought sensitive in plant.

TABLE 20

Drought tolerance assay of OsPRP1 transgenic rice plants under greenhouse conditions (2nd experiment)

| Line ID | Number of survived plants | Number of total plants | Survival rate (%) | Average recovery degree | CK = ZH11-TC P value | CK = ZH11-TC P ≤ 0.05 | CK = DP0158 P value | CK = DP0158 P ≤ 0.05 |
|---|---|---|---|---|---|---|---|---|
| DP0086 (Construct) | 52 | 108 | 48.1 | 0.61 | 0.0000 | Y | 0.0036 | Y |
| ZH11-TC | 20 | 24 | 83.3 | 1.30 | | | | |
| DP0158 | 10 | 12 | 83.3 | 1.23 | | | | |
| DP0086.01 | 4 | 12 | 33.3 | 0.45 | 0.0000 | Y | 0.0012 | Y |
| DP0086.02 | 4 | 12 | 33.3 | 0.50 | 0.0001 | Y | 0.0024 | Y |
| DP0086.05 | 5 | 12 | 41.7 | 0.51 | 0.0001 | Y | 0.0027 | Y |
| DP0086.06 | 6 | 12 | 50.0 | 0.54 | 0.0002 | Y | 0.0046 | Y |
| DP0086.07 | 7 | 12 | 58.3 | 0.70 | 0.0030 | Y | 0.0289 | Y |
| DP0086.25 | 3 | 12 | 25.0 | 0.45 | 0.0000 | Y | 0.0012 | Y |
| DP0086.27 | 10 | 12 | 83.3 | 0.96 | 0.0923 | | 0.2665 | |
| DP0086.33 | 5 | 12 | 41.7 | 0.59 | 0.0005 | Y | 0.0085 | Y |
| DP0086.36 | 8 | 12 | 66.7 | 0.79 | 0.0105 | Y | 0.0657 | |

2) GH DRT Validation Results of OsPP2C64 Over-Expressed (DP0297) Transgenic Rice Nine OsPP2C64 transgenic lines were tested. When the rice plants grew to 3-leaf stage, the plants were removed to a dry place. 16 days later, the rice plants were placed in water and were recovered for about six days. Table 21 shows that the OsPP2C64 transgenic plants showed lower survival rate and recovery degree than ZH11-TC plants and higher than DP0158 plants at the construct level. Five lines showed lower survival rates and significantly lower recovery degrees than ZH11-TC control. These results indicate that OsPP2C64 transgenic rice was sensitive to drought condition.

TABLE 21

Drought tolerance assay of OsPP2C64 transgenic rice plants under greenhouse conditions

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0297 (Construct) | 94 | 216 | 43.52 | 0.50 | 0.0231 | Y | 0.2174 | |
| ZH11-TC | 30 | 48 | 62.50 | 0.74 | | | | |
| DP0158 | 8 | 24 | 33.33 | 0.33 | | | | |
| DP0297.01 | 15 | 24 | 62.50 | 0.68 | 0.6418 | | 0.0241 | |
| DP0297.07 | 10 | 24 | 41.67 | 0.46 | 0.0257 | Y | 0.4272 | |
| DP0297.10 | 8 | 24 | 33.33 | 0.44 | 0.0195 | Y | 0.4795 | |
| DP0297.11 | 11 | 24 | 45.83 | 0.50 | 0.0553 | | 0.2917 | |
| DP0297.15 | 9 | 24 | 37.50 | 0.44 | 0.0195 | Y | 0.4795 | |
| DP0297.16 | 15 | 24 | 62.50 | 0.61 | 0.3223 | | 0.0686 | |
| DP0297.18 | 8 | 24 | 33.33 | 0.45 | 0.0214 | Y | 0.4617 | |
| DP0297.20 | 6 | 24 | 25.00 | 0.38 | 0.0047 | Y | 0.7627 | |
| DP0297.21 | 12 | 24 | 50.00 | 0.55 | 0.1438 | | 0.1525 | |

3) GH DRT Validation Results of OsOPPL1 Over-Expressed (DP0328) Transgenic Rice

Nine OsOPPL1 transgenic lines were tested with two repeats. When the plants grew to 3-leaf stage, the water was withdrawn for 20 days, and the plants were recovered in water for seven days. As shown in Table 22, the OsOPPL1 transgenic rice exhibited lower survival rate and recovery degree than both ZH11-TC and DP0158 controls at the construct level. Six OsOPPL1 transgenic lines showed lower survival rates and recovery degrees at the line level. These results indicate that OsOPPL1 transgenic rice may sensitive to drought conditions at seedling stage.

TABLE 22

Drought tolerance assay of OsOPPL1 transgenic rice plants under greenhouse conditions ($1^{st}$ experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0328 (Construct) | 81 | 216 | 37.5 | 0.60 | 0.1095 | | 0.0689 | |
| ZH11-TC | 24 | 48 | 50.0 | 0.86 | | | | |
| DP0158 | 14 | 24 | 58.3 | 0.97 | | | | |
| DP0328.12 | 4 | 24 | 16.7 | 0.29 | 0.0038 | Y | 0.0034 | Y |
| DP0328.15 | 13 | 24 | 54.2 | 0.68 | 0.3589 | | 0.2089 | |
| DP0328.17 | 14 | 24 | 58.3 | 0.73 | 0.5170 | | 0.3035 | |
| DP0328.21 | 13 | 24 | 54.2 | 0.83 | 0.8659 | | 0.5323 | |
| DP0328.25 | 11 | 24 | 45.8 | 0.76 | 0.5870 | | 0.3470 | |
| DP0328.30 | 2 | 24 | 8.3 | 0.23 | 0.0014 | Y | 0.0015 | Y |
| DP0328.31 | 5 | 24 | 20.8 | 0.41 | 0.0209 | Y | 0.0150 | Y |
| DP0328.32 | 8 | 24 | 33.3 | 0.59 | 0.1625 | | 0.0967 | |
| DP0328.44 | 11 | 24 | 45.8 | 0.85 | 0.9490 | | 0.5920 | |

In the second experiment, the plants were drought stressed for 42 days and recovered in water for five days. As shown in Table 23, OsOPPL1 transgenic rice exhibited slightly lower survival rate and recovery degree than ZH11-TC control and DP0158 control at construct level. Analysis at the transgenic line level showed that the difference among the OsOPPL1 transgenic lines, ZH11-TC and DP0158 were not reaching significant level. These results further demonstrate that OsOPPL1 transgenic rice didn't have drought tolerance at seedling stage.

TABLE 23

Drought tolerance assay of OsOPPL1 transgenic rice plants under greenhouse conditions ($2^{nd}$ experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0328 (Construct) | 61 | 108 | 56.5 | 0.57 | 0.9050 | | 0.7318 | |
| ZH11-TC | 14 | 24 | 58.3 | 0.58 | | | | |
| DP0158 | 7 | 12 | 58.3 | 0.63 | | | | |
| DP0328.12 | 3 | 12 | 25.0 | 0.48 | 0.4723 | | 0.4213 | |
| DP0328.15 | 8 | 12 | 66.7 | 0.60 | 0.9321 | | 0.8684 | |
| DP0328.17 | 5 | 12 | 41.7 | 0.53 | 0.6911 | | 0.5830 | |
| DP0328.21 | 8 | 12 | 66.7 | 0.60 | 0.9321 | | 0.8684 | |
| DP0328.25 | 9 | 12 | 75.0 | 0.62 | 0.7808 | | 0.9902 | |
| DP0328.30 | 6 | 12 | 50.0 | 0.55 | 0.8134 | | 0.6739 | |
| DP0328.32 | 8 | 12 | 66.7 | 0.60 | 0.9321 | | 0.8684 | |
| DP0328.44 | 5 | 12 | 41.7 | 0.53 | 0.6911 | | 0.5830 | |
| DP0328.49 | 9 | 12 | 75.0 | 0.62 | 0.7808 | | 0.9902 | |

4) GH DRT Validation Results of OsMFS9 Over-Expressed (DP0343) Transgenic Rice

Nine OsMFS9 transgenic lines were tested. When the plants grew to 3-leaf stage, the plants were transferred to a dry place without watering for 16 days, and then the plants were recovered in water for seven days. Table 24 shows the OsMFS9 transgenic plants exhibited lower survival rate and recovery degree than both ZH11-TC and DP0158 controls at the construct level. Six transgenic lines exhibited lower survival rates and eight lines exhibited lower recovery degrees at the line level. These results indicate that OsMFS9 transgenic rice plants were sensitive to drought conditions at seedling stage.

TABLE 24

Drought tolerance assay of OsMFS9 transgenic rice plants under greenhouse conditions

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0343 (Construct) | 53 | 108 | 49.1 | 0.88 | 0.0670 | | 0.1944 | |
| ZH11-TC | 16 | 24 | 66.7 | 1.21 | | | | |
| DP0158 | 8 | 12 | 66.7 | 1.18 | | | | |
| DP0343.01 | 11 | 12 | 91.2 | 1.20 | 0.9501 | | 0.9550 | |
| DP0343.03 | 2 | 12 | 16.7 | 0.68 | 0.0179 | Y | 0.0631 | |
| DP0343.07 | 4 | 12 | 33.3 | 0.69 | 0.0189 | Y | 0.0656 | |
| DP0343.08 | 8 | 12 | 66.7 | 0.95 | 0.2490 | | 0.3960 | |
| DP0343.09 | 4 | 12 | 33.3 | 0.76 | 0.0420 | Y | 0.1141 | |
| DP0343.17 | 6 | 12 | 50.0 | 0.79 | 0.0592 | | 0.1448 | |
| DP0343.18 | 9 | 12 | 75.0 | 1.10 | 0.6298 | | 0.7704 | |
| DP0343.19 | 3 | 12 | 25.0 | 0.81 | 0.0748 | | 0.1704 | |
| DP0343.20 | 6 | 12 | 50.0 | 0.88 | 0.1424 | | 0.2670 | |

5) GH DRT Validation Results of OsLAO1 Over-Expressed (DP0451) Transgenic Rice

Nine OsLAO1 transgenic lines were tested. When the plants grew to 3-leaf stage, the plants were removed to a dry place. 16 days later, the plants were recovered in water for five days, and the recovery degrees were counted. Table 25 shows that OsLAO1 transgenic rice exhibited lower survival rate and recovery degree at the construct level. The differences among eight transgenic lines, ZH11-TC and DP0158 control didn't reach the significant level. These results indicate that OsLAO1 transgenic rice plants were not drought tolerance plants.

TABLE 25

Drought tolerance assay of OsLAO1 transgenic rice plants under greenhouse conditions ($1^{st}$ experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0451 (Construct) | 82 | 108 | 75.9 | 0.91 | 0.1442 | | 0.1356 | |
| ZH11-TC | 18 | 24 | 75.0 | 1.11 | | | | |
| DP0158 | 10 | 12 | 83.3 | 1.18 | | | | |
| DP0451.01 | 9 | 12 | 75.0 | 0.91 | 0.2133 | | 0.1759 | |
| DP0451.03 | 11 | 12 | 91.7 | 1.06 | 0.7504 | | 0.5516 | |
| DP0451.04 | 8 | 12 | 66.7 | 0.81 | 0.0648 | | 0.0648 | |
| DP0451.06 | 9 | 12 | 75.0 | 0.86 | 0.1338 | | 0.1182 | |
| DP0451.07 | 9 | 12 | 75.0 | 0.88 | 0.1527 | | 0.1322 | |
| DP0451.08 | 7 | 12 | 58.3 | 0.77 | 0.0376 | Y | 0.0417 | Y |
| DP0451.10 | 9 | 12 | 75.0 | 0.94 | 0.3000 | | 0.2367 | |
| DP0451.13 | 9 | 12 | 75.0 | 0.91 | 0.2307 | | 0.1882 | |
| DP0451.14 | 11 | 12 | 91.7 | 1.06 | 0.7682 | | 0.5644 | |

In the second experiment, the transgenic rice plant, ZH11-TC and DP0158 rice plants were drought stressed for 20 days, and recovered in water for five days. As shown in Table 26, 51 of the 95 OsLAO1 transgenic rice plants survived, while 20 of the 24 ZH11-TC seedlings and all the DP0158 seedlings survived. The OsLAO1 transgenic rice exhibited lower survival rate and significantly lower recovery degree than both ZH11-TC and DP0158 controls at construct level. Analysis at line level showed that all the nine lines exhibited lower survival rates and average recovery degrees than both ZH11-TC and DP0158 controls. These results demonstrate that OsLAO1 transgenic rice plants were drought sensitive and over-expression of OsLAO1 gene may resulted in increasing drought sensitive in plant.

TABLE 26

Drought tolerance assay of OsLAO1 transgenic rice plants under greenhouse conditions ($2^{nd}$ experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0451 (Construct) | 51 | 95 | 53.7 | 0.56 | 0.0100 | Y | 0.0015 | Y |
| ZH11-TC | 20 | 24 | 83.3 | 0.83 | | | | |
| DP0158 | 12 | 12 | 100.0 | 1.00 | | | | |
| DP0451.01 | 7 | 12 | 58.3 | 0.57 | 0.0437 | Y | 0.0065 | Y |
| DP0451.03 | 9 | 12 | 75.0 | 0.66 | 0.1750 | | 0.0297 | Y |
| DP0451.04 | 8 | 11 | 72.7 | 0.66 | 0.1750 | | 0.0297 | Y |
| DP0451.06 | 2 | 12 | 16.7 | 0.35 | 0.0002 | Y | 0.0000 | Y |
| DP0451.07 | 7 | 12 | 58.3 | 0.57 | 0.0437 | Y | 0.0065 | Y |
| DP0451.08 | 6 | 12 | 50.0 | 0.53 | 0.0189 | Y | 0.0028 | Y |
| DP0451.10 | 7 | 12 | 58.3 | 0.57 | 0.0437 | Y | 0.0065 | Y |
| DP0451.13 | 5 | 12 | 41.7 | 0.48 | 0.0074 | Y | 0.0011 | Y |
| DP0451.14 | 8 | 12 | 66.7 | 0.61 | 0.0917 | | 0.0144 | Y |

6) GH DRT Validation Results of OsDN-DSP1 Over-Expressed (DP0505) Transgenic Rice Nine transgenic lines, ZH11-TC and DP0158 plants were planted. When grew to 3-leaf stage, the plants were drought stressed for 16 days, recovered in water for five days. 90 of the 216 OsDN-DSP1 transgenic rice survived, while 43 of the 48 ZH11-TC and 17 of the 24 DP0158 seedlings survived. OsDN-DSP1 transgenic rice exhibited lower survival rate and exhibited significantly lower average recovery degree than both ZH11-TC and DP0158 seedlings (Table 27). Analysis at line level showed that six lines exhibited lower survival rates and average recovery degrees than both controls. These results demonstrate that OsDN-DSP1 transgenic rice plants were sensitive to drought conditions.

TABLE 27

Drought tolerance assay of OsDN-DSP1 transgenic rice plants under greenhouse conditions

| Line ID | Number of survived plants | Number of total plants | Survival rate (%) | Average recovery degree | CK = ZH11-TC | | CK = DP0158 | |
|---|---|---|---|---|---|---|---|---|
| | | | | | P value | P ≤ 0.05 | P value | P ≤ 0.05 |
| DP0505 (Construct) | 90 | 216 | 41.7 | 0.55 | 0.0000 | Y | 0.0081 | Y |
| ZH11-TC | 43 | 48 | 89.6 | 1.42 | | | | |
| DP0158 | 17 | 24 | 70.8 | 1.11 | | | | |
| DP0505.03 | 4 | 24 | 16.7 | 0.18 | 0.0000 | Y | 0.0000 | Y |
| DP0505.05 | 21 | 24 | 87.5 | 1.28 | 0.3253 | | 0.2731 | |
| DP0505.08 | 22 | 24 | 91.7 | 1.33 | 0.5101 | | 0.1686 | |
| DP0505.09 | 19 | 24 | 79.2 | 1.09 | 0.0150 | Y | 0.8779 | |
| DP0505.10 | 5 | 24 | 20.8 | 0.23 | 0.0000 | Y | 0.0000 | Y |
| DP0505.12 | 5 | 24 | 20.8 | 0.22 | 0.0000 | Y | 0.0000 | Y |
| DP0505.13 | 5 | 24 | 20.8 | 0.22 | 0.0000 | Y | 0.0000 | Y |
| DP0505.14 | 6 | 24 | 25.0 | 0.26 | 0.0000 | Y | 0.0000 | Y |
| DP0505.15 | 3 | 24 | 12.5 | 0.14 | 0.0000 | Y | 0.0000 | Y |

Example 6

Laboratory Paraquat Assays of Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress and cold stress usually leads to increased reactive oxygen species (ROS) in plants and sometimes, the drought and/or cold tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant and cold tolerant transgenic rice plants was tested.

Paraquat Assay Methods:

Transgenic rice plants from eight to ten transgenic lines were tested by paraquat assay. Tissue-cultured Zhonghua 11 plants (ZH11-TC) and empty vector transgenic plants (DP0158) were used as controls. T2 transgenic seeds were sterilized and germinated as described in Example 4, and this assay was carried out in growth room with temperature at 28-30° C. and humidity ~30%. The germinated seeds were placed in a tube with a hole at the bottom, and water cultured at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 µM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS® PROC GLIMMIX".

Paraquat Assay Results:

1) Paraquat Validation Results of OsPRP1 Over-Expressed (DP0086) Transgenic Rice Plants In the first experiment, after paraquat solution treated for seven days, 194 of the 600 OsPRP1 transgenic seedlings (32%) kept green and showed tolerant phenotype, while 90 of the 180 (50%) seedlings from ZH11-TC showed tolerant phenotype, and 66 of the 180 (37%) DP0158 seedlings showed tolerant phenotype. The tolerance rate of all screened OsPRP1 transgenic seedlings was significantly lower than ZH11-TC control (P value=0.0000) and lower than DP0158 control (P value=0.2883).

Further analysis at transgenic line level indicates that nine lines had lower tolerance rates compared with ZH11-TC control, and six lines had lower tolerance rates than DP0158 control (Table 28). These results demonstrate that OsPRP1 transgenic rice plants were not tolerance to Paraquat condition at seedling stages. OsPRP1 transgenic rice plants may sensitive to oxidative conditions.

TABLE 28

Paraquat tolerance assay of OsPRP1 transgenic rice plants under laboratory conditions
($1^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0086 (Construct) | 194 | 600 | 32 | 0.0000 | | 0.2883 | |
| ZH11-TC | 90 | 180 | 50 | | | | |
| DP0158 | 66 | 180 | 37 | | | | |
| DP0086.01 | 22 | 60 | 37 | 0.0794 | | 1.0000 | |
| DP0086.02 | 12 | 60 | 20 | 0.0002 | | 0.0221 | |
| DP0086.03 | 15 | 60 | 25 | 0.0016 | | 0.1051 | |
| DP0086.05 | 22 | 60 | 37 | 0.0794 | | 1.0000 | |
| DP0086.06 | 17 | 60 | 28 | 0.0055 | | 0.2457 | |
| DP0086.07 | 17 | 60 | 28 | 0.0055 | | 0.2457 | |
| DP0086.25 | 20 | 60 | 33 | 0.0298 | | 0.6427 | |
| DP0086.27 | 19 | 60 | 32 | 0.0174 | | 0.4861 | |
| DP0086.33 | 22 | 60 | 37 | 0.0794 | | 1.0000 | |
| DP0086.36 | 31 | 60 | 52 | 0.8238 | | 0.0458 | |

In the second experiment, after paraquat solution treated for seven days, 228 of the 540 OsPRP1 transgenic seedlings (42%) kept green and showed tolerant phenotype, while 145 of the 240 (60%) seedlings from ZH11-TC showed tolerant phenotype, and 98 of the 180 (54%) DP0158 seedlings showed tolerant phenotype. The tolerance rate of all screened OsPRP1 transgenic seedlings was significantly lower than ZH11-TC control (P value=0.0000) and DP0158 control (P value=0.0070).

Further analysis at transgenic line level indicates that all the nine lines had lower tolerance rates compared with ZH11-TC control, and six lines had lower tolerance rates than DP0158 control; six lines had significantly lower tolerance rates than ZH11-TC control, and four lines had significantly lower tolerance rates than DP0158 control (Table 29). These results demonstrate that OsPRP1 transgenic rice plants were sensitive to Paraquat condition at seedling stages. OsPRP1 transgenic rice plants may sensitive to oxidative conditions.

TABLE 29

Paraquat tolerance assay of OsPRP1 transgenic rice plants under laboratory conditions
($1^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0086 (Construct) | 228 | 540 | 42 | 0.0000 | | 0.0070 | |
| ZH11-TC | 145 | 240 | 60 | | | | |
| DP0158 | 98 | 180 | 54 | | | | |
| DP0086.01 | 20 | 60 | 33 | 0.0008 | | 0.0069 | |
| DP0086.02 | 23 | 60 | 38 | 0.0057 | | 0.0357 | |
| DP0086.03 | 11 | 60 | 18 | 0.0000 | | 0.0002 | |
| DP0086.06 | 25 | 60 | 42 | 0.0186 | | 0.0927 | |
| DP0086.07 | 34 | 60 | 57 | 0.7262 | | 0.7654 | |
| DP0086.25 | 24 | 60 | 40 | 0.0105 | | 0.0585 | |
| DP0086.27 | 35 | 60 | 58 | 0.9069 | | 0.6016 | |
| DP0086.33 | 22 | 60 | 37 | 0.0031 | | 0.0212 | |
| DP0086.36 | 34 | 60 | 57 | 0.7262 | | 0.7654 | |

2) Paraquat Validation Results of OsPP2C64 Over-Expressed (DP0297) Transgenic Rice Plants For OsPP2C64 transgenic rice, in the first experiment, 11% transgenic seedlings kept green and showed tolerant phenotype after treated with 0.8 μM paraquat solutions for 7 days, while 18% ZH11-TC seedlings and 10% DP0158 seedlings showed tolerant phenotype. The tolerance rate of OsPP2C64 transgenic seedlings was significantly lower than ZH11-TC control.

Analysis at transgenic line level is displayed in Table 30. Eight transgenic lines had lower tolerance rates than ZH11-TC control. These results indicate that OsPP2C64 transgenic rice were not paraquat tolerance plants.

TABLE 30

Paraquat tolerance assay of OsPP2C64 transgenic rice plants under laboratory conditions ($1^{st}$ experiment)

| Line ID | Number of tolerant seedlings | Number of total seedlings | Tolerance rate (%) | CK = ZH11-TC | | CK = DP0158 | |
|---|---|---|---|---|---|---|---|
| | | | | P value | P ≤ 0.05 | P value | P ≤ 0.05 |
| DP0297 (Construct) | 62 | 588 | 11 | 0.0024 | | 0.6990 | |
| ZH11-TC | 34 | 192 | 18 | | | | |
| DP0158 | 18 | 180 | 10 | | | | |
| DP0297.01 | 9 | 60 | 15 | 0.6290 | | 0.2948 | |
| DP0297.04 | 4 | 48 | 8 | 0.1258 | | 0.7305 | |
| DP0297.05 | 13 | 60 | 22 | 0.4946 | | 0.0258 | Y |
| DP0297.06 | 5 | 60 | 8 | 0.0922 | | 0.7067 | |
| DP0297.07 | 12 | 60 | 20 | 0.6891 | | 0.0505 | |
| DP0297.09 | 2 | 60 | 4 | 0.0165 | | 0.1292 | |
| DP0297.10 | 7 | 60 | 12 | 0.2764 | | 0.7147 | |
| DP0297.11 | 3 | 60 | 5 | 0.0269 | | 0.2494 | |
| DP0297.15 | 4 | 60 | 7 | 0.0496 | | 0.4450 | |
| DP0297.16 | 3 | 60 | 5 | 0.0269 | | 0.2493 | |

In the second experiment, 131 of the 504 transgenic seedlings (26%) kept green and showed tolerant phenotype after treated with paraquat solutions for 7 days, while 99 of the 228 (43%) seedlings from ZH11-TC showed tolerant phenotype and 81 of the 228 (36%) seedlings from DP0158 showed tolerant phenotype. The tolerance rate of OsPP2C64 transgenic seedlings was significantly lower than ZH11-TC and DP0158 controls. Analysis at transgenic line level shows that eight transgenic lines exhibited lower tolerance rates than ZH11-TC and DP0158 controls (Table 31). Seven lines exhibited significantly lower tolerant rates than ZH11-TC control. These results further demonstrate that OsPP2C64 transgenic rice were not paraquat tolerance, and over-expression OsPP2C64 gene resulted in paraquat sensitive or oxidative sensitive of the transgenic plants.

TABLE 31

Paraquat tolerance assay of OsPP2C64 transgenic rice plants under laboratory conditions ($2^{nd}$ experiment)

| Line ID | Number of tolerant seedlings | Number of total seedlings | Tolerance rate (%) | CK = ZH11-TC | | CK = DP0158 | |
|---|---|---|---|---|---|---|---|
| | | | | P value | P ≤ 0.05 | P value | P ≤ 0.05 |
| DP0297 (Construct) | 131 | 504 | 26 | 0.0000 | | 0.0163 | |
| ZH11-TC | 99 | 228 | 43 | | | | |
| DP0158 | 81 | 228 | 36 | | | | |
| DP0297.01 | 14 | 60 | 23 | 0.0049 | | 0.0763 | |
| DP0297.04 | 13 | 24 | 54 | 0.6173 | | 0.1838 | |
| DP0297.05 | 18 | 36 | 50 | 0.8294 | | 0.2242 | |
| DP0297.06 | 11 | 48 | 23 | 0.0124 | | 0.1232 | |
| DP0297.07 | 17 | 60 | 28 | 0.0282 | | 0.2866 | |
| DP0297.09 | 13 | 60 | 22 | 0.0026 | | 0.0452 | |
| DP0297.10 | 8 | 60 | 13 | 0.0001 | | 0.0022 | |
| DP0297.11 | 8 | 60 | 13 | 0.0001 | | 0.0022 | |
| DP0297.16 | 11 | 36 | 31 | 0.0665 | | 0.3515 | |
| DP0297.21 | 18 | 60 | 30 | 0.0481 | | 0.4102 | |

3) Paraquat Validation Results of OsOPPL1 Over-Expressed (DP0328) Transgenic Rice Plants In the first experiment, 285 of the 576 OsOPPL1 transgenic seedlings (49%) kept green and showed tolerant phenotype after treated with paraquat solution, whereas 75 of the 204 (37%) ZH11-TC seedlings, and 65 of the 180 (36%) DP0158 seedlings showed tolerant phenotype. The tolerance rate of OsOPPL1 transgenic plants was significantly higher than that of the ZH11-TC and DP0158 controls. The OsOPPL1 transgenic seedlings grew better after paraquat solution treatment when compared to either ZH11-TC or DP0158 seedlings. The analysis at transgenic line level is displayed in Table 32. Seven lines had greater tolerance rates than either ZH11-TC or DP0158 seedlings, which demonstrates that OsOPPL1 transgenic rice plants had enhanced paraquat tolerance at construct and transgenic line level at seedling stages. Over-expression of OsOPPL1 gene improved the paraquat tolerance of the transgenic plants.

TABLE 32

Paraquat tolerance assay of OsOPPL1 transgenic rice plants under laboratory conditions (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0328 (construct) | 285 | 576 | 49 | 0.0023 | Y | 0.0031 | Y |
| ZH11-TC | 75 | 204 | 37 | | | | |
| DP0158 | 65 | 180 | 36 | | | | |
| DP0328.12 | 39 | 60 | 65 | 0.0003 | Y | 0.0003 | Y |
| DP0328.15 | 38 | 60 | 63 | 0.0005 | Y | 0.0006 | Y |
| DP0328.17 | 29 | 60 | 48 | 0.0969 | | 0.0978 | |
| DP0328.21 | 14 | 60 | 23 | 0.0677 | | 0.0740 | |
| DP0328.25 | 17 | 60 | 28 | 0.2596 | | 0.2746 | |
| DP0328.30 | 41 | 60 | 68 | 0.0000 | Y | 0.0000 | Y |
| DP0328.31 | 41 | 60 | 68 | 0.0000 | Y | 0.0000 | Y |
| DP0328.32 | 19 | 36 | 53 | 0.0348 | Y | 0.0343 | Y |
| DP0328.44 | 15 | 60 | 25 | 0.1104 | | 0.1194 | |
| DP0328.49 | 32 | 60 | 53 | 0.0214 | Y | 0.0221 | Y |

In the second experiment, 393 of the 600 OsOPPL1 transgenic seedlings (66%) kept green and showed tolerant phenotype after treated with paraquat solution, whereas 68 of the 180 (38%) ZH11-TC seedlings, and 78 of the 180 (43%) DP0158 seedlings showed tolerant phenotype. The tolerance rate of OsOPPL1 transgenic plants was significantly higher than ZH11-TC and DP0158 controls.

The analysis at transgenic line level shows that nine lines had greater tolerance rates than both ZH11-TC and DP0158 seedlings, eight lines exhibited significantly higher tolerance rates than ZH11-TC control, and seven lines exhibited significantly higher tolerance rates than DP0158 control (Table 33). These results further demonstrate that OsOPPL1 transgenic rice plants had enhanced paraquat tolerance at construct and transgenic line level at seedling stage. Over-expression of OsOPPL1 gene improved the paraquat tolerance of the transgenic plants.

TABLE 33

Paraquat tolerance assay of OsOPPL1 transgenic rice plants under laboratory conditions (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0328 (Construct) | 393 | 600 | 66 | 0.0000 | Y | 0.0000 | Y |
| ZH11-TC | 68 | 180 | 38 | | | | |
| DP0158 | 78 | 180 | 43 | | | | |
| DP0328.12 | 50 | 60 | 83 | 0.0000 | Y | 0.0000 | Y |
| DP0328.15 | 47 | 60 | 78 | 0.0000 | Y | 0.0000 | Y |
| DP0328.17 | 44 | 60 | 73 | 0.0000 | Y | 0.0002 | Y |
| DP0328.21 | 29 | 60 | 48 | 0.1553 | | 0.5018 | |
| DP0328.25 | 38 | 60 | 63 | 0.0012 | Y | 0.0101 | Y |
| DP0328.30 | 32 | 60 | 53 | 0.0396 | Y | 0.1840 | |

TABLE 33-continued

Paraquat tolerance assay of OsOPPL1 transgenic rice plants under laboratory conditions
($2^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0328.31 | 44 | 60 | 73 | 0.0000 | Y | 0.0002 | Y |
| DP0328.32 | 39 | 60 | 65 | 0.0006 | Y | 0.0056 | Y |
| DP0328.44 | 25 | 60 | 42 | 0.5938 |   | 0.8235 |   |
| DP0328.49 | 45 | 60 | 75 | 0.0000 | Y | 0.0001 | Y |

4) Paraquat Validation Results of OsMFS9 Over-Expressed (DP0343) Transgenic Rice Plants In the first experiment, after paraquat solution treated for seven days, 214 of the 540 OsMFS9 transgenic seedlings (40%) kept green and showed tolerant phenotype, while 138 of the 240 (58%) seedlings from ZH11-TC showed tolerant phenotype, and 99 of the 180 (55%) DP0158 seedlings showed tolerant phenotype. The tolerance rate of all screened OsMFS9 transgenic seedlings was significantly lower than ZH11-TC control (P value=0.0002) and DP0158 control (P value=0.0013).

Further analysis at transgenic line level indicates that eight lines had lower tolerance rates compared with ZH11-TC and DP0158 controls; five lines had significantly lower tolerance rates than ZH11-TC control, and four lines had significantly lower tolerance rates than DP0158 control (Table 34). These results demonstrate that OsMFS9 transgenic rice plants were sensitive to Paraquat condition at seedling stages. OsMFS9 transgenic rice plants may sensitive to oxidative conditions.

TABLE 34

Paraquat tolerance assay of OsMFS9 transgenic rice plants under laboratory conditions
($1^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0343 (Construct) | 214 | 540 | 40 | 0.0002 |   | 0.0013 |   |
| ZH11-TC | 138 | 240 | 58 |   |   |   |   |
| DP0158 | 99 | 180 | 55 |   |   |   |   |
| DP0343.01 | 10 | 60 | 17 | 0.0000 |   | 0.0000 |   |
| DP0343.02 | 13 | 60 | 22 | 0.0000 |   | 0.0000 |   |
| DP0343.03 | 23 | 48 | 48 | 0.5160 |   | 0.6164 |   |
| DP0343.06 | 23 | 36 | 64 | 0.1316 |   | 0.1089 |   |
| DP0343.07 | 40 | 60 | 67 | 0.1348 |   | 0.1103 |   |
| DP0343.08 | 15 | 60 | 25 | 0.0000 |   | 0.0002 |   |
| DP0343.10 | 15 | 60 | 25 | 0.0000 |   | 0.0002 |   |
| DP0343.16. | 21 | 48 | 44 | 0.0481 |   | 0.0722 |   |
| DP0343.18 | 32 | 60 | 53 | 0.6969 |   | 0.8184 |   |
| DP0343.20 | 22 | 48 | 46 | 0.3621 |   | 0.4480 |   |

In the second experiment, after paraquat solution treated for seven days, 395 of the 600 OsMFS9 transgenic seedlings (66%) kept green and showed tolerant phenotype, while 128 of the 180 (71%) seedlings from ZH11-TC showed tolerant phenotype, and 140 of the 180 (78%) DP0158 seedlings showed tolerant phenotype. The tolerance rate of all screened OsMFS9 transgenic seedlings was lower than ZH11-TC control (P value=0.2373) and significantly lower than DP0158 control (P value=0.0055).

Further analysis at transgenic line level indicates that seven lines had lower tolerance rates compared with ZH11-TC and ten lines had lower tolerance rates than DP0158 controls; two lines had significantly lower tolerance rates than ZH11-TC control, and three lines had significantly lower tolerance rates than DP0158 control (Table 35). These results demonstrate that OsMFS9 transgenic rice plants were sensitive to Paraquat condition at seedling stages. OsMFS9 transgenic rice plants may sensitive to oxidative conditions.

TABLE 35

Paraquat tolerance assay of OsMFS9 transgenic rice plants under laboratory conditions (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0343 (Construct) | 395 | 600 | 66 | 0.2373 | | 0.0055 | |
| ZH11-TC | 128 | 180 | 71 | | | | |
| DP0158 | 140 | 180 | 78 | | | | |
| DP0343.01 | 42 | 60 | 70 | 0.8701 | | 0.2289 | |
| DP0343.02 | 42 | 60 | 70 | 0.8701 | | 0.2289 | |
| DP0343.03 | 45 | 60 | 75 | 0.5633 | | 0.6588 | |
| DP0343.06 | 37 | 60 | 62 | 0.1779 | | 0.0180 | |
| DP0343.07 | 26 | 60 | 43 | 0.0003 | | 0.0000 | |
| DP0343.08 | 39 | 60 | 65 | 0.3768 | | 0.0552 | |
| DP0343.10 | 40 | 60 | 67 | 0.5179 | | 0.0920 | |
| DP0343.16 | 44 | 60 | 73 | 0.7420 | | 0.4837 | |
| DP0343.18 | 46 | 60 | 77 | 0.4080 | | 0.8585 | |
| DP0343.20 | 34 | 60 | 57 | 0.0442 | | 0.0028 | |

5) Paraquat Validation Results of OsLAO1 Over-Expressed (DP0451) Transgenic Rice In the first experiment, 351 of the 600 OsLAO1 transgenic seedlings (59%) kept green and showed tolerant phenotype after treated with paraquat solutions, whereas 62 of the 180 (34%) ZH11-TC seedlings showed tolerant phenotype, and 33 of the 180 (18%) DP0158 seedlings showed tolerant phenotype. The tolerance rate of OsLAO1 transgenic seedlings was significantly higher than that of the ZH11-TC and DP0158 controls. Table 36 illustrates the analysis at line level. Nine tested lines had higher tolerance rates than either ZH11-TC or DP0158 controls. Seven lines had significantly higher tolerance rates. These results demonstrate that OsLAO1 transgenic rice plants were paraquat tolerant at seedling stage.

TABLE 36

Paraquat tolerance assay of OsLAO1 transgenic rice plants under laboratory conditions (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0451 (Construct) | 351 | 600 | 59 | 0.0000 | Y | 0.0000 | Y |
| ZH11-TC | 62 | 180 | 34 | | | | |
| DP0158 | 33 | 180 | 18 | | | | |
| DP0451.01 | 36 | 60 | 60 | 0.0011 | Y | 0.0000 | Y |
| DP0451.03 | 19 | 60 | 32 | 0.6946 | | 0.0352 | Y |
| DP0451.04 | 35 | 60 | 58 | 0.0020 | Y | 0.0000 | Y |
| DP0451.06 | 44 | 60 | 73 | 0.0000 | Y | 0.0000 | Y |
| DP0451.07 | 37 | 60 | 62 | 0.0005 | Y | 0.0000 | Y |
| DP0451.08 | 35 | 60 | 58 | 0.0020 | Y | 0.0000 | Y |
| DP0451.10 | 41 | 60 | 68 | 0.0000 | Y | 0.0000 | Y |
| DP0451.12 | 52 | 60 | 87 | 0.0000 | Y | 0.0000 | Y |
| DP0451.13 | 27 | 60 | 45 | 0.1484 | | 0.0002 | Y |
| DP0451.14 | 25 | 60 | 42 | 0.3154 | | 0.0007 | Y |

In the second experiment, 493 of the 600 OsLAO1 transgenic seedlings (82%) kept green and showed tolerant phenotype after treated with paraquat solutions, whereas 110 of the 180 (61%) ZH11-TC seedlings showed tolerant phenotype, and 137 of the 180 (76%) DP0158 seedlings showed tolerant phenotype. The tolerance rate of OsLAO1 transgenic seedlings was significantly higher than ZH11-TC control and higher than DP0158 control.

Table 37 illustrates the analysis at line level. eight tested lines had significantly higher tolerance rates than ZH11-TC control and eight lines had higher tolerance rates than DP0158 control. These results demonstrate that OsLAO1 transgenic rice plants were paraquat tolerant at seedling stage.

TABLE 37

Paraquat tolerance assay of OsLAO1 transgenic rice plants under laboratory conditions (2$^{nd}$ experiment)

| Line ID | Number of tolerant seedlings | Number of total seedlings | Tolerant rate (%) | CK = ZH11-TC P value | P ≤ 0.05 | CK= DP0158 P value | P ≤ 0.05 |
|---|---|---|---|---|---|---|---|
| DP0451 (Construct) | 493 | 600 | 82 | 0.0000 | Y | 0.0514 | |
| ZH11-TC | 110 | 180 | 61 | | | | |
| DP0158 | 137 | 180 | 76 | | | | |
| DP0451.01 | 53 | 60 | 88 | 0.0005 | Y | 0.0527 | |
| DP0451.03 | 49 | 60 | 82 | 0.0061 | Y | 0.3769 | |
| DP0451.04 | 52 | 60 | 87 | 0.0009 | Y | 0.0930 | |
| DP0451.06 | 53 | 60 | 88 | 0.0005 | Y | 0.0527 | |
| DP0451.07 | 52 | 60 | 87 | 0.0009 | Y | 0.0930 | |
| DP0451.08 | 48 | 60 | 80 | 0.0111 | Y | 0.5376 | |
| DP0451.10 | 45 | 60 | 75 | 0.0581 | | 0.8623 | |
| DP0451.12 | 48 | 60 | 80 | 0.0111 | Y | 0.5376 | |
| DP0451.13 | 43 | 60 | 72 | 0.1476 | | 0.4941 | |
| DP0451.14 | 50 | 60 | 83 | 0.0033 | Y | 0.2498 | |

6) Paraquat Validation Results of OsDN-DSP1 Over-Expressed (DP0505) Transgenic Rice Plants In the first experiment, 197 of the 600 OsDN-DSP1 transgenic seedlings (33%) kept green and showed tolerant phenotype after treated with paraquat solutions, whereas 65 of the 180 (36%) ZH11-TC seedlings showed tolerant phenotype, and 72 of the 180 (40%) DP0158 seedlings showed tolerant phenotype. The tolerance rate of OsDN-DSP1 transgenic seedlings was lower than that of the ZH11-TC and DP0158 controls at construct level. Analysis at transgenic line level shows that five lines had lower tolerance rates than ZH11-TC and eight lines had lower tolerance rates than DP0158 control (Table 38). These results demonstrate that OsDN-DSP1 transgenic rice plants were not paraquat tolerant.

TABLE 38

Paraquat tolerance assay of OsDN-DSP1 transgenic rice plants under laboratory conditions (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0505 (Construct) | 197 | 600 | 33 | 0.2921 | | 0.0488 | |
| ZH11-TC | 65 | 180 | 36 | | | | |
| DP0158 | 72 | 180 | 40 | | | | |
| DP0505.02 | 23 | 60 | 38 | 0.7581 | | 0.8199 | |
| DP0505.03 | 21 | 60 | 35 | 0.8770 | | 0.4940 | |
| DP0505.05 | 26 | 60 | 43 | 0.3226 | | 0.6508 | |
| DP0505.08 | 15 | 60 | 25 | 0.1211 | | 0.0424 | |
| DP0505.09 | 13 | 60 | 22 | 0.0451 | | 0.0140 | |
| DP0505.10 | 8 | 60 | 13 | 0.0023 | | 0.0007 | |
| DP0505.12 | 27 | 60 | 45 | 0.2257 | | 0.4984 | |
| DP0505.13 | 23 | 60 | 38 | 0.7581 | | 0.8199 | |
| DP0505.14 | 23 | 60 | 38 | 0.7581 | | 0.8199 | |
| DP0505.15 | 18 | 60 | 30 | 0.3927 | | 0.1724 | |

In the second experiment, 188 of the 600 OsDN-DSP1 transgenic seedlings (31%) kept green and showed tolerant phenotype after treated with paraquat solutions, whereas 121 of the 180 (67%) ZH11-TC seedlings showed tolerant phenotype, and 98 of the 180 (54%) DP0158 seedlings showed tolerant phenotype. The tolerance rate of OsDN-DSP1 transgenic seedlings was significantly lower than ZH11-TC and DP0158 controls at construct level.

Analysis at transgenic line level shows that all the ten lines had significantly lower tolerance rates than ZH11-TC and nine lines had significantly lower tolerance rates than DP0158 control (Table 39). These results demonstrate that OsDN-DSP1 transgenic rice plants were sensitive to paraquat solution. OsDN-DSP1 transgenic rice plants may sensitive to oxidative conditions.

TABLE 39

Paraquat tolerance assay of OsDN-DSP1 transgenic rice plants under laboratory conditions (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0505 (Construct) | 188 | 600 | 31 | 0.0000 | | 0.0000 | |
| ZH11-TC | 121 | 180 | 67 | | | | |
| DP0158 | 98 | 180 | 54 | | | | |
| DP0505.03 | 23 | 60 | 38 | 0.0002 | | 0.0312 | |
| DP0505.05 | 17 | 60 | 28 | 0.0000 | | 0.0008 | |
| DP0505.07 | 21 | 60 | 35 | 0.0000 | | 0.0102 | |
| DP0505.08 | 23 | 60 | 38 | 0.0002 | | 0.0312 | |
| DP0505.09 | 19 | 60 | 32 | 0.0000 | | 0.0030 | |
| DP0505.10 | 11 | 60 | 18 | 0.0000 | | 0.0000 | |
| DP0505.12 | 16 | 60 | 27 | 0.0000 | | 0.0004 | |
| DP0505.13 | 15 | 60 | 25 | 0.0000 | | 0.0002 | |
| DP0505.14 | 15 | 60 | 25 | 0.0000 | | 0.0002 | |
| DP0505.15 | 28 | 60 | 47 | 0.0055 | | 0.2880 | |

Example 7

Construction of RNAi and CRISPR/Cas9 Constructs

To investigate whether reducing the expression levels can modify the gene function, RNAi and CRISPR/Cas9 constructs were constructed.

Construction of RNAi Constructs:

The forward cDNA fragments and reverse cDNA fragments were cloned using the templates and primers listed in Table 40 and 41. Then the forward cDNA fragments, intron (SEQ ID NO: 44) and the reverse cDNA fragments were ligated together, and ligated with TA vector. After the sequences and orientation in the construct were confirmed by sequencing, the RNAi structure fragments (forward cDNA-intron-reverse cDNA) were cloned into plant binary construct DP0158 to obtain the RNAi constructs.

TABLE 40

Rice fragment for constructing RNAi constructs

| Gene name | Template SEQ ID NO: | RNAi Construct ID |
|---|---|---|
| OsPRP1 | 45 | DP2108 |
| OsPP2C64 | 46 | DP1549 |
| OsOPPL1 | 47 | DP2111 |
| OsMFS9 | 48 | DP0687 |
| OsLAO1 | 49 | DP2113 |
| OsDN-DSP1 | 50 | DP2116 |

TABLE 41

Primers for cloning fragment constructing RNAi constructs

| Primer | Sequence | SEQ ID NO: | Fragment | Length of amplified fragment (bp) |
|---|---|---|---|---|
| F-rg-463 | 5'-CTGCTGAGGGCTACTCGT ATCCACCACCCCAAG-3' | 51 | Forward cDNA for | 161 |
| F-rg-464 | 5'-GCTTGCTGAGGGTCGCAG CAGCACTCGTCGAT-3' | 52 | DP2108 | |
| R-rg-463 | 5'-CCGCTGAGGGCTACTCGT ATCCACCACCCCAAG-3' | 53 | Reverse cDNA for | 161 |
| R-rg-464 | 5'-GCCTGCTGAGGGTCGCAG CAGCACTCGTCGAT-3' | 54 | DP2108 | |
| FRiPP2C-I | 5'-CTGCTGAGGGAAGATCAG CTCGGGATGG-3' | 55 | Forward cDNA for | 105 |
| FRiPP2C-II | 5'-GCTTGCTGAGGGTCCTGG TTGATCCCCTTG-3' | 56 | DP1549 | |
| RRiPP2C-I | 5'-CCGCTGAGGGAAGATCAG CTCGGGATGG-3' | 57 | Reverse cDNA for | 105 |
| RRiPP2C-II | 5'-GCCTGCTGAGGGTCCTGG TTGATCCCCTTG-3' | 58 | DP1549 | |
| F-rg-483 | 5'-CTGCTGAGGAGAGGATGA CAAAGATTCTGAGCA-3'-3' | 59 | Forward cDNA for | 173 |
| F-rg-484 | 5'-GCTTGCTGAGGCCATTGG TGTTAAAGTTGGGTATCC-3' | 60 | DP2111 | |
| R-rg-483 | 5'-CCGCTGAGGAGAGGATGA CAAAGATTCTGAGCA-3' | 61 | Reverse cDNA for | 173 |
| R-rg-484 | 5'-GCCTGCTGAGGCCATTGG TGTTAAAGTTGGGTATCC-3' | 62 | DP2111 | |
| F-rg-027 | 5'-CTGCTGAGGATCACATTC TCCAAGGCTAT-3' | 63 | Forward cDNA for | 195 |
| F-rg-028 | 5'-GCTTGCTGAGGGCTTTCA GATGGGTCTCC-3' | 64 | DP0687 | |
| R-rg-027 | 5'-CCGCTGAGGATCACATTC TCCAAGGCTAT-3' | 65 | Reverse cDNA for | 195 |
| R-rg-028 | 5'-GCCTGCTGAGGGCTTTCA GATGGGTCTCC-3' | 66 | DP0687 | |
| F-rg-498 | 5'-CTGCTGAGGCTCATCAAT GGCATGCCGTCG-3' | 67 | Forward cDNA for | 173 |
| F-rg-499 | 5'-GCTTGCTGAGGGAGTCGT ACACGTTCTGCACCGG-3' | 68 | DP2113 | |
| R-rg-498 | 5'-CCGCTGAGGCTCATCAAT GGCATGCCGTCG-3' | 69 | Reverse cDNA for | 173 |
| R-rg-499 | 5'-GCCTGCTGAGGGAGTCGT ACACGTTCTGCACCGG-3' | 70 | DP2113 | |
| F-rg-513 | 5'-CTGCTGAGGGTGTTCCTC AACTATTTCGTCGCC-3' | 71 | Forward cDNA for | 264 |
| F-rg-514 | 5'-GCTTGCTGAGGGTTTTCC TCACGCTCCATCACTCTG-3' | 72 | DP2116 | |
| R-rg-513 | 5'-CCGCTGAGGGTGTTCCTC AACTATTTCGTCGCC-3' | 73 | Reverse cDNA for | 264 |
| R-rg-514 | 5'-GCCTGCTGAGGGTTTTCC TCACGCTCCATCACTCTG-3' | 74 | DP2116 | |

Construction of CRISPR/Cas9 Constructs:

Genome Editing of OsMFS9 Gene and its Regulatory Element

Target genomic sequences are analyzed using available tools to generate candidate sgRNA sequences. The sgRNA sequences can also be generated by other web-tools including, but not limited to, the web site cbi.hzau.edu.cn/crispr/ and CRISPR-PLANT, available online.

In this application, the sequence of OsMFS9 gene and its regulatory element (SEQ ID NO: 11, SEQ ID NO: 12 and SEQ ID NO: 102) was analyzed to generate the sgRNA sequences. The sequence of OsMFS9 gene and its regulatory element includes promoter, exon, intron, 5'-UTR, and 3'-UTR, and many sgRNA sequences were generated. 22 sgRNA sequences were selected and the distributions were shown in FIG. 16. The sgRNA sequences were listed in SEQ ID NO: 75-96.

In the CRISPR-Cas9 system, maize Ubi promoter (SEQ ID NO: 97) drives the optimized coding sequence (SEQ ID NO: 98) of Cas9 protein; CaMV35S 3'-UTR (SEQ ID NO: 99) improves the expression level of Cas9 protein; and rice U6 promoter (SEQ ID NO: 100) drives the expression of gRNA (gRNA scaffold, SEQ ID NO: 101).

One sgRNA can be used to make the genome editing construct (FIG. 17); the sgRNA can be selected from any region of the fragment such as promoter, exon, intron and UTR. The single sgRNA can guide the Cas9 enzyme to the target region and generate the double strand break at the target DNA sequence, non-homologous end-joining (NHEJ) repairing mechanism and homology directed repair (HDR) will be triggered, and it often induces random insertion, deletion and substitution at the target site. This edit, for example, can remove an expression element in the regulatory element region of OsMFS9 to reduce the mRNA levels or can result in a structural change in the OsMFS9 polypeptide that may result in reduced activity of the OsMFS9 protein.

Two sgRNAs can be used to make the genome editing construct (FIG. 18.); two or more sgRNAs can be selected from any region of the fragment such as promoter, exon, intron and UTR. This construct can lead to fragment deletion, point mutation (small insertion, deletion and substitution).

Table 42 showed the primer sequence, target position and the specific strand for genome editing of OsMFS9 gene and its regulatory element. DP2318, DP2389 and DP2410 are constructs for editing OsMFS9 gene; and DP2409, DP2411, DP2412, DP2421, DP2423 and DP2508 are constructs for editing OsMFS9 gene's regulatory element. For the construct DP2318 and DP2389, one position in OsMFS9 gene is edited. The target primers first anneal to form short double strand fragment, then the fragment is inserted in pHSG396GW-URS-UC-mpCas9&U6-DsRed. After confirmed the nucleotide sequence of gRNA fragment, the gRNA fragments are ligated with the expression vector Pcambia13000DsRed-GW-Adv.ccdB. For editing two target positions, the different primers should first anneal to form the double strand fragments, and then the two gRNA fragments stack together and insert in the cloning vector, and then are inserted in the expression vector to form DP2410, DP2409, DP2411, DP2412, DP2421, DP2423 and DP2508.

TABLE 42

Primers for constructing CRISPR/Cas9 constructs for
OsMFS9 gene and its regulatory element editing

| Construct ID | Target site ID | Target position | Strand (+/-) | Target site primer sequence | SEQ ID NO: |
|---|---|---|---|---|---|
| DP2318 | gRNA1 | Chr3: 844865-844885 | - | 5'-GCCCGGATACAATTGCGACC-3' | 75 |
| DP2389 | gRNA16 | Chr3: 845335-845355 | + | 5'-CTTGTTAGCCCGAAAGCTGA-3' | 90 |
| DP2410 | gRNA1 | Chr3: 844865-844885 | - | 5'-GCCCGGATACAATTGCGACC-3' | 75 |
|  | gRNA16 | Chr3: 845335-845355 | + | 5'-CTTGTTAGCCCGAAAGCTGA-3' | 90 |
| DP2409 | gRNA6 | Chr3: 842144-842163 | - | 5'-GCGCGCTGTGAAACAAGTGT-3' | 80 |
|  | gRNA9 | Chr3: 842551-842570 | + | 5'-GTGCGTGCCGGCCGAAGATT-3' | 83 |
| DP2412 | gRNA6 | Chr3: 842144-842163 | - | 5'-GCGCGCTGTGAAACAAGTGT-3' | 80 |
|  | gRNA5 | Chr3: 842679-842698 | + | 5'-GTATAAATCCCACCGGCTTG-3' | 79 |
| DP2421 | gRNA8 | Chr3: 842668-842687 | - | 5'-GATTTATACGCGCGTTTCTT-3' | 82 |
|  | gRNA5 | Chr3: 842679-842698 | + | 5'-GTATAAATCCCACCGGCTTG-3' | 79 |
| DP2423 | gRNA9 | Chr3: 842551-842570 | + | 5'-GTGCGTGCCGGCCGAAGATT-3' | 83 |
|  | gRNA5 | Chr3: 842679-842698 | + | 5'-GTATAAATCCCACCGGCTTG-3' | 79 |
| DP2508 | gRNA2 | Chr3: 841766-841785 | - | 5'-GAGCCGAGTCGCACACGGTT-3' | 76 |
|  | gRNA5 | Chr3: 842679-842698 | + | 5'-GTATAAATCCCACCGGCTTG-3' | 79 |
| DP2411 | gRNA2 | Chr3: 841766-841785 | - | 5'-gagccgagtcgcacacggtt-3' | 76 |
|  | gRNA9 | Chr3: 842551-842570 | + | 5'-gtgcgtgccggccgaagatt-3' | 83 |

Example 8

Transformation to Get Transgenic Rice Plants and Gene Expression Analysis

The RNAi and CRISPR/Cas9 constructs were transformed into the rice plants as described in Example 2.

The gene expression analyses were performed as described in Example 3.

The relative expression levels of OsMFS9 gene in leaves of different OsMFS9 suppressed transgenic rice lines were determined by real-time PCR analyses. The base expression level in ZH11-TC was set at 1.00, and the expression levels in other OsMFS9 suppressed lines ranged from about 0.07-0.53 compared to ZH11-TC. The expression levels in the OsMSF9 suppressed transgenic rice plants were lower than ZH11-TC. The primers used were listed in SEQ ID NO: 38 and 39.

DP0343-F1:
(SEQ ID NO: 38)
5'-GGAGGTAGCATCTCATTTGGAG-3'

DP0343-R1:
(SEQ ID NO: 39)
5'-GCCAGAATATGCCAACGC-3'

The relative expression levels of OsMFS9 gene in leaves of different OsMFS9 promoter edited rice lines (DP2421) were also determined using primers of SEQ ID NO: 38 and 39 and ranged from about 0.50 to 0.81 as compared to the base expression level in ZH11-TC (control, set at 1.00) (Table 21). The expression levels of OsMFS9 in the regulatory element edited lines were less than that in ZH11-TC rice plants.

Example 9

Identification the Cleavage Sites and the Modifications of OsMFS9 Gene or its Regulatory Element in Rice Plants The primers were designed to amplified the target sequence near the genome editing target sites using the genome DNA of the transformed seedlings as template. The amplified target sequences were sequenced to confirm the editing results. Part of the sequences were shown in FIG. 19. Modifications such as insertion of at least one nucleotide, deletion of at least one nucleotide, replacement of at least one nucleotide were produced, which resulted the early termination of the coding sequence, translation shift and/or deletion of at least one amino acid residues. Modifications such as insertion of at least one nucleotide, deletion of a DNA fragment, or substitution of a DNA fragment were produced in the regulatory element sequence to regulate the expression level of OsMFS9 in the transformed rice plants.

As shown in FIG. 19 (SEQ ID NO: 109-115), there are seven modifications produced at the expect site in DP2389 rice plants (ZH11). One nucleotide inserted at the expect site in mutation types 1 to 3 and resulted in early stops of the ORF. The predicted translated polypeptide has 345 amino acids. Short DNA fragments were deleted in mutation type 3 to 6, and resulted in translation shift. The predicted translated polypeptide has 454 and 453 amino acids for mutation 4 and 6, respectively. Translation shift was produced in mutation type 7, and resulted in early stop of the ORF and resulted a short predicted polypeptides with 322 amino acids.

A fragment about 400 bp, 800 bp, 128 bp in length were deleted at the expected sites in DP2409, DP2411 and DP2423 rice plants, respectively. In some cases, one nucleotide was inserted or several nucleotides were deleted at the expected sited. The DP2409, DP2411 and DP2423 rice plants used in the following validation experiments have long fragment deletion.

As shown in FIG. 20 (SEQ ID NO: 117-118), one nucleotide was inserted in the two mutation types of DP2421 rice plants.

Example 10

Field Drought Assays of Gene Expression Suppressed or Genome Edited Rice Plants T1 or T2 seeds were screened in the field to validate whether reducing the gene expression can enhance drought tolerance of the transgenic rice plants.

The screening method was described in Example 4.

Screening Results:

1) Field DRT Validation Results of OsMFS9 Suppressed Transgenic Rice (DP0687)

T2 OsMFS9 transgenic lines were tested in Beijing field, and ZH11-TC and DP0158 rice plants were used as controls. When the plants grew to main stem panicle initiation stage II watering was stopped. 17 days later, the main stem panicle reached panicle initiation stage VI, and the rice plants started to show drought stress phenotype. 31 days after stopping watering, the rice plants were watered again. The changes of soli volumetric water content were showed in FIG. 13. Transgenic line DP0687.02 showed drought tolerance phenotype and DP0687.11 showed good setting rate. The OsMFS9 transgenic rice plants obtained significantly greater grain yield per plant than DP0158 plants at the construct level (Table 43). Eight OsMFS9 suppressed transgenic lines showed significantly greater grain yields per plant than DP0158 control.

TABLE 43

Grain yield analysis of OsMFS9 suppressed (DP687) transgenic rice plants at under field drought conditions ($1^{st}$ experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0687 (Construct) | | | 6.10 | −0.45 | 0.544 | | 1.29 | 0.090 | Y |
| ZH11-TC | 24 | 14 | 6.55 | | | | | | |
| DP0158 | 24 | 9 | 4.81 | | | | | | |
| DP0687.02 | 24 | 14 | 6.92 | 0.36 | 0.700 | | 2.11 | 0.028 | Y |
| DP0687.03 | 24 | 11 | 4.32 | −2.23 | 0.037 | | −0.49 | 0.653 | |
| DP0687.04 | 24 | 17 | 6.91 | 0.36 | 0.707 | | 2.10 | 0.029 | Y |
| DP0687.05 | 24 | 14 | 6.41 | −0.14 | 0.883 | | 1.61 | 0.091 | Y |
| DP0687.06 | 24 | 15 | 5.16 | −1.39 | 0.125 | | 0.35 | 0.698 | |
| DP0687.07 | 24 | 13 | 4.93 | −1.62 | 0.069 | | 0.12 | 0.893 | |
| DP0687.08 | 24 | 15 | 6.52 | −0.03 | 0.972 | | 1.71 | 0.072 | Y |
| DP0687.09 | 24 | 13 | 6.29 | −0.26 | 0.765 | | 1.48 | 0.095 | Y |
| DP0687.11 | 16 | 9 | 7.42 | 0.87 | 0.392 | | 2.61 | 0.011 | Y |

The OsMFS9 suppressed transgenic rice plants were drought tested again in Hainan province. When the rice plants were at main stem panicle initiation stage III, watering were stopped. 23 days later, the main stem panicles headed out, the tiller panicles were at panicle initiation stage VI, and the rice plants started to show leaf rolling phenotypes. The changes of soil volumetric water content were showed in FIG. 14. Table 44 showed that OsMFS9 suppressed transgenic rice plants obtained more grain yield per plant than both ZH11-TC and DP0158 controls at the construct level. Seven lines showed greater grain yields per plant than ZH11-TC and significantly greater grain yields per plant than DP0158 control.

TABLE 44

Grain yield analysis of OsMFS9 suppressed (DP687) transgenic rice plants at under field drought conditions ($2^{nd}$ experiment)

| Line ID | Number of survived plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0687 (Construct) | | | 3.85 | 0.36 | 0.622 | | 1.71 | 0.020 | Y |
| ZH11-TC | 36 | 20 | 3.49 | | | | | | |
| DP0158 | 36 | 20 | 2.14 | | | | | | |

TABLE 44-continued

Grain yield analysis of OsMFS9 suppressed (DP687) transgenic rice plants at under field drought conditions ($2^{nd}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0687.01 | 36 | 20 | 3.18 | −0.31 | 0.720 | | 1.04 | 0.230 | |
| DP0687.02 | 36 | 20 | 4.63 | 1.14 | 0.183 | | 2.49 | 0.003 | Y |
| DP0687.03 | 36 | 20 | 3.02 | −0.47 | 0.587 | | 0.88 | 0.306 | |
| DP0687.04 | 36 | 20 | 3.79 | 0.30 | 0.717 | | 1.65 | 0.054 | Y |
| DP0687.05 | 36 | 19 | 2.41 | −1.07 | 0.203 | | 0.27 | 0.750 | |
| DP0687.06 | 36 | 19 | 4.70 | 1.21 | 0.159 | | 2.56 | 0.003 | Y |
| DP0687.07 | 36 | 20 | 2.83 | −0.66 | 0.443 | | 0.69 | 0.421 | |
| DP0687.08 | 35 | 20 | 4.67 | 1.19 | 0.158 | | 2.53 | 0.003 | Y |
| DP0687.09 | 36 | 18 | 5.72 | 2.24 | 0.008 | Y | 3.58 | 0.000 | Y |
| DP0687.10 | 36 | 19 | 2.89 | −0.60 | 0.473 | | 0.74 | 0.373 | |
| DP0687.11 | 36 | 20 | 4.17 | 0.68 | 0.423 | | 2.03 | 0.015 | Y |
| DP0687.13 | 36 | 20 | 4.18 | 0.69 | 0.420 | | 2.04 | 0.015 | Y |

2) Field DRT Validation Results of OsMFS9 Gene's Regulatory Element Edited Rice (DP2421)

The OsMFS9 gene's regulatory element edited lines (DP2421) were tested in Hainan Province; ZH11-TC rice plants and the genome edited negative rice plants which went through the transformation process and have the wild-type (un-mutated, Negative) planted nearby were used as controls. Watering was stopped when the main stem panicles were at panicle initiation stage III. The soil volumetric water content decreased slowly from 16% to 6% (FIG. 12). 22 days later, the rice plants were at heading stage. The OsMFS9 gene's regulatory element edited (DP2421) rice plants did not show drought stress phenotype before dough stage. Four DP2421 lines DP2421H.02A, DP2421H.10A, DP2421H.11A and DP2421.14A showed good setting rate at the maturity stage. Table 45 showed that the DP2421 plants obtained significantly greater grain yield per plant than ZH11-TC and negative control at the construct level. Six rice lines showed greater grain yields per plant than ZH11-TC control and five lines showed greater grain yields per plant than Negative control at the line level.

TABLE 45

Grain yield analysis of OsMFS9 gene's regulatory element edited (DP2421) rice plants at T1 generation under field drought conditions

| Line ID | Number of survival plants | Number of harvested plants | Yield per plant (g) | CK = ZH11-TC | | | CK = Negative | | |
|---|---|---|---|---|---|---|---|---|---|
| | | | | Diff | P value | P ≤ 0.1 | Diff | P value | P ≤ 0.1 |
| DP2421 (Construct) | | | 6.29 | 1.85 | 0.000 | Y | 2.46 | 0.000 | Y |
| ZH11-TC | 82 | 55 | 3.83 | | | | | | |
| Negative | 631 | 303 | 4.45 | | | | | | |
| DP2421H.02A | 66 | 50 | 7.40 | 3.57 | 0.000 | Y | 2.95 | 0.000 | Y |
| DP2421H.05A | 70 | 44 | 5.24 | 1.41 | 0.136 | | 0.79 | 0.313 | |
| DP2421H.07A | 69 | 49 | 4.41 | 0.58 | 0.539 | | −0.04 | 0.964 | |
| DP2421H.08A | 68 | 49 | 3.28 | −0.55 | 0.566 | | −1.16 | 0.134 | |
| DP2421H.10A | 71 | 55 | 6.71 | 2.88 | 0.002 | Y | 2.27 | 0.004 | Y |
| DP2421H.11A | 72 | 53 | 9.67 | 5.84 | 0.000 | Y | 5.22 | 0.000 | Y |
| DP2421H.13A | 54 | 40 | 2.27 | −1.56 | 0.131 | | −2.18 | 0.015 | Y |
| DP2421H.14A | 55 | 40 | 11.36 | 7.53 | 0.000 | Y | 6.92 | 0.000 | Y |

The OsMFS9 gene's regulatory element edited lines (DP2421) were tested again in Hainan Province; the genome edited negative rice plants (un-mutated, Negative) planted nearby were used as controls. Watering was stopped when the main stem panicles were at panicle initiation stage III. The soil volumetric water content decreased slowly from 35% to 8%. 22 days later, the rice plants were at heading stage. The OsMFS9 promoter edited (DP2421) rice plants did not show drought stress phenotype before dough stage. The same four DP2421 lines DP2421H.02A, DP2421H.10A, DP2421H.11A and DP2421.14A showed good setting rate at the maturity stage. Table 46 showed that the DP2421 plants obtained equal grain yield per plant to negative control at the construct level. Four rice lines showed the greater grain yields per plant than Negative control at the line level.

OsMFS9 gene's regulatory element edited (DP2409) rice plants did not show drought stress phenotype before dough stage. One line DP2409H.01A showed good setting rate at the maturity stage. Table 47 showed that the DP2409 plants obtained significantly greater grain yield per plant than ZH11-TC and negative control at the construct level. These rice lines showed the greater grain yields per plant than ZH11-TC control and Negative control at the line level.

TABLE 47

Grain yield analysis of OsMFS9 gene's regulatory element edited (DP2409) rice plants at T1 generation under field drought conditions

| Line ID | Number of survival plants | Number of harvested plants | Yield per plant (g) | CK = ZH11-TC Diff | P value | P ≤ 0.1 | CK = Negative Diff | P value | P ≤ 0.1 |
|---|---|---|---|---|---|---|---|---|---|
| DP2409 | | | 7.58 | 3.75 | 0.000 | Y | 3.13 | 0.000 | Y |
| ZH11-TC | 82 | 55 | 3.83 | | | | | | |
| Negative | 631 | 303 | 4.45 | | | | | | |
| DP2409H.01A | 40 | 29 | 9.64 | 5.81 | 0.000 | Y | 5.20 | 0.000 | Y |
| DP2409H.02A | 67 | 47 | 5.52 | 1.69 | 0.075 | Y | 1.07 | 0.173 | |

TABLE 46

Grain yield analysis of OsMFS9 gene's regulatory element edited (DP2421) rice plants at T2 generation under field drought conditions

| Line ID | Number of survival plants | Number of harvested Plants | Yield per plant (g) | Diff | P value | P ≤ 0.1 |
|---|---|---|---|---|---|---|
| DP2421 (Construct) | | | 9.63 | −0.13 | 0.658 | |
| Negative | 480 | 288 | 9.76 | | | |
| DP2421H.01B.03 | 74 | 48 | 8.85 | −0.90 | 0.284 | |
| DP2421H.02B.03 | 79 | 48 | 11.55 | 1.79 | 0.031 | Y |
| DP2421H.02B.05 | 80 | 48 | 9.53 | −0.22 | 0.787 | |
| DP2421H.03B.01 | 60 | 36 | 7.77 | −1.99 | 0.033 | |
| DP2421H.06B.01 | 80 | 48 | 9.49 | −0.27 | 0.748 | |
| DP2421H.08B.01 | 80 | 48 | 6.22 | −3.54 | 0.000 | |
| DP2421H.08B.05 | 55 | 36 | 9.52 | −0.23 | 0.805 | |
| DP2421H.10B.01 | 80 | 48 | 10.83 | 1.07 | 0.195 | |
| DP2421H.11B.06 | 80 | 48 | 11.21 | 1.45 | 0.098 | Y |
| DP2421H.12B.06 | 80 | 48 | 8.55 | −1.20 | 0.146 | |
| DP2421H.13B.02 | 24 | 17 | 7.30 | −2.46 | 0.033 | |
| DP2421H.14B.01 | 80 | 48 | 14.15 | 4.40 | 0.000 | Y |

3) Field DRT Validation Results of OsMFS9 Gene's Regulatory Element Edited Rice (DP2409)

Tow OsMFS9 gene's regulatory element edited lines (DP2409) were tested in Hainan Province; ZH11-TC rice plants and the genome edited negative rice plants which went through the transformation process and have the wild-type (un-mutated, Negative) planted nearby were used as controls. Watering was stopped when the main stem panicles were at panicle initiation stage III. The soil volumetric water content decreased slowly from 16% to 6% (FIG. 12). 22 days later, the rice plants were at heading stage. The OsMFS9 gene's regulatory element edited lines (DP2409) were tested again in Hainan Province; the genome edited negative rice plants (un-mutated, Negative) planted nearby were used as controls. Watering was stopped when the main stem panicles were at panicle initiation stage III. The soil volumetric water content decreased slowly from 35% to 8%. 22 days later, the rice plants were at heading stage. The OsMFS9 gene's regulatory element edited (DP2409) rice plants did not show drought stress phenotype before dough stage. One line DP2409H.01B showed good setting rate at the maturity stage. Table 48 showed that the DP2409 plants obtained equal grain yield per plant to negative control at the construct level. Four rice lines showed the greater grain yields per plant than Negative control at the line level.

TABLE 48

Grain yield analysis of OsMFS9 gene's regulatory element edited (DP2409) rice plants at T2 generation under field drought conditions

| Line ID | Number of survival plants | Number of harvested plants | Yield per plant (g) | Diff | P value | P ≤ 0.1 |
|---|---|---|---|---|---|---|
| DP2409 (Construct) | | | 9.97 | 0.21 | 0.466 | |
| Negative | 480 | 288 | 9.76 | | | |
| DP2409H.01B.01 | 80 | 48 | 10.33 | 0.58 | 0.493 | |
| DP2409H.01B.02 | 80 | 48 | 9.24 | −0.52 | 0.537 | |
| DP2409H.02B.03 | 80 | 49 | 11.76 | 2.00 | 0.018 | Y |
| DP2409P.02B.11 | 80 | 48 | 6.73 | −3.02 | 0.000 | |
| DP2409P.03B.06 | 80 | 48 | 6.17 | −3.59 | 0.000 | |
| DP2409P.03B.10 | 80 | 48 | 8.30 | −1.46 | 0.085 | |
| DP2409P.04B.03 | 80 | 48 | 11.59 | 1.84 | 0.030 | Y |

4) Field DRT Validation Results of OsMFS9 Gene's Regulatory Element Edited Rice (DP2411)

one OsMFS9 gene's regulatory element edited line (DP2411) was tested in Hainan Province; ZH11-TC rice plants and the genome edited negative rice plants which went through the transformation process and have the wild-type (un-mutated, Negative) planted nearby were used as controls. Watering was stopped when the main stem panicles were at panicle initiation stage III. The soil volumetric water content decreased slowly from 16% to 6% (FIG. 12). 22 days later, the rice plants were at heading stage. Table 49 showed that the DP2411 plants obtained significantly greater grain yield per plant than ZH11-TC and negative control.

TABLE 49

Grain yield analysis of OsMFS9 gene's regulatory element edited (DP2411) rice plants at T1 generation under field drought conditions

| Line ID | Number of survival plants | Number of harvested plants | Yield per plant (g) | CK = ZH11-TC Diff | P value | P ≤ 0.1 | CK = Negative Diff | P value | P ≤ 0.0 |
|---|---|---|---|---|---|---|---|---|---|
| DP2411H.01A | 68 | 48 | 6.15 | 2.32 | 0.014 | Y | 1.71 | 0.029 | Y |
| Negative | 631 | 303 | 4.45 | | | | | | |
| ZH11-TC | 82 | 55 | 3.83 | | | | | | |

The OsMFS9 gene's regulatory element edited lines (DP2411) were tested again in Hainan Province; the genome edited negative rice plants (un-mutated, Negative) planted nearby were used as controls. Watering was stopped when the main stem panicles were at panicle initiation stage III. The soil volumetric water content decreased slowly from 35% to 8%. One line DP2411H.01B showed good setting rate at the maturity stage. Table 50 showed that the DP2411 plants obtained equal grain yield per plant to negative control at the construct level. One rice lines showed the greater grain yields per plant than Negative control at the line level.

TABLE 50

Grain yield analysis of OsMFS9 gene's regulatory element edited (DP2411) rice plants at T2 generation under field drought conditions

| Line ID | Number of survival plants | Number of harvested plants | Yield per plant (g) | Diff | P value | P ≤ 0.1 |
|---|---|---|---|---|---|---|
| DP2411 (Construct) | | | 8.95 | −0.80 | 0.124 | |
| Negative | 480 | 288 | 9.76 | | | |
| DP2411H.01B.02 | 80 | 48 | 9.60 | −0.15 | 0.852 | |
| DP2411H.01B.05 | 80 | 48 | 11.45 | 1.69 | 0.042 | Y |
| DP2411P.02B.20 | 80 | 48 | 8.13 | −1.63 | 0.049 | |
| DP2411P.08B.25 | 80 | 48 | 6.81 | −2.94 | 0.000 | |

5) Field DRT Validation Results of OsMFS9 Gene's Regulatory Element Edited Rice (DP2423)

The OsMFS9 gene's regulatory element edited lines (DP2423) were tested again in Hainan Province; the genome edited negative rice plants (un-mutated, Negative) planted nearby were used as controls. Watering was stopped when the main stem panicles were at panicle initiation stage III. The soil volumetric water content decreased slowly from 35% to 8%. Three lines DP2423P.02B.01, DP2423P.02B.03 and DP2423P.10B.03 showed good setting rate at the maturity stage. Table 51 showed that the DP2423 plants obtained significantly greater grain yield per plant than negative control at the construct level. two rice lines showed significantly greater grain yields per plant than Negative control at the line level.

TABLE 51

Grain yield analysis of OsMFS9 gene's regulatory element edited (DP2423) rice plants at T2 generation under field drought conditions

| Line ID | Number of survival plants | Number of harvested plants | Yield per plant (g) | Diff | P value | P ≤ 0.1 |
|---|---|---|---|---|---|---|
| DP2423 (Construct) | | | 11.16 | 1.41 | 0.007 | Y |
| Negative | 480 | 288 | 9.76 | | | |
| DP2423P.02B.01 | 80 | 48 | 12.52 | 2.77 | 0.001 | Y |
| DP2423P.02B.03 | 80 | 48 | 12.87 | 3.12 | 0.000 | Y |
| DP2423P.02B.04 | 80 | 48 | 9.37 | −0.38 | 0.648 | |
| DP2423P.10B.03 | 80 | 48 | 9.75 | −0.01 | 0.993 | |

6) Field DRT Validation Results of OsMFS9 Gene Edited Rice (DP2389)

The OsMFS9 gene edited lines (DP2389) were tested in Ningxia Province; ZH11-TC rice plants and the genome edited negative rice plants which went through the transformation process and have the wild-type (un-mutated, Negative) planted nearby were used as controls. Watering was stopped when the main stem panicles were at panicle initiation stage I. The soil volumetric water content decreased slowly from 44% to 20%, the following rain affected the soil volumetric water content after stopping watering for 38 days. 32 days after stopping watering, the rice plants showed leaf rolling phenotype. The OsMFS9 gene edited (DP2389) rice plants did not show drought stress phenotype. Four DP2389 lines DP2389P.03B.11, DP2389P.13B.03, DP2389P.14B.09 and DP2389P.18B.02 showed good setting rate at the maturity stage. Table 52 showed that the DP2389 plants obtained greater grain yield per plant than negative control at the construct level. Four rice lines showed the greater grain yields per plant than Negative control at the line level.

TABLE 52

Grain yield analysis of OsMFS9 gene edited (DP2389) rice plants at T2 generation under field drought conditions (1$^{st}$ experiment)

| Line ID | Number of survival plants | Number of harvested plants | Yield per plant (g) | CK = ZH11-TC Diff | CK = ZH11-TC P value | CK = ZH11-TC P ≤ 0.1 | CK = Negative Diff | CK = Negative P value | CK = Negative P ≤ 0.1 |
|---|---|---|---|---|---|---|---|---|---|
| DP2389 (Construct) | | | 9.19 | −1.41 | 0.104 | | 1.49 | 0.115 | |
| ZH11-TC | | | 10.60 | | | | | | |
| Negative | | | 7.69 | | | | | | |
| DP2389P.03B.11 | 60 | 36 | 10.80 | 0.20 | 0.908 | | 3.10 | 0.089 | Y |
| DP2389P.13B.03 | 80 | 48 | 9.83 | −0.76 | 0.602 | | 2.14 | 0.156 | |
| DP2389P.14B.09 | 80 | 48 | 9.01 | −1.58 | 0.288 | | 1.32 | 0.390 | |
| DP2389P.17B.09 | 40 | 24 | 7.30 | −3.29 | 0.115 | | −0.39 | 0.853 | |
| DP2389P.18B.02 | 67 | 42 | 8.99 | −1.61 | 0.333 | | 1.30 | 0.445 | |

The OsMFS9 gene edited lines (DP2389) were tested in Hainan Province again, the genome edited negative rice plants which went through the transformation process and have the wild-type (un-mutated, Negative) planted nearby were used as controls. Watering was stopped when the main stem panicles were at panicle initiation stage I. Four DP2389 lines DP2389H.01B.04, DP2389H.03B.01, DP2389P.10B.04 and DP2389P.14B.10 showed good setting rate at the maturity stage. Table 53 showed that the DP2389 plants obtained equal grain yield per plant to negative control at the construct level. Five rice lines showed the greater grain yields per plant than Negative control at the line level.

TABLE 53

Grain yield analysis of OsMFS9 gene edited (DP2389) rice plants at T2 generation under field drought conditions (2$^{nd}$ experiment)

| Line ID | Number of survival plants | Number of harvested plants | Yield per plant (g) | Diff | P value | P ≤ 0.1 |
|---|---|---|---|---|---|---|
| DP2389 | | | 9.97 | 0.21 | 0.466 | |
| Negative | 480 | 288 | 9.76 | | | |
| DP2389H.0113.04 | 80 | 48 | 11.04 | 1.29 | 0.117 | |
| DP2389H.0213.04 | 80 | 48 | 8.21 | −1.55 | 0.070 | |
| DP2389H.0313.01 | 74 | 48 | 12.16 | 2.41 | 0.012 | Y |
| DP2389P.0313.04 | 80 | 48 | 8.15 | −1.60 | 0.055 | |
| DP2389P.1013.04 | 80 | 48 | 9.32 | −0.44 | 0.602 | |
| DP2389P.1013.14 | 80 | 48 | 10.01 | 0.26 | 0.753 | |
| DP2389P.1413.10 | 80 | 48 | 12.70 | 2.95 | 0.000 | Y |
| DP2389P.1713.03 | 76 | 48 | 8.92 | −0.84 | 0.312 | |
| DP2389P.1913.10 | 80 | 48 | 10.02 | 0.27 | 0.745 | |

7) Field DRT Validation Results of OsLAO1 Suppressed Transgenic Rice (DP2113)

T2 eleven OsLAO1 suppressed transgenic lines were tested in Hainan Province, ZH11-TC and DP0158 rice plants planted nearby were used as controls. Watering was stopped when the main stem panicles were at panicle initiation stage III. The soil volumetric water content decreased slowly from 16% to 6% (FIG. 12). 50 days after stopping watering, the main stem panicles were at milk stage and the rice plants started to show leaf rolling phenotypes. As shown in Table 54, the difference among OsLAO1 suppressed transgenic rice plant, ZH11-TC and DP0158 control were small at the construct level. Six suppressed transgenic lines showed greater grain yields per plant than both ZH11-TC and DP0158 controls at the line level.

TABLE 54

Grain yield analysis of OsLAO1 suppressed (DP2113) transgenic rice plants at T1 generation under field drought conditions

| Line ID | Number of survived plants | Number of harvested plants | Yield per plant (g) | CK = ZH11-TC Diff | CK = ZH11-TC P value | CK = ZH11-TC P ≤ 0.1 | CK = DP0158 Diff | CK = DP0158 P value | CK = DP0158 P ≤ 0.1 |
|---|---|---|---|---|---|---|---|---|---|
| DP2113 (Construct) | | | 7.90 | −0.02 | 0.98 | | 0.38 | 0.76 | |
| ZH11-TC | 38 | 24 | 7.93 | | | | | | |
| DP0158 | 38 | 24 | 7.52 | | | | | | |
| DP2113.02 | 14 | 9 | 8.50 | 0.57 | 0.721 | | 0.98 | 0.545 | |
| DP2113.03 | 20 | 12 | 5.88 | −2.05 | 0.202 | | −1.64 | 0.306 | |
| DP2113.04 | 30 | 18 | 8.22 | 0.29 | 0.846 | | 0.69 | 0.642 | |
| DP2113.05 | 16 | 9 | 5.84 | −2.09 | 0.189 | | −1.69 | 0.273 | |
| DP2113.06 | 38 | 24 | 10.49 | 2.57 | 0.069 | Y | 2.97 | 0.031 | Y |
| DP2113.07 | 33 | 22 | 8.03 | 0.10 | 0.940 | | 0.50 | 0.722 | |
| DP2113.10 | 27 | 17 | 8.56 | 0.63 | 0.650 | | 1.03 | 0.469 | |
| DP2113.11 | 23 | 14 | 7.83 | −0.10 | 0.944 | | 0.30 | 0.831 | |

TABLE 54-continued

Grain yield analysis of OsLAO1 suppressed (DP2113) transgenic
rice plants at T1 generation under field drought conditions

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP2113.13 | 34 | 21 | 7.70 | −0.23 | 0.868 | | 0.17 | 0.904 | |
| DP2113.15 | 35 | 23 | 6.70 | −1.23 | 0.385 | | −0.83 | 0.562 | |
| DP2113.16 | 27 | 21 | 8.66 | 0.73 | 0.602 | | 1.13 | 0.384 | |

8) Field DRT Validation Results of OsDN-DSP1 Suppressed Transgenic Rice (DP2116)

T2 twelve OsDN-DSP1 suppressed transgenic lines were tested in Hainan Province, ZH11-TC and DP0158 rice plants planted nearby were used as controls. Watering was stopped when the main stem panicles were at panicle initiation stage III. The soil volumetric water content decreased slowly from 16% to 6% (FIG. 12). 50 days after stopping watering, the main stem panicles were at milk stage and the rice plants started to show leaf rolling phenotypes. Seven suppressed transgenic lines DP2116.01, DP2116.03, DP2116.04, DP2116.05, DP2116.09, DP2116.10 and DP2116.12 showed drought tolerance phenotype and good setting rate after the drought stress. As shown in Table 55, the OsDN-DSP1 suppressed transgenic rice plant obtained more grain yield per plant than both ZH11-TC and DP0158 controls at the construct level. Six transgenic lines obtained more grain yields per plant than both ZH11-TC and DP0158 controls at the line level.

T2 OsDN-DSP1 suppressed transgenic lines were tested in Ningxia Province again, ZH11-TC and DP0158 rice plants planted nearby were used as controls. Watering was stopped when the main stem panicles were at panicle initiation stage I. The soil volumetric water content decreased slowly from 45% to 20%. The following rain affected the soil volumetric water content 38 days after stopping watering. 27 days after stopping watering, the rice plants were at milk stage and show leaf rolling phenotype. Three suppressed transgenic lines DP2116.07, DP2116.10 and DP2116.13 showed drought tolerance phenotype and good setting rate after the drought stress. As shown in Table 56, the OsDN-DSP1 suppressed transgenic rice plant obtained significantly more grain yield per plant than DP0158 control at the construct level.

TABLE 55

Grain yield analysis of OsDN-DSP1 suppressed (DP2116) transgenic rice
plants at T1 generation under field drought conditions (1$^{st}$ experiment)

| Line ID | Number of survived plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP2116 (Construct) | | | 8.95 | 0.70 | 0.568 | | 0.20 | 0.886 | |
| ZH11-TC | 38 | 24 | 8.24 | | | | | | |
| DP0158 | 30 | 18 | 8.75 | | | | | | |
| DP2116.01 | 24 | 15 | 11.14 | 2.90 | 0.052 | Y | 2.40 | 0.138 | |
| DP2116.02 | 25 | 16 | 7.94 | −0.31 | 0.848 | | −0.81 | 0.636 | |
| DP2116.03 | 40 | 24 | 9.91 | 1.67 | 0.226 | | 1.16 | 0.449 | |
| DP2116.04 | 33 | 20 | 6.99 | −1.25 | 0.380 | | −1.75 | 0.262 | |
| DP2116.05 | 20 | 12 | 10.83 | 2.59 | 0.105 | | 2.09 | 0.224 | |
| DP2116.07 | 14 | 10 | 12.22 | 3.98 | 0.012 | Y | 3.48 | 0.041 | Y |
| DP2116.08 | 30 | 18 | 7.11 | −1.14 | 0.432 | | −1.64 | 0.307 | |
| DP2116.09 | 40 | 24 | 6.78 | −1.46 | 0.304 | | −1.97 | 0.206 | |
| DP2116.10 | 40 | 24 | 9.64 | 1.39 | 0.321 | | 0.89 | 0.554 | |
| DP2116.11 | 31 | 19 | 8.34 | 0.09 | 0.944 | | −0.41 | 0.782 | |
| DP2116.12 | 19 | 12 | 10.54 | 2.29 | 0.135 | | 1.79 | 0.290 | |
| DP2116.14 | 23 | 14 | 5.91 | −2.34 | 0.115 | | −2.84 | 0.076 | |

TABLE 56

Grain yield analysis of OsDN-DSP1 suppressed (DP2116) transgenic rice plants under field drought conditions (2$^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP2116 (Construct) | | | 10.04 | −0.28 | 0.874 | | 3.62 | 0.065 | Y |
| ZH11-TC | 36 | 24 | 10.33 | | | | | | |
| DP0158 | 28 | 18 | 6.42 | | | | | | |
| DP2116.02 | 10 | 6 | 9.81 | −0.52 | 0.819 | | 3.39 | 0.158 | |
| DP2116.03 | 19 | 12 | 10.00 | −0.33 | 0.870 | | 3.58 | 0.100 | Y |
| DP2116.07 | 40 | 24 | 10.76 | 0.43 | 0.809 | | 4.34 | 0.026 | Y |
| DP2116.10 | 40 | 24 | 9.34 | −0.99 | 0.577 | | 2.92 | 0.134 | |
| DP2116.13 | 37 | 24 | 10.32 | −0.01 | 0.994 | | 3.90 | 0.043 | Y |

9) Field DRT Validation Results of OsPP2C64 Suppressed Transgenic Rice (DP1549)

T2 eleven OsPP2C64 suppressed transgenic lines were tested in Hainan Province, ZH11-TC and DP0158 rice plants planted nearby were used as controls. Watering was stopped when the main stem panicles were at panicle initiation stage III. The soil volumetric water content decreased slowly from 16% to 6% (FIG. 12). 50 days after stopping watering, the main stem panicles were at milk stage and the rice plants started to show leaf rolling phenotypes. Five suppressed transgenic lines DP1549.03, DP1549.04, DP1549.06, DP1549.10 and DP1549.13 showed drought tolerance phenotype and good setting rate after the drought stress. As shown in Table 57, the OsPP2C64 suppressed transgenic rice plant didn't obtain more grain yield per plant than ZH11-TC and DP0158 controls at the construct level.

T2 OsPP2C64 suppressed transgenic lines were tested in Ningxia Province again, ZH11-TC and DP0158 rice plants planted nearby were used as controls. Watering was stopped when the main stem panicles were at panicle initiation stage I. The soil volumetric water content decreased slowly from 45% to 20%. The following rain affected the soil volumetric water content 38 days after stopping watering. 27 days after stopping watering, the rice plants were at milk stage and show leaf rolling phenotype. All the tested suppressed transgenic lines showed good setting rate after the drought stress. As shown in Table 58, the OsPP2C64 suppressed transgenic rice plant obtained equal grain yield per plant to DP0158 control at the construct level.

TABLE 57

Grain yield analysis of OsPP2C64 suppressed (DP1549) transgenic rice plants under field drought conditions (1$^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1549 (Construct) | | | 8.44 | −3.10 | 0.010 | | 0.14 | 0.908 | |
| ZH11-TC | 36 | 23 | 11.54 | | | | | | |
| DP0158 | 40 | 24 | 8.30 | | | | | | |
| DP1549.03 | 35 | 24 | 9.54 | −1.99 | 0.149 | | 1.24 | 0.370 | |
| DP1549.04 | 38 | 24 | 8.83 | −2.71 | 0.052 | | 0.53 | 0.704 | |
| DP1549.05 | 40 | 24 | 5.65 | −5.89 | 0.000 | | −2.65 | 0.058 | |
| DP1549.06 | 37 | 24 | 8.98 | −2.56 | 0.066 | | 0.68 | 0.626 | |
| DP1549.07 | 40 | 24 | 7.97 | −3.56 | 0.010 | | −0.32 | 0.818 | |
| DP1549.08 | 27 | 21 | 8.69 | −2.84 | 0.040 | | 0.40 | 0.779 | |
| DP1549.09 | 39 | 24 | 6.65 | −4.88 | 0.000 | | −1.64 | 0.241 | |
| DP1549.10 | 38 | 24 | 10.73 | −0.80 | 0.582 | | 2.43 | 0.098 | Y |
| DP1549.11 | 30 | 18 | 8.47 | −3.06 | 0.036 | | 0.17 | 0.906 | |
| DP1549.12 | 25 | 16 | 7.86 | −3.68 | 0.012 | | −0.44 | 0.763 | |
| DP1549.13 | 40 | 24 | 11.11 | −0.42 | 0.761 | | 2.82 | 0.044 | Y |

TABLE 58

Grain yield analysis of OsPP2C64 suppressed (DP1549) transgenic rice plants under field drought conditions (2$^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1549 (Construct) | | | 15.63 | −5.60 | 0.001 | | 0.54 | 0.755 | |
| ZH11-TC | 39 | 24 | 21.23 | | | | | | |
| DP0158 | 35 | 24 | 15.09 | | | | | | |
| DP1549.01 | 30 | 18 | 16.20 | −5.03 | 0.014 | | 1.11 | 0.580 | |
| DP1549.03 | 38 | 24 | 17.34 | −3.89 | 0.047 | | 2.25 | 0.255 | |
| DP1549.04 | 38 | 24 | 14.45 | −6.78 | 0.000 | | −0.63 | 0.748 | |
| DP1549.05 | 33 | 24 | 13.45 | −7.78 | 0.000 | | −1.64 | 0.407 | |
| DP1549.06 | 38 | 24 | 16.06 | −5.17 | 0.008 | | 0.97 | 0.624 | |
| DP1549.07 | 33 | 22 | 14.73 | −6.50 | 0.001 | | −0.36 | 0.857 | |
| DP1549.08 | 26 | 18 | 18.58 | −2.65 | 0.199 | | 3.49 | 0.095 | Y |
| DP1549.09 | 31 | 21 | 13.82 | −7.41 | 0.000 | | −1.27 | 0.522 | |
| DP1549.10 | 31 | 18 | 18.23 | −3.00 | 0.147 | | 3.15 | 0.132 | |
| DP1549.11 | 29 | 18 | 14.68 | −6.55 | 0.001 | | −0.41 | 0.844 | |
| DP1549.12 | 31 | 22 | 15.09 | −6.14 | 0.002 | | 0.01 | 0.997 | |
| DP1549.13 | 39 | 24 | 14.92 | −6.31 | 0.001 | | −0.17 | 0.927 | |

10) Field DRT Validation Results of OsPPL1 Suppressed Transgenic Rice (DP2111)

T2 eleven OsPPL1 suppressed transgenic lines were tested in Hainan Province, ZH11-TC and DP0158 rice plants planted nearby were used as controls. Watering was stopped when the main stem panicles were at panicle initiation stage III. The soil volumetric water content decreased slowly from 16% to 6% (FIG. 12). 50 days after stopping watering, the main stem panicles were at milk stage and the rice plants started to show leaf rolling phenotypes. As shown in Table 59, the OsPPL1 suppressed transgenic rice plant obtained equal grain yield per plant to ZH11-TC and DP0158 controls at the construct level. Two lines showed significantly greater grain yield per plant than DP158 control.

TABLE 59

Grain yield analysis of OsPPL1 suppressed (DP2111) transgenic rice plants under field drought conditions

| Line ID | Number of survival plants | Number of harvested plants | Yield per plant (g) | CK = ZH11-TC Difff | P value | P ≤ 0.1 | CK = DP0158 Diff | P value | P ≤ 0.1 |
|---|---|---|---|---|---|---|---|---|---|
| DP2111 (Construct) | | | 7.73 | −0.84 | 0.48 | | 0.40 | 0.73 | |
| ZH11-TC | 38 | 24 | 8.57 | | | | | | |
| DP0158 | 36 | 23 | 7.32 | | | | | | |
| DP2111.01 | 34 | 22 | 6.43 | −2.14 | 0.124 | | −0.89 | 0.518 | |
| DP2111.02 | 20 | 12 | 8.89 | 0.32 | 0.837 | | 1.57 | 0.315 | |
| DP2111.03 | 37 | 24 | 9.69 | 1.12 | 0.420 | | 2.37 | 0.078 | Y |
| DP2111.04 | 40 | 24 | 6.37 | −2.20 | 0.096 | | −0.96 | 0.480 | |
| DP2111.05 | 29 | 18 | 10.38 | 1.81 | 0.216 | | 3.06 | 0.029 | Y |
| DP2111.06 | 28 | 18 | 8.10 | −0.47 | 0.752 | | 0.78 | 0.594 | |
| DP2111.08 | 30 | 18 | 8.11 | −0.46 | 0.756 | | 0.79 | 0.578 | |
| DP2111.09 | 15 | 10 | 6.57 | −2.00 | 0.190 | | −0.75 | 0.630 | |
| DP2111.10 | 40 | 24 | 7.59 | −0.98 | 0.467 | | 0.26 | 0.846 | |
| DP2111.11 | 39 | 24 | 5.93 | −2.64 | 0.057 | | −1.40 | 0.313 | |
| DP2111.12 | 40 | 24 | 8.54 | −0.03 | 0.985 | | 1.22 | 0.366 | |
| DP2111.13 | 40 | 24 | 6.13 | −2.44 | 0.069 | | −1.20 | 0.370 | |

Example 11

Laboratory Paraquat Assays of Gene Expression Suppressed or Genome Edited Rice Plants Transgenic Rice Plants T2 seeds were screened in paraquat solution to validate whether reducing the gene expression can enhance paraquat tolerance of the transgenic rice plants.

The screening method was described in Example 6.

Results:

1) Paraquat Validation Results of OsPRP1 Suppressed (DP2108) Transgenic Rice Plants After paraquat solution treated for seven days, 403 of the 540 OsPRP1 suppressed transgenic seedlings (74%) kept green and showed tolerant phenotype, while 128 of the 180 (71%) seedlings from ZH11-TC showed tolerant phenotype, and 129 of the 180 (72%) DP0158 seedlings showed tolerant phenotype. The tolerance rate of all screened OsPRP1 suppressed transgenic seedlings was more than ZH11-TC and DP0158 controls.

Further analysis at transgenic line level indicates that six lines had greater tolerance rates compared with ZH11-TC and DP0158 controls, and one line had significantly greater tolerance rates than ZH11-TC and DP0158 controls (Table 60). These results demonstrate that OsPRP1 suppressed transgenic rice plants may tolerance to Paraquat condition at seedling stages. Data in Example 6 shown over-expression OsPRP1 gene resulted in sensitive to paraquat condition. The validation of OsPRP1 suppressed rice plants indicated reducing the expression level of OsPRP1 gene may enhance paraquat tolerance and enhance tolerance to oxidative conditions.

TABLE 60

Paraquat tolerance assay of OsPRP1 suppressed transgenic rice plants under laboratory conditions

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2108 | 403 | 540 | 74 | 0.4426 | | 0.5314 | |
| ZH11-TC | 128 | 180 | 71 | | | | |
| DP0158 | 129 | 180 | 72 | | | | |
| DP2108.01 | 53 | 60 | 88 | 0.0120 | Y | 0.0142 | Y |
| DP2108.03 | 37 | 60 | 62 | 0.1780 | | 0.1529 | |
| DP2108.05 | 46 | 60 | 77 | 0.4080 | | 0.4539 | |
| DP2108.07 | 44 | 60 | 73 | 0.7419 | | 0.8040 | |
| DP2108.08 | 37 | 60 | 62 | 0.1780 | | 0.1529 | |
| DP2108.10 | 47 | 60 | 78 | 0.2814 | | 0.3172 | |
| DP2108.11 | 47 | 60 | 78 | 0.2814 | | 0.3172 | |
| DP2108.12 | 40 | 60 | 67 | 0.5180 | | 0.4656 | |
| DP2108.14 | 44 | 60 | 73 | 0.7419 | | 0.8040 | |

2) Paraquat Validation Results of OsPPL1 Suppressed (DP2111) Transgenic Rice Plants After paraquat solution treated for seven days, 452 of the 600 OsPPL1 suppressed transgenic seedlings (75%) kept green and showed tolerant phenotype, while 121 of the 180 (67%) seedlings from ZH11-TC showed tolerant phenotype, and 118 of the 180 (66%) DP0158 seedlings showed tolerant phenotype. The tolerance rate of all screened OsPPL1 suppressed transgenic seedlings was significantly greater than ZH11-TC and DP0158 controls.

Further analysis at transgenic line level indicates that seven lines had greater tolerance rates compared with ZH11-TC and DP0158 controls, and four lines had significantly greater tolerance rates than ZH11-TC and DP0158 controls (Table 61). These results demonstrate that OsPPL1 suppressed transgenic rice plants were tolerance to Paraquat condition at seedling stages.

TABLE 61

Paraquat tolerance assay of OsPPL1 suppressed transgenic rice plants under laboratory conditions (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2111 (Construct) | 452 | 600 | 75 | 0.0118 | Y | 0.0037 | Y |
| ZH11-TC | 121 | 180 | 67 | | | | |
| DP0158 | 118 | 180 | 66 | | | | |

TABLE 61-continued

Paraquat tolerance assay of OsPPL1 suppressed transgenic rice plants under laboratory conditions (1st experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2111.01 | 37 | 60 | 62 | 0.4349 | | 0.5869 | |
| DP2111.02 | 46 | 60 | 77 | 0.1751 | | 0.1162 | |
| DP2111.03 | 46 | 60 | 77 | 0.1751 | | 0.1162 | |
| DP2111.05 | 49 | 60 | 82 | 0.0394 | Y | 0.0241 | Y |
| DP2111.06 | 53 | 60 | 88 | 0.0036 | Y | 0.0021 | Y |
| DP2111.08 | 53 | 60 | 88 | 0.0036 | Y | 0.0021 | Y |
| DP2111.09 | 52 | 60 | 87 | 0.0066 | Y | 0.0039 | Y |
| DP2111.10 | 40 | 60 | 67 | 0.9362 | | 0.8764 | |
| DP2111.11 | 42 | 60 | 70 | 0.6916 | | 0.5301 | |
| DP2111.12 | 34 | 60 | 57 | 0.1460 | | 0.2228 | |

In the second experiment, after paraquat solution treated for seven days, 461 of the 600 OsPPL1 suppressed transgenic seedlings (77%) kept green and showed tolerant phenotype, while 108 of the 180 (60%) seedlings from ZH11-TC showed tolerant phenotype, and 123 of the 180 (68%) DP0158 seedlings showed tolerant phenotype. The tolerance rate of all screened OsPPL1 suppressed transgenic seedlings was significantly greater than ZH11-TC control (P value=0.0000) and DP0158 control (P value=0.0000).

Further analysis at transgenic line level indicates that eight lines had greater tolerance rates compared with ZH11-TC and DP0158 controls, and six lines had significantly greater tolerance rates than ZH11-TC control and four lines had significantly greater tolerance rates than DP0158 control (Table 62). These results demonstrate that OsPPL1 suppressed transgenic rice plants were tolerant to Paraquat condition at seedling stages. OsPPL1 suppressed transgenic rice plants were tolerance to oxidative conditions.

TABLE 62

Paraquat tolerance assay of OsPPL1 suppressed transgenic rice plants under laboratory conditions (2nd experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2111 (Construct) | 461 | 600 | 77 | 0.0000 | Y | 0.0000 | Y |
| ZH11-TC | 108 | 180 | 60 | | | | |
| DP0158 | 123 | 180 | 68 | | | | |
| DP2111.01 | 41 | 60 | 68 | 0.2532 | | 0.9996 | |
| DP2111.02 | 47 | 60 | 78 | 0.0137 | Y | 0.1462 | |
| DP2111.03 | 38 | 60 | 63 | 0.6470 | | 0.4771 | |
| DP2111.05 | 51 | 60 | 85 | 0.0003 | Y | 0.0050 | Y |
| DP2111.06 | 41 | 60 | 68 | 0.2532 | | 0.9996 | |
| DP2111.08 | 55 | 60 | 92 | 0.0001 | Y | 0.0015 | Y |
| DP2111.09 | 55 | 60 | 92 | 0.0001 | Y | 0.0015 | Y |
| DP2111.10 | 50 | 60 | 83 | 0.0022 | Y | 0.0308 | Y |
| DP2111.11 | 48 | 60 | 80 | 0.0076 | Y | 0.0906 | |
| DP2111.12 | 35 | 60 | 58 | 0.8206 | | 0.1623 | |

3) Paraquat Validation Results of OsMFS9 Suppressed (DP0687) Transgenic Rice Plants After paraquat solution treated for seven days, 225 of the 600 OsMFS9 suppressed transgenic seedlings (38%) kept green and showed tolerant phenotype, while 54 of the 180 (30%) ZH11-TC seedlings showed tolerant phenotype. The tolerance rate of all screened OsMFS9 suppressed transgenic seedlings was greater than ZH11-TC control.

Further analysis at transgenic line level indicates that six lines had greater tolerance rates compared with ZH11-TC control, and four lines had significantly greater tolerance rates than ZH11-TC control (Table 63). These results demonstrate that OsMFS9 suppressed transgenic rice plants were tolerance to Paraquat condition at seedling stages.

TABLE 63

Paraquat tolerance assay of OsMFS9 suppressed transgenic rice plants under laboratory conditions ($1^{st}$ experiment)

| Line ID | Number of tolerant seedlings | Number of total seedlings | Tolerant rate (%) | P value | P ≤ 0.05 |
|---|---|---|---|---|---|
| DP0687 (Construct) | 225 | 600 | 38 | 0.1193 | |
| ZH11-TC | 54 | 180 | 30 | | |
| DP0687.01 | 28 | 60 | 47 | 0.0227 | Y |
| DP0687.02 | 17 | 60 | 28 | 0.8073 | |
| DP0687.03 | 29 | 60 | 48 | 0.0129 | Y |
| DP0687.04 | 9 | 60 | 15 | 0.0287 | |
| DP0687.05 | 21 | 60 | 35 | 0.4724 | |
| DP0687.06 | 16 | 60 | 27 | 0.6247 | |
| DP0687.07 | 28 | 60 | 47 | 0.0227 | Y |
| DP0687.08 | 37 | 60 | 62 | 0.0000 | Y |
| DP0687.09 | 18 | 60 | 30 | 1.0000 | |
| DP0687.10 | 22 | 60 | 37 | 0.3409 | |

In the second experiment, after paraquat solution treated for seven days, 252 of the 600 OsMFS9 suppressed transgenic seedlings (42%) kept green and showed tolerant phenotype, while 55 of the 180 (31%) ZH11-TC seedlings showed tolerant phenotype. The tolerance rate of all screened OsMFS9 suppressed transgenic seedlings was significantly greater than ZH11-TC control.

Further analysis at transgenic line level indicates that nine lines had greater tolerance rates compared with ZH11-TC control, and three lines had significantly greater tolerance rates than ZH11-TC control (Table 63). These results demonstrate that OsMFS9 suppressed transgenic rice plants were tolerance to Paraquat condition at seedling stages.

TABLE 64

Paraquat tolerance assay of OsMFS9 suppressed transgenic rice plants under laboratory conditions ($2^{nd}$ experiment)

| Line ID | Number of tolerant seedlings | Number of total seedlings | Tolerant rate (%) | P value | P ≤ 0.05 |
|---|---|---|---|---|---|
| DP0687 | 252 | 600 | 42 | 0.0091 | Y |
| ZH11-TC | 55 | 180 | 31 | | |
| DP0687.01 | 23 | 60 | 38 | 0.2692 | |
| DP0687.02 | 32 | 60 | 53 | 0.0026 | Y |
| DP0687.03 | 20 | 60 | 33 | 0.6884 | |
| DP0687.04 | 25 | 60 | 42 | 0.1193 | |
| DP0687.05 | 31 | 60 | 52 | 0.0048 | Y |
| DP0687.06 | 23 | 60 | 38 | 0.2692 | |
| DP0687.07 | 17 | 60 | 28 | 0.7452 | |
| DP0687.08 | 34 | 60 | 57 | 0.0007 | Y |
| DP0687.09 | 22 | 60 | 37 | 0.3825 | |
| DP0687.10 | 25 | 60 | 42 | 0.1194 | |

4) Paraquat Validation Results of OsMFS9 Gene Edited (DP2389) Rice Plants

After paraquat solution treated for seven days, 351 of the 480 OsMFS9 gene edited (DP2389) seedlings (73%) kept green and showed tolerant phenotype, while 111 of the 180 (62%) ZH11-TC seedlings showed tolerant phenotype, 82 of the 120 (68%) DP0158 seedlings showed tolerant phenotype. The tolerance rate of all screened OsMFS9 gene edited (DP2389) seedlings was significantly greater than ZH11-TC control.

Further analysis at transgenic line level indicates that eight lines had greater tolerance rates compared with ZH11-TC control, and five lines had greater tolerance rates than DP0158 control (Table 65). These results demonstrate that OsMFS9 gene edited (DP2389) rice plants were tolerance to Paraquat condition at seedling stages

TABLE 65

Paraquat tolerance assay of OsMFS9 gene edited (DP2389) rice plants under laboratory conditions ($1^{st}$ experiment)

| Line ID | Number of tolerant seedlings | Number of total seedlings | Tolerant rate (%) | CK = ZH11-TC | | CK = DP0158 | |
|---|---|---|---|---|---|---|---|
| | | | | P value | P ≤ 0.05 | P value | P ≤ 0.05 |
| DP2389 (Construct) | 351 | 480 | 73 | 0.0040 | Y | 0.2411 | |
| ZH11-TC | 111 | 180 | 62 | | | | |
| DP0158 | 82 | 120 | 68 | | | | |
| DP2389P.03B.11 | 40 | 60 | 67 | 0.4904 | | 0.8223 | |
| DP2389P.10B.02 | 40 | 60 | 67 | 0.4904 | | 0.8223 | |
| DP2389P.13B.03 | 52 | 60 | 87 | 0.0011 | Y | 0.0122 | Y |
| DP2389P.14B.07 | 42 | 60 | 70 | 0.2506 | | 0.8206 | |
| DP2389P.14B.09 | 46 | 60 | 77 | 0.0405 | Y | 0.2509 | |
| DP2389P.17B.09 | 46 | 60 | 77 | 0.0405 | Y | 0.2509 | |
| DP2389P.17B.15 | 41 | 60 | 68 | 0.3577 | | 1.0000 | |
| DP2389P.18B.02 | 44 | 60 | 73 | 0.1089 | | 0.4931 | |

In the second experiment, after paraquat solution treated for seven days, 376 of the 540 OsMFS9 gene edited (DP2389) seedlings (70%) kept green and showed tolerant phenotype, while 119 of the 180 (66%) ZH11-TC seedlings showed tolerant phenotype, 73 of the 120 (61%) DP0158 seedlings showed tolerant phenotype. The tolerance rate of all screened OsMFS9 gene edited (DP2389) seedlings was greater than ZH11-TC and DP0158 controls.

Further analysis at transgenic line level indicates that seven lines had greater tolerance rates compared with ZH11-TC and DP0158 controls, and two lines had significantly greater tolerance rates than ZH11-TC and DP0158 controls (Table 66). These results demonstrate that OsMFS9 gene edited (DP2389) rice plants were tolerance to Paraquat condition at seedling stages

6) Paraquat Validation Results of OsMFS9 Promoter Edited (DP2421) Rice Plants After paraquat solution treated for seven days, 197 of the 240 OsMFS9 promoter edited (DP2421) seedlings (82%) kept green and showed tolerant phenotype, while 150 of the 228 (66%) ZH11-TC seedlings showed tolerant phenotype, 101 of the 180 (56%) DP0158 seedlings showed tolerant phenotype. The tolerance rate of all screened OsMFS9 promoter edited (DP2421) seedlings was significantly greater than ZH11-TC and DP0158 controls.

Further analysis at transgenic line level indicates that three lines had significantly greater tolerance rates compared with ZH11-TC and DP0158 controls (Table 65). These results demonstrate that OsMFS9 promoter edited (DP2421) rice plants were tolerance to Paraquat condition at seedling stages

TABLE 66

Paraquat tolerance assay of OsMFS9 gene edited (DP2389) rice plants under laboratory conditions (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2389 (Construct) | 376 | 540 | 70 | 0.3703 | | 0.0664 | |
| ZH11-TC | 119 | 180 | 66 | | | | |
| DP0158 | 73 | 120 | 61 | | | | |
| DP2389P.03B.11 | 36 | 60 | 60 | 0.3942 | | 0.9144 | |
| DP2389P.10B.02 | 41 | 60 | 68 | 0.7523 | | 0.3284 | |
| DP2389P.13B.03 | 48 | 60 | 80 | 0.0495 | Y | 0.0135 | Y |
| DP2389P.14B.07 | 33 | 60 | 55 | 0.1276 | | 0.4555 | |
| DP2389P.14B.09 | 48 | 60 | 80 | 0.0495 | Y | 0.0135 | Y |
| DP2389P.17B.09 | 44 | 60 | 73 | 0.3036 | | 0.1036 | |
| DP2389P.17B.15 | 41 | 60 | 68 | 0.7523 | | 0.3284 | |

5) Paraquat Validation Results of OsMFS9 Promoter Edited (DP2408) Rice Plants After paraquat solution treated for seven days, 340 of the 480 OsMFS9 promoter edited (DP2408) seedlings (71%) kept green and showed tolerant phenotype, while 126 of the 180 (70%) ZH11-TC seedlings showed tolerant phenotype, 79 of the 120 (66%) DP0158 seedlings showed tolerant phenotype. The tolerance rate of all screened promoter edited (DP2408) seedlings was little greater than ZH11-TC and DP0158 controls.

Further analysis at transgenic line level indicates that four lines had greater tolerance rates compared with ZH11-TC control, and six lines had greater tolerance rates than DP0158 control (Table 67).

TABLE 67

Paraquat tolerance assay of OsMFS9 promoter edited (DP2408) rice plants under laboratory conditions

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2409 (Construct) | 340 | 480 | 71 | 0.7619 | | 0.2544 | |
| ZH11-TC | 126 | 180 | 70 | | | | |
| DP0158 | 79 | 120 | 66 | | | | |
| DP2409H.01B.08 | 42 | 60 | 70 | 0.9990 | | 0.5744 | |
| DP2409H.02B.02 | 38 | 60 | 63 | 0.3393 | | 0.7408 | |
| DP2409P.01B.08 | 46 | 60 | 77 | 0.3238 | | 0.1423 | |
| DP2409P.01B.12 | 44 | 60 | 73 | 0.6224 | | 0.3104 | |
| DP2409P.02B.09 | 36 | 60 | 60 | 0.1569 | | 0.4438 | |
| DP2409P.03B.02 | 44 | 60 | 73 | 0.6224 | | 0.3104 | |
| DP2409P.03B.05 | 42 | 60 | 70 | 0.9990 | | 0.5744 | |
| DP2409P.04B.09 | 48 | 60 | 80 | 0.1412 | | 0.0562 | |

TABLE 68

Paraquat tolerance assay of OsMFS9 promoter edited
(DP2421) rice plants under laboratory conditions

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2421 (Construct) | 197 | 240 | 82 | 0.0000 | Y | 0.0000 | Y |
| ZH11-TC | 150 | 228 | 66 | | | | |
| DP0158 | 101 | 180 | 56 | | | | |
| DP2421H.02A.01 | 57 | 60 | 95 | Y | | 0.0000 | Y |
| DP2421H.11A.01 | 32 | 60 | 53 | | | 0.7094 | |
| DP2421H.14A.01 | 51 | 60 | 85 | Y | | 0.0003 | Y |
| DP2421H.10B3.01 | 57 | 60 | 95 | Y | | 0.0000 | Y |

Data in Example 6 shown over-expression OsMFS9 gene resulted in sensitive to paraquat condition. The validation of OsMFS9 suppressed rice plants and the promoter edited rice indicated that reducing the expression level of OsMFS9 gene enhance paraquat tolerance and enhance tolerance to oxidative conditions.

7) Paraquat Validation Results of OsDN-DSP1 Suppressed (DP2116) Transgenic Rice Plants After paraquat solution treated for seven days, 330 of the 600 OsDN-DSP1 suppressed transgenic seedlings (55%) kept green and showed tolerant phenotype, while 84 of the 180 (47%) seedlings from ZH11-TC showed tolerant phenotype, and 102 of the 180 (57%) DP0158 seedlings showed tolerant phenotype. The tolerance rate of all screened OsDN-DSP1 suppressed transgenic seedlings was significantly greater than ZH11-TC control.

Further analysis at transgenic line level indicates that eight lines had greater tolerance rates compared with ZH11-TC control, and five lines had greater tolerance rates than DP0158 control (Table 69). These results demonstrate that OsDN-DSP1 suppressed transgenic rice plants were tolerance to Paraquat condition at seedling stages.

In the second experiment, after paraquat solution treated for seven days, 353 of the 600 OsDN-DSP1 suppressed transgenic seedlings (59%) kept green and showed tolerant phenotype, while 87 of the 180 (48%) seedlings from ZH11-TC showed tolerant phenotype, and 87 of the 180 (48%) DP0158 seedlings showed tolerant phenotype. The tolerance rate of all screened OsDN-DSP1 suppressed transgenic seedlings was significantly greater than ZH11-TC and DP0158 controls.

Further analysis at transgenic line level indicates that all the ten lines had greater tolerance rates compared with ZH11-TC and DP1058 controls, and two lines had significantly greater tolerance rates than ZH11-TC and DP0158 control (Table 70). These results demonstrate that OsDN-DSP1 suppressed transgenic rice plants were tolerance to Paraquat condition at seedling stages.

TABLE 69

Paraquat tolerance assay of OsDN-DSP1 suppressed transgenic
rice plants under laboratory conditions (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP2116 (Construct) | 330 | 600 | 55 | 0.0493 | Y | 0.7034 | |
| ZH11-TC | 84 | 180 | 47 | | | | |
| DP0158 | 102 | 180 | 57 | | | | |
| DP2116.01 | 36 | 60 | 60 | 0.0754 | | 0.6478 | |
| DP2116.02 | 32 | 60 | 53 | 0.3673 | | 0.6492 | |
| DP2116.03 | 27 | 60 | 45 | 0.8205 | | 0.1173 | |
| DP2116.04 | 36 | 60 | 60 | 0.0754 | | 0.6478 | |
| DP2116.05 | 35 | 60 | 58 | 0.1182 | | 0.8194 | |
| DP2116.07 | 30 | 60 | 50 | 0.6508 | | 0.3654 | |
| DP2116.08 | 39 | 60 | 65 | 0.0161 | Y | 0.2546 | |
| DP2116.09 | 31 | 60 | 52 | 0.4979 | | 0.4960 | |
| DP2116.10 | 28 | 60 | 47 | 1.0000 | | 0.1776 | |
| DP2116.12 | 36 | 60 | 60 | 0.0754 | | 0.6478 | |

TABLE 70

Paraquat tolerance assay of OsDN-DSP1 suppressed transgenic rice plants under laboratory conditions (2nd experiment)

| Line ID | Number of tolerant seedlings | Number of total seedlings | Tolerant rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP2116 (Construct) | 353 | 600 | 59 | 0.0161 | Y | 0.0161 | Y |
| ZH11-TC | 87 | 180 | 48 | | | | |
| DP0158 | 87 | 180 | 48 | | | | |
| DP2116.02 | 35 | 60 | 58 | 0.1857 | | 0.1857 | |
| DP2116.03 | 39 | 60 | 65 | 0.0300 | Y | 0.0300 | Y |
| DP2116.04 | 31 | 60 | 52 | 0.6563 | | 0.6563 | |
| DP2116.05 | 31 | 60 | 52 | 0.6563 | | 0.6563 | |
| DP2116.07 | 31 | 60 | 52 | 0.6563 | | 0.6563 | |
| DP2116.08 | 37 | 60 | 62 | 0.0798 | | 0.0798 | |
| DP2116.10 | 37 | 60 | 62 | 0.0798 | | 0.0798 | |
| DP2116.11 | 42 | 60 | 70 | 0.0056 | Y | 0.0056 | Y |
| DP2116.12 | 36 | 60 | 60 | 0.1239 | | 0.1239 | |
| DP2116.14 | 34 | 60 | 57 | 0.3751 | | 0.3750 | |

Example 12

Evaluation the Function of Rice Genes in Maize Plants

Maize plants can be transformed or be modified to suppress *Oryza sativa* drought sensitive genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The suppression DNA construct can be introduced into maize cells by particle bombardment substantially as described in International Patent Publication WO 2009/006276. Alternatively, maize plants can be transformed with the suppression DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as T1 plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

What is claimed is:

1. A transgenic plant transformed with a recombinant nucleic acid molecule comprising an expression cassette which comprises a heterologous promoter operably linked to a DNA sequence encoding a gRNA molecule which targets one or more nucleotides in a regulatory element of a genomic region of a gene, wherein said gene encodes a polypeptide comprising an amino acid sequence that is at least 95% identical to the amino acid sequence as set forth in SEQ ID NO: 13, wherein said gRNA molecule produces genetic modifications in said regulatory element of said gene which is endogenous to said transformed plant, wherein said gRNA molecule and said genetic modifications are produced using CRISPR/Cas system, wherein the genetic modifications decreases the expression of said polypeptide when compared to the expression of the polypeptide in a control plant of the same species lacking said recombinant nucleic acid molecule, and wherein said genetic modifications in said transgenic plant result in at least one phenotype selected from the group consisting of increased drought tolerance, increased grain yield, increased abiotic stress tolerance and increased biomass, as compared to the control plant.

2. The transgenic plant of claim 1, wherein the genetic modifications comprising one or more nucleotide modifications in the genomic region of the gene comprising a nucleotide sequence having at least 90% nucleotide sequence identity to the nucleotide sequence as set forth in SEQ ID NO: 12.

3. The transgenic plant of claim 1, wherein the transgenic plant exhibits increased drought tolerance.

4. The transgenic plant of claim 1, wherein the transgenic plant is selected from the group consisting of rice, maize, soybean, sunflower, sorghum, canola, wheat, alfalfa, cotton, barley, millet, sugarcane and switchgrass.

5. A method of increasing drought tolerance in a plant, comprising:
   (i) transforming plant cells with a recombinant nucleic acid molecule comprising an expression cassette which comprises a heterologous promoter operably linked to a DNA sequence encoding a gRNA molecule which targets one or more nucleotides in a regulatory element of a genomic region of a gene, wherein said gene encodes a polypeptide comprising an amino acid sequence that is at least 95% identical to the amino acid sequence as set forth in SEQ ID NO: 13, wherein said gRNA molecule produces genetic modifications in said regulatory element of said gene which is endogenous to said transformed plant, wherein said gRNA molecule and said genetic modifications are produced using CRISPR/Cas system, wherein the genetic modifications decrease the expression of said polypeptide when compared to the expression of the polypeptide in a control plant of the same species lacking said recombinant nucleic acid molecule;
   (ii) regenerating transgenic plants from said transformed plant cells of step (i); and
   (iii) selecting a transgenic plant from said regenerated transgenic plants of step (ii) that expresses said gRNA molecule in said selected transgenic plant and exhibits increase in drought tolerance as compared to the control plant of the same species lacking said recombinant nucleic acid molecule.

6. The method of claim 5, wherein the genetic modifications comprising one or more nucleotide modifications in the genomic region of the gene comprising a nucleotide sequence having at least 90% nucleotide sequence identity to the nucleotide sequence as set forth in SEQ ID NO: 12.

7. The method of claim 5, wherein the said transgenic plant is selected from the group consisting of rice, maize, soybean, sunflower, sorghum, canola, wheat, alfalfa, cotton, barley, millet, sugar cane and switchgrass.

8. The method of claim 5, further comprising harvesting transgenic plant seeds from the selected transgenic plant of step (iii) and obtaining transgenic progeny plants.

* * * * *